US012742193B2

(12) United States Patent
Feinberg et al.

(10) Patent No.: US 12,742,193 B2
(45) Date of Patent: Sep. 22, 2026

(54) HETEROLOGOUS CAROTENOID PRODUCTION IN MICROORGANISMS

(71) Applicant: KnipBio, Inc., Lowell, MA (US)

(72) Inventors: Lawrence F. Feinberg, Lowell, MA (US); Daniel R. Smith, Lowell, MA (US); Bonnie D. McAvoy, Lowell, MA (US); Catherine J. Pujol-Baxley, Lowell, MA (US); Christopher J. Marx, Lowell, MA (US)

(73) Assignee: KnipBio, Inc., Lowell, MA (US)

( * ) Notice: Subject to any disclaimer, the term of this patent is extended or adjusted under 35 U.S.C. 154(b) by 684 days.

(21) Appl. No.: 18/071,945

(22) Filed: Nov. 30, 2022

(65) Prior Publication Data

US 2023/0348948 A1 Nov. 2, 2023

Related U.S. Application Data

(62) Division of application No. 16/618,048, filed as application No. PCT/US2018/035505 on May 31, 2018, now Pat. No. 11,560,583.

(60) Provisional application No. 62/513,892, filed on Jun. 1, 2017.

(51) Int. Cl.

| | |
|---|---|
| ***C12P 23/00*** | (2006.01) |
| ***A23K 20/179*** | (2016.01) |
| ***A23K 50/80*** | (2016.01) |
| ***A61K 9/00*** | (2006.01) |
| ***A61K 31/122*** | (2006.01) |
| ***B01D 3/00*** | (2006.01) |
| ***C12N 15/74*** | (2006.01) |

(52) U.S. Cl.

CPC ............ *C12P 23/00* (2013.01); *A23K 20/179* (2016.05); *A23K 50/80* (2016.05); *A61K 9/0056* (2013.01); *A61K 31/122* (2013.01); *B01D 3/001* (2013.01); *C12N 15/74* (2013.01)

(58) Field of Classification Search

CPC ........................................................ C12P 23/00

See application file for complete search history.

(56) References Cited

U.S. PATENT DOCUMENTS 5,968,251 A * 10/1999 Auweter .................. A23L 5/44 106/498

OTHER PUBLICATIONS

Shinichi Takaichi, Advances in Photosynthesis and Respiration, 2009, 8: 97-117.*
Astaxanthin supplement from Amazon.*

* cited by examiner

*Primary Examiner* — Rei Tsang Shiao
(74) *Attorney, Agent, or Firm* — Fountainhead Law Group, PC; Jill A. Jacobson

(57) ABSTRACT

Non-naturally occurring microorganisms are provided that produce C40 carotenoid compound(s), utilizing exogenously added enzyme activities. Methods of producing C40 carotenoid compounds in microbial cultures, and feed and nutritional supplement compositions that include the C40 carotenoid compounds produced in the microbial cultures, are also provided.

16 Claims, 9 Drawing Sheets

Specification includes a Sequence Listing.

| | Str05 | Str06 | Str05 + pD10 |
|---|---|---|---|
| Methanol | 1719 | 2931 | 2243 |
| Methanol/Ethanol | 1530 | 2203 | 1935 |

HETEROLOGOUS CAROTENOID PRODUCTION IN MICROORGANISMS

CROSS-REFERENCE TO RELATED APPLICATIONS

This application is a divisional of U.S. application Ser. No. 16/618,048, filed on Nov. 11, 2019, which issued as U.S. Pat. No. 11,560,583 B2 on Jan. 24, 2023, which is a U.S. National Phase application under 35 U.S.C. § 371 of PCT Application No. US2018/035505, filed on May 31, 2018, which claims the benefit of U.S. Provisional Application No. 62/513,892, filed on Jun. 1, 2017, which is incorporated by reference herein in its entirety.

SEQUENCE LISTING

The instant application contains a Sequence Listing which has been submitted electronically in XML file format and is hereby incorporated by reference in its entirety. Said XML copy, created on May 7, 2026, is named 000238-000303US_SL.xml and is 116,429 bytes in size.

FIELD OF THE INVENTION

The invention relates to production of carotenoid compounds in microbial organisms, and use in feed compositions, in particular for aquaculture, animal feeds and human nutrition.

BACKGROUND

Carotenoids are a class of ubiquitous and structurally diverse natural pigments ranging in color from light yellow to orange to red. Carotenoids are responsible for the coloring of carrots, tomatoes, red peppers, and the petals of daffodils and marigolds, as well as lobsters, salmon, and other marine life.

Carotenoids are produced by all photosynthetic organisms, as well as by some bacteria and fungi. Carotenoids have roles in photosynthesis, nutrition, and protection against photooxidative damage. Animals cannot produce carotenoids themselves, but must obtain these nutritionally important compounds through their diet. Carotenoids include 40-carbon ($C_{40}$) terpenoids ultimately derived from the isoprene biosynthetic pathway, specifically from isopentenyl pyrophosphate (IPP), a five-carbon building block. This biosynthetic pathway can be divided into two portions: the upper isoprene pathway, which leads to the formation of IPP, and the lower carotenoid biosynthetic pathway, responsible for converting IPP into long chain (e.g., $C_{30}$ and $C_{40}$) carotenogenic compounds.

Carotenoid compounds, such as 0-carotene, astaxanthin, canthaxanthin, zeaxanthin, and lutein, are used industrially as ingredients for food and feed stocks, both serving a nutritional role, and often increasing desirability of the product to consumers. Carotenoids, such as astaxanthin and canthaxanthin, are often added to aquaculture feeds for the purpose of providing color to the flesh of aquacultured organisms; their wild counterparts have colored flesh resulting from consumption of carotenoids that occur naturally in crustacea or algae, or in other fish that have consumed algae. For example, astaxanthin is widely used in salmon aquaculture to produce the orange to red coloration of the flesh found in wild salmon. The deposition of carotenoids in animals is dependent on the dosing, chemical species, purity of the compound, and the individual organism's biology (see, e.g., Matthews, et al. (2006) *Comp. Biochem. Physiol.* 206-14; Per Foss, et al. (1984) *Aquaculture* 41(3):213-26). Some carotenoids are also precursors of vitamin A. Moreover, some carotenoids have antioxidant properties, and may have health benefits, for example, against cardio-vascular problems, different types of cancer and some diseases of the immunological system (see, e.g., Jyonouchi, et al. (1991) *Nutr. Cancer* 16:93; Giovannucci, et al. (1995) *J. Natl. Cancer Inst.* 87:1767; Miki (1991) *Pure Appl. Chem* 63:141; Chew, et al. (1999) *Anticancer Res.* 19:1849; Wang, et al. (2000) *Antimicrob. Agents Chemother.* 44:2452; Higuera-Ciapara, et al. (2006) *Crit. Rev. in Food Science & Nutr.* 46(2):185-96). Several carotenoids (e.g., β-carotene, lycopene, and lutein) are currently sold as nutritional supplements.

A number of carotenoids have been produced in microbial organisms. For example, PCT Application No. WO 02/18617 describes a method of production of carotenoid compounds using microorganisms that metabolize single carbon substrates. Genes encoding elements of the carotenoid biosynthetic pathway have been cloned and expressed in fungi, yeast, and microbes. For example, lycopene has been produced from genetically engineered *Escherichia coli* and *Candida utilis* (see, e.g., Farmer, et al. (2001) *Biotechnol. Prog.* 17: 57-61; Wang, et al., (2000) *Biotechnol. Prog.* 16: 922-926; Misawa & Shimada (1998) *J Biotechnol.* 59: 169-181; Shimada, et al. (1998) *Appl. Environm. Microbiol.* 64: 2676-2680). Zeaxanthin has been produced from recombinant *E. coli* and *C. utilis* (see, e.g., Albrecht, et al. (1999) *Biotechnol. Lett.* 21:791-795; Miura, et al. (1998) *Appl. Environm. Microbiol.* 64: 1226-1229). Astaxanthin has been produced from *E. coli* and *Pfaffia rhodozyma* (see, e.g., U.S. Pat. No. 5,466,599). The nutrient O-carotene has been produced from *E. coli, C. utilis*, and *P. rhodozyma* (see, e.g., Albrecht, et al. (1999) *Biotechnol. Lett.* 21:791-795; Miura, et al. (1998) *Appl. Environm. Microbiol.* 64:1226-1229; U.S. Pat. No. 5,691,190).

Genes encoding geranylgeranyl pyrophosphate synthase, lycopene cyclase, and phytoene dehydrogenase from *Erwinia herbicola* have been expressed in *E. coli* (see, e.g., U.S. Pat. Nos. 5,545,816, 5,656,472, 5,530,189, and 5,530,188). Genes encoding such carotenoid products as geranylgeranyl pyrophosphate, phytoene, lycopene, β-carotene, and zeaxanthin-diglucoside, from *Erwinia uredovora*, have been expressed in *E. coli, Zymomonas mobilis*, and *Saccharomyces cerevisiae* (U.S. Pat. No. 5,429,939). Carotenoid biosynthetic genes including crtE, crtB, crtI, crtY, and crtZ taken from *Flavobacterium*, have been recombinantly expressed (see U.S. Pat. No. 6,124,113).

Although the above methods can produce useful amounts of carotenoids, a need exists for improved processes. A particular long-appreciated need is for a process that produces useful yields of carotenoids from an inexpensive feedstock and also produces one or more nutrients (e.g., lipids or protein). The resulting carotenoid- and nutrient-rich microbial or plant biomass could then be processed into feed for aquaculture or agriculture, or used as a nutrient source for humans.

There are several microorganisms that utilize single-carbon substrates as their sole energy sources. Examples of single-carbon substrates include methane, methanol, formate, thiols, and methylated amines. These organisms are referred to as methylotrophs and also herein as "C1 metabolizers." Few methylotrophs have been successfully utilized to produce nutrients on an industrial scale. Despite the fact that single-carbon substrates are cost-effective energy sources, the lack of information about methylotroph genetics and the resulting difficulty in their manipulation has limited their use primarily to the synthesis of native products.

There is also a need for and an economic benefit to be able to utilize process streams and waste effluents that result from ethanol production as alternative carbon substrates. Ethanol is commonly produced by fermenting sugars extracted from plant biomass into 'beer' from which the ethanol is removed and concentrated by distillation. The major residual material from this distillation process is called whole stillage. During production of ethanol from dry milled corn, this whole stillage is further separated by centrifugation into dry solids (wet cake or wet distiller grains (WDG)) and a liquid component called thin stillage. Thin stillage is further evaporated to form stillage syrup or condensed distiller solubles (CDS). These products are often combined to form wet distiller grains with solids (WDGS) and further dried to form dried distillers grains with solids (DDGS) to improve shelf life. WDG, CDS, WDGS, and/or DDGS are mixed into animal feed. Beer, thin stillage, and stillage syrup contains many potential carbon substrates including alcohols (glycerol, ethanol, butanediol), carbohydrates (glucose, glucan, xylose, xylan, arabinose, arabinan, galactose, galactan, maltose, cellulose, starch), organic acids (lactic acids, acetic acid), protein, peptides, amino acids and fat (see, e.g., Kim, et al. (2008) *Bioresource Technology* 99:5165-5176).

A need also exists for low-cost, complete nutrition for use in aquaculture. Aquaculture is the propagation, cultivation and marketing of aquatic animals and plants in a controlled environment. The aquaculture industry is currently the fastest growing animal protein production sector in the world. World aquaculture produces approximately 60 million tons of seafood at an annual value of more than $110 billion (USD). Presently, fish farming produces about half of all fish consumed globally and this percentage is growing as a result of declining yields from wild-caught fish in both marine and freshwater environments and the need to provide more protein to a swelling human population. Species groups produced in aquaculture include: carps and other cyprinids; oysters; clams, cockles and ark shells; scallops; shrimps and prawns; salmons, trouts and smelts; mussels; and tilapias and other cichlids.

While certain species (e.g., tilapia) can be fed an exclusively vegetarian diet, others require a carnivorous diet. Feed for carnivorous fish typically comprises fishmeal and fish oil derived from wild caught species of small pelagic fish (predominantly anchovy, jack mackerel, blue whiting, capelin, sand eel and menhaden). The fishmeal is processed into a pelleted or flaked feed, depending on the size of the fish to which it will be fed (e.g., fry, juveniles, adults). Other components of the aquaculture feed composition may include carotenoid pigments, vegetable protein, vitamins, and minerals.

Many organizations recognize the limitations to fishmeal availability and aquaculture sustainability. The National Oceanic and Atmospheric Administration and the United States Department of Agriculture have collaborated in an Alternative Feeds Initiative to " . . . identify alternative dietary ingredients that will reduce the amount of fishmeal contained in aquaculture feeds while maintaining the important human health benefits of farmed seafood." (NOAA Technical memorandum NMFS F/SPO-124, 2011).

U.S. Pat. Appl. Pub. No. 2007/0226814 discloses fish food containing at least one biomass obtained from fermenting microorganisms wherein the biomass contains at least 20% DHA relative to the total fatty acid content. Microorganisms from the genus Stramenopiles are mentioned as sources of DHA. U.S. Pat. Appl. Pub. No. 2009/0202672 discloses that stearidonic acid ("SDA"; 18:4 omega-3) can be added to aquaculture feed. This fatty acid can be obtained from a transgenic plant. Unfortunately, SDA is not converted efficiently to DHA in fish. U.S. Pat. No. 7,932,077 discloses that recombinantly engineered *Yarrowia lipolytica* may be a useful addition to most animal feeds, including aquaculture feeds, because it provides necessary omega-3 and/or omega-6 PUFAs, and offers unique protein:lipid:carbohydrate composition, as well as unique complex carbohydrate profile (comprising an approximate 1:4:4.6 ratio of mannan: beta-glucans:chitin).

If the growing aquaculture industry is to sustain and even increase its contribution to world fish supplies, there is a need for alternative aquaculture feed compositions that: (i) reduce wild fish inputs by replacing fish meal with non-fish derived sources; and (ii) use pigments that are not chemically synthesized, or otherwise derived from petroleum-based feedstocks, to provide pigmentation.

BRIEF SUMMARY OF THE INVENTION

Microorganisms and methods for production of C40 carotenoid compounds and compositions containing the C40 carotenoid compounds are provided.

In one aspect, a microorganism is provided that includes a heterologous polynucleotide, including a polynucleotide sequence from *Paracoccus zeaxanthinifaciens, Escherichia vulnaris*, or *Pantoea ananatis* that encodes a polypeptide of a C40 carotenoid biosynthetic pathway or including a polynucleotide sequence with at least about 70% sequence identity thereof or including a polynucleotide sequence that encodes a polypeptide including at least about 70% sequence identity to the polypeptide of the C40 carotenoid biosynthetic pathway, operably linked to a promoter for expression of said polynucleotide sequence, wherein the microorganism is a bacterial cell from the class Alphaproteobacteria, and wherein the bacterial cell expresses said heterologous polynucleotide sequence to produce at least one C40 carotenoid compound.

In some embodiments, the microorganism further includes a polynucleotide sequence that expresses the heterologous gene sequence idi from *Escherichia vulneris* or includes a polynucleotide sequence with at least about 70% sequence identity thereof or includes a polynucleotide sequence that encodes a polypeptide comprising at least about 70% sequence identity to the polypeptide encoded by idi from *Escherichia vulneris*.

In another aspect, a microorganism is provided that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived, wherein the microorganism is a bacterial cell from the class Alphaproteobacteria.

In some embodiments, the microorganism further comprises a heterologous polynucleotide that encodes a polypeptide of a heterologous C40 carotenoid biosynthetic production pathway, wherein the microorganism expresses the heterologous polynucleotide to produce one or more C40 carotenoid compound.

In another aspect, a microorganism is provided that includes a heterologous polynucleotide containing a polynucleotide sequence that includes the gene sequence crtW from *Fulvimarina pelagi* or includes a polynucleotide sequence with at least about 70% sequence identity thereof or includes a polynucleotide sequence that encodes a polypeptide including at least about 70% sequence identity to the polypeptide encoded by crtW from *Fulvimarina pelagi*, operably linked to a promoter for expression of the polynucleotide sequence, wherein the microorganism is a Gram-negative bacterial cell, and wherein the bacterial cell expresses the heterologous polynucleotide to produce at least one C40 carotenoid compound.

In some embodiments, the microorganism further includes heterologous polynucleotide sequences that include the gene sequences crtY, crtI, and crtB from *Fulvimarina pelagi* or include polynucleotide sequences with at least about 70% sequence identity thereof or include polynucleotide sequences that encode polypeptides comprising at least about 75% sequence identity to the polypeptides encoded by crtY, crtI, and crtB from *Fulvimarina pelagi.*

In some embodiments, the microorganism includes the gene sequences crtW and crtZ from *Fulvimarina pelagi* or includes polynucleotide sequences with at least about 70% sequence identity thereof or includes polynucleotide sequences that encode polypeptides that include at least about 70% sequence identity to the polypeptides encoded by crtW and crtZ from *Fulvimarina pelagi.*

In some embodiments, the Gram-negative bacterial cell is from the phylum Proteobacteria. In some embodiments, the Gram-negative bacterial cell is from the class Alphaproteobacteria.

In some embodiments, a microorganism as disclosed herein expresses a heterologous polynucleotide to produce at least one C40 carotenoid compound selected from astaxanthin, canthaxanthin, zeaxanthin, phoenicoxanthin, adonixanthin, 3-hydroxyechinenone, echinenone, β-carotene, and lycopene.

In some embodiments, a microorganism as disclosed herein includes at least one heterologous polynucleotide including polynucleotide sequences that include the gene sequences crtZ, crtY, crtI, crtB, and crtE from *Paracoccus zeaxanthinifaciens, Escherichia vulneris*, and/or *Pantoea ananatis* or including polynucleotide sequences with at least about 70% sequence identity thereof or including polynucleotide sequences that that encode polypeptides comprising at least about 70% identity to the polypeptides encoded by crtZ, crtY, crtI, crtB, and crtE from *Paracoccus zeaxanthinifaciens, Escherichia vulneris*, and/or *Pantoea ananatis*, operably linked to a promoter for expression of said polynucleotide sequences, wherein the microorganism produces zeaxanthin.

In some embodiments, a microorganism as disclosed herein includes at least one heterologous polynucleotide including polynucleotide sequences that include the gene sequence crtW from *Fulvimarina pelagi* or including a polynucleotide sequence with at least about 70% sequence identity thereof or including a polynucleotide sequence that encodes a polypeptide comprising at least about 70% sequence identity to the polypeptide encoded by crtW from *Fulvimarina pelagi*, wherein the microorganism produces astaxanthin.

In some embodiments, a microorganism as disclosed herein includes at least one heterologous polynucleotide including polynucleotide sequences that include the gene sequences crtY, crtI, crtB, and crtE from *Paracoccus zeaxanthinifaciens, Escherichia vulneris*, and/or *Pantoea ananatis* or including polynucleotide sequences with at least about 70% sequence identity thereof or including polynucleotide sequences that encode polypeptides include at least about 70% identity to the polypeptides encoded by crtY, crtI, crtB, and crtE from *Paracoccus zeaxanthinifaciens, Escherichia vulnearis*, and/or *Pantoea ananatis*, operably linked to a promoter for expression of said polynucleotide sequences, wherein the microorganism produces β-carotene.

In some embodiments, a microorganism as disclosed herein includes a heterologous sequence that includes the gene sequence crtW from *Fulvimarina pelagi* or includes a polynucleotide sequence with at least about 70% sequence identity thereof or includes a polynucleotide sequence that encodes a polypeptide including at least about 70% sequence identity to the polypeptide encoded by crtW from *Fulvimarina pelagi*, wherein the microorganism produces canthaxanthin.

In another aspect, a microorganism is provided that includes a heterologous polynucleotide including a polynucleotide sequence from *Sphingomonas astaxanthinifaciens, Siansivirga zeaxanthinifaciens*, or *Mesoflavibacter zeaxanthinifaciens* that encodes a polypeptide of a C40 carotenoid biosynthetic pathway or including a polynucleotide sequence with at least about 70% sequence identity thereof or including a polynucleotide sequence that encodes a polypeptide including at least about 70% sequence identity to the polypeptide of the C40 carotenoid biosynthetic pathway, operably linked to a promoter for expression of the polynucleotide sequence, wherein the microorganism expresses the heterologous polynucleotide sequence to produce at least one C40 carotenoid compound.

In some embodiments, the microorganism is a bacterial cell. In some embodiments, the bacterial cell is from the phylum Proteobacteria. In some embodiments, the bacterial cell is from the class Alphaproteobacteria.

In some embodiment, the microorganism comprising a heterologous polynucleotide including polynucleotide sequences that encode the gene sequences crtZ, crtY, crtI, and crtB from *Siansivirga zeaxanthinifaciens*, and/or *Mesoflavibacter zeaxanthinifaciens* or including polynucleotide sequences with at least about 70% sequence identity thereof or including polynucleotide sequences that encode polypeptides including at least about 70% sequence identity to the polypeptides encoded by crtZ, crtY, crtI, and crtB from *Siansivirga zeaxanthinifaciens* and/or *Mesoflavibacter zeaxanthinifaciens*, wherein the microorganism produces astaxanthin, canthaxanthin, zeaxanthin, lycopene, beta-carotene or intermediates of these C40 carotenoids.

In some embodiment, the microorganism includes a heterologous polynucleotide including polynucleotide sequences that encode the gene sequences crtZ, crtY, crtI, crtB, and crtW from *Sphingomonas astaxanthinifaciens* or including polynucleotide sequences with at least about 70% sequence identity thereof or including polynucleotide sequences that encodes polypeptides comprising at least about 70% identity to the polypeptides encoded by crtZ, crtY, crtI, crtB, and crtW from *Sphingomonas astaxanthinifaciens*, wherein the microorganism produces astaxanthin, canthaxanthin, zeaxanthin, lycopene, beta-carotene or intermediates of these C40 carotenoids.

In some embodiments, a microorganism as disclosed herein is capable of producing at least one C40 carotenoid compound utilizing at least one C1 carbon sources, such as, but not limited to, methanol, methane, methylamine, and/or formate. In some embodiments, a microorganism as disclosed herein is capable of producing at least one C40 carotenoid compound utilizing at least one C2 carbon source, such as, but not limited to, ethanol, ethylamine, ethylene glycol, and/or acetate. In some embodiments, a microorganism as disclosed herein is capable of producing at least one C40 carotenoid compound utilizing a combination of C1 and C2 carbon sources. In some embodiment, a microorganism as disclosed herein is capable of producing at least one C40 carotenoid compound utilizing at least one C1 and/or C2 alcohol, such as, but not limited to, methanol and/or ethanol.

In some embodiments, a microorganism as disclosed herein is capable of producing at least one C40 carotenoid compound utilizing one or more process streams of fermentation to produce a bioproduct of interest, such as an alcohol or a biofuel, for example, ethanol fermentation and/or distillation, such as beer, wet stillage, thin stillage, and/or thin stillage syrup as a carbon source or media component for growth. In some embodiments, a microorganism as disclosed herein is capable of producing at least one C40 carotenoid compound utilizing one of more process streams of ethanol fermentation and/or distillation, in combination with additional C1 and/or C2 carbon sources, such as, but not limited to, methanol, ethanol, methane, methylamine, formate, ethylamine, ethylene glycol, and/or acetate. In some embodiments, a microorganism as disclosed herein is capable of producing at least one C40 carotenoid compound utilizing ethanol beer resulting from fermentation of plant biomass, and one or more alcohols, such as, but not limited to, methanol and/or ethanol. In some embodiments, a microorganism as disclosed herein is capable of producing at least one C40 carotenoid compound utilizing wet stillage resulting from distillation following fermentation of plant biomass, and one or more alcohols, such as, but not limited to, methanol and/or ethanol. In some embodiments, a microorganism as disclosed herein is capable of producing at least one C40 carotenoid compound utilizing thin stillage resulting from distillation following fermentation of plant biomass, and one or more alcohols, such as, but not limited to, methanol and/or ethanol. In some embodiments, a microorganism as disclosed herein is capable of producing at least one C40 carotenoid compound utilizing thin stillage syrup resulting from distillation following fermentation of plant biomass, and one or more alcohols, such as, but not limited to methanol and/or ethanol.

In some embodiments, a microorganism as disclosed herein is a bacterial cell in the genus *Methylobacteria*, such as, but not limited to, a *Methylobacterium extorquens* cell.

In another aspect, a method is provided for producing biomass that includes at least one C40 carotenoid compound, including culturing a microorganism as disclosed herein that includes a heterologous polynucleotide for C40 carotenoid in a culture medium under conditions suitable for growth of the bacterial cell or microorganism and production of the C40 carotenoid compound, wherein biomass including the C40 carotenoid compound is produced in the culture.

In some embodiments, the method includes utilizing at least one C1 compound and/or at least one C2 compound as carbon source(s) for the microorganism culture. In some embodiments, the method includes utilizing at least one C1 and/or C2 alcohol as carbon source(s) for the microorganism culture.

In some embodiments, the method includes utilizing at least one process stream of a fermentation to produce a bioproduct of interest, such as an alcohol or a biofuel, e.g., ethanol fermentation and/or distillation as carbon source(s) for the microorganism culture. In some embodiments, the method includes utilizing at least one process stream of ethanol fermentation and/or distillation as carbon source(s), in combination with at least one C1 and/or or C2 compound as carbon source(s) for the microorganism culture. In some embodiments, the method includes utilizing at least one process stream of ethanol fermentation and/or distillation as carbon source(s), in combination with at least one C1 and/or C2 alcohol as carbon source(s) for the microorganism culture.

In some embodiments, the microorganism is in the genus *Methylobacteria*, such as, but not limited to, *Methylobacterium extorquens*.

In another aspect, biomass that includes at least one C40 carotenoid compound is provided, wherein the biomass is produced according to a method as described herein for producing biomass in a microorganism that includes a heterologous polynucleotide for C40 carotenoid production.

In another aspect, a feed or nutritional supplement composition is provided that includes biomass produced according to a method as described herein for producing biomass in a microorganism that includes a heterologous polynucleotide for C40 carotenoid production In another aspect, a method is provided for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived, including culturing the microorganism according in a culture medium under conditions suitable for growth of the microorganism, wherein said biomass is produced in the culture.

In some embodiments, the method includes utilizing at least one C1 compound and/or at least one C2 compound as carbon source(s) for the microorganism culture. In some embodiments, the method includes utilizing at least one C1 and/or C2 alcohol as carbon source(s) for the microorganism culture.

In some embodiments, the method includes utilizing at least one process stream of a fermentation to produce a bioproduct of interest, such as an alcohol or a biofuel, e.g., ethanol fermentation and/or distillation as carbon source(s) for the microorganism culture. In some embodiments, the method includes utilizing at least one process stream of ethanol fermentation and/or distillation as carbon source(s), in combination with at least one C1 and/or or C2 compound as carbon source(s) for the microorganism culture. In some embodiments, the method includes utilizing at least one process stream of ethanol fermentation and/or distillation as carbon source(s), in combination with at least one C1 and/or C2 alcohol as carbon source(s) for the microorganism culture.

In some embodiments, the microorganism is in the genus *Methylobacteria*, such as, but not limited to, *Methylobacterium extorquens*.

In another aspect, biomass is provided, wherein the biomass is produced according to a method as described herein for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived.

In another aspect, a feed or nutritional supplement composition is provided that includes biomass produced according to a method as described herein for producing biomass in a microorganism that is derived from a parent microorganism that expresses a native pathway for C30 carotenoid production, wherein at least one gene sequence that encodes an enzyme of the native pathway for C30 carotenoid production has been disrupted or deleted such that C30 carotenoid production is reduced or eliminated in the microorganism in comparison to the parent microorganism from which it is derived

a. Absorbance trace of lycopene standard.
b. Absorbance trace of Str08 extract.
c. Absorbance trace of Str09 extract. Minor peak with retention time 3.12 minutes predicted to be cis-isomer of canthaxanthin.
d. Absorbance trace of Str06 extract. Minor peak with retention time 2.60 minutes predicted to be cis-isomer of zeaxanthin.
e. Absorbance trace of reference mixture of standard compounds (all trans-isomers).
f. Mass spectrometry trace of 565.24 m/z ions of Str07 extract. Exact mass of canthaxanthin ($C_{40}H_{52}O_2$) is 564.40 Da.
g. Mass spectrometry trace of 580.2 m/z ions of Str07 extract. Exact mass of phoenicaxanthin ($C_{40}H_{52}O_3$ is 580.39.
h. Mass spectrometry trace of 597.4 m/z ions of Str07 extract. Exact mass of astaxanthin ($C_{40}H_{52}O_4$) is 597.38.
i. Absorbance trace of Str07 extract.
j. Absorbance trace of reference mixture of standard compounds (all trans-isomers): astaxanthin (retention time 1.96 minutes); zeaxanthin (retention time 2.36 minutes); canthaxanthin (retention time 2.56 minutes); beta-carotene (retention time 4.14 minutes).

Figure 10A:
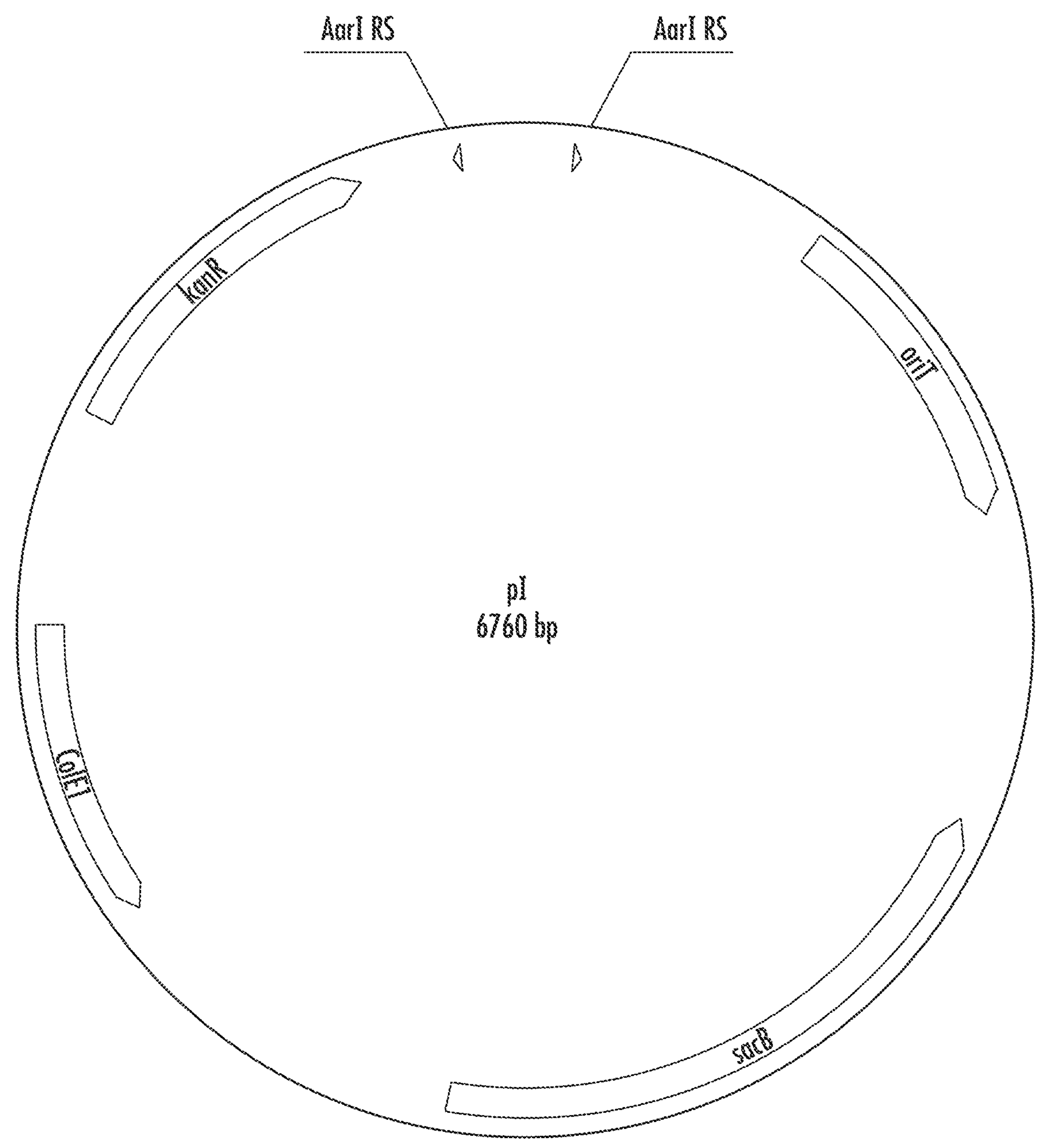
Figure 10B:
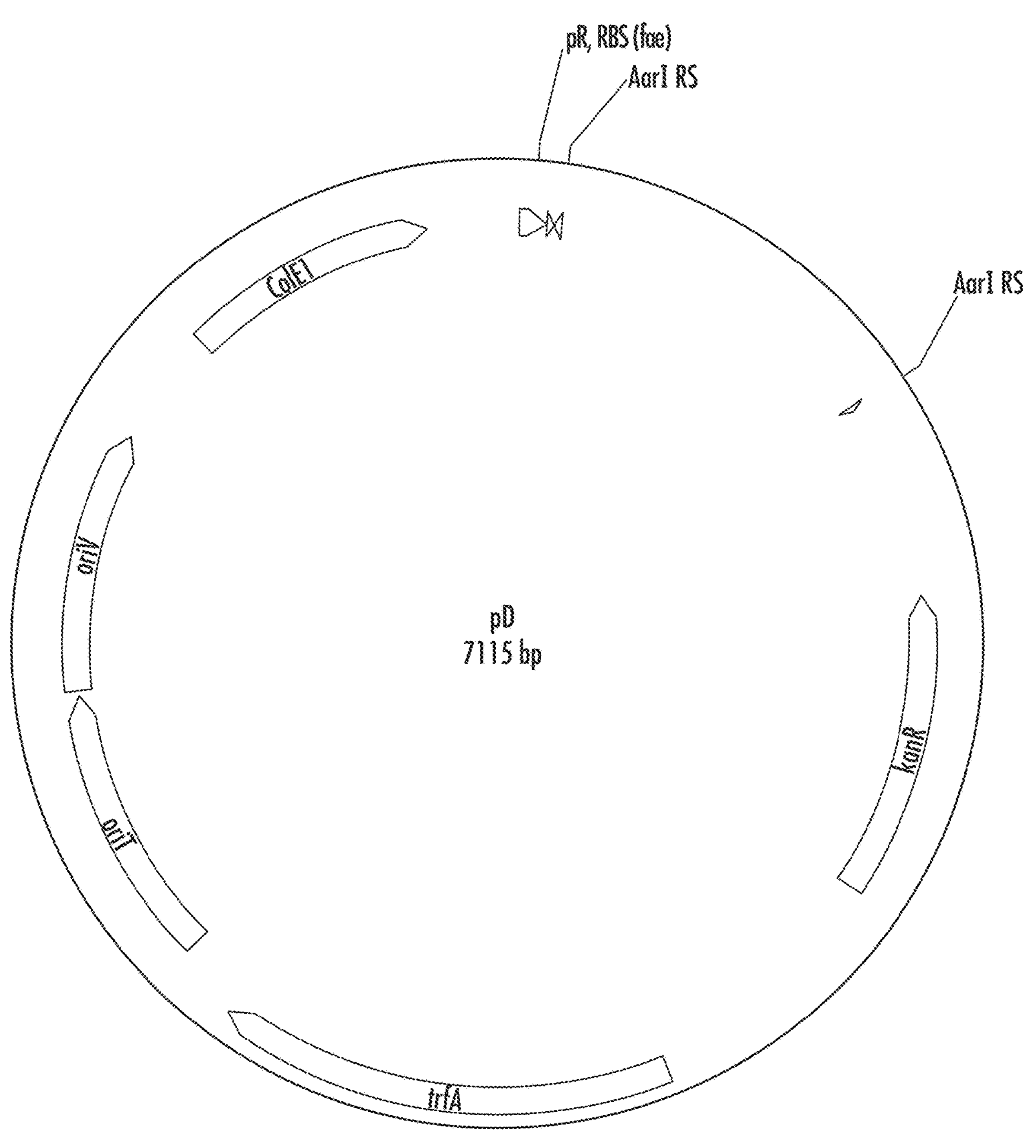
Figure 10C:
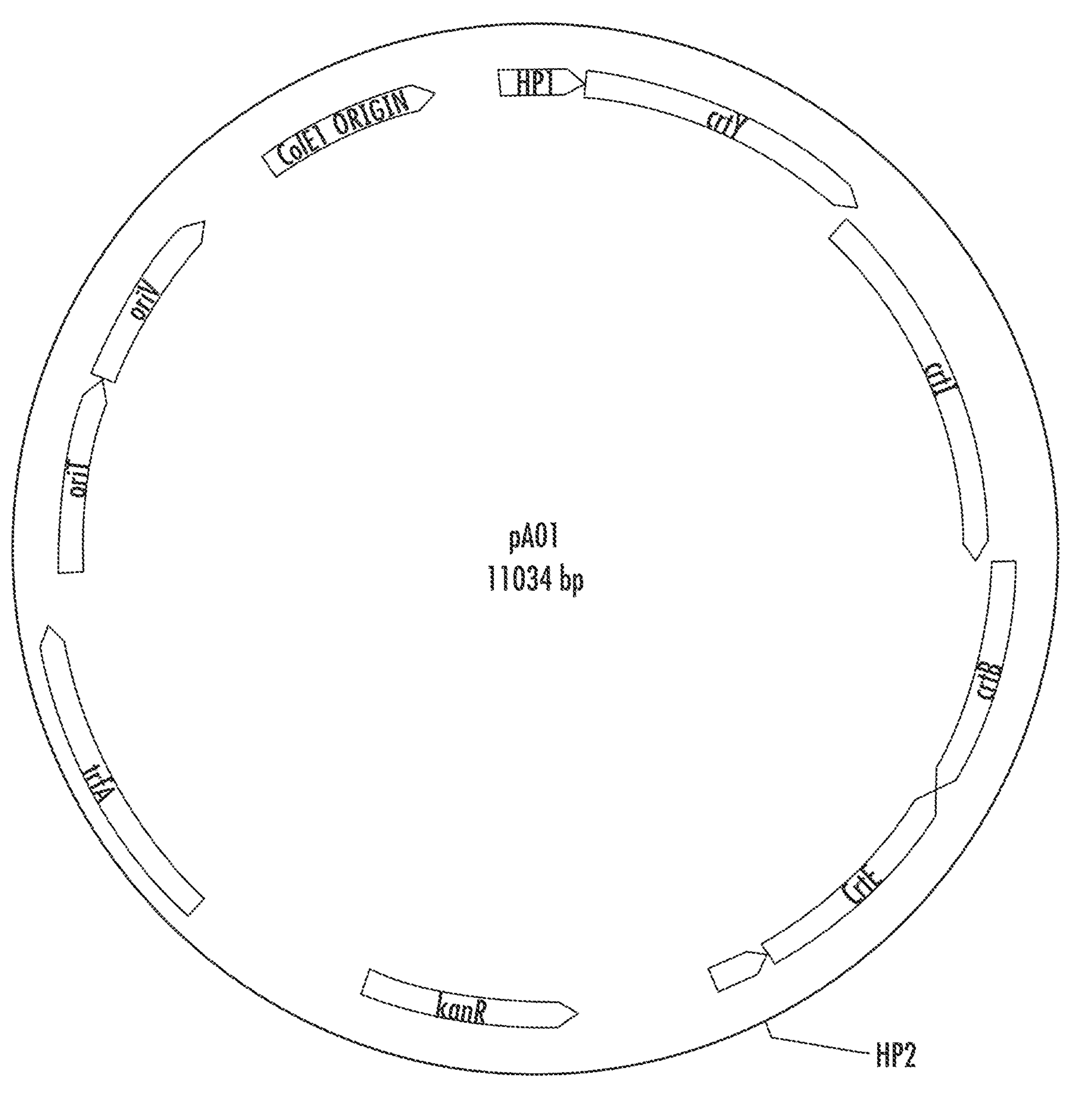

FIG. 10A shows a map of plasmid pI, as described in Example 3. FIG. 10B shows a map of plasmid pD, as described in Examples 1 and 5. FIG. 10C shows a map of plasmid pA01, as described in Example 2. Location of AarI restriction sites labeled "AarI-RS."

DETAILED DESCRIPTION

Provided herein are non-naturally occurring microorganisms that are capable of producing C40 carotenoid compound(s), e.g., astaxanthin, canthaxanthin, zeaxanthin, adonixanthin, 3-hydroxyechinenone, echinenone, β-carotene, lycopene, or any combinations thereof.

Also provided are methods of engineering and culturing such microorganisms, methods of using such microorganisms to produce C40 carotenoid compounds, and methods of producing C40 carotenoid-containing compositions, such as feed or nutritional compositions that contain the microorganisms or compositions that contain C40 carotenoid compounds recovered from such organisms.

Also provided herein are non-naturally occurring microorganisms in which C30 carotenoid production has been reduced or eliminated, methods of culturing such microorganisms, and compositions, such as feed or nutritional compositions, that contain the microorganisms.

One aspect pertains to the field of aquaculture. Another aspect is the field of pet foods, for example, for cats and dogs. A further aspect is in the field of human nutrition and supplements. More specifically, aquaculture feeds, pet food, and nutritional supplement compositions are provided that include C40 carotenoid-containing microbial biomass and/or biomass from microorganisms in which C30 carotenoid production has been reduced or eliminated, and a complete protein nutrition, that is, containing most or all amino acids necessary for healthy growth of the animal to which it is administered. The microbial biomass can be blended with other ingredients to form a portion or whole of a feed, or may be consumed directly as a protein-rich powder.

In some embodiments, microorganisms that are capable of being grown on inexpensive C1 and/or C2 feed stocks at an industrial scale that replace the (i) protein and (ii) pigment components are described.

In some embodiments, microorganisms that are capable of being grown on a process stream from a fermentation to produce a bioproduct of interest, such as an alcohol or a biofuel, e.g., inexpensive ethanol fermentation and/or distillation process streams (e.g., one or more of ethanol beer, wet stillage, thin stillage, thin stillage syrup) at an industrial scale that replace the (i) protein and (ii) pigment components are described. In some embodiments, microorganisms that are capable of being grown on ethanol fermentation and/or distillation process streams (e.g., one or more of ethanol beer, wet stillage, thin stillage, thin stillage syrup) in combination with C1 and/or C2 feed stocks at an industrial scale that replace the (i) protein and (ii) pigment components are described.

Definitions

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, The Harper *Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques).

"A," "an" and "the" include plural references unless the context clearly dictates otherwise.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

"Under translational control" is a term well understood in the art that indicates a regulatory process which occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" or "parent cell," used interchangeably herein, refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a protein which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "derived from" encompasses the terms "originated from," "obtained from," "obtainable from," "isolated from," and "created from," and generally indicates that one specified material finds its origin in another specified material or has features that can be described with reference to another specified material.

The term "culturing" refers to growing a population of cells, e.g., microbial cells, under suitable conditions for growth, in a liquid or solid medium.

The term "heterologous" or "exogenous," with reference to a polynucleotide or protein, refers to a polynucleotide or protein that does not naturally occur in a specified cell, e.g., a host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the cell.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

"Transfection" or "transformation" refers to the insertion of an exogenous polynucleotide into a host cell. The exogenous polynucleotide may be maintained as a non-integrated vector, for example, a plasmid, or alternatively, may be integrated into the host cell genome. The term "transfecting" or "transfection" is intended to encompass all conventional techniques for introducing nucleic acid into host cells. Examples of transfection techniques include, but are not limited to, calcium phosphate precipitation, DEAE-dextran-mediated transfection, lipofection, electroporation, and microinjection.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system.

A "signal sequence" (also termed "presequence," "signal peptide," "leader sequence," or "leader peptide") refers to a sequence of amino acids at the amino terminus of a nascent polypeptide that targets the polypeptide to the secretory pathway and is cleaved from the nascent polypeptide once it is translocated in the endoplasmic reticulum membrane.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively, or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%6, 65%, 70%, 75%, 80%, 85%, 86%, 87%, 88%, 89%0, 90%, 91%, 92%, 93%, 94%, 95%, 96%, 97%, 98%, 99%, or even 99.5% amino acid sequence identity with a reference sequence.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein that has similar function and/or structure as a reference protein. Homologs may be from evolutionarily related or unrelated species. In some embodiments, a homolog has a quintenary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide, polypeptide, or region or domain of a polypeptide that comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide, polypeptide, or region or domain of a polypeptide. A region or domain of a polypeptide may contain, for example, at least about 20, 50, 100, or 200 amino acids within a longer polypeptide sequence. Sequence identity may be determined using known programs such as BLAST, ALIGN, and CLUSTAL using standard parameters. (See, e.g., Altshul, et al. (1990) *J. Mol. Biol.* 215:403-410; Henikoff, et al. (1989) *Proc. Nail. Acad. Sci.* 89:10915; Karin, et al. (1993) *Proc. Natl. Acad. Sci.* 90:5873; and Higgins, et al. (1988) *Gene* 73:237). Software for performing BLAST analyses is publicly available through the National Center for Biotechnology Information. Also, databases may be searched using FASTA (Pearson, et al. (1988) *Proc. Natl. Acad. Sci.* 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{80}$-$C_{100}$ [See Sliwka et al. (2012) Acta ABP Biochimica Polonica 59:1 p 17-20; Zeeshan et al. (2012) Organic Letters 14:21 p 5496-5498]. Diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature. Carotenoids include but are not limited to: antheraxanthin, adonirubin, adonixanthin, astaxanthin, canthaxanthin, capsorubin, θ-cryptoxanthin, α-carotene, β-carotene, β,ψ-carotene, δ-carotene, ε-carotene, echinenone, β-hydroxyechinenone, 3'-hydroxyechinenone, γ-carotene, ψ-carotene, 4-keto-Y-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and $C_{30}$ carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway." The term "isoprenoid pathway" is sufficiently general to encompass both types of pathway. Biosynthesis of isoprenoids from IPP occurs by polymerization of several five-carbon isoprene subunits. Isoprenoid metabolites derived from IPP vary greatly in chemical structure, including both cyclic and acyclic molecules. Isoprenoid metabolites include, but are not limited to, monoterpenes, sesquiterpenes, diterpenes, sterols, and polyprenols such as carotenoids.

The term "isoprenoid compound" refers to any compound which is derived via the pathway beginning with isopentenyl pyrophosphate (IPP) and formed by the head-to-tail condensation of isoprene units which may be of 5, 10, 15, 20, 30 or 40 carbons in length. There term "isoprenoid pigment" refers to a class of isoprenoid compounds which typically have strong light absorbing properties.

The term "feed premix" refers to the crude mixture of aquaculture feed or animal/pet food components prior to processing, optionally at high temperature, into an aquaculture feed or animal or pet food composition that is in the form of pellets or flakes.

An aquaculture feed composition is used in the production of an "aquaculture product," wherein the product is a harvestable aquacultured species (e.g., finfish, crustaceans), which is often sold for human consumption. For example, salmon are intensively produced in aquaculture and thus are aquaculture products. Aquaculture compositions may also be used as feed for aquaculture feed organisms such as small fish like krill, rotifers, and the like, that are food sources for larger aquaculture organisms such as carnivorous fish. In addition, aquaculture compositions described herein can be used as feed for ornamental fish, shrimp, hobbyist aquaculture, and the like, that are not intended as food for other organisms.

The term "aquaculture meat product" refers to food products intended for human consumption comprising at least a portion of meat from an aquaculture product as defined above. An aquaculture meat product may be, for example, a whole fish or a filet cut from a fish, each of which may be consumed as food. In some embodiments, such a product can be referred to as a fish or seafood product.

The term "biomass" refers to microbial cellular material. Biomass may be produced naturally, or may be produced from the fermentation of a native host or a recombinant production host. The biomass may be in the form of whole cells, whole cell lysates, homogenized cells, partially hydrolyzed cellular material, and/or partially purified cellular material.

The term "processed biomass" refers to biomass that has been subjected to additional processing such as drying, pasteurization, disruption, etc., each of which is discussed in greater detail below.

The term "C1 carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "C1 metabolizer" refers to a microorganism that has the ability to use a single carbon substrate as a sole source of energy and biomass. C1 metabolizers include methylotrophs and/or methanotrophs capable of growth on a single carbon substrate.

The term "C2 carbon substrate" refers to any carbon-containing molecule that contain two linked carbon molecules. Examples include ethanol, ethylamine, acetate, acetic acid, acetylaldehyde, ethylene glycol, and ethanethiol. Diethylamine and triethylamine can also be considered C2 carbon substrates.

The term "methylotroph" means an organism capable of oxidizing organic compounds which do not contain carbon-carbon bonds. Where the methylotroph is able to oxidize CH4, the methylotroph is also a methanotroph.

The term "methanotroph" means a prokaryote capable of utilizing methane as a substrate. Complete oxidation of methane to carbon dioxide occurs by aerobic degradation pathways. Examples of methanotrophs include, but are not limited to, the genera *Methylomonas, Methylobacter, Methylococcus*, and *Methylosinus.*

The term "high growth methanotrophic bacterial strain" refers to a bacterium capable of growth using methane as its sole carbon and energy source.

The term "Gram-negative bacteria" are bacteria that do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane. In contrast, Gram-positive bacteria such as most bacteria in the phyla Actinobacteria or Firmicutes retain crystal violet due to their relatively thicker peptidoglycan cell wall layer. In general, Gram-positive bacteria are monoderms and have a single lipid bilayer whereas Gram-negative bacteria are diderms and have two lipid bilayers. As used here "Gram-negative bacteria" refers to all bacteria except those in the phyla Actinobacteria, Firmicutes, or Tenericutes. Examples of Gram-negative phyla include Proteobacteria, Aquificae, Bacteroidetes, Chlamydiae, Chlorobi, Cyanobacteria, *Deinococcus-Thermus*, Fibrobacteres, Fusobacteria, Gemmatimonadetes, Nitrospirae, Planctomycetes, Spirochaetes, Synergistetes, and Verrucomicrobia.

The term "process stream" (e.g., "ethanol fermentation and/or distillation process stream") refers to the products or waste effluents generated during the fermentation of sugars extracted from biomass to a bioproduct of interest, e.g., ethanol, distillation to remove and concentrate the bioproduct (e.g., ethanol), or the solid separation and drying of the resulting residuals. Examples include beer (e.g., ethanol beer), an alcohol (e.g., ethanol), whole stillage, wet cake or wet distiller grains (WDG), thin stillage, thin stillage syrup or condensed distiller solubles (CDS), wet distillers grains with solubles (WDGS), and dried distiller grains with solubles (DDGS).

The term "ethanol beer" refers to the result of fermentation of biomass containing sugars into a liquid containing an increased content of ethanol.

The term "whole stillage" refers to the residuals or left-overs from distillation of "ethanol beer" to remove and concentrate the ethanol.

The term "wet cake" or "wet distiller grains" or "WDG" refers to the solid component of "whole stillage" that is separated by centrifugation.

The term "thin stillage" refers to the liquid component of "whole stillage" that is separated from the solid "wet cake" or "wet distiller grains" by centrifugation.

The term "thin stillage syrup" or "syrup" or "condensed distiller solids" or "CDS" refers to concentrated "thin stillage" where liquid (e.g., water) has been removed.

The term "wet distiller grains with solubles" or "WDGS" refers to a combination of "thin stillage syrup" with "wet distiller grains"

The term "dried distiller grains with solids" or "DDGS" refers to "wet distiller grains with solubles" that have been further dried.

Microorganisms

Non-naturally occurring microorganisms are provided for the production of C40 carotenoid compound(s) and/or for reduced or eliminated production of C30 carotenoid compound(s). In some embodiments, non-naturally occurring, e.g., recombinant, microorganisms herein include, e.g., bacteria, yeast, Archaea, that have been engineered to express at least one (i.e., one or more) enzyme(s) for biosynthesis of one or more C40 carotenoid compound(s) and that produce the C40 carotenoid compound(s) when cultured under conditions suitable for microbial growth and carotenoid production.

Non-naturally occurring microorganisms as described herein include one or more exogenous polynucleotide(s) that encode and express one or more enzyme or enzyme activity for biosynthesis of C40 carotenoid compound(s). The exogenous polynucleotide(s) may include one or more coding sequence for one or more enzyme or enzyme activity for biosynthesis of C40 carotenoid compound(s), operably linked to one or more promoter for expression in the non-naturally occurring microorganism. Such promoters may include, but are not limited to PR and PmxaF. In some embodiments, the polynucleotide(s) are codon optimized for expression in the microorganism.

In some embodiments, the non-naturally occurring microorganism includes one or more exogenous polynucleotide(s) that encodes one or more enzymes or enzyme activities for C40 carotenoid biosynthesis, as described herein, that has been modified for improved stability and/or activity relative to the stability and/or activity of the enzyme or enzyme activity in the host cell from which it is derived or relative to the wild-type stability and/or activity of the enzyme or enzyme activity. For example, the non-naturally occurring microorganism may express a variant of an enzyme of C40 carotenoid biosynthesis that has greater stability and/or activity than the wild-type enzyme from which it is derived.

In some embodiments, the host cell from which anon-naturally occurring microorganism as described herein is derived produces one or more C30 carotenoid compound(s). In some embodiments, the non-naturally occurring microorganism includes deletion or inactivation of one or more gene(s) that encode enzyme(s) of C30 carotenoid biosynthesis. In some embodiments, the host cell is *Methylobacterium extorquens* and the non-naturally occurring microorganism derived from the host cell includes deletion or modification of one or more gene(s) that encode squalene synthase, diapophytoene synthase, diapophytoene desaturase, C30 carotenoid oxidase, glycosyl transferase, or phospholipid glycerol acetyltransferase in the host cell. In some embodiments, a deletion or replacement of the region encompassing Mext_3434 to Mext_3441 in *M. extorquens* PA1 removes the C30 carotenoid oxidase, diaphophytoene desaturase, glycosyl transferase, and phospholipid glyercol acetyltransferase, resulting in complete blockage of C30 carotenoid production.

In certain embodiments, the host cell comprises one or more endogenous gene(s) in the described pathway, and the exogenous gene(s) that are added complement the endogenous pathway for production of C40 carotenoid compound(s).

Microorganisms herein may be bacterial or fungal. In some embodiments, the microorganism is a bacterial microorganism from the phylum Proteobacteria. In some embodiments, the microorganism is a bacterial microorganism from the class Alphaproteobacteria. In some embodiments, the microorganism is a Gram-negative bacterium.

Non-limiting examples of genera from which the non-naturally occurring microorganism may be derived include *Methylobacterium, Methylomonas, Methylobacter. Methylococcus, Methylosinus, Methylocyctis, Methylomicrobium, Methylophilus, Methylobacillus, Hyphomicrobium, Xanthobacter, Bacillus, Paracoccus, Nocardia, Arthrobacter, Rhodopseudomonas, Pseudomonas, Candida, Hansenula, Pichia, Torulopsis, Rhodotorula, Escherichia*, and *Saccharomyces*. Non-limiting examples of microbial species from which the non-naturally occurring microorganism may be derived include *Methylobacterium extorquens* (e.g., strains AM1, DM4, DSMZ1340, CM4, PA1, or BJ001 (formerly *Methylobacterium populi*)), *Methylobacterium radiotolerans, Methylobacterium nodulans, Methylobacterium* spp. 4-46, and *Escherichia coli.*

In some embodiments, the non-naturally occurring microorganism is a methylotrophic bacterium.

In various embodiments, genes of C40 carotenoid biosynthesis may be incorporated into a host microorganism for production of C40 carotenoid(s). For example, one or more of the gene(s) crtZ, crtY, crtI, crtB, crtE, idi, and crtW, or polynucleotides that encode polypeptides with functionally equivalent activities thereof may be introduced (e.g., transformed) into a host cell, thereby producing a cell that produces C40 carotenoid compound(s). Introduction of different subsets of these genes or functional equivalents thereof will result in production of different predominant C40 carotenoid compound(s). For example, expression of crtZYIBE will produce zeaxanthin. Expression of crtYIBE will produce β-carotene. Expression of crtIBE will produce lycopene. Expression of crtYIBEW will produce canthaxanthin and/or echinenone. Expression of crtZYIBEW will produce astaxanthin. Expression of crtZYIBW of *S. astaxanthinifaciens* will produce astaxanthin in a strain that expresses a native or heterologous crtE on a plasmid or second integration site. Expression of crtZYIB of *S. zeaxanthinifaciens* or *M. zeaxanthinifaciens* will produce zeaxanthin in a strain that expresses native of heterologous crtE on a plasmid or second integration site. Expression of crtYIB and crtWZ from *F. pelagi* will produce astaxanthin in a strain that expresses a native or heterologous crtE on a plasmid or second integration site. The gene or functional equivalents thereof that are introduced into a host microorganism may be derived from the same or different microorganism species or strain.

In some embodiments, the host microorganism may be a non-naturally occurring microorganism that has been engineered to reduce or eliminate native C30 carotenoid production, which may, in some embodiments, increase flux to C40 carotenoid compound(s).

In some embodiments, the gene idi or a polynucleotide that encodes a polypeptide with functionally equivalent isopentenyl-diphosphate delta-isomerase activity may be incorporated, which may increase carotenoid biosynthesis, in comparison with an identical cell that does not include or express the idi gene or functional equivalent thereof.

In one embodiment, the non-naturally occurring microorganism includes at least one heterologous polynucleotide that encodes one or more polypeptide encoded by the gene(s) crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*, or one or more polypeptide having at least about 70%, 75%, 80%, 85%, 90%, 95%, 98%, or 99% amino acid sequence identity to the polypeptide(s) encoded by crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*, and retaining the functional activity thereof for production of C40 carotenoid compound(s). In some embodiments, the heterologous polynucleotide(s) includes one or more polynucleotide sequence(s) having at least about 70%, 75%, 80%, 85%, 90%, 95%, 98%, or 99% nucleotide sequence identity to the gene sequence(s) crtZ, crtY, crtI, crtB, and/or crtE of *Paracoccus zeaxanthinifaciens* or *Pantoea ananatis*, e.g., *P. ananatis* ATCC 19321, or crtZ, crtY, crtI, crtB, crtE, and/or idi of *Escherichia vulneris*. In some embodiments, the microorganism is a bacterial microorganism. In some examples, the bacterial microorganism may be from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens.*

In one embodiment, the microorganism includes and expresses heterologous crtZYIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces zeaxanthin. In some embodiments, the microorganism further includes and expresses a heterologous polynucleotide that encodes a crtW gene, for example the crtW gene from *Fulvimarina pelagi*, or a polypeptide having at least about 70%, 75%, 80%, 85%, 90%, 95%, 98%, or 99% identity to the polypeptide encoded by crtW of *Fulvimarina pelagi* and retaining the functional activity thereof for production of C40 carotenoid compound(s), or having a polynucleotide sequence having at least about 70% sequence identity with the polynucleotide sequence of crtW of *Fulvimarina pelagi*, and the microorganism produces astaxanthin. In some embodiments, the microorganism further includes and expresses a heterologous polynucleotide that encodes a idi gene, for example, the idi gene from *Escherichia vulneris*, or a polypeptide having at least about 70% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the microorganism includes and expresses heterologous crtYIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces β-carotene. In some embodiments, the microorganism further includes a heterologous polynucleotide that encodes a crtW gene, for example the crtW gene from *Fulvimarina pelagi*, or a polypeptide having at least about 70%, 75%, 80%, 85%, 90%, 95%, 98%, or 99% identity to the polypeptide encoded by crtW of *Fulvimarina pelagi* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of crtW of *Fulvimarina pelagi*, and the microorganism produces canthaxanthin and/or echinenone. In some embodiments, the microorganism further includes and expresses a heterologous polynucleotide that encodes a idi gene, for example, the idi gene from *Escherichia vulneris*, or a polypeptide having at least about 70%, 75%, 80%, 85%, 90%, 95%, 98%, or 99% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the microorganism includes and expresses heterologous crtIBE from *Paracoccus zeaxanthinifaciens, Pantoea ananatis*, e.g., *P. ananatis* ATCC 19321, and/or *Escherichia vulneris*, or polypeptides having at least about 70%, 75%, 80%, 85%, 90%, 95%, 98%, or 99% sequence identity thereof and retaining the functional activity thereof, and the microorganism produces lycopene. In some embodiments, the microorganism further includes and expresses a heterologous polynucleotide that encodes a idi gene, for example, the idi gene from *Escherichia vulneris*, or a polypeptide having at least about 70% identity to the polypeptide encoded by idi of *Escherichia vulneris* and retaining the functional activity thereof for production of C40 carotenoid compound(s), or having a polynucleotide sequence having at least about 70%, 75%, 80%, 85%, 90%, 95%, 98%, or 99% sequence identity with the polynucleotide sequence of idi of *Escherichia vulneris*, and the microorganism produces a greater amount of C40 carotenoid compound(s) than an identical microorganism that does not include the idi gene or functional equivalent thereof.

In one embodiment, the non-naturally occurring microorganism includes at least one heterologous polynucleotide that encodes the polypeptides encoded by the gene(s) crtYIB and crtWZ of *Fulvimarina pelagi*, or polypeptides having at least about 75%, 80%, 85%, 90%, 95%, 98%, or 99% amino acid sequence identity to the polypeptides encoded by crtYIB and crtWZ of *Fulvimarina pelagi*, and retaining the functional activities thereof for production of C40 carotenoid compound(s), and the microorganism produces astaxanthin, canthaxanthin, zeaxanthin, lycopene, or beta-carotene or intermediates of these C40 carotenoids. In some embodiments, the heterologous polynucleotide(s) includes polynucleotide sequences having at least about 70%, 75%, 80%, 85%, 90%, 95%, 98%, or 99% nucleotide sequence identity to the gene sequence(s) crtYIB and crtWZ of *Fulvimarina pelagi*. In some embodiments, the microorganism is a bacterial microorganism. In some examples, the bacterial microorganism may be a Gram-negative bacterial microorganism. In one example, the bacterial microorganism may be from the phylum Proteobacteria. In one example the bacterial microorganism may be from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens*.

In one embodiment, the non-naturally occurring microorganism includes at least one heterologous polynucleotide that encodes one or more polypeptide encoded by the gene(s) crtZ, crtY, crtI, crtB, and/or crtW of *Sphingomonas astaxanthinifaciens*, e.g., *S. astaxanthinifaciens* DSM 22298, or one or more polypeptide having at least about 70% amino acid sequence identity to the polypeptide(s) encoded by crtZ, crtY, crtI, crtB, and/or crtW of *Sphingomonas astaxanthinifaciens*, e.g., *S. astaxanthinifaciens* DSM 22298 and retaining the functional activity thereof for production of C40 carotenoid compound(s). In some embodiments, the heterologous polynucleotide includes one or more polynucleotide sequence(s) having at least about 70%, 75%, 80%, 85%, 90%, 95%, 98%, or 99% nucleotide sequence identity to the gene sequence(s) crtZ, crtY, crtI, crtB, and/or crtW of *Sphingomonas astaxanthinifaciens*, e.g., *S. astaxanthinifaciens* DSM 22298. In one embodiment, the microorganism includes and expresses heterologous crtZYIBW from *Sphingomonas astaxanthinifaciens* or polypeptides having at least about 70%, 75%, 80%, 85%, 90%, 95%, 98%, or 99% sequence identity thereof and retaining the functional activity thereof, and the microorganism produces astaxanthin, canthaxanthin, zeaxanthin, lycopene, beta-carotene, or intermediates of these C40 carotenoids. In some embodiments, the microorganism expresses crt Y, crtI, and crtB of *Sphingomonas astaxanthinifaciens* or polypeptides having at least about 70%, 75%, 80%, 85%, 90%, 95%, 98%, or 99% sequence identity thereof and retaining the functional activity thereof, and the microorganism produces beta-carotene. In some embodiments, crtW is expressed that results in production of canthaxanthin. In some embodiments, crtZ is expressed that results in production of zeaxanthin. In some embodiments, crtW and crtZ are expressed to produce a ratio of the gene products thereof that produces astaxanthin. In some embodiments, the microorganism is a bacterial microorganism. In some examples, the bacterial microorganism may be from the phylum proteobacteria, optionally from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens*.

In one embodiment, the non-naturally occurring microorganism includes at least one heterologous polynucleotide that encodes one or more polypeptide encoded by the gene(s) crtZ, crtY, crtI, and/or crtB of *Siansivirga zeaxanthinifaciens*, e.g., *S. zeaxanthinifaciens* CC-SAMT-1, or of *Mesoflavibacterzeaxanthinifaciens*, e.g., *M. zeaxanthinifa-*

*ciens* DSM 18436, or one or more polypeptide having at least about 70%, 75%, 80%, 85%, 90%, 95%, 98%, or 99% amino acid sequence identity to the polypeptide(s) encoded by crtZ, crtY, crtI, and/or crtB, of *Siansivirga zeaxanthinifaciens*, e.g., *S. zeaxanthinifaciens* CC-SAMT-1, or of *Mesoflavibacterzeaxanthinifaciens*, e.g., *M. zeaxanthinifaciens* DSM 18436, and retaining the functional activity thereof for production of C40 carotenoid compound(s). In some embodiments, the heterologous polynucleotide includes one or more polynucleotide sequence(s) having at least about 70%, 75%, 80%, 85%, 90%, 95%, 98%, or 99% nucleotide sequence identity to the gene sequence(s) crtZ, crtY, crtI, and/or crtB of *Siansivirga zeaxanthinifaciens*, e.g., *S. zeaxanthinifaciens* CC-SAMT-1, or of *Mesoflavibacter zeaxanthinifaciens*, e.g., *M. zeaxanthinifaciens* DSM 18436. In one embodiment, the microorganism includes and expresses heterologous crtZYIB from *Siansivirga zeaxanthinifaciens*, e.g., *S. zeaxanthinifaciens* CC-SAMT-1, or of *Mesoflavibacter zeaxanthinifaciens*, e.g., *M. zeaxanthinifaciens* DSM 18436 or polypeptides having at least about 70% sequence identity thereof and retaining the functional activity thereof, and the microorganism produces astaxanthin, canthaxanthin, zeaxanthin, lycopene, beta-carotene, or intermediates of these C40 carotenoids. In some embodiments, the microorganism is a bacterial microorganism. In some examples, the bacterial microorganism may be from the phylum Proteobacteria, optionally from the class Alphaproteobacteria. In one example, the bacterial microorganism is from the genus *Methylobacterium*, for example, *Methylobacterium extorquens*. In some embodiments, the coding sequences of the heterologous polynucleotide(s) are codon optimized for expression in the microorganism, for example, codon optimized for expression in *Methylobacterium extorquens*.

Transformation of Microorganisms

Numerous transformation protocols and constructs for introducing and expressing exogenous polynucleotides in host cells are known in the art.

In certain embodiments, genetic modifications will take advantage of freely replicating plasmid vectors for cloning. These may include small IncP vectors developed for use in *Methylobacterium*. These vectors may include pCM62, pCM66, or pHC41 for cloning. (Marx & Lidstrom (2001) Microbiology 147:2065-2075; Chou, et al. (2009) *PLoS Genetics* 5: e1000652).

In certain embodiments, genetic modifications will take advantage of freely replicating expression plasmids such as pCM80, pCM160, pHC90, or pHC91. (Marx & Lidstrom (2001) *Microbiology* 147:2065-2075; Chou, et al. (2009) *PLoS Genetics* 5: e1000652).

In certain embodiments, genetic modifications will utilize freely replicating expression plasmids that have the ability to respond to levels of inducing molecules such as cumate or anhydrotetracycline. These include pHC115, pLC290, pLC291. (Chou, et al. (2009) *PLoS Genetics* 5: e1000652; Chubiz, et al. (2013) *BMC Research Notes* 6:183).

In certain embodiments, genetic modifications will utilize recyclable antibiotic marker systems such as the cre-lox system. This may include use of the pCM157, pCM158, pCM184, pCM351 series of plasmids developed for use *M. extorquens*. (Marx & Lidstrom (2002) *BioTechniques* 33:1062-1067).

In certain embodiments, genetic modifications will utilize transposon mutagenesis. This may include mini-Tn5 delivery systems such as pCM639 (D'Argenio, et al. (2001) *J Bacteriol.* 183: 1466-1471) demonstrated in *M. extorquens*. (Marx, et al. (2003) *J Bacteriol.* 185: 669-673).

In certain embodiments, genetic modifications will utilize expression systems introduced directly into a chromosomal locus. This may include pCM168, pCM172, and pHC01 plasmids developed for *M. extorquens* AM1. (Marx & Lidstrom (2001) *Microbiology* 147: 2065-2075; Lee, et al. (2009) *Evolution* 63: 2813-2830).

In certain embodiments, genetic modifications will utilize a sacB-based system for unmarked exchange of alleles due to the sucrose sensitivity provided by sacB expression. This may include the pCM433 vector originally tested with *M. extorquens*. (Marx, et al. (2008) *BMC Research Notes* 1:1).

Microbial Cultures

Methods for producing biomass are provided. The methods include culturing a microorganism as described herein in a culture medium under conditions suitable for growth of the microorganism and production of biomass that contains one or more C40 carotenoid compound(s) as described herein. In some embodiments, one or more of the C40 carotenoid compound(s) astaxanthin, canthaxanthin, zeaxanthin, phoenicoxanthin, adonixanthin, 3-hydroxyechinenone, echinenone, β-carotene, and lycopene, or a combination thereof, is produced.

The microorganisms herein are non-naturally occurring and contain at least one heterologous polynucleotide that encodes one or more heterologous enzyme for C40 carotenoid production in the microorganism. In some embodiments, the microorganism produces C40 carotenoid compound(s) exclusively from enzymes that are encoded by the heterologous polynucleotide(s). In some embodiments, the microorganism produces carotenoid compound(s) from a combination of enzymes that are encoded by the heterologous polynucleotide(s) and native enzyme(s) encoded by the genome of the parent microorganism. In some embodiments, the microorganism also produces one or more C30 carotenoid compound from a native biosynthetic pathway in the parent microorganism. In some embodiments, the native C30 carotenoid pathway of the parent microorganism has been disrupted or deleted such that C30 carotenoid production is reduced or eliminated in comparison to the parent microorganism.

The culture medium includes carbon source(s), nitrogen source(s), inorganic substances (e.g., inorganic salts), and any other substances required for the growth of the microorganism (e.g., vitamins, amino acids, etc.).

The carbon source may include sugars, such as glucose, sucrose, lactose, fructose, trehalose, mannose, mannitol, and maltose; organic acids, such as acetic acid, lactic acid, fumaric acid, citric acid, propionic acid, malic acid, pyruvic acid, malonic acid, succinic acid and ascorbic acid; alcohols, such as methanol, ethanol, propanol, butanol, pentanol, hexanol, isobutanol, and glycerol; oil or fat, such as soybean oil, rice bran oil, olive oil, corn oil, sesame oil, linseed oil, and the like. The amount of the carbon source added varies according to the kind of the carbon source, for example, about 1 to about 100 gm, or about 2 to about 50 gm per liter of medium.

In various embodiments, the culture conditions may include one or more of: aeration of the culture medium (e.g., resulting in a dissolved oxygen concentration of about 5% to about 50%); temperature of the culture medium (e.g., temperature of about 20° C. to about 50° C.); carbon source comprising, consisting of, or consisting essentially of one or more alcohol(s) (e.g., methanol, ethanol, glycerol, or a combination thereof); or semi-continuous or continuous fermentation conditions.

In some embodiments, a C1 carbon substrate is provided to a microorganism that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the C1 carbon substrate is selected from methane, methanol, formaldehyde, formic acid, methylated amines, methylated thiols, and carbon dioxide. In certain embodiments, the C1 carbon substrate is selected from methanol, formaldehyde, and methylated amines. In certain embodiments, the C1 carbon substrate is methanol.

In some embodiments, a C2 carbon substrate is provided to a microorganism that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the C2 carbon substrate is selected from ethylamine, acetate, acetic acid, acetaldehyde, ethylene glycol, and ethanethiol. Diethylamine and triethylamine can also be considered C2 carbon substrates. In certain embodiments, the C1 carbon substrate is selected from methanol.

In some embodiments, one or more C1 and C2 carbon substrate are provided together or sequentially to a microorganism that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the C1 and C2 source(s) may include methane, methanol, formaldehyde, formic acid, methylated amines, methylated thiols, carbon dioxide, ethanol, ethylamine, acetate, acetic acid, acetaldehyde, ethylene glycol, ethanethiol, diethylamine, or triethylamine. In some embodiments the C1 and C2 sources are methanol and ethanol, respectively.

In some embodiments, one or more process stream from a fermentation to produce a bioproduct of interest, such as an alcohol or a biofuel (e.g., ethanol fermentation and/or distillation process stream(s)) is provided as a carbon substrate to a microorganism that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the ethanol fermentation and/or distillation process stream is selected from one or more of ethanol beer, ethanol, whole stillage, wet cake or wet distiller grains (WDG), thin stillage, thin stillage syrup or condensed distiller solubles (CDS), wet distillers grains with solubles (WDGS), and dried distiller grains with solubles (DDGS). In certain embodiments, the ethanol fermentation and/or distillation process stream is selected from thin stillage or thin stillage syrup. In certain embodiments, the ethanol fermentation and/or distillation process stream is thin stillage syrup.

In some embodiments, one or more C1, one or more C2, or one or more C1 and C2 carbon substrate are provided together or sequentially to a microorganism with one or more process stream from a fermentation to produce a bioproduct of interest, such as an alcohol or a biofuel (e.g., ethanol fermentation and/or distillation process stream(s)) that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the C1, C2, or C1 and C2 source(s), and ethanol fermentation and/or distillation process stream(s) may include methane, methanol, formaldehyde, formic acid, methylated amines, methylated thiols, carbon dioxide, ethanol, ethylamine, acetate, acetic acid, acetaldehyde, ethylene glycol, ethanethiol, diethylamine, triethylamine, ethanol beer, ethanol, whole stillage, wet cake or wet distiller grains (WDG), thin stillage, thin stillage syrup or condensed distiller solubles (CDS), wet distillers grains with solubles (WDGS), and/or dried distiller grains with solubles (DDGS). In some embodiments, the C1 and C2 sources are methanol and ethanol, respectively and the ethanol fermentation and/or distillation process stream is thin stillage. In some embodiments the C1 and C2 sources are methanol and ethanol, respectively, and the ethanol fermentation and/or distillation process stream is thin stillage syrup.

The nitrogen source may include potassium nitrate, ammonium nitrate, ammonium chloride, ammonium sulfate, ammonium phosphate, ammonia, urea, spent yeast cells and the like, alone or in combination. Amount of the nitrogen source added varies according to the kind of the nitrogen source, for example, about 0.1 to about 30 μm, or about 1 to about 10 μm per liter of medium.

Inorganic salts may include potassium dihydrogen phosphate, dipotassium hydrogen phosphate, disodium hydrogen phosphate, sodium dihydrogen phosphate, magnesium sulfate, magnesium chloride, ferric sulfate, ferrous sulfate, ferric chloride, ferrous chloride, manganese sulfate, manganese chloride, zinc sulfate, zinc chloride, cupric sulfate, calcium chloride, calcium carbonate, sodium carbonate, sodium sulfate, and the like, alone or in combination. Amount of inorganic salt varies according to the kind of the inorganic salt, for example, about 0.00001 to about 10 μm per liter of medium.

Special required substances, for example, vitamins, nucleic acids, yeast extract, peptone, meat extract, malt extract, corn steep liquor, soybean meal, dried yeast etc., may be included alone or in combination. Amount of the special required substance used varies according to the kind of the substance, for example, about 0.2 μm to about 200 μm, or about 3 μm to about 10 μm per liter of medium.

In some embodiments, the culture conditions include a carbon source that comprises, consists of, or consists essentially of one or more alcohol(s), such as, but not limited to, methanol, ethanol, and/or glycerol, or a combination thereof, e.g., a combination of methanol and ethanol.

In some embodiments, culture conditions that result in a desired C40 carotenoid level are employed. For example, a total C40 carotenoid level of 0.1-1% (w/v) or greater in the biomass may be achieved.

Figure 1:
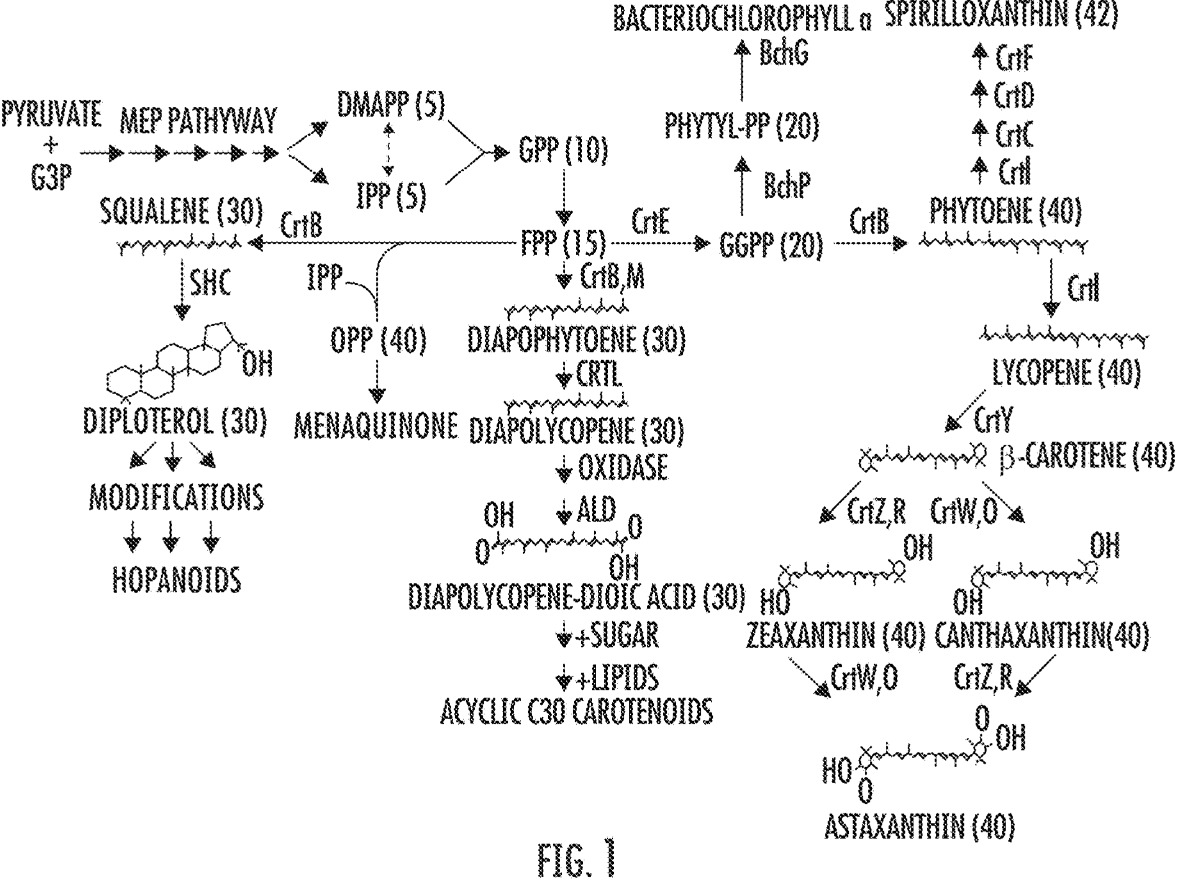
FIG. 1 schematically depicts the carotenoid biosynthetic pathway for production of C30 and C40 carotenoid compounds.
Figure 2:
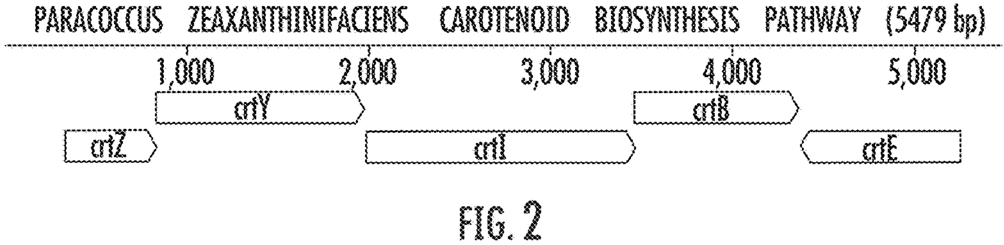
FIG. 2 schematically depicts the C40 carotenoid biosynthetic gene cluster in *Paracoccus zeaxanthinifaciens.*

In some embodiments, the pH of the culture medium is adjusted to pH about 2 to about 12, or about 6 to about 9. The medium may further include one or more buffer(s) to maintain the culture at the desired pH. Numerous buffers are known in the art and include phosphate, carbonate, acetate, PIPES, HEPES, and Tris buffers. A suitable buffer for a given microorganism can easily be determined by one of ordinary skill in the art. For *Methylobacterium*, a common medium, described by Lee, et al. (2009) *Evolution* 63:2813-2830, is a phosphate buffered medium that consists of 1 mL of trace metal solution (to 1 liter of deionized water the following are added in this order: 12.738 μm of EDTA disodium salt dihydrate, 4.4 μm of $ZnS0\text{-}7H_20$, 1.466 μm of $CaCl_2)\text{-}2H_2O$, 1.012 μm of $MnCl_2\text{-}4H_20$, 0.22 μm of $(NH_4)_6Mo_7O_{24}\text{-}4H_20$, 0.314 μm of $CuSO_4\text{-}5H_20$, 0.322 μm of $CoCl_2\text{-}6H_20$, and 0.998 μm of $Fe_3(SO_4)_2\text{-}7H_20$; pH 5.0 is maintained after every addition), 100 mL of phosphate buffer (25.3 g of $K_2HPO_4$ and 22.5 g of NaH2PO4 in 1 liter of deionized water), 100 mL of sulfate solution (5 μm of $(NH_4)_2(SO_4)$ and 0.98 μm of $Mg(SO_4)_2$ in 1 liter of deionized water), and 799 mL of deionized water. All components are heat sterilized separately and then pooled together. An alternative medium recently developed for use with *Methylobacterium extorquens* takes advantage of an organic buffer and has a citrate-chelated trace metal mix. Culturing is carried out at temperature of 15° to 40° C., and preferably 20° to 35° C., usually for 1 to 20 days, and preferably 1 to 4 days, under aerobic conditions provided by shaking or aeration/agitation. Common practice with *Methylobacterium* is at 30° C. The protocol for making M-PIPES medium is described in Table Si of Delaney et al. (2013) *PLoS One* 8:e62957. FIG. 2 in U.S. Ser. No. 61/863,701 shows an exemplary recipe for medium optimized for use with *M. extorquens*.

In order to generate dense cultures of microorganisms, such as *Methylobacterium*, it may be advantageous to use a fed-batch method. Methanol can be tolerated well at 0.1-10% v/v (~24.7 mM-2.47M), and thus this step size of addition can be used repeatedly. Ethanol can be tolerated well at 0.1-20% v/v (~1.71 mM-3.42M), and thus this step size of addition can be used repeatedly. Critically, pH levels drop during culturing on methanol and/or ethanol, such that the use of a base such as KOH, NH40H, or NaOH would be important to maintain the pH around 6.5. Aeration can be achieved via physical agitation, such as an impeller, via bubbling of filtered air or pure oxygen, or in combination. In order to reduce production costs, the buffer can be replaced from phosphates or PIPES to a carbonate-buffered medium.

In some embodiments, a "fill and draw" method is used, in which a portion of the culture medium (e.g., about 10% to about 90%) is removed when the culture reaches a desired optical density at 600 nm (e.g., about 50 to about 200), followed by replacement with an equivalent amount of fresh medium, thereby maintaining C40 carotenoids at a relatively constant level in the culture, thereby resulting in biomass that contains a desired level of C40 carotenoids.

In some embodiments, a "continuous" method is used, in which fresh medium is continuously added, while culture medium and microorganisms are continuously removed at the same rate, keeping the culture volume relatively constant, thereby resulting in biomass that contains a desired level of C40 carotenoids.

Microbial cells may be separated from the culture, for example, by a conventional means such as centrifugation or filtration. The cells may be isolated whole, or may be lysed to release their contents for extraction or further processing. The cells or the medium may be subjected to an extraction with a suitable solvent.

Compositions

Compositions are provided for use as feed in aquaculture, or as animal feed, or as human nutritional supplements containing processed or unprocessed biomass from microorganism cells cultured as described herein, as are methods of preparation of the feed or nutritional supplement compositions.

In some embodiments, the feed compositions or nutritional supplements include C40 carotenoid-containing biomass, produced by culturing one or more microorganism(s) as described herein, i.e., produced by culturing a non-naturally occurring microorganism as described herein that result in a desired C40 carotenoid level, as described herein.

In some embodiments in which the C30 carotenoid biosynthetic pathway has been disrupted or deleted, the feed composition or nutritional supplement contains biomass that does not contain C30 carotenoids or which contains reduced levels of C30 carotenoids in comparison to the biomass produced from the parent strain from which the microorganism is derived under identical culture conditions.

In some embodiments, the microbial cell produces a polyhydroxyalkanoate (PHA), e.g., polyhydroxybutyrate (PHB), and the composition contains PHA (e.g., PHB) in the biomass that is incorporated into the composition. In some embodiments, the composition contains one or more C40 carotenoid(s) and contains PHA (e.g., PHB).

In various embodiments, the composition contains one or more of astaxanthin, canthaxanthin, zeaxanthin, phoenicoxanthin, adonixanthin, 3-hydroyechinenone, echinenone, β-carotene, and lycopene, or combinations thereof.

In certain embodiments, biomass that is incorporated into a feed or nutritional supplement composition can be in a dry, or substantially dry, form, e.g., containing less than about 20%, 10%, 5%, or 2% of moisture. In certain embodiments, the cultures are isolated by removing substantially all supernatant, such as by filtering, sedimentation, or centrifugation. In certain embodiments, the collection of cultures and further processing of biomass includes a bacterial lysis step, e.g., by use of detergents or ultrasound. In certain embodiments, the processed microbial cells maintain substantially whole cell membranes. In some embodiments, a substantial portion (e.g., more than about 5%, 10%, 20%, 30%, 50%, or 80%) of bacterial cells may maintain viability in the processed biomass.

The feed composition may contain at least about 1% of the biomass by weight. In certain embodiments, the feed composition is optimized for consumption by fish, seafood, humans, poultry, swine, cattle or other animals. For example, the feed may include one or more of EPA, DHA, and one or more essential amino acids.

Methods for preparing a feed composition are also provided. In some embodiments, the method includes: (a) culturing in an appropriate medium at least one non-naturally occurring microorganism as described above; (b) concentrating the medium to provide a biomass; (c) optionally providing additional feed components; and (d) producing the feed composition from the biomass. In certain embodiments, step (b) includes centrifugation. In certain embodiments, step (b) includes allowing the biomass to settle. In certain embodiments, step (b) includes filtration. In certain embodiments, the method further includes a pre-treatment of the biomass after step (a) with a chemical agent (e.g., a surfactant or solvent) to disrupt the cell membranes of the biomass. In certain embodiments, the method further includes mechanical disruption of the cell membranes of the biomass after step (a).

Examples of feedstuffs into which single cell protein enriched with one or more C40 carotenoid compound(s), produced as described herein, may be incorporated include, for example, pet foods, such as cat foods, dog foods and the like, feeds for aquarium fish, cultured fish or crustaceans, etc., feed for farm-raised animals (including livestock and further including fish or crustaceans raised in aquaculture). The state of the biomass can be in whole cell, lysed or partially processed. C40 carotenoid-enriched biomass or C40 carotenoid-enriched protein, produced as described herein can also be incorporated into food or vitamin supplements for human consumption, optionally with additional caloric or nutritional supplements. Food or feed material that includes one or more C40 carotenoid compound(s) or biomass that includes one or more C40 carotenoid compound(s), produced as described herein is incorporated, is preferably palatable to the organism that is the intended recipient. This food or feed material may have any physical properties currently known for a food material (e.g., solid, liquid, soft). In some embodiments, feed produced as described herein will undergo a pelletization process, e.g., through a hot or cold extrusion process at an inclusion rate of less than about 1%, 5%, 10%, 20%, 25%, 30%, 40%, 50%, 60%, or 75%. In other scenarios, C40 carotenoid-enriched biomass or C40 carotenoid-enriched protein, produced as described herein, can be consumed directly at 100% or combined with another substance in the form of liquid, baked goods or other to form, including but not limited to, various types of tablets, capsules, drinkable agents, gargles, etc.

In some embodiments, the feed or nutritional composition or the biomass that is incorporated into the feed or nutritional composition includes about 0.0001% to about 1% C40 carotenoids by weight. In some embodiments the final feed composition, the C40 carotenoids are by weight 0.00001% to 0.0001%.

In some embodiments, all of the C40 carotenoids in the final feed are provided by biomass of the microorganisms described herein. In some embodiments, at least 1% (w/w) of the C40 carotenoids in the final feed composition are provided by the biomass of the microorganisms described herein.

In some embodiments, a feed or nutritional composition as described herein includes a plurality of microorganisms that each produce different levels of different C40 carotenoid compound(s) as described herein, which may be cultured together or may be cultured separately and combined for production of the feed or nutritional composition.

Methods of producing fish or seafood are also provided, including farming fish or seafood, and providing a diet, which includes a feed composition as described herein, to the fish or seafood.

The following examples are intended to illustrate, but not limit, the invention.

EXAMPLES

Vectors and nucleotide sequences used in the examples below are provided in Table 1. Gene or gene cluster origin is noted by initials of the native organism.

TABLE 1

| Plasmid name | Insert Origin | Description | Example | SEQ ID NO: |
|---|---|---|---|---|
| pI | | Integration plasmid backbone | | |
| pA | | Circulating plasmid backbone with HP1 promoter | | 7 |
| pB | | Circulating plasmid back bone with HP2 promoter | | 8 |
| pC | | Circulating plasmid backbone with pmxaF promoter | | 3 |
| pD | | Circulating plasmid backbone with pR-faeRBS promoter | | 2, 4 |
| pD00 | *Paracoccus zeaxanthinifaciens* | pR-faeRBS-crtZYIB_Pz-pmxaF-crtE_Pz | 1 | 4, 10, 11, 12, 13, 14, 3 |
| pD00* | *Paracoccus zeaxanthinifaciens* | pR-facRBS-crZ*YIB_Pz-pmxaF-crtE_Pz | | 4, 10, 11, 12, 13, 14, 3 |
| pA01 | *P. zeaxanthinifaciens* | HP1-crtYIB_Pz-HP2-crtE_Pz | 2 | 7, 11, 12, 13, 8, 14 |
| pA02 | *E. vulneris, P. zeaxanthinifaciens* | HPI-crtYIB_Ev-HP2-crtE_Pz | 2 | 7, 33, 34, 35, 8, 14 |
| pA03 | *P. ananatis, P. zeaxanthinifaciens* | HP1-crtYIB_Pa-HP2-crtE_Pz | 2 | 7, 40, 41, 42, 8, 14 |
| pA04 | *S. zeaxanthinifaciens, P. zeaxanthinifaciens* | HPI-crtIBZY_Sz-HP2-crtE_Pz | 2 | 7, 22, 23, 24, 25, 8, 14 |
| pA05 | *S. astaxanthinifaciens, P. zeaxanthinifaciens* | HP1-crtYIB_Sa-HP2-crtE_Pz | 2 | 7, 17, 18, 19, 8, 14 |
| pA06 | *F. pelagi, P. zeaxanthinifaciens* | HPI-crtYIB_Fp-HP2-crtE_Pz | 2 | 7. 46, 47, 48, 8, 14 |
| pA07 | *M. zeaxanthinifaciens, P. zeaxanthinifaciens* | HP1-crtIBY_Mz-HP2-crtE_Pz | 3 | 7, 28, 29, 30, 8, 14 |
| pI08 | *P. zeaxanthinifaciens, M. extorquens* | HPI-crtZYIB_Pz-HP2-crtE_Pz (C30 integration flanks) | 3 | 1, 5, 9, 6 |
| pB09 | *E. vulneris* | HP2-idi_Ev | 4 | 8, 37 |
| pD10 | *F. pelagi* | pR-faeRBS-criWZ_Fp | 5 | 4, 49, 50 |
| pC11 | *S. astaxanthinifaciens* | pmxaF-crtW_Sa | 6 | 3, 20 |
| pI12 | *F. pelagi* | pR-faeRBS-crtW_Fp (3010-3011 integration flanks) | 8 | 1, 51, 4, 49, 52 |
| pI13 | *P. zeaxanthinifaciens* | ΔcrtZ (integration) | 8 | 1, 7, 11 (partial) |
| pI14 | *P. zeaxanthinifaciens* | crtIBE_Pz-HPI-HP2 (C30 integration flanks) | 8 | 1, 5, 7, 12, 13, 14, 8, 6 |
| pA15 | *S. astaxanthinifaciens* | HP1-crtZ_Sa-crtY_Pz | 9 | 7, 16, 11 |
| pA16 | *F. pelagi* | HP1-crtZ_Fp-crtY_Pz | 9 | 7, 50, 11 |
| pA17 | *E. vulneris* | HP1-crtZ_Ev-crtY_Pz | 9 | 7, 32, 11 |
| pA18 | *M. zeaxanthinifaciens* | HPI-crtZ_Mz-crtY_Pz | 9 | 7, 27, 11 |
| pB19 | *E. vulneris* | HP2-crtE_Ev | 10 | 8, 36 |
| pB20 | *P. ananatis* | HP2-crtE_Pa | 10 | 8, 43 |

A list of strains used in the examples below with genotypes related to carotenoid production is provided in Table 2.

TABLE 2

| Strain Name | Relevant Genotype | Strain derived from | Main carotenoid produced |
|---|---|---|---|
| Str01 | | PA1 | C30 mix |
| Str02 | Δbch-cluster | Str01 | C30 mix |
| Str03 | ΔC30 Δbch-cluster Δhpt:: PR-crtY_Pz pR-faeRBS-crtEBI_Me | Str01 | B-carotene |
| Str04 | ΔC30 | Str01 | — |
| Str05 | HP1-crtZYIB_Pz-HP2-crt_ Pz | Str03 | Zeaxanthin |
| Str06 | HP1-crtZYIB_Pz-HP2-crtE_Pz | Str01 | Zeaxanthin |
| Str07 | HPI-crtZYIB_Pz-HP2-crtE_Pz pR-crtW_p | Str06 | Astaxanthin |
| Str08 | HP1-crtIB_Pz-HP2-crtE_Pz pR-crtW_Fp | Str07 | Lycopene |
| Str09 | HP1-crtYIB_Pz-HP2-crtE_Pz pR-crtW_Fp | Str07 | Canthaxanthin |
| Str10 | HP1-crtIB_Pz-HP2-crtE*_Pz pR-crtW_Fp | Str07 | — |

Carotenoid production of crtYIB and crtIBZY clusters from various organisms in *E. coli* and *M. extorquens* with and without native C30 carotenoid production pathway, as described in the examples below, is shown in Table 3. Production of C40 carotenoids is reported on dry-cell basis for best producing isolates.

TABLE 3

| Plasmid | Strain | Beta carotene (ppm) | Zeaxanthin (ppm) |
|---|---|---|---|
| pA01 | Str02 | 165 | |
| | Str04 | 730 | |
| | *E. coli* BL21 | 44 | |
| pA02 | Str02 | 588 | |
| | Str04 | 111 | |
| | *E. coli* BL21 | 188 | |

TABLE 3-continued

| Plasmid | Strain | Beta carotene (ppm) | Zeaxanthin (ppm) |
|---|---|---|---|
| pA03 | Str02 | 165 | |
| | Str04 | 304 | |
| | *E. coli* BL21 | 289 | |
| pA04 | Str04 | | 200 |
| | *E. coli* BL21 | | 120 |
| pA05 | Str02 | 15 | |
| | *E. coli* BL21 | 114 | |
| pA06 | Str04 | 895 | |
| pA07 | Str02 | 739 | |
| | *E. coli* BL21 | 39 | |

Carotenoid production of various integrated strains with plasmid-based overexpression of various genes, as described in the examples below, is provided in Table 4. crtE* indicates non-functional mutant.

TABLE 4

| Strain | Plasmid | Lycopene (ppm) | Beta Carotene (ppm) | Zea-xanthin (ppm) | Cantha-xanthin (ppm) | Asta-xanthin (ppm) |
|---|---|---|---|---|---|---|
| Str06 | pB | | | 1,475 | | |
| Str06 | pB09 | | | 2,743 | | |
| Str06 | pD10 | | | 668 | | 1,424 |
| Str06 | pC11 | | | | | 1,232 |
| Str08 | pA | 4,896 | | | | |
| Str08 | pA15 | | 99 | | 2,048 | 216 |
| Str08 | pA16 | | 4 | | | 1,404 |
| Str08 | pA17 | | 64 | | | 776 |
| Str08 | pA18 | | 12 | | | 169 |
| Str10 | pB | | | | | |
| Str10 | pB19 | | | | 321 | 1,097 |
| Str10 | pB20 | | | | 38 | 579 |

Carotenoid production of integrated pathways in *M. extorquens* on various media compositions, as described in the examples below, is provided in Table 5.

TABLE 5

| Sample Name | Carbon Source | Total Carotenoids (ppm) 2500E | Lycopene (ppm) | Zea-xanthin (ppm) | Cantha-xanthin (ppm) | Asta-xanthin (ppm) |
|---|---|---|---|---|---|---|
| Str06 | Methanol | 2,726 | | 2,295 | | |
| Str06 | Cofeed | | | 1,171 | | |
| Str06 | Stillage | | | 1,780 | | |
| Str06 | Stillage + Methanol | | | 2,621 | | |
| Str06 | Stillage + Cofeed | | | 1,490 | | |
| Str06 | Stillage + Ethanol | | | 533 | | |
| Str07 | Methanol | 3,669 | | 970 | 369 | 2,311 |
| Str07 | Cofeed | | | 630 | 154 | 2,570 |
| Str07 | Stillage | | | 159 | 134 | 1,630 |
| Str07 | Stillage + Methanol | | | 701 | 130 | 2,765 |
| Str07 | Stillage + Cofeed | | | 420 | 159 | 1,934 |
| Str07 | Stillage + Ethanol | | | 59 | 95 | 537 |
| Str08 | Methanol | 5,789 | 5,857 | | | |
| Str08 | Cofeed | | 5,942 | | | |
| Str08 | Stillage | | 2,271 | | | |
| Str08 | Stillage + Methanol | | 3,884 | | | |
| Str08 | Stillage + Cofeed | | 2,517 | | | |
| Str08 | Stillage + Ethanol | | 1,631 | | | |
| Str09 | Methanol | 4,652 | | | 4,470 | |
| Str09 | Cofeed | | | | 3,313 | |
| Str09 | Stillage | | | | 3,232 | |
| Str09 | Stillage + Methanol | | | | 5,363 | |
| Str09 | Stillage + Cofeed | | | | 3,463 | |
| Str09 | Stillage + Ethanol | | | | 2,609 | |

Example 1

Summary: *Paracoccus zeaxanthinifaciens* crtZYIBE genes were cloned into a plasmid with constitutive promoters previously characterized in *M. extorquens*. The plasmid was transformed into *M. extorquens*, with and without native C30 carotenoid pathway. Fermentations of these plasmid-bearing strains produced zeaxanthin.

*P. zeaxanthinifaciens* ATCC 21588 crtZYIBE genes (SEQ ID NO:9) were amplified via polymerase chain reaction (PCR) in several parts, with junctions introduced where AarI recognition sites natively occurred in the target sequence. As this gene cluster consists of two convergent operons (FIG. 2), promoter region from *M. extorquens* mxaF gene (SEQ ID NO:3) was amplified via PCR to drive the expression of the crtE gene. All amplification primers were designed with 18-25 base pair binding regions and an overhang including a recognition site, spacer regions and restriction site to enable restriction and ligation by AarI Gateway cloning. Single nucleotide polymorphisms (SNPs) were introduced at the junctions located inAarI recognition sites to remove recognition without changing coded amino acids.

Operon fragments and pmxaF were ligated with AarI Gateway assembly into vector pD (FIG. 10B), which contains the promoter-RBS region pR-faeRBS (SEQ ID NO:4) derived from the viral promoter pR and the RBS region from *M. extorquens* gene fae. Genes were assembled in their native convergent structure with crtZYIB downstream of pR-faeRBS and crtE downstream of pmxaF. (FIG. 10C shows a map of plasmid pA01 as an example schematic.) The vector backbone was derived from plasmid pLC291 (see Chubiz, et al. (2013) *BMC Research Notes,* 6(1):183), which included the gene kanR, which confers kanamycin resistance, origin of replication ColEI, which allows *E. coli* to maintain the plasmid at high copy numbers, and IncP origin of vegetation (oriV), which allows *M. extorquens* to maintain the plasmid at low copy numbers (*M. extorquens* does not recognize the ColEI origin).

Ligation products were transformed into New England Biolab's 10-beta Competent *E. coli* cells, single colonies were screened for correct assembly, and plasmid DNA was extracted by mini-prep and sequenced.

Verified plasmid. Designated pD00, was transformed into competent *M. extorquens* PA1 (Taxonomy ID: 419610) variants. All *M. extorquens* PA1 strains tested in these studies were derived from a strain designated Str01, which includes two deletions, the celABC and crtCDF deletions that reduce flocculation of cells in liquid culture and eliminate spirilloxanthin pathway, respectively. The strain used in this study is designated Str03 and includes overexpression of the native crtEBI genes on the heterologous pR promoter integrated into the crtBI locus (Mext_3011-Mext_3012) and the crtY from *P. zeaxanthinifaciens* also expressed on the heterologous pR promoter integrated at the hpt locus. Additionally, Str03 has a deleted carotenoid cluster and does not produce native C30 compounds. Most transformed colonies appeared yellow on solid media, however an orange mutant was identified and isolated for study. The mutant plasmid was designated pD00*.

Isolated colonies were picked into 3-5 mL precultures, grown with shaking 3 days at 30° C., then 250-500 L transferred to 25-50 mL minimal media in flasks for 2-3 day fermentation with shaking at 30° C. (with kanamycin selection to maintain the plasmid). Minimal media used in all fermentations was modified from Choi et al., (1989) *Kor. J Appl. Microbiol. Bioeng.* 17:392-396. Cultures were fed twice daily with 0.5% methanol as carbon source unless otherwise noted.

Absorbance at 600 nm over 1 cm path length was measured by spectrophotometry to estimate cell density, and 0.1-10 mL culture was harvested by centrifugation. Total biomass harvested was calculated from absorbance using a conversion value of 0.3 mg/($OD_{600}$*mL) according to internal data.

Carotenoids were extracted from the cell pellet and analyzed as follows: the cell pellet was resuspended in methanol, mixed with an equal volume of chloroform, and sonicated to lyse. Cell debris was removed by centrifugation and the resulting supernatant was dried completely. Residue was resuspended in dichloromethane and ethyl acetate (1:4 ratio) with sonication, debris again removed by centrifugation, and resultant supernatant dried completely. Residue was resuspended in 1:1 methanol chloroform mixture with sonication, centrifuged to remove any remaining debris, and analyzed by UPLC.

Figure 3:
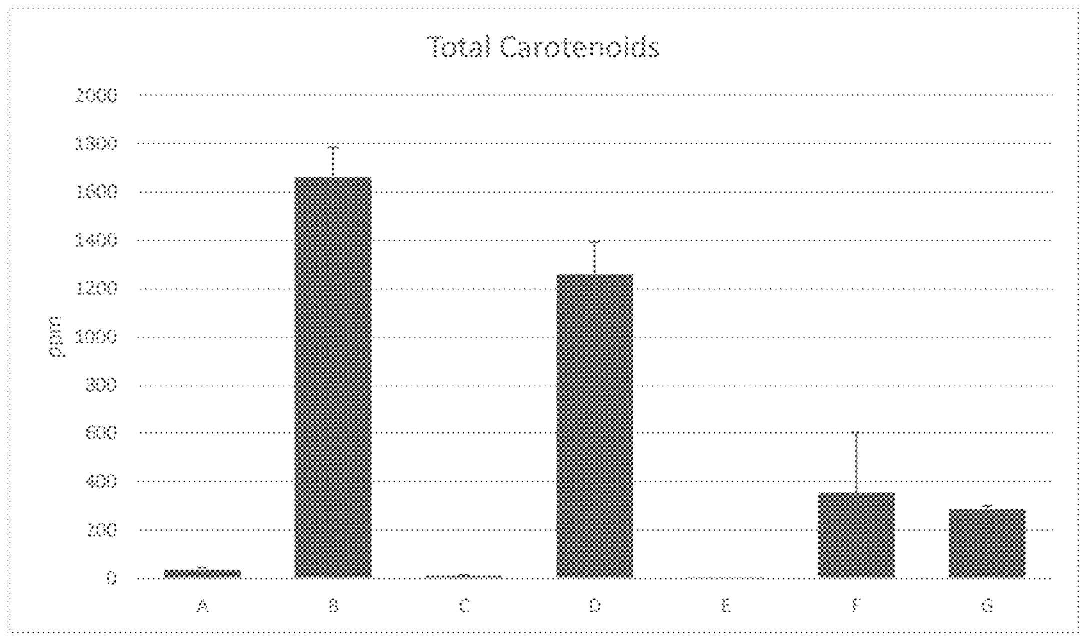
FIG. 3 shows data from the experiment described in Examples 1 and 3. (A) Str01, parent strain, *Methylobacterium extorquens* PA1, producing 100% C30 carotenoids; (B) Str06, strain (A) with C30 carotenoid production removed and *P. zeaxanthinifaciens* carotenoid gene cluster crtZYIBE integrated into the bacterial chromosome, producing >95% zeaxanthin; (C) Str03, strain (A) with C30 carotenoid production removed and *P. zeaxanthinifaciens* crtY gene integrated into the bacterial chromosome, driven by native crtEBI, producing trace amount of β-carotene; (D) Str05, strain (C) with *P. zeaxanthinifaciens* crtZYIBE integrated into the bacterial chromosome, producing >95% zeaxanthin; (E) Strain (C) with empty control plasmid, producing trace amount of β-carotene; (F) Strain (C) with plasmid pD00* containing *P. zeaxanthinifaciens* crtYIBE, producing >80% β-carotene; (G) Strain (C) with plasmid pD00 containing *P. zeaxanthinifaciens* crtZYIBE, producing >95% zeaxanthin.

1-4 μL of the cell extract was injected on Waters Acuity Ultra Performance Liquid Chromatography (UPLC) system. Analytes were separated by a gradient of ultrapure water with 0.1% formic acid, methanol with 0.1% formic acid and acetonitrile on a C18 column held at 32° C. Compounds were identified by tunable UV (TUV) detector (470 nm wavelength) and mass spectrometry. The resultant chromatography peaks were quantified by comparison of UV signal to standard curves of astaxanthin, zeaxanthin, canthaxanthin and beta-carotene. Parent strain Str03 with empty control vector produced trace beta-carotene, while this strains bearing pD00 plasmid produced zeaxanthin and those bearing pD00* produced more beta-carotene than the control vector (FIG. 3(E-G)).

Example 2

Summary: crtYIB or crtIBZY gene clusters from *Paracoccus zeaxanthinifaciens, Escherichia* vulgaris, *Pantoea ananatis, Fulvimarina pelagi, Sphingomonas astaxanthinifaciens, Siansivirga zeaxanthinifaciens* and *Mesoflavibacter zeaxanthinifaciens* were cloned into plasmids with crtE from *P. zeaxanthinifaciens* with promoter regions from *P. zeaxanthinifaciens*. The plasmids were transformed into *M. extorquens* with and without native C30 carotenoid pathway and *Escherichia coli* BL21. Fermentations of these plasmid-bearing strains produced beta carotene and zeaxanthin.

Carotenoid production genes were identified in strains *Paracoccus zeaxanthinifaciens, Escherichia vulgaris, Pantoea ananatis, Fulvimarina pelagi, Sphingomonas astaxanthinifaciens, Siansivirga zeaxanthinifaciens* and *Mesoflavibacter zeaxanthinifaciens*. crtYIB or crtIBZY gene clusters (SEQ IDs in Table 1) were amplified via polymerase chain reaction (PCR) in several parts, with junctions introduced where AarI recognition sites natively occurred in the target sequence. The crtE gene from *P. zeaxanthinifaciens* (SEQ ID NO: 14) was amplified with adjacent non-coding promoter region which was designated HP2 (SEQ ID NO: 8). As in Example 1, SNPs were introduced at junctions to remove natively-occurring AarI sites without changing coded amino acids and extension primers were designed to enable restriction and ligation by AarI Gateway cloning.

Each cluster was assembled with HP2-crtE fragment using AarI Gateway assembly into vector pA, which contains the non-coding promoter region upstream of *P. zeaxanthinifaciens* crtZYIBE cluster, designated HP1 (SEQ ID NO: 7), and shares other backbone features with plasmid pD described in Example 1. As in pD00, fragments were arranged in a convergent operon structure (FIG. 10C shows a map of plasmid pA01 as example schematic).

Ligation products were transformed into competent *E. coli* cells, single colonies were screened for correct assembly, and plasmid DNA was extracted by mini-prep and sequenced.

Verified plasmids were introduced into *M. extorquens* PA1 (Taxonomy ID: 419610) variants. Variant Str02 contains the *M. extorquens* carotenoid cluster and no bch cluster, while variant Str04 has a deleted carotenoid cluster and does not produce native C30 compounds. Plasmids were also transformed into competent *E. coli* BL21.

Isolated colonies of *M. extorquens* transformations were picked into 3 mL of minimal media in 24 deep well plates, covered with breathable film and grown with shaking at 30° C. for three days. Isolated colonies of *E. coli* transformations were picked into 3 mL of LB media in capped tubes and grown with shaking at 37° C. overnight.

Cultures were harvested as in Example 1 and extracted from the cell pellet by an abbreviated method suitable for target C40 compounds as follows: the cell pellet was resuspended in methanol, mixed with an equal volume of ethyl acetate, and sonicated to lyse. Cell debris was removed by centrifugation, the resulting supernatant was diluted in 1:1 methanol:ethyl acetate as necessary and analyzed by UPLC as in Example 1. Parent strains with empty control vector produced no detectable C40 carotenoids, while strains with plasmids produced beta carotene or zeaxanthin (Table 3).

Example 3

Summary: *P. zeaxanthinifaciens* crtZYIBE genes were cloned into an integration plasmid with non-coding regions upstream and downstream of operons from *P. zeaxanthinifaciens*. The cassette was integrated into *M. extorquens* in the C30 gene cluster region using scarless integration methods. Fermentations of these strains produced zeaxanthin.

The *P. zeaxanthinifaciens* crtZYIBE operon with up- and down-stream non-coding regions (HP1 and HP2), was amplified with PCR in fragments with junctions at natively-occurring AarI sites (SEQ ID NO:9). 500 base pair flanking regions upstream of MEXT_3434 (SEQ ID NO:5) and downstream of MEXT_3441 (SEQ ID NO:6) (flanking the C30-producing gene cluster region) were designed to target insertion of operons into *M. extorquens* chromosome.

As in Example 1, SNPs were introduced at junctions in crtZ and crtB to remove natively-occurring AarI sites without changing coded amino acids, and extension primers were designed to enable restriction and ligation by AarI Gateway cloning.

Operon fragments were assembled with flanking regions by Gateway assembly to form integration cassettes in plasmid pI (SEQ ID NO:1; FIG. 10A), which replicates in *E. coli* but not in *M. extorquens*, and which includes a kanamycin resistance cassette, a sacB counter selection cassette, and the origin of replication ColEI for maintenance in *E. coli*. Ligation products were transformed into competent *E. coli* cells, single colonies were screened for correct assembly, and plasmid DNA was extracted by mini-prep and sequenced.

The resulting plasmid, p108, was introduced into several strains of *M. extorquens* by electroporation, including Str01 (with addition of crtZYIBE cassette this was designated Str06) and Str03 (with addition of crtZYIBE cassette this was designated Str05) described in Example 1. Integrants were selected on kanamycin selective media and passaged onto sucrose media plates to remove markers. Yellow isolates were selected and the integration locus verified with PCR.

Verified integration strains and parent strains were grown with no antibiotics and assessed for zeaxanthin production as described in Example 1. Parent strains produced no zeaxanthin, while integrated strains produced zeaxanthin (FIG. 3 (A-D)).

Example 4

Summary: *E. vulneris* idi gene was cloned on a plasmid and transformed into a zeaxanthin producing strain. Fermentations with this plasmid improved production of zeaxanthin up to 70% over control plasmid fermentations.

The gene idi from *E. vulneris* (SEQ ID NO: 37) was amplified via PCR with AarI Gateway extension primers. The gene was assembled by Gateway assembly into plasmid pB, which contains promoter region HP2 and shares other backbone features with plasmid pD, described in Example 1, to generate pB09. Ligation products were transformed into competent *E. coli* cells, single colonies were screened for correct assembly, and plasmid DNA was extracted by mini-prep and sequenced.

Verified idi plasmid and empty control plasmid were transformed into integrated zeaxanthin-producing strain Str06. Transformants were grown with kanamycin and assessed for zeaxanthin production as described in Example 2. Fermentations with idi overexpression yielded elevated zeaxanthin yields when compared to control plasmid fermentations (Table 4).

Example 5

Summary: *Fulvimarina pelagi* crtWZ genes were cloned into a plasmid with a constitutive promoter previously characterized in *M. extorquens*. The plasmid was transformed into *M. extorquens* and fermentations of plasmid-bearing strains were analyzed for carotenoid content. *M. extorquens* with this plasmid produced ~1200 ppm astaxanthin.

crtW and crtZ genes from *F. pelagi* were amplified with PCR with Gateway extension primers, as described in Example 1. Gene fragments from *F. pelagi* were ligated into plasmid pD, which contains promoter/RBS pair pR-faeRBS (SEQ ID NO:4) to generate pD10 using Gateway assembly. The vector backbone was as described in Example 1, and contained a kanamycin resistance cassette and oriV for replication in *M. extorquens*. Insertion was verified by PCR and sequence verified. Ligation products were transformed into competent *E. coli* cells, single colonies were screened for correct assembly, and plasmid DNA was extracted by mini-prep and sequenced.

Verified plasmids were transformed into strain Str05 from Example 3 and isolated colonies grown in presence of kanamycin and assessed for astaxanthin production as described in Example 2. Fermentations with this plasmid-bearing strain are described in Example 7.

Example 6

Summary: *S. astaxanthinifaciens* crtW gene was cloned into plasmids and transformed alongside pD10 into zeaxanthin producing *M. extorquens*. Fermentations of plasmid-bearing strains produced astaxanthin.

crtW from *S. astaxanthinifaciens* (SEQ ID NO: 20) was amplified via PCR with Gateway extension primers as described in Example 1. The gene was ligated with Gateway assembly in plasmid pC, which contains the promoter pmxaF (SEQ ID NO: 3) and shares other backbone features with plasmid pA, described in Example 2, to generate pC11.

Ligation products were transformed into competent *E. coli* cells, single colonies were screened for correct assembly, and plasmid DNA was extracted by mini-prep and sequenced.

Verified pD10 and pC11 were transformed into Str06, described in Example 3. Transformants were grown with kanamycin and assessed for carotenoid production as in Example 2. Fermentations with these plasmids produced astaxanthin and mixed precursors (Table 4).

Example 7

Summary: Zeaxanthin and astaxanthin-producing strains were fermented as described in Example 1 with either methanol alone, or methanol and ethanol fed together. Zeaxanthin and astaxanthin production were altered in cultures fed with methanol and ethanol together versus those fed methanol alone.

Zeaxanthin producing strains Str05 and Str06 from Example 3 and plasmid-bearing strain from Example 5 were struck on solid minimal media with methanol to isolate single colonies.

Three single colonies from each plate were picked into 3-5 mL minimal media with 0.5% methanol and grown 3 days at 30° C. Flasks with minimal media containing either 0.5% methanol or 0.25% methanol and 0.1% ethanol were inoculated with 1% of preculture (each preculture used to inoculate one methanol and one methanol/ethanol flask).

Cultures were sampled and fed with additional bolus of carbon equivalent to starting quantity (0.4% methanol or 0.25% methanol and 0.1% ethanol) after one day. Additional samples were taken after three and four days. Cell density was measured by absorbance at 600 nm.

Carotenoids were harvested from cell extracts using an abbreviated method suitable for high-titer cultures: 1 mL culture was pelleted and supernatant removed. Pellet was resuspended in ethanol then lysed with equal volume of ethyl acetate and sonication. Cell debris was removed by centrifugation.

Figure 6:
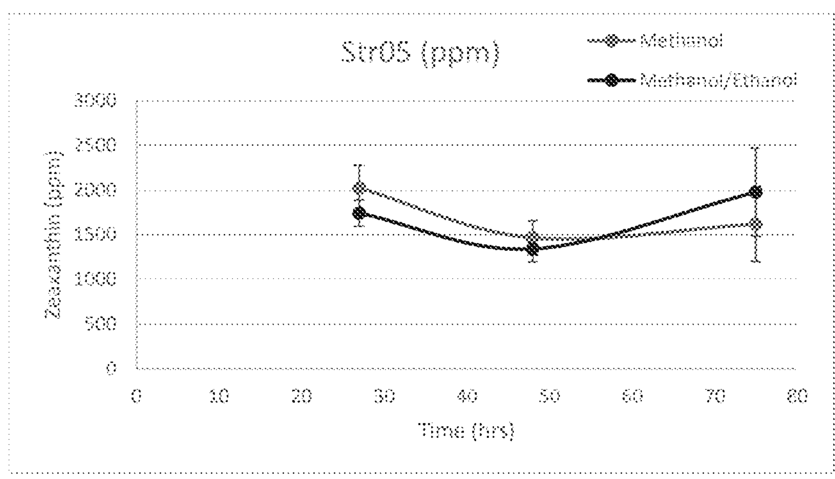
FIG. 6 shows zeaxanthin production in methanol and methanol/ethanol for strain Str05 as described in Example 7.
Figure 7:
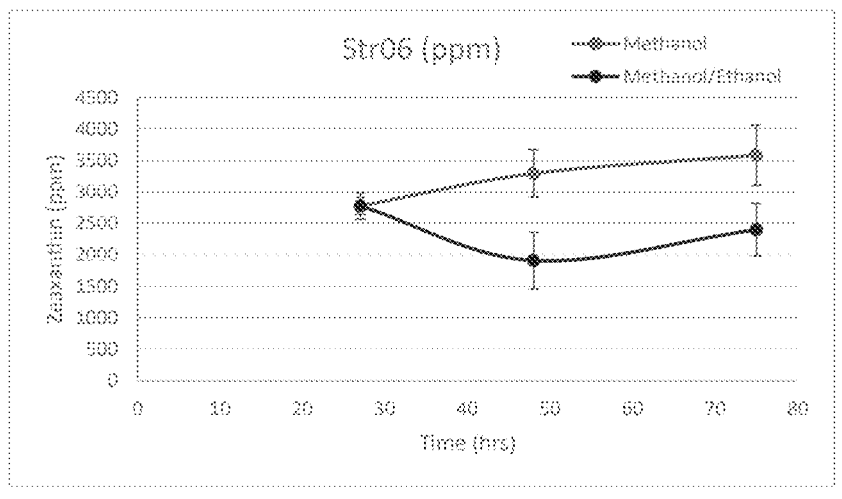
FIG. 7 shows zeaxanthin production in methanol and methanol/ethanol for strain Str06 as described in Example 7.
Figure 8:
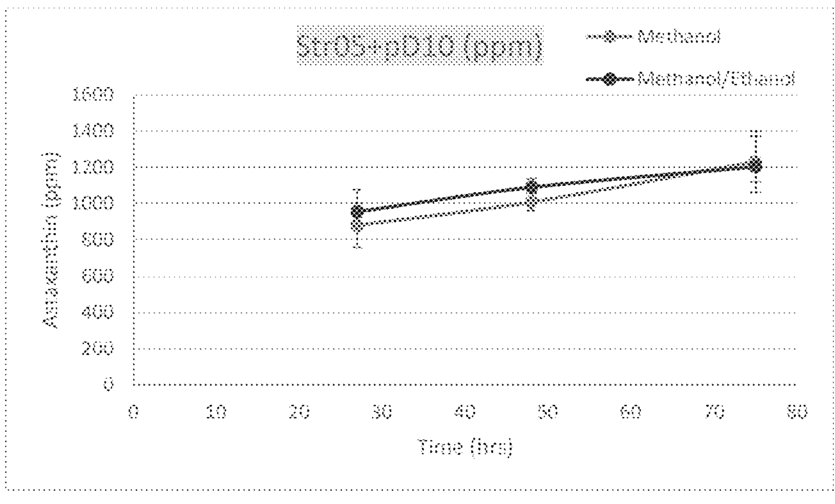
FIG. 8 shows astaxanthin production in methanol and methanol/ethanol for strain Str05+plasmid pD10 as described in Example 7.

Carotenoids were extracted from cell pellets as described in Example 2. Zeaxanthin production in strains Str05 and Str06 on methanol and methanol/ethanol is shown in FIG. 6 and FIG. 7, respectively. Astaxanthin production in strain Str05+plasmid pD10 on methanol and methanol/ethanol is shown in FIG. 8.

Figure 4A:
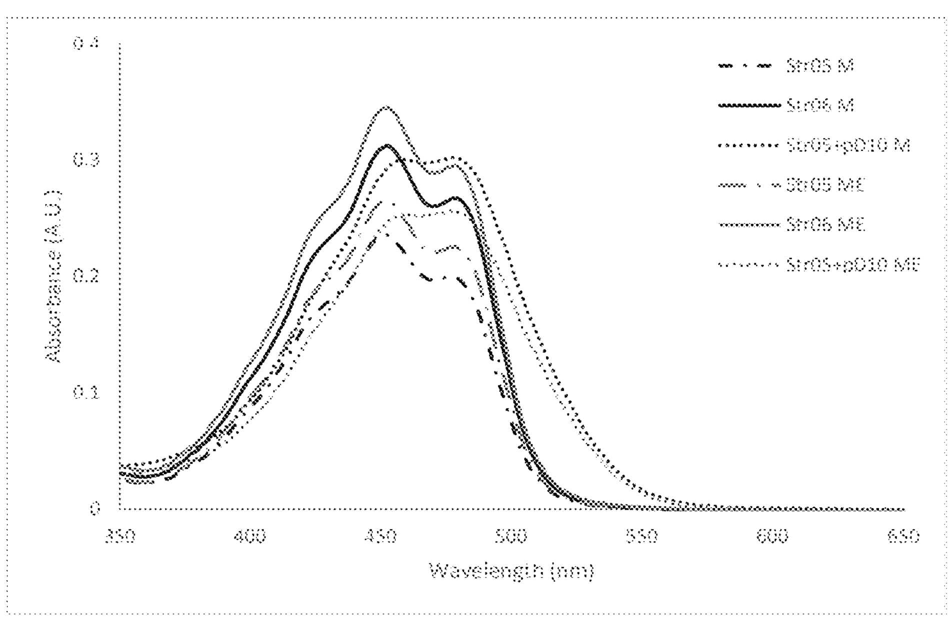
FIG. 4A shows the absorbance spectra for the strains described in Example 7.
Figure 5:
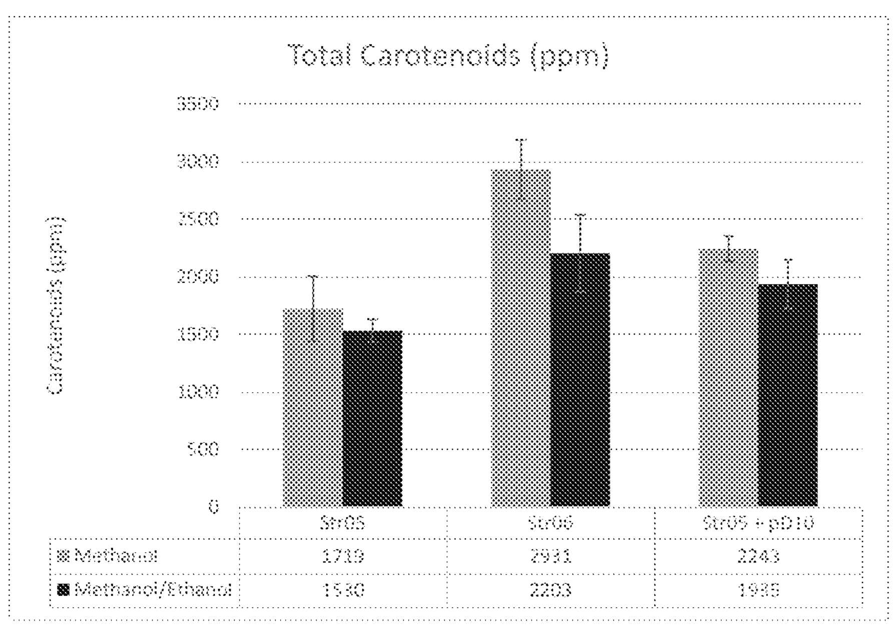
FIG. 5 shows total carotenoid production for the strains described in Example 7.

Aliquots of final time point were diluted 10× into ethyl acetate and absorbance was measured from 350-800 nm wavelengths at 1 nm intervals. Representative absorbance spectra are plotted (FIG. 4A), showing relative carotenoid levels of certain samples and peaks indicating chemical differences in carotenoids as known in the art (Rodriguez (2001) A Guide to Carotenoid Analysis in Foods). Total carotenoids were estimated based on peak absorbance and extinction coefficients reported in literature (Davies (1976) Carotenoids. In: T. W. Goodwin (Ed.) Chemistry and Biochemistry of Plant Pigments, Academic Press, London, pp. 38-165). Results are shown in FIG. 5.

Example 8

Summary: Strains that produce astaxanthin, canthaxanthin, and lycopene were generated. *Fulvimarina pelagi* crtW gene was integrated into a zeaxanthin producing strain of *M. extorquens*. The crtZ gene and the crtZY genes were removed from the astaxanthin strain. Integrated strains were fermented in six conditions: minimal media with methanol alone or methanol and ethanol cofeed; or media made with 2% stillage syrup and methanol alone, methanol and ethanol cofeed, ethanol alone or no supplemental carbon.

The *F. pelagi* crtW, pR-faeRBS fragment and two flanking regions overlapping MEXT_3010 (SEQ ID NO: 51) and MEXT 3011 (SEQ ID NO: 52) were amplified with PCR. As in Example 1, extension primers were designed to enable restriction and ligation by AarI Gateway cloning.

Promoter and crtW were assembled with flanking regions by Gateway assembly to form integration cassette in plasmid pI. Ligation products were transformed into competent *E. coli* cells, single colonies were screened for correct assembly, and plasmid DNA was extracted by mini-prep and sequenced. The plasmid was introduced into Str06 by electroporation. Integrants were selected on kanamycin selective media and passaged onto sucrose media plates to remove markers. Red-orange isolates were selected, and the integration locus verified with PCR. Verified integration strain was designated Str07.

Deletion fragments overlapping the MEXT_3434-HP1 region (SEQ ID NOs: 5 and 7) and crtY region (SEQ ID NO: 11) were designed to delete the crtZ gene from STR07. Fragments were amplified with PCR. As in Example 1, extension primers were designed to enable restriction and ligation by AarI Gateway cloning. Deletion fragments were assembled by Gateway assembly to form deletion cassette in plasmid pI. Ligation products were transformed into competent *E. coli* cells, single colonies were screened for correct assembly, and plasmid DNA was extracted by mini-prep and sequenced. The plasmid was introduced into Str07 by electroporation. Integrants were selected on kanamycin selective media and passaged onto sucrose media plates to remove markers. Isolates were screened by PCR for the absence of crtZ and the locus sequenced to confirm deletion. Verified deletion strain was designated Str09.

A truncated section of the *P. zeaxanthinifaciens* crtZYIBE operon consisting only of the crtIBE genes with up- and down-stream non-coding regions (HP1 and HP2) was amplified with PCR and assembled into pI with 500 base pair flanking regions upstream of MEXT_3434 (SEQ ID NO: 5) and downstream of MEXT_3441 (SEQ ID NO: 6) as in Example 1. Ligation products were transformed into competent *E. coli* cells, single colonies were screened for correct assembly, and plasmid DNA was extracted by mini-prep and sequenced. The plasmid was introduced into Str07 by electroporation to replace full-length crtZYIBE Pz pathway. Integrants were selected on kanamycin selective media and passaged onto sucrose media plates to remove markers. Pink isolates were selected, and the integration locus verified with PCR. Verified strain was designated Str08.

Figure 4B:
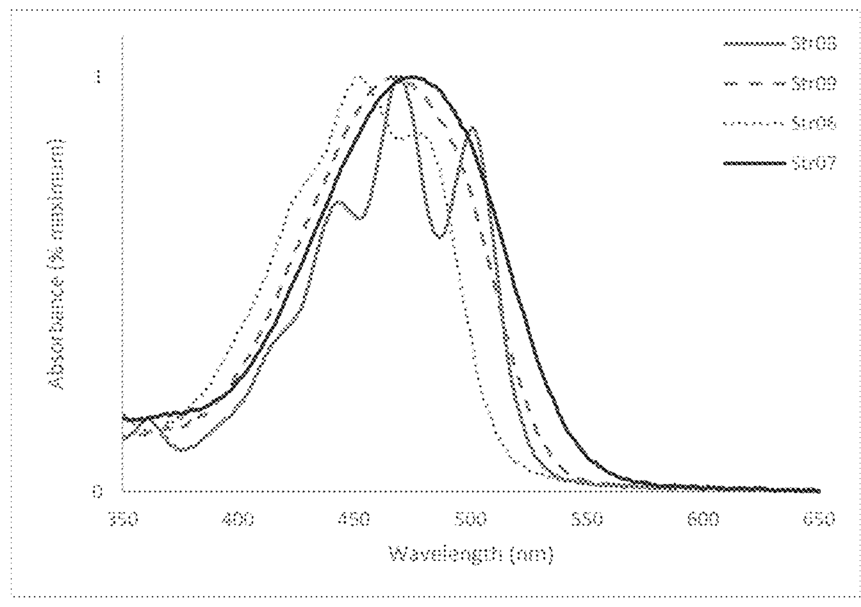
FIG. 4B shows the absorbance spectra for the strains fermented with methanol described in Example 8.

Integrated carotenoid-producing strains Str08, Str09, Str06, and Str07 were struck on solid minimal media with methanol to isolate single colonies. One colony from each plate was picked into 5 mL minimal media precultures with 0.5% methanol and grown 3 days at 30° C. Concentrated stillage syrup with sterile water and mineral solutions to a final media composition of 2% stillage syrup with supplementation of $(NH_4)_2SO_4$, $KH_2PO_4$ and $Na_2HPO_4$. Stillage media was supplemented with nothing (Stillage), 0.25% methanol (Stillage+Methanol), 0.1% methanol and 0.0625% ethanol (Stillage+Cofeed) or 0.125% ethanol (Stillage+Ethanol). Minimal media were prepared with either 0.5% methanol as the sole carbon source or 0.125% methanol and 0.2% ethanol (Cofeed). Each of the four precultures was used to inoculate one flask of each media and the set was grown with shaking for 3 days at 30° C. Cell density was measured by absorbance at 600 nm at the end of fermentation and carotenoid production assessed as described in Example 2. Absorbance spectrum measurements of extracts from minimal media methanol-fed cultures were taken as in Example 7. Representative absorbance spectra are plotted in FIG. 4B.

Figure 9:
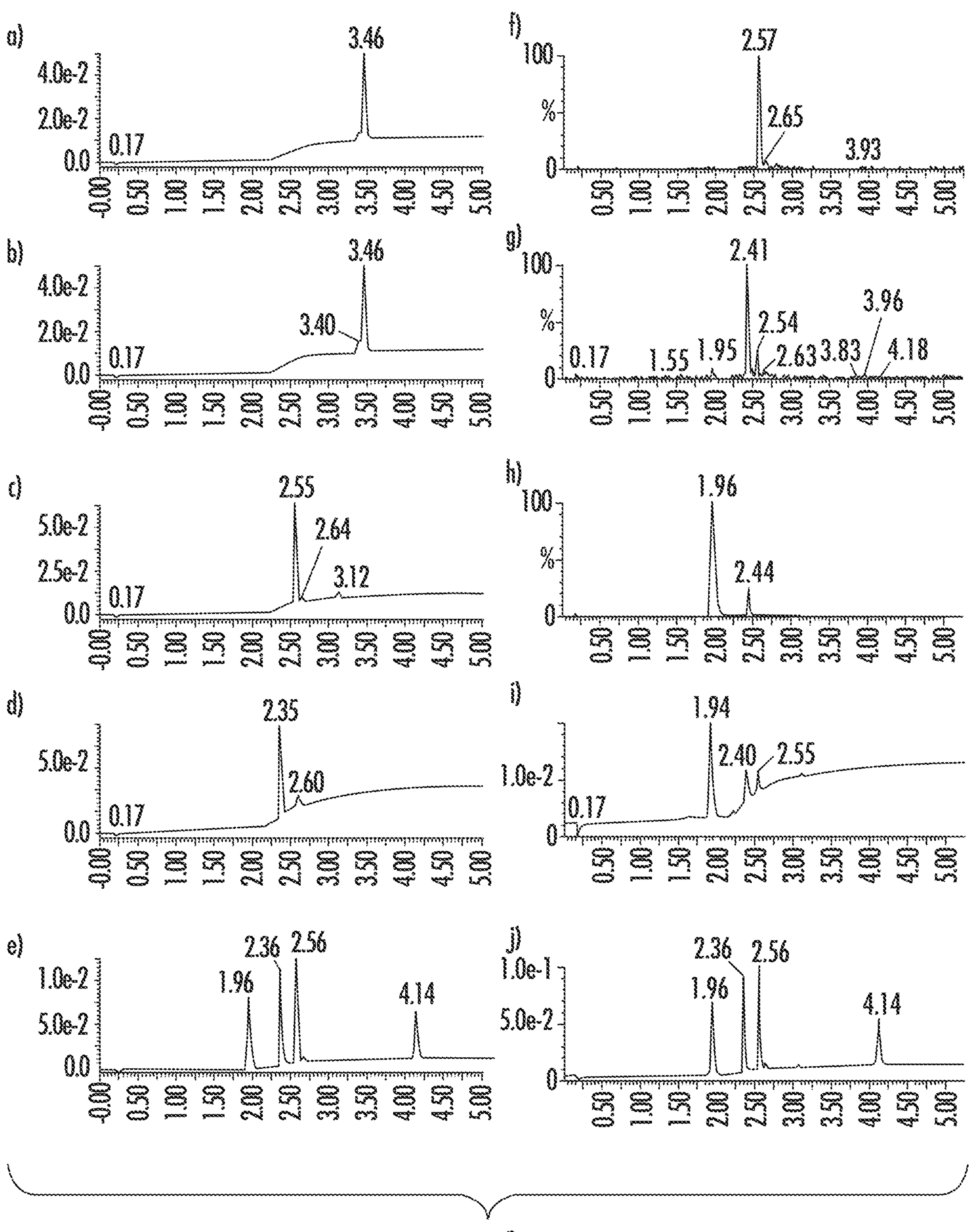
FIG. 9 shows UPLC traces of standard compound mixtures and extracts of various strains grown in minimal media with methanol as sole carbon source. Traces show absorbance at 470 nm wavelength or targeted ions.

Total carotenoid content calculated from absorbance spectra of methanol-fed samples and individual carotenoid content calculated from UPLC traces of all samples are reported in Table 5 and FIG. 9. Str06 produced zeaxanthin; Str07 produced mostly astaxanthin, some canthaxantin and another molecule predicted by mass spectrometry data to be phoenicaxanthin; Str08 produced lycopene, and Str09 produced canthaxanthin.

Example 9

Summary: *S. astaxanthinifaciens, F. pelagi, E. vulneris* and *M. zeaxanthinifaciens* crtZ genes were cloned into plasmids with crtY gene from *P. zeaxanthinifaciens*. Plasmids were transformed into lycopene-producing strain from Example 8. Fermentations of these plasmid-bearing strains produced astaxanthin.

crtZ genes from *S. astaxanthinifaciens* (SEQ ID NO: 16), *F. pelagi* (SEQ ID NO: 50), *E. vulneris* (SEQ ID NO: 32) and *M. zeaxanthinifaciens* (SEQ ID NO: 27) were amplified via PCR with Gateway extension primers as described in Example 1. The crtY from *P. zeaxanthinifaciens* (SEQ ID NO: 11) was also amplified with Gateway extension primers and the faeRBS (SEQ ID NO: 4). Each crtZ was ligated with the faeRBS-crtY fragment into plasmid pA using Gateway assembly. Ligation products were transformed into competent *E. coli* cells, single colonies were screened for correct assembly, and plasmid DNA was extracted by mini-prep and sequenced.

Verified plasmids pA15-18 were transformed into Str08 from Example 8. Transformants were grown with kanamycin and assessed for carotenoid production as in Example 1. Fermentations with these plasmids produced astaxanthin and mixed precursors (Table 4).

Example 10

Summary: Descendant of astaxanthin-producing strain from Example 8 with non-producing phenotype was identified to have null mutation in the crtE gene. Complementation of non-producer with *E. vulneris* and *P. ananatis* crtE genes expressed on plasmids recovered production of astaxanthin.

Astaxanthin-producing strain Str07 was grown in minimal media to high density and passaged to allow for random mutation before plating. Pale colonies were selected, and the carotenoid genes were sequenced. A white isolate with a frame-shift mutation in the crtE gene was identified and designated Str10.

The crtE gene from *E. vulneris* (SEQ ID NO: 36) and from *P. ananatis* (SEQ ID NO: 43) were amplified via PCR with Gateway extension primers as described in Example 1 and ligated into plasmid pB using Gateway assembly. Ligation products of *E. vulneris* gene were transformed into competent *E. coli* cells, single colonies were screened for correct assembly, and plasmid DNA was extracted by mini-prep and sequenced. The verified plasmids pB19 was transformed into Str10. Ligation products of *P. ananatis* gene were directly transformed into Str07 and pB20 containing colonies were screened for orange color.

Transformants were grown with kanamycin and assessed for carotenoid production as in Example 2. Fermentations with these plasmids produced astaxanthin and mixed precursors (Table 4).

Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

Nucleotide and Amino Acid Sequences

Nucleotide and Amino Acid Sequences pKB40 - plasmid sequences (FIG. 10A)

SEQ ID NO: 1

```
acccacgctcaccggctccagatttatcagcaataaaccagccagccggaagggccgagcgcagaagtggtcctgcaactttatccgcctccatccagtctatt

aatatccccgtgtcggacctgcagggggggggggggaaagccacgttgtgtctcaaaatctctgatgttacattgcacaagataaaatatatcatcatgaacaa

taaaactgtctgcttacataaacagtaatacaaggggtgttatgagccatattcaacgggaaacgtcttgctcgaggccgcgattaaattccaacatggatgct

gatttatatgggtataaatgggctcgcgataatgtcgggcaatcaggtgcgacaatctatcgattgtatgggaagcccgatgcgccagagttgtttctgaaaca

tggcaaaggtagcgttgccaatgatgttacagatgagatggtcagactaaactggctgacggaatttatgcctcttccgaccatcaagcattttatccgtactc

ctgatgatgcatggttactcaccactgcgatccccgggaaaacagcattccaggtattagaagaatatcctgattcaggtgaaaatattgttgatgcgctggca

gtgttcctgcgccggttgcattcgattcctgtttgtaattgtccttttaacagcgatcgcgtatttcgtctcgctcaggcgcaatcacgaatgaataacggttt

ggttgatgcgagtgattttgatgacgagcgtaatggctggcctgttgaacaagtctggaaagaaatgcataagcttttgccattctcaccggattcagtcgtca

ctcatggtgatttctcacttgataaccttatttttgacgaggggaaattaataggttgtattgatgttggacgagtcggaatcgcagaccgataccaggatctt

gccatcctatggaactgcctcggtgagttttctccttcattacagaaacggctttttcaaaaatatggtattgataatcctgatatgaataaattgcagtttca

tttgatgctcgatgagtttttctaatcagaattggttaattggttgtaacactggcagagcattacgctgacttgacgggacggaatattattgaagcatttat

cagggttattgtctcatgagcggatacatatttgaatgtatttagaaaaataaacaaataggggttccgcgcacatttccccgaaaagtgccacctgacgtcta
```

-continued gatctgaattcagctgtacaattggtaccatggatgGGAGggcagcaggtgGGAAAGCGGGCAGTGAGCGCAACGCAATTAATGTGAGTTAGCTCACTCATTAG

GCACCCCAGGCTTTACACTTTATGCTTCCGGCTCGTATGTTGTGTGGAATTGTGAGCGGATAACAATTTCA

CACAGGAAACAGCTATGACCATGATTACGCCAAGCTATTTAGGTGACACTATAGAATACTCAAG

CTATGCATCAAGCTTGGTACCGAGCTCGGATCCACTAGTAACGGCCGCCAGTGTGCTGGAATTCG

CCCTTcacctgctgccAGTAcatatgctgcagctcgagcggccgcgggccctacgtacgcgtgttaaccggtgagctcactagaggatccagccgac caggctttccacgcccgcgtgccgctccatgtcgttcgcgcggttctcggaaacgcgctgccgcgtttcgtgattgtcacgctcaagcccgtagtcccgttcg agcgtcgcgcagaggtcagcgagggcgcggtaggcccgatacggctcatggatggtgtttcgggtcgggtgaatcttgttgatggcgatatggatgtgcaggt tgtcggtgtcgtgatgcacggcactgacgcgctgatgctcggcgaagccaagcccagcgcagatgcggtcctcaatcgcgcgcaacgtctccgcgtcgggctt ctctcccgcgcggaagctaaccagcacgtgataggtcttgtcggcctcggaacgggtgttgccgtgctgggtcgccatcacctcggccatgacagcgggcagg gtgtttgcctcgcagttcgtgacgcgcacgtgacccaggcgctcggtcttgccttgctcgtcggtgatgtacttcaccagctccgcgaagtcgctcttcttga tggagcgcatggggacgtgcttggcaatcacgcgcacccccccggccgttttagcggctaaaaaagtcatggctctgccctcgggcggaccacgcccatcatga ccttgccaagctcgtcctgcttctcttcgatcttcgccagcagggcgaggatcgtggcatcaccgaaccgcgccgtgcgcgggtcgtcggtgagccagagttt cagcaggccgcccaggcggcccaggtcgccattgatgcgggccagctcgcggacgtgctcatagtccacgacgcccgtgattttgtagccctggccgacggcc agcaggtaggccgacaggctcatgccggccgccgccgccttttcctcaatcgctcttcgttcgtctggaaggcagtacaccttgataggtgggctgcccttcc tggttggcttggtttcatcagccatccgcttgccctcatctgttacgccggcggtagccggccagcctcgcagagcaggattcccgttgagcaccgccaggtg cgaataagggacagtgaagaaggaacacccgctcgcgggtgggcctacttcacctatcctgcccggctgacgccgttggatacaccaaggaaagtctacacga accctttggcaaaatcctgtatatcgtgcgaaaaaggatggatataccgaaaaaatcgctataatgaccccgaagcagggttatgcagcggaaaagcgctgct tccctgctgttttgtggaatatctaccgactggaaacaggcaaatgcaggaaattactgaactgaggggacaggcgagagacgatgccaaagagctacaccga cgagctggccgagtgggttgaatcccgcgcggccaagaagcgccggcgtgatgaggctgcggttgcgttcctggcggtgagggcggatgtcgaggcggcgtta gcgtccggctatgcgctcgtcaccatttgggagcacatgcgggaaacggggaaggtcaagttctcctacgagacgttccgctcgcacgccaggcggcacatca aggccaagcccgccgatgtgcccgcaccgcaggccaaggctgcggaacccgcgccggcacccaagacgccggagccacggcggccgaagcaggggggcaa ggctgaaaagccggcccccgctgcggccccgaccggcttcaccttcaacccaacaccggacaaaaaggatccccaattctcatgtttgacagcttatcatcgat aagctttaatgcggtagtttatcacagttaaattgctaacgcagtcaggcaccgtgtatgaaatctaacaatgcgctcatcgtcatcctcggcaccgtcaccct ggatgctgtaggcataggcttggttatgccggtactgccgggcctcttgcgggatatcggcattttcttttgcgtttttatttgttaactgttaattgtccttg ttcaaggatgctgtctttgacaacagatgttttcttgcctttgatgttcagcaggaagcttggcgcaaacgttgattgtttgtctgcgtagaatcctctgtttg tcatatagcttgtaatcacgacattgtttcctttcgcttgaggtacagcgaagtgtgagtaagtaaaggttacatcgttaggatcaagatccatttttaacaca aggccagttttgttcatgcggcttgtagggccagttaaagaattagaaacataaccaagcatgtaaatatcgttagacgtaatgccgtcaatcgtcatttttga tccgcgggagtcagtgaacaggtaccatttgccgttcattttaaagacgttcgcgcgttcaatttcatctgttactgtgttagatgcaatcagcggtttcatca ctttttcagtgtgtaatcatcgtttagctcaatcataccgagagcgccgtttgctaactcagccgtgcgtttttatcgctttgcagaagtttttgactttct tgacggaagaatgatgtgcttttgccatagtatgctttgttaaataaagattcttcgccttggtagccatcttcagttccagtgtttgcttcaaatactaagta tttgtggcctttatcttctacgtagtgaggatctctcagcgtatggttgtcgcctgagctgtagttgccttcatcgatgaactgctgtacattttgatacgttt ttccgtcaccgtcaaagattgatttataatcctctacaccgttgatgttcaaagagctgtctgatgctgatacgttaacttgtgcagttgtcagtgtttgtttg ccgtaatgtttaccggagaaatcagtgtagaataaacggatttttccgtcagatgtaaatgtggctgaacctgaccattcttgtgtttggtcttttaggataga atcatttgcatcgaatttgtcgctgtctttaaagacgcggccagcgtttttccagctgtcaatagaagtttcgccgacttttgatagaacatgtaaatcgatg tgtcatccgcattttaggatctccggctaatgcaaagacgatgtggtagccgtgatagtttgcgacagtgccgtcagcgttttgtaatggccagctgtcccaa acgtccaggccttttgcagaagagatatttttaattgtggacgaatcgaattcaggaacttgatatttttcatttttttgctgttcagggatttgcagcatatc atggcgtgtaatatgggaaatgccgtatgtttccttatatggcttttggttcgtttctttcgcaaacgcttgagttgcgcctcctgccagcagtgcggtagtaa aggttaatactgttgcttgttttgcaaactttttgatgttcatcgttcatgtctcctttttttatgtactgtgttagcggtctgcttcttccagccctcctgttt gaagatggcaagttagttacgcacaataaaaaaagacctaaaatatgtaaggggtgacgccaaagtatacactttgccctttacacattttaggtcttgcctgc tttatcagtaacaaacccgcgcgatttacttttcgacctcattctattagactctcgtttggattgcaactggtctattttcctcttttgtttgatagaaaatc -continued ataaaaggatttgcagactacgggcctaaagaactaaaaaatctatctgtttcttttcattctctgtatttttatagtttctgttgcatgggcataaagttgc ctttttaatcacaattcagaaaatatcataatatctcatttcactaaataatagtgaacggcaggtatatgtgatgggttaaaaaggatcgatcctctagccac gggtgcgcatgatcgtgctcctgtcgttgaggacccggctaggctggcggggttgccttactggttagcagaatgaatcaccgatacgcgagcgaacgtgaagc gactgctgctgcaaaacgtctgcgacctgagcaacaacatgaatggtcttcggtttccgtgtttcgtaaagtctggaaacgcggaagtcagcgctcttccgctt cctcgctcactgactcgctgcgctcggtcgttcggctgcggcgagcggtatcagctcactcaaaggcggtaatacggnatccacagaatcaggggataacgcag gaaagaacatgtgagcaaaaggccagcaaaaggccaggaaccgtaaaaaggccgcgttgctggcgttittccataggctccgcccccctgacgagcatcacaaa aatcgacgctcaagtcagaggtggcgaaacccgacaggactataaagataccaggcgtttccccctggaagctccctcgtgcgctctcctgttccgaccctgcc gcttaccggatacctgtccgcctttctcccttcgggaagcgtggcgctttctcatagctcacgctgtaggtatctcagttcggtgtaggtcgttcgctccaagc tgggctgtgtgcacgaaccccccgttcagcccgaccgctgcgccttatccggtaactatcgtcttgagtccaacccggtaagacacgacttatcgccactggca gcagccactggtaacaggattagcagagcgaggtatgtaggcggtgctacagagttcttgaagtggtggcctaactacggctacactagaaggacagtatttgg tatctgcgctctgctgaagccagttaccttcggaaaaagagttggtagctcttgatccggcaaacaaaccaccgctggtagcggtggtttttgtitgcaagca gcagattacgcgcagaaaaaaaggatctcaagaagatcctttgatcttttctacggggtctgacgctcagtggaacgaaaactcacgttaagggattnggtcat gagattatcaaaaaggatcttcacctagatcctataaattaaaaatgaagttttaaatcaatctaaagtatatatgagtaaacttggtctgacagnaccaatgc ttaatcagtgaggcacctatctcagcgatctgtctatttcgttcatccatagttgcctgactccccgtcgtgtagataactacgatacgggagggcttaccatc tggccccagtgctgcaatgataccgcgag pKB127 - plasmid sequences (FIG. 10B)

SEQ ID NO: 2 gtgtcgatggtcatcgacttcgccaaacctgccgcctcctgttcgagacgacgcgaacgctccacggcggccgatggcgcgggcagggcaggggagcca gttgcacgctgtcgcgctcgatcttggccgtagcttgctggaccatcgagccgacggactggaaggtttcgcggggcgcacgcatgacggtgcggcttgcgat ggtttcggcatcctcggcggaaaaccccgcgtcgatcagttcttgcctgtatgccttccggtcaaacgtccgattcattcaccctccttgcgggattgccccga ctcacgccggggcaatgtgcccttattcctgatttgacccgcctggtgccttggtgtccagataatccaccttatcggcaatgaagtcggtcccgtagaccgtc tggccgtccttctcgtacttggtattccgaatcttgccctgcacgaataccagctccgcgaagtcgctcttcttgatggagcgcatggggacgtgcttggcaat cacgcgcacccccggccgttttagcggctaaaaaagtcatggctctgccctcgggcggaccacgcccatcatgaccttgccaagctcgtcctgcttctcttcg atcttcgccagcagggcgaggatcgtggcatcaccgaaccgcgccgtgcgcgggtcgtcggtgagccagagtttcagcaggccgcccaggcggcccaggtcgcc attgatgcgggccagctcgcggacgtgctcatagtccacgacgcccgtgattttgtagccctggccgacggccagcaggtaggcctacaggctcatgccggccg ccgccgcctttttcctcaatcgctcttcgttcgtctggaaggcagtacaccttgataggtgggctgcccttcctggttggcttggtttcatcagccatccgcttg ccctcatctgttacgccggcggtagccggccagcctcgcagagcaggattcccgttgagcaccgccaggtgcgaataagggacagtgaagaaggaacacccgct cgcgggtgggcctacttcacctatcctgcccggctgacgccgttggatacaccaaggaaagtctacacgaaccctttggcaaaatcctgtatatcgtgcgaaaa aggatggatataccgaaaaaatcgctataatgaccccgaagcagggttatgcagcggaaaagatccgtcgacccttttccgacgctcaccgggctggttgccctc gccgctgggctggcggccgtctatggccctgcaaacgcgccagaaacgccgtcgaagccgtgtgcgagacaccgcggccgccggcgttgtggatacctcgcgga aaacttggccctcactgacagatgaggggcggacgttgacacttgaggggccgactcacccggcgcggcgttgacagatgaggggcaggctcgatttcggccg gcgacgtggagctggccagcctcgcaaatcggcgaaaacgcctgattttacgcgagtttcccacagatgatgtggacaagcctggggataagtgccctgcggt attgacacttgaggggcgcgactactgacagatgaggggcgcgatccttgacacttgaggggcagagtgctgacagatgaggggcgcacctattgacatttga ggggctgtccacaggcagaaaatccagcatttgcaagggtttccgcccgtttttcggccaccgctaacctgtcttttaacctgcttttaaaccaatatttataa accttgtttttaaccagggctgcgccctgtgcgcgtgaccgcgcacgccgaaggggggtgccccccttctcgaaccctcccggcccgctaacgcgggcctccc atcccccccaggggctgcgcccctcggccgcgaacggcctcaccccaaaaatggcagccaagctgaccacttctgcgctcggcccttccggctggctggtttatt gctgataaatctggagccggtgagcgtgggtctcgcggtatcattgcagcactggggccagatggtaagccctcccgtatcgtagttatctacacgacggggag tcaggcaactatggatgaacgaaatagacagatcgctgagataggtgcctcactgattaagcattggtaactgtcagaccaagtttactcatatatactttaga ttgatttaaaacttcatttttaatttaaaaggatctaggtgaagatcctttttgataatctcatgaccaaaatcccttaacgtgagttttcgttccactgagcg tcagaccccgtagaaaagatcaaaggatcttcttgagatcctttttttctgcgcgtaatctgctgcttgcaaacaaaaaaaccaccgctaccagcggtggtttg tttgccggatcaagagctaccaactctttttccgaaggtaactggcttcagcagagcgcagataccaaatactgttcttctagtgtagccgtagttaggccacc acttcaagaactctgtagcaccgcctacatacctcgctctgctaatcctgttaccagtggctgctgccagtggcgataagtcgtgtcttaccgggttggactca -continued agacgatagttaccggagcagcggtcgggctgaacggggggttcgtgcacacagcccagcttggagcgaacgacctacaccgaactgagatacctacagcgtga gctatgagaaagcgtaaggcccacgcttcccgaagggagaaaggcggacaggtatccggtaagcggcagggtcggaacaggagagcgcacgagggagcttccag ggggaaacgcctggtatctttatagtcctgtcgggtttcgccacctctgacttgagcgtcgatttttgtgatgctcgtcaggggggcggagcctatggaaaaac gccagcaacgcggcctttttacggttcctggccttttgctggccttttgctcacatgttctttcctgcgttatcccctgattctgtggataaccgtattaccgc ctttgagtgagctgataccgctcgccgcagccgaacgaccgagcgcagcgagtcagtgagcgaggaagcggaagagcgcccaatacgcaaaccgcctctccccg cgcgttggccgattcattaatgcagctggcacgacaggtttcccgactACTAGTccaacaacttataccatggcctacaaaaaggcaaacaatggtacttgacg actcatcacaacaattgtagngtagcagggagagaccccgaGGTACCgatCCTAGCAGGTGGTGCCGCTGGCGACCTGCGTTTCACCCTGC

CATAAAGAAACTGTTACCCGTAGGTAGTCACGCAACTCGCCGCACATCTGAACTTCAGCCTCCAG

TACAGCGCGGCTGAAATCATCATTAAAGCGAGTGGCAACATGGAAATCGCTGATTTGTGTAGTC

GGTTTATGCAGCAACGAGACGTCACGGAAAATGCCGCTCATCCGCCACATATCCTGATCTTCCAG

ATAACTGCCGTCATTCCAGCGCAGCACCATCACCGCGAGGCGGTTTTCTCCGGCGCGTAAAAATG

CGCTCAGGTCAAATTCAGACGGCAAACGACTGTCCTGGCCGTAACCGACCCAGCGCCCGTTGCA

CCACAGATGAAACGCCGAGTTAACGCCATCAAAAATAATTCGCGTCTGGCCTTCCTGTAGCCAGC

TTTCATCAACATTAAATGTGAGCGAGTAACAACCCGTCGGATTCTCCGTGGGAACAAACGGCGG

ATTGACCGTAATGGGATAGGTCACGTTGGTGTAGATGGGCGCATCGTAACCGTGCATCTGCCAGT

TTGAGGGGACGACGACAGTATCGGCCTCAGGAAGATCGCACTCCAGCCAGCTTTCCGGCACCGC

TTCTGGTGCCGGAAACCAGGCAAAGCGCCATTCGCCATTCAGGCTGCGCAACTGTTGGGAAGGG

CGATCGGTGCGGGCCTCTTCGCTATTACGCCAGCTGGCGAAAGGGGGATGTGCTGCAAGGCGAT

TAAGTTGGGTAACGCCAGGGTTTTCCCAGTCACGACGTTGTAAAACGACGGCCAGTGAATCCGT

AATCATGGTCATAGCTGTTTCCTGTGTAAAATTGTTATCCGCTCACAATTCCACACAACATACGA

GCCGGAAGCATAAAGTGTAAAGCCTGGGGTGCCTAATGAGTGAGCTAACTCACATTAATTGCGT

TGCGCTCACCTGCTAGGGCCTGGATCCATGGTTTAAACtcaggaattcacgtgcgcacctgtgctgggcgcgctgtcggat cgtdcgggcggcggccaatcttgctcgtctcgctggccggcgccactgtcgactacgccatcatggcgacagcgcctttcctttgggttctctatatcgggcgga tcgtggccggcatcaccggggcgactggggcggtagccggcgcttatattgccgatgacctgcagggggggggggcgctgaggtctgcctcgtgaagaa ggigttgctgactcataccaggcctgaatcgccccatcatccagccagaaagtgagggagccacggttgatgagagctttgngtaggtggaccagttggtgattt tgaactittgctttgccacggaacggtctgcgttgtcgggaagatgcgtgatctgatccttcaactcagcaaaagttcgatttattcaacaaagccgccgtcccg tcaagtcagcgtaatgctctgccagtgttacaaccaattaaccaattctgattagaaaaactcatcgagcatcaaatgaaactgcaatttattcatatcaggatt atcaataccatatttttgaaaaagccgtttctgtaatgaaggagaaaactcaccgaggcagttccataggatggcaagatcctggtatcggtctgcgattccgac tcgtccaacatcaatacaacctattaatttcccctcgtcaaaaataaggttatcaagtgagaaatcaccatgagtgacgactgaatccggtgagaatggcaaaag cttatgcatttctttccagacttgttcaacaggccagccattacgctcgtcatcaaaatcactcgcatcaaccaaaccgttattcattcgtgattgcgcctgagc gagacgaaatacgcgatcgctgttaaaaggacaattacaaacaggaatcgaatgcaaccggcgcaggaacactgccagcgcatcaacaatattttcacctgaatc aggatattcttctaatacctggaatgctgttttcccggggatcgcagtggtgagtaaccatgcatcatcaggagtacggataaaatgcttgatggtcggaagagg cataaattccgtcagccagtttagtctgaccatctcatctgtaacatcattggcaacgctacctttgccatgtttcagaaacaactctggcgcatcgggcttccc atacaatcgatagattgtcgcacctgattgcccgacattatcgcgagcccatttatacccatataaatcagcatccatgttggaatttaatcgcggcctcgagca agacgtttcccgttgaatatggctcataacaccccttgtattactgtttatgtaagcagacagttttattgttcatgatgatatatttttatcttgtgcaatgta acatcagagattttgagacacaacgtggctttcccccccccccctgcaggtccgacacggggatggatggcgttcccgatcatggtcctgcttgcttcgggtggc atcggaatgccggcgctgcaagcaatgttgtccaggcacgtggatgaggaacgtcaggggcagctgcaaggctcactggcggcgctcaccagcctgacctcgatc cgtcggacccctcctcttcacggcgattatgcggcttctataacaacgtggaacgggtgggcatggattgcaggcgctgccctctacttgctctgcctgccggcg ctgcgtcgcgggctttggagcggcgcagggcaacgagccgatcgctgatcgtggaaacgataggcctatgccatgcgggtcaaggcgacttccggcaagctatac gcgccctagaattgtcaattttaatcctctgtttatcggcagttcgtagagcgcgccgtgcgtcccgagcgatactgagcgaagcaagtgcgtcgagcagtgccc -continued gcttgttcctgaaatgccagtaaagcgctggctgctgaacccccagccggaactgaccccacaaggccctagcgtttgcaatgcaccaggtcatcattgacccag gcgtgttccaccaggccgctgcctcgcaactcttcgcaggcttcgccgacctgctcgcgccacttcttcacgcgggtggaatccgatccgcacatgaggcggaag gtttccagcttgagcgggtacggctcccggtgcgagctgaaatagtcgaacatccgtcgggccgtcggcgacagcttgcggtacttctcccatatgaatttcgtg tagtggtcgccagcaaacagcacgacgatttcctcgtcgatcaggacctggcaacgggacgttttcttgccacggtccaggacgcggaagcggtgcagcagcgac accgattccaggtgcccaacgcggtcggacgtgaagcccatcgccgtcgcctgtaggcgcgacaggcattcctcggccttcgtgtaataccggccattgatcgac cagcccaggtcctggcaaagctcgtagaacgtgaaggtgatcggctcgccgataggggtgcgcttcgcgtactccaacagctgctgccacaccagttcgtcatcg tcggcccgcagctcgacgccggtgtaggtgatcttcacgtccttgttgacgtggaaaatgaccttgttttgcagcgcctcgcgcgggattttcttgttgcgcgtg gtgaacagggcagagcgggccgtgtcgtttggcatcgctcgcatcgtgtccggccacggcgcaatatcgaacaaggaaagctgcatttccttgatctgctgcttc gtgtgtttcagcaacgcggcctgcttggcctcgctgacctgttttgccaggtcctcgccggcggtttttcgcttcttggtcgtcatagttcctcgc pmxaF - promoter
Source: *Methylobacterium extorquens* PA1

SEQ ID NO: 3 gttgacgacaacggtgcgatgggtcccggccccggtcaagacgatgccaatacgttgcgacactacgccttggcacttttagaattgccttatcgtcctgataag aaatgtccgaccagctaaagacatcgcgtccaatcaaagcctagaaaatataggcgaagggacgctaataagtctttcataagaccgcgcaaatctaagaatatc cttagattcacgatgcggcacttcggatgacttccgagcgagcctggaacctcagaaaaacgtctgagagataccgcgaggccgaaaggcgaggcggttcag cgaggagacgcagg Pr-faeRBS - promoter-ribosome binding site from MEXT_1384

SEQ ID NO: 4 ccaacaacttataccatggcctacaaaaaggcaaacaatggtacttgacgactcatcacaacaattgtagttgtagcagggagagaccccga Flank 1 - 500bp flanking region upstream of MEXT_3434
Source: *Methylobacterium extorquens* PA1

SEQ ID NO: 5 caccgcgcgggacttcatcttgccccggcagatgcgcagggcctccaccgtgcgctcgatcgccgcctcggtgaggcgattggaattgcccaatccctcgcc gagccggacgatgcgggagaaggcgtcgatcacccggaagccgttgggcgtcggctcggcgaccagaaggcggcaattgttggtgccgagatcgagcgc ggcataggcgtcgcgtcggccgtgccgaccggtttcgtagcggggagggaagctctcgatcgggcgtccgcccgtgaccgtgcgggaaccctcccgcgctg tctgcgggtcggcggtggggcgggccgacacggcggcggcgctctcatccctcatcgacgcgaccgaacttcctggcgatgcagcccggcaagacgccgg gccgacgtggcaccaaggctacaggcgttattcaggaactgcaaaggctggatggccggccttacacgatttgccgcatggattgtttcgcgaaaagtccc Flank2 - 500bp flanking region downstream of MEXT_3441
Source: *Methylobacterium extorquens* PA1

SEQ ID NO: 6 cgccccaagactcccaacctgatatcgtcggcgcaatcttggccggaagcgggcgaggggcaagaggcacggattgtcgcgtgccgccggtctcgaccggt tccggccgcgttcagggccgccgccgacgcagcgggagcacggcagcggcgccgatctgtgggccggtctcggcgtcgagatcgggcacggcgatgatc ggcgcgccgcgcaggtcccggcgcatgacgatagcgccgcgctcctccagatagcccagcatgcgccgggcacgccccgccgaggaggtgccgtaggc ctccgcgagcgccgcgtcggaagggcagggcgaaccttcgagcgccgtgcgggcgatgagcaggaacaacccggccagatcctccggcagaccggcgg cgatctcctgcgcccgctcccaaccgggtccctcggcggtggcgccctggacgccggcccgcgccacggcgagccgccgcttgaactcgggcaggcccat cgcc CrtZ, pPzZ, HP1
Source: *Paracoccus zeaxanthinifaciens*

SEQ ID NO: 7 gactaggtctttcccttgccggaacaatcggctaaagccttccgcagtcggggcgtagcgcagcctggtagcgcgacggttttgggtaccgtaggtcggaggtt cgaatcctctcgccccgaccatcttcgggaaaacattaatatttccagcgacggaacgcgtgatgcgcctgccg crtE, pPzE, HP2
Source: *Paracoccus zeaxanthinifaciens*

SEQ ID NO: 8 ccgcatccgtctgcatcggcgggggcgaggcgacggccatcgcgctggaacggctgagctaattcatttgcgcgaatccgcgtttttcgtgcacgatgggga accggaaacggccacgcctgttgtggttgcgtcgacctgtcttcgggccatgcccgtgacgcgatgtggcaggcgcatggggcgttgccgatccggtcgcatg actgacgcaacgaaggcaccg crtZYIBE, PzC40 cluster
Source: *Paracoccus zeaxanthinifaciens*

SEQ ID NO: 9 gactaggtctttcccttgccggaacaatcggctaaagccttccgcagtcggggcgtagcgcagcctggtagcgcgacggttttgggtaccgtaggtcggaggtt -continued cgaatcctctcgccccgaccatcttcgggaaaacattaatatttccagcgacggaacgcgtgatgcgcctgccgcgttcggcggcgaatgtcacggatgatccg cctatgagccctgaacgcagatgtcacgcgatgccctttggtcgcaccccgatgggctggtcatgcaccgcgcggcagcgtagcctgttccctgtcatatcaag caaggggccggcatgagcacttgggccgcaatcctgaccgtcatcctgaccgtcgccgcgatggagctgacggcctactccgtccatcggtggatcatgcatg gccccctgggctggggctggcataaatcgcaccacgacgaggatcacgaccacgcgctcgagaagaacgacctctatggcgtcatcttcgcggtaatctcgat cgtgctgttcgcgatcggcgcgatggggtcggatctggcctggtggctggcggtgggggtcacctgctacgggctgatctactatttcctgcatgacggcttggt gcatgggcgctggccgttccgctatgtccccaagcgcggctatcttcgtcgcgtctaccaggcacacaggatgcatcacgcggtccatggccgcgagaactgc gtcagcttcggtttcatctgggcgccctcggtcgacagcctcaaggcagagctgaaacgctcgggcgcgctgctgaaggaccgcgaaggggcggatcgcaa tacatgagccatgatctgctgatcgcgggcgcggggctgtccggtgcgctgatcgcgcttgccgttcgcgaccgcagaccggatgcgcgcatcgtgatgctcg acgcgcggtccggcccctcggaccagcacacctggtcctgccacgacacggatctttcgcccgaatggctggcgcgcctgtcgcccattcgtcgcggcgaat ggacggatcaggaggtcgcgtttcccgaccattcgcgccgcctgacgacaggctatggctcgatcgaggcgggcgcgctgatcgggctgctgcagggtgtc gatctgcggtggaatacgcatgtcgcgacgctggacgataccggcgcgacgctgacggacggctcgcggatcgaggctgcctgcgtgatcgacgcccgtgg tgccgtcgagaccccgcacctgaccgtgggtttccagaaattcgtgggcgtcgagatcgagaccgacgcccccatggcgtcgagcgcccgatgatcatgga cgcgaccgttccgcagatggacgggtaccgcttcatctatctgctgcccttcagtcccacccgcatcctgatcgaggatacgcgctacagcgacggcggcgatc tggacgatggcgcgctggcgcaggcgtcgctggactatgccgccaggcggggctggaccgggcaggagatgcggcgcgaaaggggcatcctgcccatcg cgctggcccatgacgccataggcttctggcgcgaccacgcgcagggggcggtgccggttgggctgggggcagggctgttccaccccgtcaccggatattcg ctgccctatgccgcgcaggtcgcggatgccatcgcggcgcgcgacctgacgaccgcgtccgcccgtcgcgcggtgcgcggctgggccatcgatcgcgcgg atcgcgaccgcttcctgcggctgctgaaccggatgctgttccgcggctgcccgcccgaccgtcgctatcgcctgctgcagcggttctaccgcctgccgcagcc gctgatcgagcgcttctatgccgggcgcctgacattggccgaccggcttcgcatcgtcaccggacgcccgcccattccgctgtcgcaggccgtgcgctgcctg cccgaacgcccccctgctgcaggagagagcatgagttccgccatcgtcatcggcgcaggtttcggcgggcttgcgcttgccatccgcctgcaatcggccggcat cgcgaccaccatcgtcgaggcccgcgacaagcccggcggccgcgcctatgtctggaacgatcagggccacgtcttcgatgcaggcccgacggtcgtgacc gaccccgacagcctgcgagagctgtgggccctcagcggccaaccgatggagcgtgacgtgacgctgctgccggtctcgcccttctaccggctgacatgggc ggacggccgcagcttcgaatacgtgaacgacgacgacgagctgatccgccaggtcgcctccttcaatcccgccgatgtcgatggctatcgccgcttccacgatt acgccgaggaggtctatcgcgaggggtatctgaagctggggaccacgcccttcctgaagctgggccagatgctgaacgccgcgcccgcgctgatgcgcctg caggcataccgctcggtccacagcatggtggcgcgcttcatccaggacccgcatctgcggcaggccttctcgttccacacgctgctggtcggcgggaacccgt tttcgaccagctcgatctatgcgctgatccatgcgctggaacggcgcggcggcgtctggttcgccaagggcggcaccaaccagctggtcgcgggcatggtcg ccctgttcgagcgtcttggcggcacgctgctgctgaatgcccgcgtcacgcggatcgacaccgagggcgatcgcgccacgggcgtcacgctgctggacggg cggcagttgcgcgcggatacggtggccagcaacggcgacgtgatgcacagctatcgcgacctgctgggccatacccgccgcgggcgcaccaaggccgcg atcctgaaccggcagcgctggtcgatgtcgctgttcgtgctgcatttcggcctgtccaagcgccccgagaacctggcccaccacagcgtcatcttcggcccgcg ctacaaggggctggtgaacgagatcttcaacgggccacgcctgccggacgatttctcgatgtatctgcattcgccctgcgtgaccgatcccagcctggcccccg aggggatgtccacgcattacgtccttgcgcccgttccgcatctgggccgcgccgatgtcgattgggaagccgaggccccgggctatgccgagcgcatcttcga ggaactggagcgccgcgccatccccgacctgcgcaagcacctgaccgtcagccgcatcttcagccccgccgatttcagcaccgaactgtcggcccatcacgg cagcgccttctcggtcgagccgatcctgacgcaatccgcctggttccgcccgcataaccgcgaccgcgcgatcccgaacttctacatcgtgggggcgggcac gcatccgggtgcgggcatcccgggtgtcgttggcagcgccaaggccacggcgcaggtcatgctgtcggacctggccgtcgcatgaccgatctgacggcgac ttccgaagcggccatcgcgcagggttcgcaaagcttcgcgcaggcggccaagctgatgccgcccggcatccgcgaggatacggtcatgctctatgcctggtg caggcatgcggatgacgtgatcgacgggcaggtCatgggttctgcccccgaggcgggcggcgacccacaggcgcggctggatgcgctgcgcgccgacac gctggccgcgctgcacgaggacggcccgatgtcgccgcccttcgcggcgctgcgccaggtcgcccggcggcatgatttcccggacctttggccgatggacc tgatcgagggtttcgcgatggatgtcgcggatcgcgaataccgcagcctggatgacgtgctggaatattcctaccacgtcgcgggggtcgtgggcgtgatgatg gcgcgggtgatgggcgtgcaggacgatgcggtgctggatcgcgcctgcgatctgggccttgcgttccagctgacgaacatcgctcgcgacgtgatcgacgat gccgccatcgggcgctgctatctgcctgccgactggctggccgaggcgggggcgacggttgagggtccggtgccttcggacgcgctctattccgtcatcatcc gcctgcttgacgcggccgagccctattatgcctcggcgcggcaggggcttccgcatctgccgccgcgctgcgcgtggtcgatcgccgccgcgctgcgtatcta -continued

```
tcgcgcaatcgggacgcgcatccggcagggtggccccgaggcctatcgccagcggatcagcacgtcgaaggctgccaagatcgggcttctggcgcgcgga

ggcttggacgcggccgcatcgcgcctgcgcggcggtgaaatcagccgcgacggcctgtggacccgaccgcgcgcctaggcgctgcggcggatgtcatgc

ggcagcacgcgggccagcaggtccgcgatctgccccccgcggaacagccgggtgcgcatcagctcgtccagttgcgcgcggctggcgcggtaatgctgcg

ccacgtcgcccatctgtccgaccgccatcaggccgcgctttgggccgggggcggcggtgtcgcgccccgtatccttgccggtgctggccttgtcgccgatcac

gtccagcaggtcgtcataggactggaagacccgaccaagctgacgcccgaaggccatgagctgctcggtctcggccttgtccagacccttaataatggacagc

atctcgaggcccgcgacgaacagcacgccggtcttgaggtcctgttcacgttcgatcccggcggcgtccttgggggcgtgcaggtccagatcctgccctgcgc

acagccccaccggtcccatcgcgcgcgacatggatgcgaccagccttgcgcgctgatccggcgtcgcgccgcgcgcctcgcccaaaatccgcatggcctcg

gtgatcagggcgatgcccgcaagcaccgcgcgcccctcgccatgggcgacatgggtggcgggctgaccgcgacgggtcctggcatcgtccatgcagggca

tgtcgtcgaagatcagcgatgcggcatggaccatctcgaccgcgcaggcggcatcgaccatcgcatcgcagaccccgcccgagctttcggcgaccatcagca

tcagcacggcgcgaaagcgtttgccgggggacagggcggcatcgctcatggccgcgccgagcggggccgagaccacgccgaactggcccgagatctgc

gccagcctgatctcgaccagatcgcgtaggggggaattgctgcttgggcgtcatcggtgccttcgttgcgtcagtcatgcgaccggatcggcaacgccccatgcg

cctgccacatcgcgtcacgggcatggcccgaagacaggtcgacgcaaccacaacaggcgtggccgtttccggttcccccatcgtgcacgaaaaacgcggatt

cgcgcaaatgaattagctcagccgttccagcgcgatggccgtcgcctcgcccccgccgatgcagacggatgcgg
```

crtZ_Pz
Source: *Paracoccus zeaxanthinifaciens*

SEQ ID NO: 10

```
MSTWAAILTVILTVAAMELTAYSVHRWIMEGPLGWGWHKSHHDEDHDHALEKNDLYGVIFAVISIV

LFAIGAMGSDLAWWLAVGVTCYGLIYYFLHDGLVHGRWPFRYVPKRGYLRRVYQAHRMHHAVHG

RENCVSFGFIWAPSVDSLKAELKRSGALLKDREGADRNT*
```

crtY_Pz
Source: *Paracoccus zeaxanthinifaciens*

SEQ ID NO: 11

```
MSHDLLIAGAGLSGALIALAVRDRRPDARIVMLDARSGPSDQHTWSCHDTDLSPEWLARLSPIRRGE

WTDQEVAFPDHSRRLTTGYGSIEAGALIGLLQGVDLRWNTHVATLDDTGATLTDGSRIEAACVIDAR

GAVETPHLTVGFQKFVGVEIETDAPHGVERPMIMDATVPQMDGYRFIYLLPFSPTRILIEDTRYSDGG

DLDDGALAQASLDYAARRGWTGQEMRRERGILPIALAHDAIGFWRDHAQGAVPVGLGAGLFHPVT

GYSLPYAAQVADAIAARDLTTASARRAVRGWAIDRADRDRFLRLLNRMLFRGCPPDRRYRLLQRFY

RLPQPLIERFYAGRLTLADRLRIVTGRPPIPLSQAVRCLPERPLLQERA*
```

crtI_Pz
Source: *Paracoccus zeaxanthinifaciens*

SEQ ID NO: 12

```
MSSAIVIGAGFGGLALAIRLQSAGIATTIVEARDKPGGRAYVWNDQGHVFDAGPTVVTDPDSLRELW

ALSGQPMERDVTLLPVSPFYRLTWADGRSFEYVNDDDELIRQVASFNPADVDGYRRFHDYAEEVYR

EGYLKLGTTPFLKLGQMLNAAPALMRLQAYRSVHSMVARFIQDPHLRQAFSFHTLLVGGNPFSTSSI

YALIHALERRGGVWFAKGGTNQLVAGMVALFERLGGTLLLNARVTRIDTEGDRATGVTLLDGRQLR

ADTVASNGDVMESYRDLLGHTRRGRTKAAILNRQRWSMSLFVLHFGLSKRPENLAHHSVIFGPRYK

GLVNEIFNGPRLPDDFSMYLHSPCVTDPSLAPEGMSTHYVLAPVPHLGRADVDWEAEAPGYAERIFE

ELERRAIPDLRKHLTVSRIFSPADFSTELSAHHGSAFSVEPILTQSAWFRPHNRDRAIPNFYIVGAGTHP

GAGIPGVVGSAKATAQVMLSDLAVA*
```

crtB_Pz
Source: *Paracoccus zeaxanthinifaciens*

SEQ ID NO: 13

```
MTDLTATSEAAIAQGSQSFAQAAKLMPPGIREDTVMLYAWCRHADDVIDGQVMGSAPEAGGDPQA

RLDALRADTLAALHEDGPMSPPFAALRQVARRHDFPDLWPMDLIEGFAMDVADREYRSLDDVLEYS

YHVAGVVGVMMARVMGVQDDAVLDRACDLGLAFQLTNIARDVIDDAAIGRCYLPADWLAEAGAT

VEGPVPSDALYSVIIRLLDAAEPYYASARQGLPHLPPRCAWSIAAALRIYRAIGTRIRQGGPEAYRQRIS

TSKAAKIGLLARGGLDAAASRLRGGEISRDGLWTRPRA*
```

-continued crtE_Pz
Source: *Paracoccus zeaxanthinifaciens*

SEQ ID NO: 14

MTPKQQFPLRDLVEIRLAQISGQFGVVSAPLGAAMSDAALSPGKRFRAVLMLMVAESSGGVCDAMV

DAACAVEMVHAASLIFDDMPCMDDARTRRGQPATHVAHGEGRAVLAGIALITEAMRILGEARGATP

DQRARLVASMSRAMGPVGLCAGQDLDLHAPKDAAGIEREQDLKTGVLFVAGLEMLSIIKGLDKAET

EQLMAFGRQLGRVFQSYDDLLDVIGDKASTGKDTGRDTAAPGPKRGLMAVGQMGDVAQHYRASR

AQLDELMRTRLFRGGQIADLLARVLPHDIRRSA* crtZYIBW, Sa C40 cluster
Source: *Sphingomonas astaxanthinifaciens* DSM 22298

SEQ ID NO: 15 atgatgaagcgcgcggacctggtgatcgtcggtggaggactggccggcggcctgtgcgccctcgcccttcgccgccgccgccctgacctcaggctgctgctg gtcgagccggggccaagcatcggcggcaaccatctctggtccttcttcgaaagcgacgtcgcccccgccgaccgctggctgaccgacccgctgatccggcat cgctggcccgattacgaggtccgcttcccggcgcaccagcgccacctcgccgaagcctatcagaccatcgagagcgaggcgctcgacgaggccgtgcgca aggccctttccgccgaggagatcgtccgggccgaagccaccgaccttggcccgacccacgtcaccctcgcgaccggcgagcggatcgaggcgaaggcgg tgctcgacgcgcgcgggggcaaagccgaggggctcgatctcggctggcagaaattcctcggccagctgctgaccatcccgcagggccacggcctcacccgt ccgatcgtgatggacgcgacggtcgaccagcatgacggctatcgcttcgtctactgcctgcccttcagcccgaccgaactcttcgtcgaggacacttattacagc gacgggcccgagctcgaccacgaccgattgcgtgaccggatcggcgattatgccgcggcacagggctggcaggtcgcggaccgcagccgcgaggagcat ggcgcgctgccagtggtgatcggcggcgatttcgaccggctgtggcccgccgccgaccatgtcgcccgggccggcgcgcgcggcggtttcttccatccgct gaccagctattcgctgcccgacgcggtccgcttcgccatctggctggcggacaaggccacgttcgacgcccggctcggggccgcgacccgcgcgcggggc cgccgccactggaggtcgggtgccttctaccggctgctcaccgcgctcctgttccacgccgccgagcccggccagcgctacctcgtgctggagcgtttctacc gcctttccggccccttgatcggccgcttctacgcggggatgagcaccggctatgacaaggcgcgcgtgctcgcgggcaagccgccggtgcccttcttccggg cactcagggtattgagggacagcttgtgaagagtgcaatcgtgatcggtgccggcttcggcggcctggcgctggccatccgcctccagtcggccggggtgaa gaccaccatcgtcgaggcccgcgaccggcccggcggccgcgcctatgtctgggaaaaggacggccacgtgttcgacgcgggcccgaccgtgatcaccgat cccgactgtctccagcggctgtggaagctgtcgggccacgacatgtcggaggatgtcgagctcgtcccggtcaagcccttctaccggctctcctggcccgacg gcgtggtgttcgattacaccaatgacgacgccgagctcaaagccgcgatggacgcactcaatcccgacgactgggcgggctaccagcgcttcctcgcctatag cgccggggtctataacgagggctatgtgaagctcgggaccaaggcgtttgaaagcctcggcgacatgctcaaggccgcgcccgcgctcgccaaatatcagg cttggcggtcggtctattcgatcgtgtcgagcttcgtgaaggacgagcacctgcgccagaccttgtccttccacacgctgctggtcggcggcaatccgatgacct gctcgtcgatctacgcgctgatccacaagctcgagcgcgacggcggggtgtggttcgccaagggcgggaccaacaagctgatcgccggcatggtccgccag ttcgagcggatcggcgggaccattcgccttggcgatccggtcactgcgatcctggccgagaacgatcgggtcaccggggtgcgcaccgcctcgggttggagc gccaccgccgacgcggtcgcctccaatggcgacgtggtccacagctatggcctgatcgagggttccgaccgcggccagcaacaggtccgcgccctcaagc gcaagcgtttctcgcccggcctgttcgtgctccatttcgggctcgaggggacgtcggacctcgcccaccacacgatcctgttcggcccgcgctacggcggcctc gtcaacgacatctacaagaccgggcggctcgcgaccgacccgtcgctctacatccaccacccgaccatcaccgacccgtccatggcgccgccgggctgctc gaccttctacgcgcttgcccccgtccccaatgccggcaaggccgatgtcgactgggcggtcgaggggccgaaatatcaggaggtcgtgctcgacacgatcgc cgagcggctgatccccgacgtgcgccagcggatccggaccatcttccattacaccccggccgatttctcggccgacctcgccgcccacctcggctccgcattc agcctcgagccggtgctgtggcagtcggcctggttccgcacccacaatcgcgacgacaagctcaggaacctctatttcgtcggtgccggcactcacccaggcg cggggatcccgggggtggtcggaagcgccgaggcgactgcggggctgatgctggcgtgagcgaagctgacgaacgggcacggctggtccaggccgcgc tggaaagcatttcggcgggctccaagagttttcgcttcgccagccagttgttcgaccagcagacccgagagcgcagctggctgctctacagctggtgccgcgc ctgcgacgacgtgaccgacggccagaccctgggccatgatgcggagcgggtcgacgatcccgccgcccgcctcgccttcctcaaggcgaagaccgccgag gcgttcgcgggccaaccgacgggacttgtccccttcgacgcactgcgcgtggtcgccgccgaatgcgcgattccccaggccgtcgccggcgaccatctcgcc gggttcgagcgcgacgccgggggtggcggccgaccacgaccgacgacctcctctcttattgctaccaggttgctggcgcggtgggcgtgatgatggcgca cgtcatgggcgtgccgcccgaggacgaggacacgctcaaccgcgcagccgacttggggatcgccttccagctcgccaatatcgcccgcgacatcgtcgacg atgccaaggtcgggcgggtctatctgcccgccgaatggcttgccgccgaggggctggccggggccgacctcgccgatcccgcgcatcgcccggccctcgc -continued gcgcctcgcccaccgcctcgccgacatggccgacgcctatcgccgctcggcccgggtcggcgcggcccgcctgcccttccgcagccgctgggcggtgctc gcggccagcggcatctacggcgagatcgcgacccgcgccgccgcgctcgggccccgcgcctgggacgagcggatcaccacctcgaaggcggaaaaggc cgcgctggtgatggaggccttctgggaagccttgtggcgggtcaggcccgctcctcgtgacgggctgtggacccgccccgcgcacgcctgagctgcgcctc gcggctggcctggagcgcctgcttcagccgctcgaccggcggggcgtaaaggaagccgaagctcaccgccccgtcgcggctctcgaccgcatggtgcagc ttgtgcgcctggacgatccgcttgaaataggtcgaacgcggcacgatccggtgcggcagccggccgtggacgatgacgtcgtgaaagccgaaatagatcacc ccgtagaaggccaccccggcccccatccacgtcgcccagtcgccccagccgccattgagcccgccccagatcagcaggatcgagggcaaagcgaagacc acggcatagaggtcgttccgctcgaaccagccggtccgcgcgcgatgatggctttcgtgccagttccagccgagccgcgagtgcatcacgaagcggtggag gacataggcgaagccctccatcagaaggaccgtcgatacgaacagggcgagaccggcaggccaggacat crtZ_Sa
Source: *Sphingomonas astaxanthinifaciens* DSM 22298

SEQ ID NO: 16

MSWPAGLALFVSTVLLMEGFAYVLHRFVMHSRLGWNWHESHHRARTGWFERNDLYAVVFALPSIL

LIWGGLNGGWGDWATWMGAGVAFYGVIYFGFHDVIVHGRLPHRIVPRSTYFKRIVQAHKLHHAVE

SRDGAVSFGFLYAPPVERLKQALQASREAQLRRARGGSTARHEERA* crtY_Sa
Source: *Sphingomonas astaxanthinifaciens* DSM 22298

SEQ ID NO: 17

MMKRADLVIVGGGLAGGLCALALRRRRPDLRLLLVEPGPSIGGNHLWSFFESDVAPADRWLTDPLIR

HRWPDYEVRFPAHQRHLAEAYQTIESEALDEAVRKALSAEEIVRAEATDLGPTHVTLATGERIEAKA

VLDARGGKAEGLDLGWQKFLGQLLTIPQGHGLTRPIVMDATVDQHDGYRFVYCLPFSPTELFVEDTY

YSDGPELDHDRLRDRIGDYAAAQGWQVADRSREEHGALPVVIGGDFDRLWPAADHVARAGARGGF

FHPLTSYSLPDAVRFAIWLADKATFDARLGAATRARGRRHWRSGAFYRLLTALLFHAAEPGQRYLV

LERFYRLSGPLIGRFYAGMSTGYDKARVLAGKPPVPFFRALRVLRDSL* crtI_Sa
Source: *Sphingomonas astaxanthinifaciens* DSM 22298

SEQ ID NO: 18

VKSAIVIGAGFGGLALAIRLQSAGVKTTIVEARDRPGGRAYVWEKDGHVFDAGPTVITDPDCLQRLW

KLSGHDMSEDVELVPVKPFYRLSWPDGVVFDYTNDDAELKAAMDALNPDDWAGYQRFLAYSAGV

YNEGYVKLGTKAFESLGDMLKAAPALAKYQAWRSVYSIVSSFVKDEHLRQTLSFHTLLVGGNPMTC

SSIYALIHKLERDGGVWFAKGGTNKLIAGMVRQFERIGGTIRLGDPVTAILAENDRVTGVRTASGWS

ATADAVASNGDVVHSYGLIEGSDRGQQQVRALKRKRFSPGLFVLHFGLEGTSDLAHHTILFGPRYGG

LVNDIYKTGRLATDPSLYIHHPTITDPSMAPPGCSTFYALAPVPNAGKADVDWAVEGPKYQEVVLDTI

AERLIPDVRQRIRTIFHYTPADFSADLAAHLGSAFSLEPVLWQSAWFRTHNRDDKLRNLYFVGAGTHP

GAGIPGVVGSAEATAGLMLA* crtB_Sa
Source: *Sphingomonas astaxanthinifaciens* DSM 22298

SEQ ID NO: 19

VSEADERARLVQAALESISAGSKSFRFASQLFDQQTRERSWLLYSWCRACDDVTDGQTLGHDAERV

DDPAARLAFLKAKTAEAFAGQPTGLVPFDALRVVAAECAIPQAVAGDHLAGFERDAGGWRPTTTDD

LLSYCYQVAGAVGVMMAHVMGVPPEDEDTLNRAADLGIAFQLANIARDIVDDAKVGRVYLPAEWL

AAEGLAGADLADPAHRPALARLAHRLADMADAYRRSARVGAARLPFRSRWAVLAASGIYGEIATR

AAALGPRAWDERITTSKAEKAALVMEAFWEALWRVRPAPRDGLWTRPAHA* crtW_Sa
Source: *Sphingomonas astaxanthinifaciens* DSM 22298

SEQ ID NO: 20

MAPMLSDAQRRRQAMIGLGLAAAITAAFVALHVWSVFFLPLEGAGWWLALPIVAVQTWLSVGLFIV

AHDAMHGSLAPGRPATNLFWGRLTLLLYAGFWLDRLSPKHFDHHRHVGTERDPDFSVDHPTRFWP

-continued

WYYAFMRRYFGLREYLVLNALVLAYVLVLKAPLGNLLLFWALPSILSSIQLFYFGTYLPHRHEDAPF

ADQHNARSNDFPVWLSLLTCFHFGYHREHHLSPGTPWWQLPRRRRELALPA crtZYIB, Sz cluster
Source: *Siansivirga zeaxanthinifaciens* CC-SAMT-1

SEQ ID NO: 21 atgaaaaaagaaataataattatcggttcaggtttttcgtctctagcagcatcctgctatttggcgaaagcaggttataatgtaactttattagaaaaaaacaa cactattggaggcagagctcgacaattagttaaagacggttttactttcgatataggtccaacttggtattggatgcccgatgtatttgaacgcttcttcaatg attttgataaaaaaccttcagattactatagtcttgaaaaactgaatcccgcatacagtgtttattttggaaaaaacgactacattaccattgaagatacatta gcgaaaatttctgaagcatttgaaaaagaagaacctggaagttcaaaaaaactaaacacctttattgaaaaagctaaaagcaactacgatatagcaattaaaga tttggtttataaccctggcgtatcgcctctagaattggttactattgctactataaaaaaattagaccaattctttagtaacataaaaagagatgttagaaaag aatttaaaaatgaaaggttagtaaaaattcttgaatttcctgttttatttttaggagcaaaaccaagcgatacaccttcgttttatagttttatgaattatgca gattttggccttgggacgtttcatccaaaaaaaggcatgtatcaagttatcctagcgcttgaaaatctggcaaaatctcttggtgttattataaaaacaaatgc tcccatagaaaaaattatcattgaaaacaacgaagtaaaaggtgttatttcaaatggaaaaacaataaataccaacattgttgttagtggagccgattaccatc ataccgaaacgttattagataaaacatacagacaatatagtgagtcttactggagtaaaaagacttttgcaccgtcatcactactattttatgtaggtttcgat aaaaagattcaaaatgtaaatcatcacacattatttttgatgtagatttttgatgtacatgcagaagccatatacgatactccaaaatggcccgaagaaccact tttttacgcaagttttcctagtataacggatgctaacagcgccccagaaggtaaagaagctggcatatttttaatacccttagcgccaggattagaagatacag aagcgttaagagaagcctattttgaaaaaattatgacacgttttgaggccttaactagtcaaaatattaaaaaacatgttatatttaaagagagtttttgtatc aatgattttataaaagattataattcttacaaaggaaacgcttacggaatggctaatacaattacccaaaccgcatttttaagacccaaattaaaaagtaaaaa agttaaaggtttatttttttacaggtcaattaacagttcctggtcccggtgtaccaccatcattaatttcaggaaagttagtagcagatttagtaaccaaacacc attctttatgaaagcattatttgataccgtttcatacaattgcagcaaattagtaacaaaatcttatagcacttcattttcgcttgctactaaaatgctataca aatctataagacccgatatttacaacatttacggatttgttagatttgctgatgagattgtagattcgtttcatgattttaataaagaagaactacttaacaaa tttgaagccgatttagagcatgctctcgaacatagggtaagtttaaaccctattttaaatgccttccagtacacataccataagaataaaatagagaaaagcat ggtcgatgcttttatgaaaagtatgcgacttgatttacataaaactcaatacctaacaaacgaagagtacaaagaatacatttacggttctgcagatgttgtag gacttatgtgtttaaaggttttgtgaatggtgataacgaaaaatttgaagctttaaaagatacagccatggcacttggttctgcttttcaaaaagttaacttt ttaagagatttaaaagatgattacgaaggtttaaacagaacatatttcccgaataccgatttaaataaccttgatgaacaatcgaaactagatattattcaaga tattgaaaaagatttgaaaaaggcttaacaggaattaaaaaattaccaattgaggctaaatttggtgtttttatggcttacagatattatcatcaattgctta aaaaacttaaaaaaacacctgcttttaatattaaaaacaccagaatacgcgtttcaaatcctaaaaaaatagaattattaatgcgtagttatgtaaaatatcaa ttaaaattaatgtaaatttatagtatgcaaacactattatggataatcatttttttagcaacgtattgtatcatggaatttatggcgtggtttacgcataaata cattatgcatggctttttatggagtttacacaaagaccatcacaagaaagatcacgatagttggttcgaaagaaacgatgctttttttatattttatgctattg ttagcataggttgtttttttactttggaaatacgacatattttgggctggtttacccattggcgttggtattttttgcttatggattatcatactttttggtacac gatatatttattcatcaacgttttaaattatttagaaatgccaataactggtatgctaaaggtgtaagacgtgctcacaaaatgcaccacaaacatattggaaa agaagatggcgaatgctttggtatgttgtttgttccttttaaatacttcaagaaataattttctattaattacatgatatctaacacccatttcgattatatca ttattggaaatggattagcagggcttcagttggcattaaaaatgagtgctgatgtttattttaaagataaacgcatcgctttaatagatggttctaacaaaaac acaaacgataaaacctggagtttttgggaagaaaactcatctcaatgggatgccattacaactaaaagttggaatattgccaacatttacacttccaaaaaaca tatttcattagcactttgcccctataaatataaatctatacgttctatagatttatataattatgcgaaattcgagcttcaaaaacattctaattttttcattta taattgattttgtatgtactaccacagaaacagaagataaaaaggtattagtagaaacttcctctaataaattcactgcctcacatgtttttgatagtagaatt ccagaagatttttttcaaaaaaataaaaattacacacacataattcaacactttaaaggctatgtaattaaaacagaagaagcctattttaatgacgacacctt cacgatgatggattatcgattgaaagatggtgaacaaaccacatttacctatgtactgcctttttcaaaaacagaagctttaatagaatttacctattttacag aaaatttagttaatgaagccgtttatgatgcattcattgaaaaatacataaaaaactatcttaaaattgactcgtatttaattatggaaacagaaataggtcaa -continued attcctatgactaatttcccatttgcaaggttcaatacaaaaaatataacgaaaataggcactggtggtggatgggtaaaggggtctacgggttattcttttaa acataccgaaaaaaaaatatctaaaatcatcgaaaatattaaagctaacaacataccaagcgctcacttatttaagaaaaggtatcgtttttatgacaaaatat ttttaaaggttttaaaagataacaaccacaaaggcgaatggatttttgagcaattttacaacaaaaattctcctcaaaatatgtttaaatttcttgatgaagaa tctactttttttgatgaattaaaaattatgtattcattattctctttgccttttattaaagcatttttcaagacccttttcaaataa crtZ_Sz
Source: *Siansivirga zeaxanthinifaciens* CC-SAMT-1

SEQ ID NO: 22

MQTLLWIIIFLATYCIMEFMAWFTHKYIMEGFLWSLHKDHHKKDHDSWFERNDAFFIFYAIVSIGCFL

LWKYDIFWAGLPIGVGIFAYGLSYFLVHDIFIHQRFKLFRNANNWYAKGVRRAHKMEHKHIGKEDG

ECFGMLFVPFKYFKK* crtY_Sz
Source: *Siansivirga zeaxanthinifaciens* CC-SAMT-1

SEQ ID NO: 23

MISNTHFDYIIIGNGLAGLQLALKMSADVYFKDKRIALIDGSNKNTNDKTWSFWEENSSQWDAITTKS

WNIANIYTSKKHISLALCPYKYKSIRSIDLYNYAKFELQKHSNFSFIIDFVCTTTETEDKKVLVETSSNK

FTASHVFDSRIPEDFFQKNKNYTHIIQHFKGYVIKTEEAYFNDDTFTMMDYRLKDGEQTTFTYVLPFS

KTEALIEFTYFTENLVNEAVYDAFIEKYIKNYLKIDSYLIMETEIGQIPMTNFPFARFNTKNITKIGTGG

GWVKGSTGYSFKHTEKKISKIIENIKANNIPSAHLFKKRYRFYDKIFLKVLKDNNHKGEWIFEQFYNK

NSPQNMFKFLDEESTFFDELKIMYSLFSLPFIKAFFKTLFK* crtI_Sz
Source: *Siansivirga zeaxanthinifaciens* CC-SAMT-1

SEQ ID NO: 24

MKKEIIIIGSGFSSLAASCYLAKAGYNVTLLEKNNTIGGRARQLVKDGFTFDIGPTWYWMPDVFERFF

NDFDKKPSDYYSLEKLNPAYSVYFGKNDYITIEDTLAKISEAFEKEEPGSSKKLNTFIEKAKSNYDIAIK

DLVYNPGVSPLELVTIATIKKLDQFFSNIKRDVRKEFKNERLVKILEFPVLFLGAKPSDTPSFYSFMNY

ADFGLGTFHPKKGMYQVILALENLAKSLGVIIKTNAPIEKIIIENNEVKGVISNGKTINTNIVVSGADYH

HTETLLDKTYRQYSESYWSKKTFAPSSLLFYVGFDKKIQNVNHHTLFFDVDFDVHAEAIYDTPKWPE

EPLFYASFPSITDANSAPEGKEAGIFLIPLAPGLEDTEALREAYFEKIMTRFEALTSQNIKKHVIFKESFCI

NDFIKDYNSYKGNAYGMANTITQTAFLRPKLKSKKVKGLFFTGQLTVPGPGVPPSLISGKLVADLVT

KHHSL* crtB_Sz
Source: *Siansivirga zeaxanthinifaciens* CC-SAMT-1

SEQ ID NO: 25

MKALFDTVSYNCSKLVTKSYSTSFSLATKMLYKSIRPDIYNIYGFVRFADEIVDSFHDFNKEELLNKFE

ADLEHALEHRVSLNPILNAFQYTYHKNKIEKSMVDAFMKSMRLDLHKTQYLTNEEYKEYIYGSADV

VGLMCLKVFVNGDNEKFEALKDTAMALGSAFQKVNFLRDLKDDYEGLNRTYFPNTDLNNLDEQSK

LDIIQDIEKDFEKGLTGIKKLPIEAKFGVFMAYRYYHQLLKKLKKTPAFNIKNTRIRVSNPKKIELLMRS

YVKYQLKLM* crtZYIB, Mz C40 cluster
Source: *Mesoflavibacter zeaxanthinifaciens* DSM 18436

SEQ ID NO: 26 atgaaaaataaaatagcaataataggttctgggttttctgctttatctgctgcatgttatcttgctaaggatggatttaatgtttcagtttttgaaaaaaatga tactgtaggaggacgttgtagacagtttaaaaaagatggatttacttttgatatgggaccaagctggtattggatgcctgatatatttgataagtttttaatg atttgataaaaaaacttcagatttttatcagctagacaagctttctcctgcgtataaaattttctttaatgatgaagttatcaccataggagatacaatggag aaaatttgcgaagaatttgaacgcatagaaaaaggaagttcaattcctcttaaaaaatttataaataaagctgcagataattataacattgccataaacaaaat tgtattaaaaccaggtgtttcacccttagaattggttactaaagatactgttactagactagatcaatttttaaaacaataagcagtgatgttagacgccagt ttaaaaaccctaaactaatatctactttagagtttcctgttttgtttttgggtgcaaaaccaagcaatacaccttctttttatagttttatgaattacgccgat tttggcttaggtacttggcatcctaaaggcggaatgtatcaaataattcttgcaatgagacaacttgcagaagaattaggtgtttcaataaatgtaaactctaa -continued tgttactaatattaatgttgaaaataatacatcaacatcaattactgttaacggtaaaactttaaagtttgatgttgttttaagcggtgcagattatcatcact cagaaacgttgttagatagaaaatatagacagtattcagaaaaatattggaacaataaaacctttgctccttcttctcctattttacgtaggttttgataag aaattgaaaaatgtaaaccatcataacttatttttgataccaactttgaaacgcatgcagaagatatttacgataatccaaaatggcctaaagaacctctatt ttatgccaatttcccatctgtaacagataacagcatggcgcctaatggtaaagaaaatggtttttcttaataccaattgctcctaacttagaagatacacctc aattaagagaacaatattttgatataatcatgtctcgttttgaaaaattaactcaacaagatgttaaaaatagtattatctttaaagaaagcttttgtgttaaa gattttattgaagcatataattcctacaaaggaaacgcatacggaatggctaatacgctaacgcaaaccgctttttaagaccaaatttaaagagtaaaaaagt taacaacctctactttacaggacaattaactgttcctggtccaggtgtgccgccagcacttatatctggaaaattagtagcagaattaatccaaaaacaccacc aaaaactatgaaagcaatatttgattctgtgtcgtacaattgtagtaaagttgttactacatcttacagcacttcgttttctttagctacaaaaatgcttgcaa agtctatcagacaggatatttataatatttatggttttgtgaggtttgcagatgagattgtagacacttttcatgattatgataaagaaactttatttaacaat tttgaaaatgatttagaattagctctaaaaaacaaaattagcctaaatccaatattaaatgcgtttcaacatacatatcacaagtataacatcgaaaaacatat ggttgatgcttttatgaaaagtatgcgactagatttatctaaaactaaatacactacagaccaagagtataaagattatatttatggttctgcagacgtagttg gactaatgtgtttaaaagtctttgttaaaggagataatgatcaatacgaaaaacttaaagacacagcaatgtcattaggttctgcttttcaaaaggtgaatttt ttacgagacttaaaagctgatcacgaattacttgatagaacttatttcccaaatacagatttaaataatctaactgaagaagataaactattcatcattaatga tattgaaaacgatttaaaaaaggcttagaaggtataaaacaattacctatggaggctaaatttggagtatttatggcttatagatactatcaccagttactgg caaagcttaaaaaaacaccagcattagaaattaaaaatactagaataagagtaccaaactacaaaaaggcagaacttttaactagaagctacgtaaagtatcag ttaaatttattataattagacatgaaaacattgtattggatattaatatttttaggcacattttctatcatggaatttatggcatggtttacacataaatacat catgcacggatttttatggtcactacataaagaccatcatctaaaagatcacgatagctggtttgagcgtaatgatgcctttttttatcttttatgcaattgtaa gtatgacttgcttttacttatggagttacgaagatatatggtatacattaccaataggcttaggcattatggcttatggtgcagcttacttcttagtacacgat atttttatccatcaacgctttaaaatgtttagaaatgctaataattggtacgcacgtggtgttagacgtgcacacaaaatacatcacaagcatataggcaaaga agatggagaaaactttggcatgttagtcgtaccatttaagtacttcaaaaaatagactaaatgtctcaaaaacattatgattatatcatagttggcaatggttt agctggacttcaattagccttagcttttgccaaggattcatatttaataataaatccattgctttaatagacgcttctactaaaactgaaaatgataaaactt ggagtttttgggaacaaaacaatagcacttttagtcatttaacttaccaatcctggcaacatgcaactatctacgcagaagaccaaaaaataagcttaaatcta aaaccttatacttataaatctatacgtgcaatagacttttatacggaagctaaagcacaactcaatcagcaagacaatattacatttttggtggaaaccgtgac ttcggttaaagaaaaagaaatagttgaagtcacaaccaaaacaaacaactatacgacaaatcatgtttttgatagtcggattccagacgcgtttttaaagatg aaaaagccacaactttaatacaacattttaaaggctggattatagaagctgaaaacgatgtttttaatgaaaacagcttaacaatgatggattatcgattaaaa gataataatcaaacaacctttatgtatgtgttaccgcatacaaaaaataaagcgttagtagaatttacatattttacggaaaacactgttaaaagtgaccatta cgacaactatttaaagcaatatatttcagaatatttaaacattaataattataatattgtcgaaactgaagttggtcaaataccaatgacaacttttaattttc aattgtttaactcttccaaaatcactaaaattggtacagctggcggttgggtaaaaccttctacgggatattcttttaaactcacagaaaaaagagttgcaaaa attattgagaatataaaaaccaatcaaccaaccacaaacggatttttaaaaacaagtataaattttacgacaaagtatttttacaagttttaaaagataataa tgaaaaaggcgaatgggtttttaatcaattttacagtaaaaatagcacaccaaccatgtttaaatttttagatgaagagtcttcacttttgaagacattaaaa ttatgtggtcgttatttagtttcagttttattaaagctttttttaaaacgctttaa crtZ_Mz
Source: *Mesoflavibacter zeaxanthinifaciens* DSM 18436

SEQ ID NO: 27

MKTLYWILIFLGTFSIMEFMAWFTHKYIMEGFLWSLHKDHHLKDHDSWFERNDAFFIFYAIVSMTCF

YLWSYEDIWYTLPIGLGIMAYGAAYFLVHDIFIHQRFKMFRNANNWYARGVRRAHKIHHKHIGKED

GENFGMLVVPFKYFKK* crtY_Mz
Source: *Mesoflavibacter zeaxanthinifaciens* DSM 18436

SEQ ID NO: 28

MSQKHYDYIIVGNGLAGLQLALAFAKDSYFNNKSIALIDASTKTENDKTWSFWEQNNSTFSHLTYQS

WQHATIYAEDQKISLNLKPYTYKSIRAIDFYTEAKAQLNQQDNITFLVETVTSVKEKEIVEVTTKTNN

YTTNHVFDSRIPDAFFKDEKATTLIQHFKGWITEAENDVFNENSLTMMDYRLKDNNQTTFMYVLPHT

KNKALVEFTYFTENTVKSDHYDNYLKQYISEYLNINNYNIVETEVGQIPMTTFNFQLFNSSKITKIGTA

-continued

GGWVKPSTGYSFKLTEKRVAKIIENIKTNQPTTNGFFKNKYKFYDKVFLQVLKDNNEKGEWVFNQF

YSKNSTPTMFKFLDEESSLFEDIKIMWSLFSFSFIKAFFKTL* crtI_Mz
Source: *Mesoflavibacter zeaxanthinifaciens* DSM 18436

SEQ ID NO: 29

MKNKIAIIGSGFSALSAACYLAKDGFNVSVFEKNDTVGGRCRQFKKDGFTFDMGPSWYWMPDIFDK

FFNDFDKKTSDFYQLDKLSPAYKIFFNDEVITIGDTMEKICEEFERIEKGSSIPLKKFINKAADNYNIAIN

KIVLKPGVSPLELVTKDTVTRLDQFFKTISSDVRRQFKNPKLISTLEFPVLFLGAKPSNTPSFYSFMNYA

DFGLGTWHPKGGMYQIILAMRQLAEELGVSINVNSNVTNINVENNTSTSITVNGKTLKFDVVLSGAD

YHHSETLLDRKYRQYSEKYWNNKTFAPSSLLFYVGFDKKLKNVNHHNLFFDTNFETHAEDIYDNPK

WPKEPLFYANFPSVTDNSMAPNGKENGFFLIPIAPNLEDTPQLREQYFDIIMSRFEKLTQQDVKNSIIFK

ESFCVKDFIEAYNSYKGNAYGMANTLTQTAFLRPNLKSKKVNNLYFTGQLTVPGPGVPPALISGKLV

AELIQKHHQKL* crtB_Mz
Source: *Mesoflavibacter zeaxanthinifaciens* DSM 18436

SEQ ID NO: 30

MKAIFDSVSYNCSKVVTTSYSTSFSLATKMLAKSIRQDIYNIYGFVRFADEIVDTFHDYDKETLFNNFE

NDLELALKNKISLNPILNAFQHTYHKYNIEKHMVDAFMKSMRLDLSKTKYTTDQEYKDYIYGSADV

VGLMCLKVFVKGDNDQYEKLKDTAMSLGSAFQKVNFLRDLKADHELLDRTYFPNTDLNNLTEEDK

LFIINDIENDFKKGLEGIKQLPMEAKFGVFMAYRYYHQLLAKLKKTPALEIKNTRIRVPNYKKAELLT

RSYVKYQLNLL* crtZYIBE-idi, Ev C40 cluster
Source: *Escherichia vulneris*

SEQ ID NO: 31 atggtgagtggcagtaaagcgggcgtttcgcctcatcgcgaaatagaagtaatgagacaatccattgacgatcacctggctggcctgttacctgaaaccgacag ccaggatatcgtcagccttgcgatgcgtgaaggcgtcatggcacccggtaaacggatccgtccgctgctgatgctgctggccgcccgcgacctccgctaccag ggcagtatgcctacgctgctcgatctcgcctgcgccgttgaactgacccataccgcgtcgctgatgctcgacgacatgccctgcatggacaacgccgagctgc gccgcggtcagcccactacccacaaaaaatttggtgagagcgtggcgatccttgcctccgttgggctgctctctaaagcctttggtctgatcgccgccaccggcg atctgccgggggagaggcgtgcccaggcggtcaacgagctctctaccgccgtgggcgtgcagggcctggtactggggcagtttcgcgatcttaacgatgccg ccctcgaccgtacccctgacgctatcctcagcaccaaccacctcaagaccggcattctgttcagcgcgatgctgcagatcgtcgccattgcttccgcctcgtcgc cgagcacgcgagagacgctgcacgccttcgccctcgacttcggccaggcgtttcaactgctggacgatctgcgtgacgatcacccggaaaccggtaaagatc gcaataaggacgcgggaaaatcgacgctggtcaaccggctgggcgcagacgcggcccggcaaaagctgcgcgagcatattgattccgccgacaaacacct cacttttgcctgtccgcagggcggcgccatccgacagtttatgcatctgtggtttggccatcaccttgccgactggtcaccggtcatgaaaatcgcctgataccg cccttttgggttcaagcagtacataacgatggaaccacattacaggagtagtgatgaatgaaggacgagcgccttgttcagcgtaagaacgatcatctggatatc gttctcgacccccgtcgcgccgtaactcaggctagcgcaggttttgagcgctggcgctttacccactgcgccctgccagagctgaattttagcgacatcacgctg gaaaccaccttcctgaatcggcagctacaggctccgctgctgatcagctccatgaccggcggcgttgagcgctcgcgccatatcaaccgccacctcgccgaggcg gcgcaggtgctaaaaattgcgatgggggtgggctcccagcgcgtcgccattgagagcgacgcgggcttagggctggataaaaccctgcggcagctggctcc ggacgtgccgctgctggcgaacctcggcgcggcgcagctgaccggcagaaaaggtattgattacgcccgacgggccgtggagatgatcgaggcggatgcg ctgattgtgcacctaaacccgctgcaggaggcgctacagcccggcggcgatcgcgactggcgcggacggctggcggctattgaaactctggtccgcgagct gcccgttccgctggtggtgaaagaggtgggagccggtatctcccgaaccgtggccgggcagctgatcgatgccggcgttaccgtgattgacgtcgcgggcgc gggcggcaccagctgggccgccgttgaaggcgagcgggcggccaccgagcagcagcgcagcgtggccaacgtctttgccgactgggggatccccaccg ctgaggcgctggttgacattgccgaggcctggccgcagatgccccttattgcctcgggcgggattaaaaacggcgtcgacgcggcgaaagcgctgcggctcg gcgcgtgcatggtagggcaggccgccgccgtgctcggcagcgcaggcgtctccacggagaaggtgatcgatcacttcaacgtgattattgagcagctgcggg tggcctgcttctgcaccggcagccgcagcctgagcgatctaaagcaggctgatatccgctatgtgcgggatacgccatgagccattttgccattgtggcaccgc cgctctacagtcatgcggtggcgctgcatgccctggcgctggagatggcccaacgcggccaccgggtgacctttctcaccggcaacgtcgcctcgctggcag -continued agcaggaaacggagcgggtggcgttctatccacttcccgccagcgtgcaacaggcccagcgcaacgtccagcagcagagtaacggcaacctgctgcggct gattgcggccatgtcatccctgaccgatgtgctctgccagcagttgcccgctattctacagcggctggcggtggacgcgctgattgtcgatgagatggagcccg ccggaagcctggtcgccgaggcgctgggactaccatttatctctattgcctgcgcgctgccggtcaaccgcgagccgggtctgccgctgccggtgatgccgttt cactacgccgaggataagagagccctgcggcgttttcaggtcagcgaacggatctacgatgcgctgatgtacccgcacgggcagacgatcctgcgccacgcc cagcgctttggtttgccggagcgcaggcgtctcgacgagtgtctctcgccgctggcgcagattagccagtccgttccggccctcgacttcccacgccgggcgct gccgaactgttttcactacgtgggagcactgcgctatcagccgccgccgcaggtagaacgctcgccacgcagcacgccgcggatctttgcctcgctgggcacc ctccagggccaccgtctacgcctgtttcagaagatcgcccgcgcctgtgccagcgtgggggcggaggtgaccattgcccactgcgatggcctgacgcccgcc caggccgactcgctctacgcctgcggcgcgacggaggtggtcagctttgtcgaccagccgcgctacgttgccgaggctaatctggtgatcacccacggcggt ctcaataccgtactggatgcgctggctgccgcgacgccggtgctggcggtgccactctctttcgaccagcccgccgtggctgcccggctggtctataacgggct gggtcgccgggtatcgcgctttgccagacagcagacgctggcggatgagattgcccaactgctgggggatgagacgctgcatcagcgtctggcgacggccc gccagcagcttaacgacgccgggggcacgccccgtgcggcgaccctgattgaacaggccatagcagggagtgagagcgtatcgtgagggatctgattttagt cggcggcggcctggccaacgggctgatcgcctggcgtctgcgccagcgctacccgcagcttaacctgctgctgatcgaggccggggagcagcccggcggg aaccatacctggtcattccatgaagacgatctgactcccgggcagcacgcctggctggccccgctggtggcccacgcctggccgggctatgaggtgcagtttc ccgatcttcgccgtcgcctcgcgcgcggctactactccattacctcagagcgctttgccgaggccctgcatcaggcgctgggggagaacatctggctaaactgtt cggtgagcgaggtgttacccaatagcgtgcgccttgccaacggtgaggcgctgcttgccggagcggtgattgacggacgcggcgtgaccgccagttcggcg atgcaaaccggctatcagctctttcttggtcagcagtggcggctgacacagccccacggcctgaccgtaccgatcctgatggatgccacggtggcgcagcagc agggctatcgctttgtctacacgctgccgctctccgccgacacgctgctgatcgaggatacgcgctacgccaatgtcccgcagcgtgatgataatgccctacgc cagacggttaccgactatgctcacagcaaagggtggcagctggcccagcttgaacgcgaggagaccggctgtctgccgattaccctggcgggtgacatccag gctctgtgggccgatgcgccgggcgtgccgcgctcgggaatgcgggctgggctatttcaccctaccactggctattcgctgccgctggcggtggcccttgccg acgcgattgccgacagcccgcggctgggcagcgttccgctctatcagctcacccggcagtttgccgaacgccactggcgcaggcagggattcttccgcctgct gaaccggatgcttttcctggccgggcgcgaggagaaccgctggcgggtgatgcagcgcttttatgggctgccggagcccaccgtagagcgcttttacgccggt cggctctctctctttgataaggcccgcattttgacgggcaagccaccggttccgctgggcgaagcctggcgggcggcgctgaaccattttcctgacagacgaga taaaggatgaaaaaaaccgttgtgattggcgcaggctttggtggcctggcgctggcgattcgcctgcaggcggcagggatcccaaccgtactgctggagcagc gggacaagcccggcggtcgggcctacgtctggcatgaccagggctttacctttgacgccgggccgacggtgatcaccgatcctaccgcgcttgaggcgctgtt caccctggccggcaggcgcatggaggattacgtcaggctgctgccggtaaaacccttctaccgactctgctgggagtccgggaagaccctcgactatgctaac gacagcgccgagcttgaggcgcagattacccagttcaacccccgcgacgtcgagggctaccggcgctttctggcttactcccaggcggtattccaggagggat atttgcgcctcggcagcgtgccgttcctctcttttcgcgacatgctgcgcgccgggccgcagctgcttaagctccaggcgtggcagagcgtctaccagtcggttt cgcgctttattgaggatgagcatctgcggcaggccttctcgttccactccctgctggtaggcggcaaccccttcaccacctcgtccatctacaccctgatccacg cccttgagcgggagtggggggtctggttccctgagggcggcaccggggcgctggtgaacggcatggtgaagctgtttaccgatctgggcggggagatcgaac tcaacgcccgggtcgaagagctggtggtggccgataaccgcgtaagccaggtccggctggcggatggtcggatctttgacaccgacgccgtagcctcgaac gctgacgtggtgaacacctataaaaagctgctcggccaccatccggtggggcagaagcgggcggcagcgctggagcgcaagagcatgagcaactcgctgtt tgtgctctacttcggcctgaaccagcctcattcccagctggcgcaccataccatctgttttggtccccgctaccgggagctgatcgacgagatctttaccggcag cgcgctggcggatgacttctcgctctacctgcactcgccctgcgtgaccgatccctcgctcgcgcctcccggctgcgccagcttctacgtgctggccccggtgcc gcatcttggcaacgcgccgctggactgggcgcaggaggggccgaagctgcgcgaccgcatctttgactaccttgaagagcgctatatgcccggcctgcgtag ccagctggtgacccagcggatctttaccccggcagacttccacgacacgctggatgcgcatctgggatcggccttctccatcgagccgctgctgacccaaagc gcctggttccgcccgcacaaccgcgacagcgacattgccaacctctacctggtgggcgcaggtactcaccctggggcgggcattcctggcgtagtggcctcg gcgaaagccaccgccagcctgatgattgaggatctgcaatgagccaaccgccgctgcttgaccacgccacgcagaccatggccaacggctcgaaaagttttg ccaccgctgcgaagctgttcgacccggccacccgccgtagcgtgctgatgctctacacctggtgccgccactgcgatgacgtcattgacgaccagacccacg gcttcgccagcgaggccgcggcggaggaggaggccacccagcgcctggcccggctgcgcacgctgaccctggcggcgtttgaaggggccgagatgcag gatccggccttcgctgcctttcaggaggtggcgctgacccacggtattacgccccgcatggcgctcgatcacctcgacggctttgcgatggacgtggctcagac -continued ccgctatgtcacctttgaggatacgctgcgctactgctatcacgtggcgggcgtggtgggtctgatgatggccagggtgatgggcgtgcgggatgagcgggtg ctggatcgcgcctgcgatctggggctggccttccagctgacgaatatcgcccgggatattattgacgatgcggctattgaccgctgctatctgcccgccgagtgg ctgcaggatgccgggctgaccccggagaactatgccgcgcgggagaatcgggccgcgctggcgcgggtggcggagcggcttattgatgccgcagagccgt actacatctcctcccaggccgggctacacgatctgccgccgcgctgcgcctgggcgatcgccaccgcccgcagcgtctaccgggagatcggtattaaggtaa aagcggcgggaggcagcgcctgggatcgccgccagcacaccagcaaaggtgaaaaaattgccatgctgatggcggcaccggggcaggttattcgggcga agacgacgagggtgacgccgcgtccggccggtctttggcagcgtcccgtttaggcgggcggccatgacgttcacgcaggatcgcctgtaggtcggcaggctt gcgggcgtaaataaaaccgaaggagacgcagccctcccggccgcgcaccgcgtggtgcaggcggtgggcgacgtagagccgcttcaggtagccccggcg cgggatccagtggaagggccagcgctgatgcaccagaccgtcgtgcaccaggaagtagagcaggccatagaccgtcatgccgcagccaatccactgcagg ggccaaacgcccgccgtgcccacggcaatcagcgcgatagccaccccggcaaacaccaccgcaaagagatcgtttagctcaaatacgcccttgcgcggggt atggtgtgactcatgccagcgccatccccagccgtgcataatgtagcggtgggtaaacgcggcgatgccctccatcgcaataacgctcaagatgacgattaaac tatttactagcat crtZ_Ev
Source: *Escherichia vulneris*

SEQ ID NO: 32

MLVNSLIVILSVIAMEGIAAFTHRYIMEGWGWRWHESHHTPRKGVFELNDLFAVVFAGVAIALIAVG

TAGVWPLQWIGCGMTVYGLLYFLVHDGLVHQRWPFHWIPRRGYLKRLYVAHRLHHAVRGREGCV

SFGFIYARKPADLQAILRERHGRPPKRDAAKDRPDAASPSSSSPE* crtY_Ev
Source: *Escherichia vulneris*

SEQ ID NO: 33

VRDLILVGGGLANGLIAWRLRQRYPQLNLLLIEAGEQPGGNHTWSFHEDDLTPGQHAWLAPLVAHA

WPGYEVQFPDLRRRLARGYYSITSERFAEALHQALGENIWLNCSVSEVLPNSVRLANGEALLAGAVI

DGRGVTASSAMQTGYQLFLGQQWRLTQPHGLTVPILMDATVAQQQGYRFVYTLPLSADTLLIEDTR

YANVPQRDDNALRQTVTDYAHSKGWQLAQLEREETGCLPITLAGDIQALWADAPGVPRSGMRAGL

FHPTTGYSLPLAVALADAIADSPRLGSVPLYQLTRQFAERHWRRQGFFRLLNRMLFLAGREENRWRV

MQRFYGLPEPTVERFYAGRLSLFDKARILTGKPPVPLGEAWRAALNHFPDRRDKG* crtI_Ev
Source: *Escherichia vulneris*

SEQ ID NO: 34

MKKTVVIGAGFGGLALAIRLQAAGIPTVLLEQRDKPGGRAYVWHDQGFTFDAGPTVITDPTALEALF

TLAGRRMEDYVRLLPVKPFYRLCWESGKTLDYANDSAELEAQITQFNPRDVEGYRRFLAYSQAVFQ

EGYLRLGSVPFLSFRDMLRAGPQLLKLQAWQSVYQSVSRFIEDEHLRQAFSFHSLLVGGNPFTTSSIYT

LIHALEREWGVWFPEGGTGALVNGMVKLFTDLGGEIELNARVEELVVADNRVSQVRLADGRIFDTD

AVASNADVVNTYKKLLGHHPVGQKRAAALERKSMSNSLFVLYFGLNQPHSQLAHHTICFGPRYRELI

DEIFTGSALADDFSLYLHSPCVTDPSLAPPGCASFYVLAPVPHLGNAPLDWAQEGPKLRDRIFDYLEE

RYMPGLRSQLVTQRIFTPADFHDTLDAHLGSAFSIEPLLTQSAWFRPHNRDSDIANLYLVGAGTHPGA

GIPGVVASAKATASL crtB_Ev
Source: *Escherichia vulneris*

SEQ ID NO: 35

MSQPPLLDHATQTMANGSKSFATAAKLFDPATRRSVLMLYTWCRHCDDVIDDQTHGFASEAAAEEE

ATQRLARLRTLTLAAFEGAEMQDPAFAAFQEVALTHGITPRMALDHLDGFAMDVAQTRYVTFEDTL

RYCYHVAGVVGLMMARVMGVRDERVLDRACDLGLAFQLTNIARDIIDDAAIDRCYLPAEWLQDAG

LTPENYAARENRAALARVAERLIDAAEPYYISSQAGLHDLPPRCAWAIATARSVYREIGIKVKAAGGS

AWDRRQHTSKGEKIAMLMAAPGQVIRAKTTRVTPRPAGLWQRPV*

-continued crtE_Ev
Source: *Escherichia vulneris*

SEQ ID NO: 36

MVSGSKAGVSPHREIEVMRQSIDDHLAGLLPETDSQDIVSLAMREGVMAPGKRIRPLLMLLAARDLR

YQGSMPTLLDLACAVELTHTASLMLDDMPCMDNAELRRGQPTTHKKFGESVAILASVGLLSKAFGLI

AATGDLPGERRAQAVNELSTAVGVQGLVLGQFRDLNDAALDRTPDAILSTNHLKTGILFSAMLQIVA

IASASSPSTRETLHAFALDFGQAFQLLDDLRDDHPETGKDRNKDAGKSTLVNRLGADAARQKLREHI

DSADKHLTFACPQGGAIRQFMELWFGHHLADWSPVMKIA*

Idi_Ev
Source: *Escherichia vulneris*

SEQ ID NO: 37

MKDERLVQRKNDHLDIVLDPRRAVTQASAGFERWRFTHCALPELNFSDITLETTFLNRQLQAPLLISS

MTGGVERSRHINRHLAEAAQVLKIAMGVGSQRVAIESDAGLGLDKTLRQLAPDVPLLANLGAAQLT

GRKGIDYARRAVEMIEADALIVHLNPLQEALQPGGDRDWRGRLAAIETLVRELPVPLVVKEVGAGIS

RTVAGQLIDAGVTVIDVAGAGGTSWAAVEGERAATEQQRSVANVFADWGIPTAEALVDIAEAWPQ

MPLIASGGIKNGVDAAKALRLGACMVGQAAAVLGSAGVSTEKVIDHFNVIIEQLRVACFCTGSRSLS

DLKQADIRYVRDTP* crtZYIBE, Pa C40 cluster
Source: *Pantoea ananatis* ATCC 19321

SEQ ID NO: 38 atgacggtctgcgcaaaaaaacacgttcatctcactcgcgatgctgcggagcagttactggctgatattgatcgacgccttgatcagttattgcccgtggaggga gaacgggatgttgtgggtgccgcgatgcgtgaaggtgcgctggcaccgggaaaacgtattcgccccatgttgctgttgctgaccgcccgcgatctgggttgcgct gtcagccatgacggattactggatttggcctgtgcggtggaaatggtccacgcggcttcgctgatccttgacgatatgccctgcatggacgatgcgaagctgcgg cgcggacgccctaccattcattctcattacggagagcatgtggcaatactggcggcggttgccttgctgagtaaagcctttggcgtaattgccgatgcagatggc ctcacgccgctggcaaaaaatcgggcggtttctgaactgtcaaacgccatcggcatgcaaggattggttcagggtcagttcaaggatctgtctgaaggggataa gccgcgcagcgctgaagctatttgatgacgaatcactttaaaaccagcacgctgttttgtgcctccatgcagatggcctcgattgttgcgaatgcctccagcga agcgcgtgattgcctgcatcgtttttcacttgatcttggtcaggcatttcaactgctggacgatttgaccgatggcatgaccgacaccggtaaggatagcaatca ggacgccggtaaatcgacgctggtcaatctgttaggcccgagggcggttgaagaacgtctgagacaacatcttcagcttgccagtgagcatctctctgcggcctg ccaacacgggcacgccactcaacattttattcaggcctggtttgacaaaaaactcgctgccgtcagttaaggatgctgcatgagccatttcgcggcgatcgcacc gcctttttacagccatgttcgcgcattacagaatctcgctcaggaactggtcgcgcgcggtcatcgggtgacctttattcagcaatacgatattaaacacttgat cgatagcgaaaccattggatttcattccgtcgggacagacagccatcccccggcgcgttaacgcgcgtgctacacctggcggctcatcctctggggccgtcaat gctgaagctcatcaatgaaatggcgcgcaccaccgatatgctgtgccgcgaactcccccaggcatttaacgatctggccgtcgatggcgtcattgttgatcaaat ggaaccggcaggcgcgctcgttgctgaagcactgggactgccgtttatctctgtcgcctgcgcgctgcctctcaatcgtgaaccggatatgcccctggcggttat gcctttcgaatacgggaccagcgacgcggctcgcgaacgttatgccgccagtgaaaaaatttatgactggctaatgcgtcgtcatgaccgtgtcattgccgaaca cagccacagaatgggcttagcccccggcaaaagcttcaccagtgtttttcgccactggcgcaaatcagccagcttgttcctgaactggattttccccgcaaagc gttaccggcttgttttcatgccgtcgggcctctgcgcgaaacgcacgcaccgtcaacgtcttcatcccgttattttacatcctcagaaaaaccccggattttcgc ctcgctgggcacgcttcagggacaccgttatgggctgtttaaaacgatagtgaaagcctgtgaagaaattgacggtcagctcctgttagcccactgtggtcgtct tacggactctcagtgtgaagagctggcgcgaagccgtcatacacaggtggtggattttgccgatcagtcagccgcgctgtctcaggcgcagctggcgatcaccca cggcggcatgaatacggtactggacgcgattaattaccggacgccccttttagcgcttccgctggcctttgatcagcccggcgtcgcgtcacgcatcgtttatca cggcatcggcaagcgtgcttcccgctttaccaccagccatgctttggctcgtcagatgcgttcattgctgaccaacgtcgactttcagcagcgcatggcgaaaat ccagacagcccttcgtttggcaggggggcaccatggccgctgccgatatcattgagcaggttatgtgcaccggtcagcctgtcttaagtgggagcggctatgcaac cgcattatgatctgattctcgtggggggctggactcgcgaatggccttatcgccctgcgtcttcagcagcagcaacctgatatgcgtattttgcttatcgacgccg caccccaggcgggcgggaatcatacgtggtcatttcaccacgatgatttgactgagagccaacatcgttggatagctccgctggtggttcatcactggcccgact atcaggtacgctttcccacacgccgtcgtaagctgaacagcggctacttttgtattacttctcagcgtttcgctgaggttttacagcgacagtttggcccgcact tgtggatggataccgcggtcgcagaggttaatgcggaatctgttcggttgaaaaagggtcaggttatcggtgcccgcgcggtgattgacgggcggggttatgcgg -continued caaattcagcactgagcgtgggcttccaggcgtttattggccaggaatggcgattgagccacccgcatggtttatcgtctcccattatcatggatgccacggtcg atcagcaaaatggttatcgcttcgtgtacagcctgccgctctcgccgaccagattgttaattgaagacacgcactatattgataatgcgacattagatcctgaat gcgcgcggcaaaatatttgcgactatgccgcgcaacagggttggcagcttcagacactgctgcgagaagaacagggcgccttacccattactctgtcgggcaatg ccgacgcattctggcagcagcgcccccctggcctgtagtggattacgtgccggtctgttccatcctaccaccggctattcactgccgctggcggttgccgtggccg accgcctgagtgcacttgatgtctttacgtcggcctcaattcaccatgccattacgcattttgcccgcgagcgctggcagcagcagggctttttccgcatgctga atcgcatgctgtttttagccggacccgccgattcacgctggcgggttatgcagcgtttttatggtttacctgaagatttaattgcccgtttttatgcgggaaaac tcacgctgaccgatcggctacgtattctgagcggcaagccgcctgttccggtattagcagcattgcaagccattatgacgactcatcgttaaagagcgactacat gaaaccaactacggtaattggtgcaggcttcggtggcctggcactggcaattcgtctacaagctgcggggatccccgtcttactgcttgaacaacgtgataaacc cggcggtcgggcttatgtctacgaggatcaggggtttacctttgatgcaggcccgacggttatcaccgatcccagtgccattgaagaactgtttgcactggcagg aaaacagttaaaagagtatgtcgaactgctgccggttacgccgttttaccgcctgtgttgggagtcagggaaggtctttaattacgataacgatcaaacccggct cgaagcgcagattcagcagtttaatccccgcgatgtcgaaggttatcgtcagtttctggactattcacgcgcggtgtttaaagaaggctatctaaagctcggtac tgtcccttttttatcgttcagagacatgcttcgcgccgcacctcaactggcgaaactgcaggcatggagaagcgtttacagtaaggttgccagttacatcgaaga tgaacatctgcgccaggcgttttctttccactcgctgttggtgggcggcaatcccttcgccacctcatccatttatacgttgatacacgcgctggagcgtgagtg gggcgtctggtttccgcgtggcggcaccggcgcattagttcaggggatgataaagctgtttcaggatctgggtggcgaagtcgtgttaaacgccagagtcagcca tatggaaacgacaggaaacaagattgaagccgtgcatttagaggacggtcgcaggttcctgacgcaagccgtcgcgtcaaatgcagatgtggttcatacctatcg cgacctgttaagccagcaccctgccgcggttaagcagtccaacaaactgcagactaagcgcatgagtaactctctgtttgtgctctattttggtttgaatcacca tcatgatcagctcgcgcatcacacggtttgtttcggcccgcgttaccgcgagctgattgacgaaatttttaatcatgatggcctcgcagaggacttctcacttta tctgcacgcgccctgtgtcacggattcgtcactggcgcctgaaggttgcggcagttactatgtgttggcgccggtgccgcatttaggcaccgcgaacctcgactg gacggttgaggggccaaaactacgcgaccgtatttttgcgtaccttgagcagcattacatgcctggcttacggagtcagctggtcacgcaccggatgtttacgcc tgtttgattttcgcgaccagcttaatgcctatcaggctcagccttttctgtggagcccgttcttacccagagcgcctggtttcggccgcataaccgcgataaaac cattactaatctctacctggtcggcgcaggcacgcatcccggcgcaggcattcctggcgtcatcggctcggcaaaagcgacagcaggtttgatgctggaggatct gatatgaataatccgtcgttactcaatcatgcggtcgaaacgatggcagttggctcgaaaagttttgcgacagcctcaaagttatttgatgcaaaaacccggcgc agcgtactgatgctctacgcctggtgccgccattgtgacgatgttattgacgatcagacgctgggctttcaggcccggcagcctgccttacaaacgcccgaacaa cgtctgatgcaacttgagatgaaaacgcgccaggcctatgcaggatcgcagatgcacgaaccggcgtttgcggcttttcaggaagtggctatggctcatgatatc gccccggcttacgcgtttgatcatctggaaggcttcgccatggatgtacgcgaagcgcaatacagccaactggatgatacgctgcgctattgctatcacgttgca ggcgttgtcggcttgatgatggcgcaaatcatgggcgtgcgggataacgccacgctggaccgcgcctgtgaccttgggctggcatttcagttgaccaatattgct cgcgatattgtggacgatgcgcatgcgggccgctgttatctgccggcaagctggctggagcatgaaggtctgaacaaagagaattatgcggcacctgaaaaccgt caggcgctgagccgtatcgcccgtcgtttggtgcaggaagcagaaccttactatttgtctgccacagccggcctggcagggttgcccctgcgttccgcctgggca atcgctacggcgaagcaggtttaccggaaaataggtgtcaaagttgaacaggccggtcagcaagcctgggatcagcggcagtcaacgaccacgcccgaaaaatta acgctgctgctggccgcctctggtcaggcccttacttcccggatgcgggctcatcctccccgccctgcgcatctctggcagcgcccgctctagcgccatgtcttt cccggagcgtcgcctgaagttttgacaggggcggcgcatagaggaagccaaaagaaacacaaccttctttgcccctgacggcgtgatgcatacggtgcgccatat acaaccgtttgaggtagcccttgcgtggaatatagcggaatggccaacgttgatgcaccagcccgtcgtgcaccataaaatagagtaatccatacgccgtcatac ctgcgccaatccactggagcggccacattcctgtactgcccagataaatcagcaggatcgataatgcagcaaaaaccacggcataaagatcgttaacttcaaacg cacctttacgcggttcatgatgtgaaagatgccatccccaaccccagccgtgcatgatgtatttgtgtgccagtgcagcaatcacttccatgccaatcacggtaa cgaaaacgatcagggcattccaaatccacaacat crtZ_Pa
Source: *Pantoea ananahs* ATCC 19321

SEQ ID NO: 39

MLWIWNALIVFVTVIGMEVIAALAHKYIMHGWGWGWHLSHHEPRKGAFEVNDLYAVVFAALSILLI

YLGSTGMWPLQWIGAGMTAYGLLYFMVHDGLVHQRWPFRYIPRKGYLKRLYMAHRMHHAVRGK

EGCVSFGFLYAPPLSKLQATLRERHGARAGAARDAQGGEDEPASGK*

-continued crtY_Pa
Source: *Pantoea ananatis* ATCC 19321

SEQ ID NO: 40

MQPHYDLILVGAGLANGLIALRLQQQQPDMRILLIDAAPQAGGNHTWSFHHDDLTESQHRWIAPLV

VHHWPDYQVRFPTRRRKLNSGYFCITSQRFAEVLQRQFGPHLWMDTAVAEVNAESVRLKKGQVIGA

RAVIDGRGYAANSALSVGFQAFIGQEWRLSHPHGLSSPIIMDATVDQQNGYRFVYSLPLSPTRLLIEDT

HYIDNATLDPECARQNICDYAAQQGWQLQTLLREEQGALPITLSGNADAFWQQRPLACSGLRAGLF

HPTTGYSLPLAVAVADRLSALDVFTSASIHHAITHFARERWQQQGFFRMLNRMLFLAGPADSRWRV

MQRFYGLPEDLIARFYAGKLTLTDRLRILSGKPPVPVLAALQAIMTTHR* crtI_Pa
Source: *Pantoea ananatis* ATCC 19321

SEQ ID NO: 41

MKPTTVIGAGFGGLALAIRLQAAGIPVLLLEQRDKPGGRAYVYEDQGFTFDAGPTVITDPSAIEELFAL

AGKQLKEYVELLPVTPFYRLCWESGKVFNYDNDQTRLEAQIQQFNPRDVEGYRQFLDYSRAVFKEG

YLKLGTVPFLSFRDMLRAAPQLAKLQAWRSVYSKVASYIEDEHLRQAFSFHSLLVGGNPFATSSIYTL

IHALEREWGVWFPRGGTGALVQGMIKLFQDLGGEVVLNARVSHMETTGNKIEAVHLEDGRRFLTQA

VASNADVVHTYRDLLSQHPAAVKQSNKLQTKRMSNSLFVLYFGLNHHHDQLAHHTVCFGPRYRELI

DEIFNHDGLAEDFSLYLHAPCVTDSSLAPEGCGSYYVLAPVPHLGTANLDWTVEGPKLRDRIFAYLE

QHYMPGLRSQLVTHRMFTPFDFRDQLNAYHGSAFSVEPVLTQSAWFRPHNRDKTITNLYLVGAGTH

PGAGIPGVIGSAKATAGLMLEDLI* crtB_Pa
Source: Pantoea ananatis ATCC 19321

SEQ ID NO: 42

MNNPSLLNHAVETMAVGSKSFATASKLFDAKTRRSVLMLYAWCRHCDDVIDDQTLGFQARQPALQ

TPEQRLMQLEMKTRQAYAGSQMEEPAFAAFQEVAMAHDIAPAYAFDHLEGFAMDVREAQYSQLDD

TLRYCYHVAGVVGLMMAQIMGVRDNATLDRACDLGLAFQLTNIARDIVDDAHAGRCYLPASWLEH

EGLNKENYAAPENRQALSRIARRLVQEAEPYYLSATAGLAGLPLRSAWAIATAKQVYRKIGVKVEQ

AGQQAWDQRQSTTTPEKLTLLLAASGQALTSRMRAHPPRPAHLWQRPL* crtE_Pa
Source: *Pantoea ananatis* ATCC 19321

SEQ ID NO: 43

MTVCAKKHVHLTRDAAEQLLADIDRRLDQLLPVEGERDVVGAAMREGALAPGKRIRPMLLLLTARD

LGCAVSHDGLLDLACAVEMVHAASLILDDMPCMDDAKLRRGRPTIHSHYGEHVAILAAVALLSKAF

GVIADADGLTPLAKNRAVSELSNAIGMQGLVQGQFKDLSEGDKPRSAEAILMTNHFKTSTLFCASMQ

MASIVANASSEARDCLHRFSLDLGQAFQLLDDLTDGMTDTGKDSNQDAGKSTLVNLLGPRAVEERL

RQHLQLASEHLSAACQHGHATQHFIQAWFDKKLAAVS* crtYIB, Fp US (upstream) cluster
Source: *Fulvimarina pelagi*

SEQ ID NO: 44 ttgacgtctictgcgaaacagaaggtcgacattgctcttgtgggcggtggacttgccaatgggctgatcgcctggcggcttgccgaattgeggccggatctcagc atcgtcgtectcgaagccggtgaggcgcctggeggcaaccacacatggtcgtttcacgaacacgaccttacacccgccgctcatcggtggatcgcgcctttcgt cgctcatcgctggaccaccaacgaggtgcaattccccgaccgccatcgtcatctctcgacggggtatttgagcgcgtectcggatctatttcgcgaaaggctgac gacgcgtcteggettgcgtatccgcaccggctgtccggccgtttctgtcacggcgcgcaaggtgcgactcgaaaacggcgaagtgatcgaggccggctcggt gattgacgggcgcggctaccgatcgagcgaacacctcacgcteggcttcagaagtttcteggtcaggagatcgaattcgaggcaccgcacggcgttgcccga ccggtcatcatggatgctaccgteccccaggcggacggctatcggttcgtctatcttcttcccatgacgccgacgcggttgctggtcgaggacacctactatgcc gatggcgacgccctcgatcgcggaacgatccggcgcaacatcgcggcttaccgggcggcgaagggctggcctgeggggaaagtcgttcgcgaagaagatg gtgtcctgccgatcgcgctcgccggcgatatcgaggccttctgggaggagaagcagggcgtecccatccagcggcctcaacgctgcgctificcacccgacga ctgggtattecttgccggacgccgtgtatctcgccgatctgattgcaggcctgccggactattcggccgcaaccctttatgctgcgacacgccgccactcggtcg -continued caacgtggaagcggcgcggatcttccgtatgctgaaccgccttctctatctcgccggtgatccgttgaaacgttatgtcatcctccagcatttttatcgcctgcc cgaaccattggtgtcgcggttctacgctgcgcggctgacccgaggtgacaaggtgcggatcctcaccggcaagccgccggtcagtgttatcagcgcgctcaaagt tcttccccgagttctgtcgagggagcgcccgcatgaaccagatgccgcgcgaccttcctaacaagacaaagaccgcagtcgttatcggagcaggcttcggcg gactggcgcttgcgattcgacttcaggcggccggtatccaaacgacgcttctcgaaaagcgcgacaagcccggcggacgggcttacgtctacgaggatcagg gcttcaccttcgatgccggcccaaccgtgatcaccgacccctccgcgctcgaagagctgttcgagacggcgaacgccaagcttcggactatgtcgaactgctt cccgtcaagcctttctaccgtctcgcctgggaagacggcttcgtcttcgactatgcagacgatcaggaggatctcgaccgccagatcggcgcgaagaacccga aggatgtcgagggctatcgccgcttcctcgcttattcgcgggacgtgttccacgagggttacgaaaagctcggcaccgtcccttcctgaatttcaaggatatgat gcgggcagcgccccagctcgttcggctcgaggcctatcgctcggtctattcgaaggtcgcccagttcatcgaggacgaccagnacggcaggccattccttcc actcgctcctcgtcggcggcaatccgttcgccacttcttcgatctacgcgctcatccacgcgttggagcgcaaatggggcgtcttcttcccgcgcggcggcaccg gcgcgctggtccgcggcatggccaagctcttcaccgacattggcgggaggatcgaggtgaatgccgaggtcgagaatatcgcgatcgagaacgggcgcgc gaagtccgtgacgactaagggcggtcaaacctttcccgcagacttcgtcgcctcgaatgccgacgtcgtccacacctatgccaagctgatgggtcgcagcgag cgcggcaaaaagcacggcaattcgctgaagaagaagcgcttttccatgtcgctcttcgtcatctatttcggcctgaagacccaccggccggacattgcccatcac acggtctgtttcggtccgcgctatcgcccgctgatcgacgagattttcaagggcaaagagctcgcgggcgacttctcgctctatctccataacccgtgcgtcacc gatccctcgctcgcgccggagggcatgggctccttctacgttctgtcccctgtcccccatctcggtaacgccgatatagattgggcggttgaggggccgaaatat cgcgacaggatcctcgactatctggaagagctgtacatccccggcctgaaggacgatctcgtcaccagccgcatcttcaccccggctgatttcaagaccgaact gaacgcccatctcggctcggccttctcgctcgatccggtactgacgcagagcgcttggttccgccctcacaatcgcgacgatcagattcccaacctctacgtcgt cggggctggtacgcatccaggtgccggcgttccgggcgtcgtcggttcggccaaggcgactgccggcctgatgatcgaggacgcgggtctcgcgtgcgtgc ctgcatgagtttcgccgaccgcctcgacgtaccgatcgtcggcggccttccgttcgaaaagcgcgagcgcgccgcgctggccgccgaagccgaagcgacga tcgcgcaaggctcgaagagtttcgctgccgccgcccgcctgtttgatccggagatgcgggtcagcgcgcttatgctctatgcctggtgccggcattgcgacgat gtggtcgatgaccagatccttggttttcgccagccaggccgccgggaccgagccggcgatcgcgcacgtctcgatgaactcgaggccaagacccttgcggcg gttcgaggccgatccacgggcgaagcaccattcgacgcgatcggcgatgtcgccctgcggcatgagctgccggaatcgctcttgaccgcgcacctcgaagg cttccggatggatgtcgacggccgggtctacgaggtgattgaggatacgctcgattattgctaccgggtcgcaggtgtcgtcggcgtgatgatggcgcgggtca tgggcatcagggtcgaaaacggttcgaaattcgacctgacgctgaccctcgatcgagcctgcgacctcggcatggcctttcagctcaccaatatcgcacgtgac atagtcgacgacggcgaggccggacgggtctacgtgccgaagacatggctcgatgcggctggcgtcccgggcagcgccatccaccacccgcgcaatcggg aggcggcagcggtgttcgctctgcgtctcctcgatctggccgagccatactacgcgtcggcctcgaaggggctagccgcgctgccgcctcgtgccgcatggg ccgtcgcgactgcgcttggcgtctaccgtgagatcgggaccgtcatccgccggcgtggaagtcaagcctgggacgatcgttcatcgacaagcgcggcgacca agttcctgcacgccttcaagggtgtcggttggacgatgggatcacgtgtctcaagcaggcgcggcgttcggccgccggagctctggacgcgtcctcgactgctt gagctcggtgatgcgcccacaacaggtctatcggcctga crtWZ, FP DS (downstream) cluster
Source: *Fulvimarina pelagi*

SEQ ID NO: 45 ttaggactggcgagtatgcggcagagcccaccaaggcgtccatggcgccaaatggtgctcatggtggtagccaaaatggaagcaggagaatagcgaggcca cgtaaccgaattcgctcgaacgtgtgttatgcgcgtcggcaaaggtgcccgattcttcgtgtcgatgcgggcggtaggttccgaagtagaagagctgcaatgac gaaagcagtgacggcaagccgtaaaatagaaccacgttcgtcacagatgcatccagtatgacgagataaaacgtcacgacggtcgagacgaatgcgaccgat ctccatccgaaataacgtgagaagaaggtgccgaaccaaggccagaaattctccggatcatctgcgtagaaatccgggtcggccggtgtaccgggtgcgtcgt ggtgtgcgaagtgagcatctctgatctttttccacgcaaatcccgcgtagacgaacaggatgaacccgccgattacggcattcaaacgcgttcgacccggcgcc agcgaaccatgcatggcgtcgtgagccaggatgaaaagccccaccgtcaaccagcactggaacaccgtgatcaatggtgcgagaggcaacgtgctgaaatt gatgtcgaggaagaatatcgctgagacgtgtattgcgaaccacgatgccagcagcacggcacagagcgtcaggccaatcgtcgtttggtagggtctgattttgg gtgagtcggcgggtgtggatcgcggtaacgcacttgccgggatcaggcgtgaggttgggctgagggtcatgacctcgcaaataagccgaaccgtccgggtgc aaaatcgtttgccgcctcgtttggcgcggcataacgtcgtccatcctcgctctgtgcgctcgcgagaacacgatcgacggcttctgcagcagcacgcgcaccgc ctgcgttggcgatttccgcctggatcggagcgatccggttcacgaaggctgctcggtttgcaatcaaatcggaaagtgcattcgcaatggttcgcggcttggccc gcttggcggcgatagccttacccacgccgtgatggagtatacgggcaccgacacccggctgatcgtagccaattggcagcgccaacataggcgtaccgaccg -continued ccagacagtcgagaacggtgttgagccccccgtgagtcacgcagacatctgcgcgtgcgagcatcgcgcgttgatcgacgaaactgactacccacttggccg gaagcctcgaagcttgtcgtggcgagagccccccgcaatgcgcgatcatcaattgcacatcgagcgtctcgcaggcggatgcgatctttttgaataaactgtaac gatgaccttgcaccgtgccgagagacgcgaacacgaaggggcgcgtcgggtcgatcgtgagacatgtttccttcgtcagtcttgcgactgaggcactgcggat gggtccaaccggcttcagtttcgtccccctcggtctcggaaagtcgaaaacgctgacggtctgcgacaaacgcaacactggcgagagacaggcaacgtcgtc ctcccgcggccccagtccgaagcgcgtcgcccaggcttggatcaccttccgttgcttgcgcatgaagaatttgccgacacgctccccgccgcgattgcgagca agtccctcttcggtgggatcgtagggccaatcgagaaacggcagaggcatcgccacatcccgttcgattggtagggccgacgccaaggagatgtgtggcagg ccgagataagctgcgaccagaccggcgcctggctcgaattcatctgcgatgattgcatcgatttgcatcgaacgcatgatgtccggagcgatgcgacaaaactg atctgtttctcttgctcgatcggcaactgcccgcaagataccgagaatcccggcgccgccgccgtcacgccgacgatgccgaacaccagacatgattgaagca gaagccgctagcgtaacaatctcgatgtcagactggcagaccatcgtctccgcctctttcggcagtatgaagacgacgtcgtggccgcgaaccttgagcgcttg ccccagaacttcgaacgccttgatatggctgtagaacgccggacagaccaaagctatgcgtgccaattacatcaatccctcagccgaaacgaatcgacgcaga caagcaccgccctatcgatagcaaccgaccttaacatagttccgggtgacgatagtcgaggtagggtatgatcaggacattcctgaacggcgatggaagcgttc gggtcgatcgagaaacggcttttaacgtgacgaaagaggattgatgtcggccgcgcgcggttcatgctccctaagcgagatcgctagccgctcggctcggttg cgccgacctcgctcgatcgcgaaagtctggcccgtcgcttcgacacttgcatgcctgttgctgacaaacggcctcgtcgtactctacctctgggcgatcggtaga ccgttcatcgcgccgaccgaacctctcaagctgtttagcgacaacctcgccgctgcgaattcgctttatctctccgatccctactcgcttctgcacgtcatcttc ggaatcggtctcttcctgtatctcgactggatgaaacctttctggccgacgagggaaaaactgattgtcgcggtcttggggagcgcaatctgggaagtcgtcgag aacacgccatatgttgtgggtctgttcaacgacacgagtgacacggcagcttacaacggggacagtgtcgcgaattcgattggcgatacgatctctgcggtaatt ggtttttgttcgcgaatcggacagggcgccgagtttccctgttcgttgcattcgcgcttgaatcaatcgttacagtatggattggcgatggaatcgttattggc acgctcagacttctgggtctgtacccgatctgatcgacgcgactcttgcgcccatcgtcacggccatgtgtgtgtgccaagatcgagttatatatgtacctcggc ctgaacgactgaaccaaaactagaaacgtcgataagaaacgatgacgatctggactctctactacgtctgtctcaccctcgtcacgatcggtttgatggaggttt atgcatggtgggcgcacaagttcatcatgcatggcaaattcggttggggctggcataagtcccaccacgaggaaaccgaagggtggttcgagaagaacgatctct acgctgtcgtMcgccggottcgcgatagcgctgttcatggtcggacatttcctttctccgaccctgctcgccatcgcctggggcatcacgctttacggattactc tacttcgttgcccatgatggacttgtccatcagcgctggccgttcaactacgtgccgcatcgaggttatgcaaaacgcctggttcaagctcatcgtctgcaccat gcggtggaaggccgcgagcactgcgtctcgttcggctttctctatgcgccgccgattgaaaagctgaagcgcgatttgcgtgagtccggaattctcgaacgggag cgcatcgagcggtctctggaccagcaaggctccgcccacgcgccggttcggtga crtY_Fp
Source: *Fulvimarina pelagi*

SEQ ID NO: 46

LTSSAKQKVDIALVGGGLANGLIAWRLAELRPDLSIVVLEAGEAPGGNHTWSFHEHDLTPAAHRWIA

PFVAHRWTTNEVQFPDRHRHLSTGYLSASSDLFRERLTTRLGLRIRTGCPAVSVTARKVRLENGEVIE

AGSVIDGRGYRSSEHLTLGFQKFLGQEIEFEAPHGVARPVIMDATVPQADGYRFVYLLPMTPTRLLVE

DTYYADGDALDRGTIRRNIAAYRAAKGWPAGKVVREEDGVLPIALAGDIEAFWEEKQGVPSSGLNA

ALFHPTTGYSLPDAVYLADLIAGLPDYSAATLYAATRRHSVATWKRRGFFRMLNRLLYLAGDPLKR

YVILQHFYRLPEPLVSRFYAARLTRGDKVRILTGKPPVSVISALKVLSPSSVEGAPA* crtI_Fp
Source: *Fulvimarina pelagi*

SEQ ID NO: 47

MNQMPRDLPNKTKTAVVIGAGFGGLALAIRLQAAGIQTTLLEKRDKPGGRAYVYEDQGFTFDAGPT

VITDPSALEELFETANAKLSDYVELLPVKPFYRLAWEDGFVFDYADDQEDLDRQIGAKNPKDVEGYR

RFLAYSRDVFHEGYEKLGTVPFLNFKDMMRAAPQLVRLEAYRSVYSKVAQFIEDDQLRQAFSFHSLL

VGGNPFATSSIYALIHALERKWGVFFPRGGTGALVRGMAKLFTDIGGRIEVNAEVENIAIENGRAKSV

TTKGGQTFPADFVASNADVVHTYAKLMGRSERGKKHGNSLKKKRFSMSLFVIYFGLKTHRPDIAHH

TVCFGPRYRPLIDEIFKGKELAGDFSLYLHNPCVTDPSLAPEGMGSFYVLSPVPHLGNADIDWAVEGP

KYRDRILDYLEELYIPGLKDDLVTSRIFTPADFKTELNAHLGSAFSLDPVLTQSAWFRPHNRDDQIPNL

YVVGAGTHPGAGVPGVVGSAKATAGLMIEDAGLACVPA*

-continued crtB_Fp
Source: *Fulvimarina pelagi*

SEQ ID NO: 48

MSFADRLDVPIVGGLPFEKRERAALAAEAEATIAQGSKSFAAAARLFDPEMRVSALMLYAWCRHCD

DVVDDQILGFRQPGRRDRAGDRARLDELEAKTLAAVRGRSTGEAPFDAIGDVALRHELPESLLTAHL

EGFRMDVDGRVYEVIEDTLDYCYRVAGVVGVMMARVMGIRVENGSKFDLTLTLDRACDLGMAFQ

LTNIARDIVDDGEAGRVYVPKTWLDAAGVPGSAIHHPRNREAAAVFALRLLDLAEPYYASASKGLA

ALPPRAAWAVATALGVYREIGTVIRRRGSQAWDDRSSTSAATKFLHAFKGVGWTMGSRVSSRRGVR

PPELWTRPRLLELGDAPTTGLSA* crtW_Fp
Source: *Fulvimarina pelagi*

SEQ ID NO: 49

MTLSPTSRLIPASALPRSTPADSPKIRPYQTTIGLTLCAVLLASWFAIHVSAIFFLDINFSTLPLAPLITVF

QCWLTVGLFILAHDAMHGSLAPGRTRLNAVIGGFILFVYAGFAWKKIRDAHFAHHDAPGTPADPDFY

ADDPENFWPWFGTFFSRYFGWRSVAFVSTVVTFYLVILDASVTNVVLFYGLPSLLSSLQLFYFGTYRP

HRHEESGTFADAHNTRSSEFGYVASLFSCFHFGYHHEHHLAPWTPWWALPHTRQS* crtZ_Fp
Source: *Fulvimarina pelagi*

SEQ ID NO: 50

MTIWTLYYVCLTLVTIGLMEVYAWWAHKFIMHGKFGWGWHKSHHEETEGWFEKNDLYAVVFAGF

AIALFMVGHFLSPTLLAIAWGITLYGLLYFVAHDGLVHQRWPFNYVPHRGYAKRLVQAHRLHHAVE

GREHCVSFGFLYAPPIEKLKRDLRESGILERERIERSLDQQGSAHAPVR*

Flank 3, MEXT_3010
Source: *Methylobacterium extorquens* PA1

SEQ ID NO: 51 gtgtcgccagcttcctcttccccggcatcgcccggatgctgttcctgaaccccgtgacgcccaaagttttcgcctggagcgccgaccgggcggcggtgcgtcg cctcatcgacggcaccggctcgcgcctcgacccgcaggggctcgacctctaccggcggctgttcacccgccccggccatgtcgcgggcgccctcggcatga tggcgaactgggatcttccggcactcgcccgcgacctgccggggctcgaaacccgtacgctgctggtcgtcggcggggacgacaaggcgatcaagcccga cgattccttcgccttgcgcgagcggttgcggagcgcacgcgtagaattgctgcgtgggctcggccacctcgcgcacgaggaggcgccggagcgggtggcg gagatcattctggcagaagcggacgcccttggcgcctcggtatcctgagacgcctcttgcgctgacgaaaatcccagccatagtgtcaacct Flank 3, MEXT 3011
Source: *Methylobacterium extorquens* PA1

SEQ ID NO: 51 atgttgacactggccgtcaaaccgactgtcacgtccgactccgatgcccggccgcatgcggtcgtgatcggggccggcttcggcgggctggccgcggcggtt cggctcggcgcccgcggctatcgcgtcaccgttctggaacggctcgaccagcccggcggccgcgcccgcgtccaccgccaggacggcttcaccttcgatgc ggggcccaccatcgtcaccgcgccgttcctgttcgaggagctgtggcggttgtgcgggcgggagatgcgcgaggacgtgactctcgtgccgatgcagccatt ctaccgcattcgcttcgaggatgggcagagcttcgcctatagcggcgaccgcgcggcgatgcgggccgaggtcgcccgcttctcgcccgacgacgtgtccg gctacgaacgcttcatggcccatagcgaggcggtgtgccggatgggcttcgaggaactcggccacgtcccgttcggcagcctcggctcgatgctgcggatcg cgcccgatctgctgcgcttgtcgggccaccgcagcgtctacgacgtggtgtcccgcttcatccgcgacgagcggctgcgcaccatcttcagcttccatcccctg ctcatcggcggcaacccgtttcgcgccagcggcatctactgcctgatcgcccatctggagcggcaatggggcgtccatttcgccatgggcggtaccggacgac tggtggacgggctctgcggcttgatccgggggcagggaggccgcgtccgctgcggcgaggacgtttcgcgcatccgcgtcgaggatgcgcgggcgacgg gtgtggtgctggcgggcggcgaggtcatccccgccgacaccgtcgtctcgaacgccgattccgccttcacctacggcacgctgctcggcggccggacccgg cgctggagcgcgcggcgcctggcgcgcgcctcgtcctccatggggctgttcgtctggtatttcggtacccggaagaagtacccggaggtcgatcaccacatga tcctgatgggcccgcgctatcgcggcctgttgcaggacatcttcgaccgcaagcacttggcgaacgatttcagcctctatctccaccgcccgaccgcgaccgac ccgctgctcgcgccgcccggctgcgacgcgttctacgtgctcgccccggtgccgaacctcgacggcggccaggattgggcacagcttgccgagccctaccg ccagcggatcgcgcgcttcctcgaaggctcggtgctgccggggctgtccgacgccctcgtcacctcgcgggtgacgacgccgcaggacttttccgacgacttc ctgagcttccgcggctccgggttcgggctggagccggtgctgacgcaatcggcgtggttccgtccgcacaaccgctcggaagacgtggccaacctcttcctcg tcggcgcggggacgcatcccggcgccggtctgccgggcgtgctgtcctcggcgcgtgtcctcgattccgtggtgccggatgcccgtgtttgcgcctgaccctttt -continued cgccgccagcgcggcggaccgctctgcctgccgggccgcgatccgcgccggctccaagagcttcttcgcggcctcgctgctgctgccgccctcagtgcggg tctcggcctacggcctctacgccttctgccgcctttccgacgatgcggtggacgaggcgggggcaaccgtgctgcggccctcgcccgcctggaacgacggc tgacagcggcctgtgccggccggcccgacaaccacccggccgaccgggcgctcgccgaggtgctcgcccgccacgccatcccggaaaagctgccgcgg gcgctgctcgaagggttggcctgggacacgcaaggccggcgctacgacaccctgtcggagctggccgcctatgccgcccgggtcgcgggcgcggtcggg gcgatgatgacactggtgatgggggtgcgcgacggccccgcgctcgcccgcgcctgcgatctcggcgtggccatgcaattcaccaacatcgcccgcgatgtc ggcgaggatgcccgcgccgggcgcctctacctgcctcgcgagtggctcgacgcggccggcatcgacccggacgccttcctcgccgagcctcggctcggcc ccagcctgcaacgggtggtggccgagctgctggcggcggccgacgaactctacgcccgcgccgaacccggcatcgccgcgctcccgttgagctgccgccc ggcgatccgcgccgccggcctgatctacgcggagatcggccgtgccgtggaggcgaacgagctcgattcggtcacgcgccgcgcccgcgtcaccggcgc gcgcaaggccgggcttctggccaccgcgatcctgcccgcgggcggcggccagggactatcggcgccgccattgcccgagaccgccttcctcgtggaagcc gtgacgcaccatccggtcccagccgcgcggcgcttgccaccgtggtggaacgtgtcggggcaggtcgtgcgggtgctcgacctgatcgaggtgctggagga gcgcgacgccttccgccgctcggccgcgtcgtaaggaa

---

We claim:

1. A biomass that comprises at least one C40 carotenoid compound, wherein said biomass is produced according to a method that comprises culturing a bacterial cell from the class Alphaproteobacteria in a culture medium under conditions suitable for growth of the bacterial cell and production of said C40 carotenoid compound, wherein said at least one C40 carotenoid compound is astaxanthin, canthaxanthin, zeaxanthin, phoenicoxanthin, adonixanthin, 3-hydroxyechinenone, echinenone, β-carotene, or lycopene, or a combination thereof, and wherein said biomass having said C40 carotenoid compound is produced in the culture, wherein said bacterial cell comprises a heterologous polynucleotide sequence from *Paracoccus zeaxanthinfaciens, Escherichia vulneris*, or *Pantoea ananatis* that encodes a polypeptide of a C40 carotenoid biosynthetic pathway or comprises a polynucleotide sequence that has at least 70% sequence identity thereto and that retains the biological activity thereof or comprises a polynucleotide sequence that encodes a polypeptide that has at least 70% sequence identity to the polypeptide of the C40 carotenoid biosynthetic pathway and that retains the biological activity thereof, operably linked to a promoter for expression of said polynucleotide sequence, and wherein the bacterial cell expresses said heterologous polynucleotide sequence to produce said at least one C40 carotenoid compound, and wherein said bacterial cell further comprises:

(i) a polynucleotide sequence that expresses the heterologous gene sequence idi from *Escherichia vulneris* or a polynucleotide sequence that has at least about 70% sequence identity thereto and that retains the biological activity thereof or comprises a polynucleotide sequence that encodes a polypeptide that has at least 70% sequence identity to the encoded idi polypeptide from *Escherichia vulneris* and that retains the biological activity thereof, (ii) heterologous polynucleotide sequences that have the gene sequences crtY, crtI, crtB, and crtE from *Fulvimarina pelagi* or polynucleotide sequences that have at least about 70% sequence identity thereto or polynucleotide sequences that encode polypeptides that have at least 70% sequence identity to the encoded crtY, crtI, and crtB from *Fulvimarina pelagi;*

(iii) at least one heterologous polynucleotide comprising polynucleotide sequences that have the gene sequences crtZ, crtY, crtI, crtB, and crtE from *Paracoccus zeaxanthinifaciens, Escherichia vulneris*, and/or *Pantoea ananatis* or polynucleotide sequences that have at least about 70% sequence identity thereto and that retain the biological activity thereof or polynucleotide sequences that that encode polypeptides that at least about 70% identity to the encoded by crtZ, crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein the biomass comprises zeaxanthin produced by the bacterial cell; or (iv) at least one heterologous polynucleotide having the gene sequences crtY, crtI, crtB, and crtE from *Paracoccus zeaxanthinfaciens, Escherichia vulneris*, and/or *Pantoea ananatis* or polynucleotide sequences that have at least about 70% sequence identity thereto and that retain the biological activity thereof or polynucleotide sequences that have least 70% identity to the encoded crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein the biomass comprises β-carotene produced by the bacterial cell.

2. A feed or nutritional supplement composition comprising the biomass produced according to claim 1, wherein said feed or nutritional supplement comprises said at least one C40 carotenoid compound.

3. The biomass according to claim 1, wherein the bacterial cell is in the genus *Methylobacteria.*

4. The biomass according to claim 3, wherein the bacterial cell is *Methylobacterium extorquens.*

5. The biomass according to claim 1, wherein said bacterial cell comprises at least one heterologous polynucleotide comprising polynucleotide sequences that have the gene sequences crtZ, crtY, crtI, crtB, and crtE from *Paracoccus zeaxanthinifaciens, Escherichia vulneris*, and/or *Pantoea ananatis* or polynucleotide sequences that have at least about 70% sequence identity thereto and that retain the biological activity thereof or polynucleotide sequences that that encode polypeptides that have at least about 70% identity to the encoded by crtZ, crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein said bacterial cell further comprises a heterologous polynucleotide sequence that has the gene sequences crtW from *Fulvimarina pelagi* or a polynucleotide sequence that has at least about 70% sequence identity thereto and retains the biological activity thereof or a polynucleotide sequence that encodes a polypeptide that has at least about 70% sequence identity to the encoded crtW polypeptide from *Fulvimarina pelagi* and that retains the biological activity thereof, wherein the biomass comprises astaxanthin produced by the bacterial cell.

6. The biomass according to claim 1, wherein said bacterial cell comprises at least one heterologous polynucleotide having the gene sequences crtY, crtI, crtB, and crtE from *Paracoccus zeaxanthinifaciens, Escherichia vulneris*, and/or *Pantoea ananatis* or polynucleotide sequences that have at least about 70% sequence identity thereto and that retain the biological activity thereof or comprise polynucleotide sequences that have least 70% identity to the encoded crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein said bacterial cell further comprises a heterologous polynucleotide sequence that has the gene sequences crtW from *Fulvimarina pelagi* or a polynucleotide sequence that has at least about 70% sequence identity thereto and retains the biological activity thereof or a polynucleotide sequence that encodes a polypeptide that has at least about 70% sequence identity to the encoded crtW polypeptide from *Fulvimarina pelagi* and that retains the biological activity thereof, wherein the biomass comprises castaxanthin produced by the bacterial cell.

7. The biomass according to claim 1, wherein said method comprises production of said at least one C40 carotenoid compound by consuming at least one C1 compound as a carbon source.

8. The biomass according to claim 1, wherein said method comprises production of said at least one C40 carotenoid compound by consuming at least one C2 compound as a carbon source.

9. The biomass according to claim 1, wherein said method comprises production of said at least one C40 carotenoid compound by consuming at least one C1 alcohol and/or at least one C2 alcohol as a carbon source.

10. The biomass according to claim 9, wherein said at least one C1 alcohol and/or at least one C2 alcohol comprises methanol and/or ethanol.

11. A biomass that comprises at least one C40 carotenoid compound, wherein said biomass is from a bacterial cell from the class Alphaproteobacteria, wherein said bacterial cell comprises a heterologous polynucleotide sequence from *Paracoccus zeaxanthinfaciens, Escherichia vulneris*, or *Pantoea ananatis* that encodes a polypeptide of a C40 carotenoid biosynthetic pathway or a polynucleotide sequence that has at least 70% sequence identity thereto and that retains the biological activity thereof or comprises a polynucleotide sequence that encodes a polypeptide that has at least 70% sequence identity to the polypeptide of the C40 carotenoid biosynthetic pathway and that retains the biological activity thereof, operably linked to a promoter for expression of said polynucleotide sequence, and wherein the bacterial cell expresses said heterologous polynucleotide sequence to produce said at least one C40 carotenoid compound, and wherein said at least one C40 carotenoid compound is astaxanthin, canthaxanthin, zeaxanthin, phoenicoxanthin, adonixanthin, 3-hydroxyechinenone, echinenone, β-carotene, or lycopene, or a combination thereof, and wherein said bacterial cell further comprises:

(v) a polynucleotide sequence that expresses the heterologous gene sequence idi from *Escherichia vulneris* or a polynucleotide sequence that has at least about 70% sequence identity thereto and that retains the biological activity thereof or comprises a polynucleotide sequence that encodes a polypeptide that has at least 70% sequence identity to the encoded idi polypeptide from *Escherichia vulneris* and that retains the biological activity thereof, (vi) heterologous polynucleotide sequences that have the gene sequences crtY, crtI, crtB, and crtE from *Fulvimarina pelagi* or polynucleotide sequences that have at least about 70% sequence identity thereto or polynucleotide sequences that encode polypeptides that have at least 70% sequence identity to the encoded crtY, crtI, and crtB from *Fulvimarina pelagi;*

(vii) at least one heterologous polynucleotide comprising polynucleotide sequences that have the gene sequences crtZ, crtY, crtI, crtB, and crtE from *Paracoccus zeaxanthinfaciens, Escherichia vulneris*, and/or *Pantoea ananatis* or polynucleotide sequences that have at least about 70% sequence identity thereto and that retain the biological activity thereof or polynucleotide sequences that that encode polypeptides that have at least about 70% identity to the encoded by crtZ, crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein the biomass comprises zeaxanthin produced by the bacterial cell; or (viii) wherein said bacterial cell comprises at least one heterologous polynucleotide having the gene sequences crtY, crtI, crtB, and crtE from *Paracoccus zeaxanthinfaciens, Escherichia vulneris*, and/or *Pantoea ananatis* or comprises polynucleotide sequences that have at least about 70% sequence identity thereto and that retain the biological activity thereof or comprise polynucleotide sequences that have least 70% identity to the encoded crtY, crtI, crtB, and crtE polypeptides from *Paracoccus zeaxanthinifaciens, Escherichia vulneris*, and/or *Pantoea ananatis* and that retain the biological activity thereof, operably linked to a promoter for expression of said polynucleotide sequences, wherein the biomass comprises β-carotene produced by the bacterial cell.

12. A feed or nutritional supplement composition comprising the biomass produced according to claim 11, wherein said feed or nutritional supplement comprises said at least one C40 carotenoid compound.

13. The biomass according to claim 11, wherein the bacterial cell is in the genus *Methylobacteria.*

14. The biomass according to claim 11, wherein said bacterial cell comprises at least one heterologous polynucleotide comprising polynucleotide sequences that have the gene sequences crtZ, crtY, crtI, crtB, and crtE from *Paracoccus zeaxanthinfaciens, Escherichia vulneris*, and/or *Pantoea ananatis* or polynucleotide sequences that have at least about 70% sequence identity thereto and that retain the biological activity thereof or polynucleotide sequences that that encode polypeptides that have at least about 70% identity to the encoded by crtZ, crtY, crtI, crtB, and crtE polypeptides from *Paracoccus zeaxanthinfaciens, Escherichia vulneris*, and/or *Pantoea ananatis* and that retain the biological activity thereof, operably linked to a promoter for expression of said polynucleotide sequences, wherein said bacterial cell further comprises a heterologous polynucleotide sequence that has the gene sequences crtW from *Fulvimarina pelagi* or a polynucleotide sequence that has at least about 70% sequence identity thereto and retains the biological activity thereof or a polynucleotide sequence that encodes a polypeptide that has at least about 70% sequence identity to the encoded crtW polypeptide from *Fulvimarina pelagi* and that retains the biological activity thereof, wherein the biomass comprises astaxanthin produced by the bacterial cell.

15. The biomass according to claim 11, wherein said bacterial cell comprises at least one heterologous polynucleotide having the gene sequences crtY, crtI, crtB, and crtE from *Paracoccus zeaxanthinfaciens, Escherichia vulneris*, and/or *Pantoea ananatis* or polynucleotide sequences that have at least about 70% sequence identity thereto and that retain the biological activity thereof or polynucleotide sequences that have least 70% identity to the encoded crtY, crtI, crtB, and crtE polypeptides from *Paracoccus zeaxanthinfaciens, Escherichia vulnearis*, and/or *Pantoea ananatis* and that retain the biological activity thereof, operably linked to a promoter for expression of said polynucleotide sequences, wherein said bacterial cell further comprises a heterologous polynucleotide sequence that has the gene sequences crtW from *Fulvimarina pelagi* or a polynucleotide sequence that has at least about 70% sequence identity thereto and retains the biological activity thereof or a polynucleotide sequence that encodes a polypeptide that has at least about 70% sequence identity to the encoded crtW polypeptide from *Fulvimarina pelagi* and that retains the biological activity thereof, wherein the biomass comprises castaxanthin produced by the bacterial cell.

16. The biomass according to claim 13, wherein the bacterial cell is *Methylobacterium extorquens.*

* * * * *

SEQUENCE LISTING

```
Sequence total quantity: 52
SEQ ID NO: 1            moltype = DNA  length = 6760
FEATURE                 Location/Qualifiers
misc_feature            1..6760
                        note = Description of Artificial Sequence: Synthetic
                         polynucleotide
source                  1..6760
                        mol_type = other DNA
                        organism = synthetic construct
SEQUENCE: 1
acccacgctc accggctcca gatttatcag caataaacca gccagccgga agggccgagc  60
gcagaagtgg tcctgcaact ttatccgcct ccatccagtc tattaatatc cccgtgtcgg  120
acctgcaggg ggggggggga aagccacgtt gtgtctcaaa atctctgatg ttacattgca  180
caagataaaa atatatcatc atgaacaata aaactgtctg cttacataaa cagtaataca  240
aggggtgtta tgagccatat tcaacgggaa acgtcttgct cgaggccgcg attaaattcc  300
aacatggatg ctgatttata tgggtataaa tgggctcgcg ataatgtcgg gcaatcaggt  360
gcgacaatct atcgattgta tgggaagccc gatgcgccag agttgtttct gaaacatggc  420
aaaggtagcg ttgccaatga tgttacagat gagatggtca gactaaactg gctgacggaa  480
tttatgcctc ttccgaccat caagcatttt atccgtactc ctgatgatgc atggttactc  540
accactgcga tccccgggaa aacagcattc caggtattag aagaatatcc tgattcaggt  600
gaaaatattg ttgatgcgct ggcagtgttc ctgcgccggt tgcattcgat tcctgtttgt  660
aattgtcctt ttaacagcga tcgcgtattt cgtctcgctc aggcgcaatc acgaatgaat  720
aacggtttgg ttgatgcgag tgattttgat gacgagcgta atggctggcc tgttgaacaa  780
gtctggaaag aaatgcataa gcttttgcca ttctcaccgg attcagtcgt cactcatggt  840
gatttctcac ttgataacct tatttttgac gaggggaaat taataggttg tattgatgtt  900
ggacgagtcg gaatcgcaga ccgataccag gatcttgcca tcctatggaa ctgcctcggt  960
gagttttctc cttcattaca gaaacggctt tttcaaaaat atggtattga taatcctgat  1020
atgaataaat tgcagtttca tttgatgctc gatgagtttt tctaatcaga attggttaat  1080
tggttgtaac actggcagag cattacgctg acttgacggg acggaatatt attgaagcat  1140
ttatcagggt tattgtctca tgagcggata catatttgaa tgtatttaga aaaataaaca  1200
aataggggtt ccgcgcacat ttccccgaaa agtgccacct gacgtctaga tctgaattca  1260
gctgtacaat tggtaccatg gatgggaggg cagcaggtgg gaaagcgggc agtgagcgca  1320
acgcaattaa tgtgagttag ctcactcatt aggcacccca ggctttacac tttatgcttc  1380
cggctcgtat gttgtgtgga attgtgagcg gataacaatt tcacacagga aacagctatg  1440
accatgatta cgccaagcta tttaggtgac actatagaat actcaagcta tgcatcaagc  1500
ttggtaccga gctcggatcc actagtaacg gccgccagtg tgctggaatt cgcccttcac  1560
ctgctgccag tacatatgct gcagctcgag cggccgcggg ccctacgtac gcgtgttaac  1620
cggtgagctc actagaggat ccagccgacc aggctttcca cgcccgcgtg ccgctccatg  1680
tcgttcgcgc ggttctcgga aacgcgctgc cgcgtttcgt gattgtcacg ctcaagcccg  1740
tagtcccgtt cgagcgtcgc gcagaggtca gcgagggcgc ggtaggcccg atacggctca  1800
tggatggtgt ttcgggtcgg gtgaatcttg ttgatggcga tatggatgtg caggttgtcg  1860
gtgtcgtgat gcacggcact gacgcgctga tgctcggcga agccaagccc agcgcagatg  1920
cggtcctcaa tcgcgcgcaa cgtctccgcg tcgggcttct ctcccgcgcg gaagctaacc  1980
agcacgtgat aggtcttgtc ggcctcggaa cgggtgttgc cgtgctgggt cgccatcacc  2040
tcggccatga cagcgggcag ggtgtttgcc tcgcagttcg tgacgcgcac gtgacccagg  2100
cgctcggtct tgccttgctc gtcggtgatg tacttcacca gctccgcgaa gtcgctcttc  2160
ttgatggagc gcatggggac gtgcttggca atcacgcgca ccccccggcc gttttagcgg  2220
ctaaaaaagt catggctctg ccctcgggcg gaccacgccc atcatgacct tgccaagctc  2280
gtcctgcttc tcttcgatct tcgccagcag ggcgaggatc gtggcatcac cgaaccgcgc  2340
cgtgcgcggg tcgtcggtga gccagagttt cagcaggccg cccaggcggc ccaggtcgcc  2400
attgatgcgg gccagctcgc ggacgtgctc atagtccacg acgcccgtga ttttgtagcc  2460
ctggccgacg gccagcaggt aggccgacag gctcatgccg gccgccgccg cctttcctc  2520
```

-continued

```
aatcgctctt cgttcgtctg gaaggcagta caccttgata ggtgggctgc ccttcctggt  2580
tggcttggtt tcatcagcca tccgcttgcc ctcatctgtt acgccggcgg tagccggcca  2640
gcctcgcaga gcaggattcc cgttgagcac cgccaggtgc gaataaggga cagtgaagaa  2700
ggaacacccg ctcgcgggtg ggcctacttc acctatcctg cccggctgac gccgttggat  2760
acaccaagga aagtctacac gaaccctttg gcaaaatcct gtatatcgtg cgaaaaagga  2820
tggatatacc gaaaaaatcg ctataatgac cccgaagcag ggttatgcag cggaaaagcg  2880
ctgcttccct gctgttttgt ggaatatcta ccgactggaa acaggcaaat gcaggaaatt  2940
actgaactga ggggacaggc gagagacgat gccaaagagc tacaccgacg agctggccga  3000
gtgggttgaa tcccgcgcgg ccaagaagcg ccggcgtgat gaggctgcgg ttgcgttcct  3060
ggcggtgagg gcggatgtcg aggcggcgtt agcgtccggc tatgcgctcg tcaccatttg  3120
ggagcacatg cgggaaacgg ggaaggtcaa gttctcctac gagacgttcc gctcgcacgc  3180
caggcggcac atcaaggcca agcccgccga tgtgcccgca ccgcaggcca aggctgcgga  3240
acccgcgccg gcacccaaga cgccggagcc acggcggccg aagcaggggg gcaaggctga  3300
aaagccggcc cccgctgcgg ccccgaccgg cttcaccttc aacccaacac cggacaaaaa  3360
ggatccccaa ttctcatgtt tgacagctta tcatcgataa gctttaatgc ggtagtttat  3420
cacagttaaa ttgctaacgc agtcaggcac cgtgtatgaa atctaacaat gcgctcatcg  3480
tcatcctcgg caccgtcacc ctggatgctg taggcatagg cttggttatg ccggtactgc  3540
cgggcctctt gcgggatatc ggcattttct tttgcgtttt tatttgttaa ctgttaattg  3600
tccttgttca aggatgctgt ctttgacaac agatgttttc ttgcctttga tgttcagcag  3660
gaagcttggc gcaaacgttg attgtttgtc tgcgtagaat cctctgtttg tcatatagct  3720
tgtaatcacg acattgtttc ctttcgcttg aggtacagcg aagtgtgagt aagtaaaggt  3780
tacatcgtta ggatcaagat ccatttttaa cacaaggcca gttttgttca gcggcttgta  3840
tgggccagtt aaagaattag aaacataacc aagcatgtaa atatcgttag acgtaatgcc  3900
gtcaatcgtc atttttgatc cgcgggagtc agtgaacagg taccatttgc cgttcatttt  3960
aaagacgttc gcgcgttcaa tttcatctgt tactgtgtta gatgcaatca gcggtttcat  4020
cactttttc agtgtgtaat catcgtttag ctcaatcata ccgagagcgc cgtttgctaa  4080
ctcagccgtg cgttttttat cgctttgcag aagtttttga ctttcttgac ggaagaatga  4140
tgtgcttttg ccatagtatg ctttgttaaa taaagattct tcgccttggt agccatcttc  4200
agttccagtg tttgcttcaa atactaagta tttgtggcct ttatcttcta cgtagtgagg  4260
atctctcagc gtatggttgt cgcctgagct gtagttgcct tcatcgatga actgctgtac  4320
attttgatac gtttttccgt caccgtcaaa gattgattta taatcctcta caccgttgat  4380
gttcaaagag ctgtctgatg ctgatacgtt aacttgtgca gttgtcagtg tttgtttgcc  4440
gtaatgttta ccggagaaat cagtgtagaa taaacggatt tttccgtcag atgtaaatgt  4500
ggctgaacct gaccattctt gtgtttggtc ttttaggata gaatcatttg catcgaattt  4560
gtcgctgtct ttaaagacgc ggccagcgtt tttccagctg tcaatagaag tttcgccgac  4620
tttttgatag aacatgtaaa tcgatgtgtc atccgcattt ttaggatctc cggctaatgc  4680
aaagacgatg tggtagccgt gatagtttgc gacagtgccg tcagcgtttt gtaatggcca  4740
gctgtcccaa acgtccaggc cttttgcaga agagatattt ttaattgtgg acgaatcgaa  4800
ttcaggaact tgatattttt catttttttg ctgttcaggg atttgcagca tatcatggcg  4860
tgtaatatgg gaaatgccgt atgtttcctt atatggcttt tggttcgttt ctttcgcaaa  4920
cgcttgagtt gcgcctcctg ccagcagtgc ggtagtaaag gttaatactg ttgcttgttt  4980
tgcaaacttt ttgatgttca tcgttcatgt ctcctttttt atgtactgtg ttagcggtct  5040
gcttcttcca gccctcctgt ttgaagatgg caagttagtt acgcacaata aaaaaagacc  5100
taaaatatgt aaggggtgac gccaaagtat acactttgcc ctttacacat tttaggtctt  5160
gcctgcttta tcagtaacaa acccgcgcga tttacttttc gacctcattc tattagactc  5220
tcgtttggat tgcaactggt ctattttcct cttttgtttg atagaaaatc ataaaaggat  5280
ttgcagacta cgggcctaaa gaactaaaaa atctatctgt ttcttttcat tctctgtatt  5340
ttttatagtt tctgttgcat gggcataaag ttgccttttt aatcacaatt cagaaaatat  5400
cataatatct catttcacta aataatagtg aacggcaggt atatgtgatg ggttaaaaag  5460
gatcgatcct ctagccacgg gtgcgcatga tcgtgctcct gtcgttgagg acccggctag  5520
gctggcgggg ttgccttact ggttagcaga atgaatcacc gatacgcgag cgaacgtgaa  5580
gcgactgctg ctgcaaaacg tctgcgacct gagcaacaac atgaatggtc ttcggtttcc  5640
gtgtttcgta aagtctggaa acgcggaagt cagcgctctt ccgcttcctc gctcactgac  5700
tcgctgcgct cggtcgttcg gctgcggcga gcggtatcag ctcactcaaa ggcggtaata  5760
cggttatcca cagaatcagg ggataacgca ggaaagaaca tgtgagcaaa aggccagcaa  5820
aaggccagga accgtaaaaa ggccgcgttg ctggcgtttt tccataggct ccgcccccct  5880
gacgagcatc acaaaaatcg acgctcaagt cagaggtggc gaaacccgac aggactataa  5940
agataccagg cgtttccccc tggaagctcc ctcgtgcgct ctcctgttcc gaccctgccg  6000
cttaccggat acctgtccgc ctttctccct tcgggaagcg tggcgctttc tcatagctca  6060
cgctgtaggt atctcagttc ggtgtaggtc gttcgctcca agctgggctg tgtgcacgaa  6120
ccccccgttc agcccgaccg ctgcgcctta tccggtaact atcgtcttga gtccaacccg  6180
gtaagacacg acttatcgcc actggcagca gccactggta acaggattag cagagcgagg  6240
tatgtaggcg gtgctacaga gttcttgaag tggtggccta actacggcta cactagaagg  6300
acagtatttg gtatctgcgc tctgctgaag ccagttacct tcggaaaaag agttggtagc  6360
tcttgatccg gcaaacaaac caccgctggt agcggtggtt tttttgtttg caagcagcag  6420
attacgcgca gaaaaaaagg atctcaagaa gatcctttga tcttttctac ggggtctgac  6480
gctcagtgga acgaaaactc acgttaaggg attttggtca tgagattatc aaaaaggatc  6540
ttcacctaga tccttttaaa ttaaaaatga agttttaaat caatctaaag tatatatgag  6600
taaacttggt ctgacagtta ccaatgctta atcagtgagg cacctatctc agcgatctgt  6660
ctatttcgtt catccatagt tgcctgactc cccgtcgtgt agataactac gatacgggag  6720
ggcttaccat ctggccccag tgctgcaatg ataccgcgag                        6760
```

```
SEQ ID NO: 2            moltype = DNA  length = 7115
FEATURE                 Location/Qualifiers
misc_feature            1..7115
                        note = Description of Artificial Sequence: Synthetic
                         polynucleotide
source                  1..7115
                        mol_type = other DNA
```

```
                         organism = synthetic construct
SEQUENCE: 2
gtgtcgatgg tcatcgactt cgccaaacct gccgcctcct gttcgagacg acgcgaacgc  60
tccacggcgg ccgatggcgc gggcagggca gggggagcca gttgcacgct gtcgcgctcg  120
atcttggccg tagcttgctg gaccatcgag ccgacggact ggaaggtttc gcggggcgca  180
cgcatgacgg tgcggcttgc gatggtttcg gcatcctcgg cggaaaaccc cgcgtcgatc  240
agttcttgcc tgtatgcctt ccggtcaaac gtccgattca ttcaccctcc ttgcgggatt  300
gccccgactc acgccggggc aatgtgccct tattcctgat ttgacccgcc tggtgccttg  360
gtgtccagat aatccacctt atcggcaatg aagtcggtcc cgtagaccgt ctggccgtcc  420
ttctcgtact tggtattccg aatcttgccc tgcacgaata ccagctccgc gaagtcgctc  480
ttcttgatgg agcgcatggg gacgtgcttg gcaatcacgc gcacccccg gccgttttag  540
cggctaaaaa agtcatggct ctgccctcgg gcggaccacg cccatcatga ccttgccaag  600
ctcgtcctgc ttctcttcga tcttcgccag cagggcgagg atcgtggcat caccgaaccg  660
cgccgtgcgc gggtcgtcgg tgagccagag tttcagcagg ccgcccaggc ggcccaggtc  720
gccattgatg cgggccagct cgcggacgtg ctcatagtcc acgacgcccg tgattttgta  780
gccctggccg acggccagca ggtaggccta caggctcatg ccggccgccg ccgccttttc  840
ctcaatcgct cttcgttcgt ctggaaggca gtacaccttg ataggtgggc tgcccttcct  900
ggttggcttg gtttcatcag ccatccgctt gccctcatct gttacgccgg cggtagccgg  960
ccagcctcgc agagcaggat tcccgttgag caccgccagg tgcgaataag ggacagtgaa  1020
gaaggaacac ccgctcgcgg gtgggcctac ttcacctatc ctgcccggct gacgccgttg  1080
gatacaccaa ggaaagtcta cacgaaccct ttggcaaaat cctgtatatc gtgcgaaaaa  1140
ggatggatat accgaaaaaa tcgctataat gaccccgaag cagggttatg cagcggaaaa  1200
gatccgtcga ccctttccga cgctcaccgg gctggttgcc ctcgccgctg ggctggcggc  1260
cgtctatggc cctgcaaacg cgccagaaac gccgtcgaag ccgtgtgcga gacaccgcgg  1320
ccgccggcgt tgtggatacc tcgcggaaaa cttggccctc actgacagat gaggggcgga  1380
cgttgacact tgaggggccg actcacccgg cgcggcgttg acagatgagg ggcaggctcg  1440
atttcggccg gcgacgtgga gctggccagc ctcgcaaatc ggcgaaaacg cctgatttta  1500
cgcgagtttc ccacagatga tgtggacaag cctggggata agtgccctgc ggtattgaca  1560
cttgagggc gcgactactg acagatgagg ggcgcgatcc ttgacacttg aggggcagag  1620
tgctgacaga tgaggggcgc acctattgac atttgagggg ctgtccacag gcagaaaatc  1680
cagcatttgc aagggtttcc gcccgttttt cggccaccgc taacctgtct tttaacctgc  1740
ttttaaacca atatttataa accttgtttt taaccagggc tgcgccctgt gcgcgtgacc  1800
gcgcacgccg aaggggggtg cccccccttc tcgaaccctc ccggcccgct aacgcgggcc  1860
tcccatcccc ccaggggctg cgcccctcgg ccgcgaacgg cctcacccca aaaatggcag  1920
ccaagctgac cacttctgcg ctcggccctt ccggctggct ggtttattgc tgataaatct  1980
ggagccggtg agcgtgggtc tcgcggtatc attgcagcac tggggccaga tggtaagccc  2040
tcccgtatcg tagttatcta cacgacgggg agtcaggcaa ctatggatga acgaaataga  2100
cagatcgctg agataggtgc ctcactgatt aagcattggt aactgtcaga ccaagtttac  2160
tcatatatac tttagattga tttaaaactt catttttaat ttaaaaggat ctaggtgaag  2220
atcctttttg ataatctcat gaccaaaatc ccttaacgtg agttttcgtt ccactgagcg  2280
tcagaccccg tagaaaagat caaaggatct tcttgagatc cttttttct gcgcgtaatc  2340
tgctgcttgc aaacaaaaaa accaccgcta ccagcggtgg tttgtttgcc ggatcaagag  2400
ctaccaactc tttttccgaa ggtaactggc ttcagcagag cgcagatacc aaatactgtt  2460
cttctagtgt agccgtagtt aggccaccac ttcaagaact ctgtagcacc gcctacatac  2520
ctcgctctgc taatcctgtt accagtggct gctgccagtg gcgataagtc gtgtcttacc  2580
gggttggact caagacgata gttaccggat aaggcgcagc ggtcgggctg aacggggggt  2640
tcgtgcacac agcccagctt ggagcgaacg acctacaccg aactgagata cctacagcgt  2700
gagctatgag aaagcgccac gcttcccgaa gggagaaagg cggacaggta tccggtaagc  2760
ggcagggtcg gaacaggaga gcgcacgagg gagcttccag ggggaaacgc ctggtatctt  2820
tatagtcctg tcgggtttcg ccacctctga cttgagcgtc gatttttgtg atgctcgtca  2880
ggggggcgga gcctatggaa aaacgccagc aacgcggcct ttttacggtt cctggccttt  2940
tgctggcctt ttgctcacat gttctttcct gcgttatccc ctgattctgt ggataaccgt  3000
attaccgcct ttgagtgagc tgataccgct cgccgcagcc gaacgaccga gcgcagcgag  3060
tcagtgagcg aggaagcgga agagcgccca atacgcaaac cgcctctccc cgcgcgttgg  3120
ccgattcatt aatgcagctg gcacgacagg tttcccgact actagtccaa caacttatac  3180
catggcctac aaaaaggcaa acaatggtac ttgacgactc atcacaacaa ttgtagttgt  3240
agcagggaga gaccccgagg taccgcttcc tagcaggtgg tgccgctggc gacctgcgtt  3300
tcaccctgcc ataaagaaac tgttacccgt aggtagtcac gcaactcgcc gcacatctga  3360
acttcagcct ccagtacagc gcggctgaaa tcatcattaa agcgagtggc aacatggaaa  3420
tcgctgattt gtgtagtcgg tttatgcagc aacgagacgt cacggaaaat gccgctcatc  3480
cgccacatat cctgatcttc cagataactg ccgtcattcc agcgcagcac catcaccgcg  3540
aggcggtttt ctccggcgcg taaaaatgcg ctcaggtcaa attcagacgg caaacgactg  3600
tcctggccgt aaccgaccca gcgcccgttg caccacagat gaaacgccga gttaacgcca  3660
tcaaaaataa ttcgcgtctg gccttcctgt agccagcttt catcaacatt aaatgtgagc  3720
gagtaacaac ccgtcggatt ctccgtggga acaaacggcg gattgaccgt aatgggatag  3780
gtcacgttgg tgtagatggg cgcatcgtaa ccgtgcatct gccagtttga ggggacgacg  3840
acagtatcgg cctcaggaag atcgcactcc agccagcttt ccggcaccgc ttctggtgcc  3900
ggaaaccagg caaagcgcca ttcgccattc aggctgcgca actgttggga agggcgatcg  3960
gtgcgggcct cttcgctatt acgccagctg gcgaaagggg gatgtgctgc aaggcgatta  4020
agttgggtaa cgccagggtt ttcccagtca cgacgttgta aaacgacggc cagtgaatcc  4080
gtaatcatgg tcatagctgt ttcctgtgta aaattgttat ccgctcacaa ttccacacaa  4140
catacgagcc ggaagcataa agtgtaaagc ctggggtgcc taatgagtga gctaactcac  4200
attaattgcg ttgcgctcac ctgctagggc ctggatccat ggtttaaact caggaattca  4260
cgtgcgcacc tgtgctgggc gcgctgtcgg atcgtttcgg gcggcggcca atcttgctcg  4320
tctcgctggc cggcgccact gtcgactacg ccatcatggc gacagcgcct ttcctttggg  4380
ttctctatat cgggcggatc gtggccggca tcaccggggc gactggggcg gtagccggcg  4440
cttatattgc cgatgacctg caggggggggg ggggcgctga ggtctgcctc gtgaagaagg  4500
tgttgctgac tcataccagg cctgaatcgc cccatcatcc agccagaaag tgagggagcc  4560
acggttgatg agagctttgt tgtaggtgga ccagttggtg attttgaact tttgctttgc  4620
```

```
cacggaacgg tctgcgttgt cgggaagatg cgtgatctga tccttcaact cagcaaaagt  4680
tcgatttatt caacaaagcc gccgtcccgt caagtcagcg taatgctctg ccagtgttac  4740
aaccaattaa ccaattctga ttagaaaaac tcatcgagca tcaaatgaaa ctgcaattta  4800
ttcatatcag gattatcaat accatatttt tgaaaaagcc gtttctgtaa tgaaggagaa  4860
aactcaccga ggcagttcca taggatggca agatcctggt atcggtctgc gattccgact  4920
cgtccaacat caatacaacc tattaatttc ccctcgtcaa aaataaggtt atcaagtgag  4980
aaatcaccat gagtgacgac tgaatccggt gagaatggca aaagcttatg catttctttc  5040
cagacttgtt caacaggcca gccattacgc tcgtcatcaa aatcactcgc atcaaccaaa  5100
ccgttattca ttcgtgattg cgcctgagcg agacgaaata cgcgatcgct gttaaaagga  5160
caattacaaa caggaatcga atgcaaccgg cgcaggaaca ctgccagcgc atcaacaata  5220
ttttcacctg aatcaggata ttcttctaat acctggaatg ctgttttccc ggggatcgca  5280
gtggtgagta accatgcatc atcaggagta cggataaaat gcttgatggt cggaagaggc  5340
ataaattccg tcagccagtt tagtctgacc atctcatctg taacatcatt ggcaacgcta  5400
cctttgccat gtttcagaaa caactctggc gcatcgggct tcccatacaa tcgatagatt  5460
gtcgcacctg attgcccgac attatcgcga gcccatttat acccatataa atcagcatcc  5520
atgttggaat ttaatcgcgg cctcgagcaa gacgtttccc gttgaatatg gctcataaca  5580
ccccttgtat tactgtttat gtaagcagac agttttattg ttcatgatga tatattttta  5640
tcttgtgcaa tgtaacatca gagattttga gacacaacgt ggctttcccc cccccccctg  5700
caggtccgac acggggatgg atggcgttcc cgatcatggt cctgcttgct tcgggtggca  5760
tcggaatgcc ggcgctgcaa gcaatgttgt ccaggcacgt ggatgaggaa cgtcaggggc  5820
agctgcaagg ctcactggcg gcgctcacca gcctgacctc gatcgtcgga cccctcctct  5880
tcacggcgat ctatgcggct tctataacaa cgtggaacgg gtgggcatgg attgcaggcg  5940
ctgccctcta cttgctctgc ctgccggcgc tgcgtcgcgg gctttggagc ggcgcagggc  6000
aacgagccga tcgctgatcg tggaaacgat aggcctatgc catgcgggtc aaggcgactt  6060
ccggcaagct atacgcgccc tagaattgtc aattttaatc ctctgtttat cggcagttcg  6120
tagagcgcgc cgtgcgtccc gagcgatact gagcgaagca agtgcgtcga gcagtgcccg  6180
cttgttcctg aaatgccagt aaagcgctgg ctgctgaacc cccagccgga actgacccca  6240
caaggcccta gcgtttgcaa tgcaccaggt catcattgac ccaggcgtgt tccaccaggc  6300
cgctgcctcg caactcttcg caggcttcgc cgacctgctc gcgccacttc ttcacgcggg  6360
tggaatccga tccgcacatg aggcggaagg tttccagctt gagcgggtac ggctcccggt  6420
gcgagctgaa atagtcgaac atccgtcggg ccgtcggcga cagcttgcgg tacttctccc  6480
atatgaattt cgtgtagtgg tcgccagcaa acagcacgac gatttcctcg tcgatcagga  6540
cctggcaacg ggacgttttc ttgccacggt ccaggacgcg gaagcggtgc agcagcgaca  6600
ccgattccag gtgcccaacg cggtcggacg tgaagcccat cgccgtcgcc tgtaggcgcg  6660
acaggcattc ctcggccttc gtgtaatacc ggccattgat cgaccagccc aggtcctggc  6720
aaagctcgta gaacgtgaag gtgatcggct cgccgatagg ggtgcgcttc gcgtactcca  6780
acagctgctg ccacaccagt tcgtcatcgt cggcccgcag ctcgacgccg gtgtaggtga  6840
tcttcacgtc cttgttgacg tggaaaatga ccttgttttg cagcgcctcg cgcgggattt  6900
tcttgttgcg cgtggtgaac agggcagagc gggccgtgtc gtttggcatc gctcgcatcg  6960
tgtccggcca cggcgcaata tcgaacaagg aaagctgcat ttccttgatc tgctgcttcg  7020
tgtgtttcag caacgcggcc tgcttggcct cgctgacctg ttttgccagg tcctcgccgg  7080
cggtttttcg cttcttggtc gtcatagttc ctcgc                            7115
```

```
SEQ ID NO: 3            moltype = DNA  length = 326
FEATURE                 Location/Qualifiers
source                  1..326
                        mol_type = unassigned DNA
                        organism = Methylobacterium extorquens
SEQUENCE: 3
gttgacgaca acggtgcgat gggtcccggc cccggtcaag acgatgccaa tacgttgcga  60
cactacgcct tggcactttt agaattgcct tatcgtcctg ataagaaatg tccgaccagc  120
taaagacatc gcgtccaatc aaagcctaga aaatataggc gaagggacgc taataagtct  180
ttcataagac cgcgcaaatc taagaatatc cttagattca cgatgcggca cttcggatga  240
cttccgagcg agcctggaac ctcagaaaaa cgtctgagag ataccgcgag gccgaaaggc  300
gaggcggttc agcgaggaga cgcagg                                      326
```

```
SEQ ID NO: 4            moltype = DNA  length = 92
FEATURE                 Location/Qualifiers
misc_feature            1..92
                        note = Description of Artificial Sequence: Synthetic
                         oligonucleotide
source                  1..92
                        mol_type = other DNA
                        organism = synthetic construct
SEQUENCE: 4
ccaacaactt ataccatggc ctacaaaaag gcaaacaatg gtacttgacg actcatcaca  60
acaattgtag ttgtagcagg gagagacccc ga                               92
```

```
SEQ ID NO: 5            moltype = DNA  length = 503
FEATURE                 Location/Qualifiers
source                  1..503
                        mol_type = unassigned DNA
                        organism = Methylobacterium extorquens
SEQUENCE: 5
caccgcgcgg gacttcatct tgccccggca gatgcgcagg gcctccaccg tgcgctcgat  60
cgccgcctcg gtgaggcgat tggaattgcc caatccctcg ccgagccgga cgatgcggga  120
gaaggcgtcg atcacccgga agccgttggg cgtcggctcg gcgaccagaa ggcggcaatt  180
gttggtgccg agatcgagcg cggcataggc gtcgcgtcgg ccgtgccgac cggtttcgta  240
gcggggaggg aagctctcga tcgggcgtcc gcccgtgacc gtgcgggaac cctcccgcgc  300
```

```
tgtctgcggg tcggcggtgg ggcgggccga cacggcggcg gcgctctcat ccctcatcga  360
cgcgaccgaa cttcctggcg atgcagcccg gcaagacgcc gggccgacgt ggcaccaagg  420
ctacaggcgt tattcaggaa ctgcaaaggc tggatggccg gccttacacg atttgccgca  480
tggattgttt cgcgaaaagt ccc                                          503

SEQ ID NO: 6            moltype = DNA  length = 500
FEATURE                 Location/Qualifiers
source                  1..500
                        mol_type = unassigned DNA
                        organism = Methylobacterium extorquens
SEQUENCE: 6
cgcccccaaga ctcccaacct gatatcgtcg gcgcaatctt ggccggaagc gggcgagggg  60
caagaggcac ggattgtcgc gtgccgccgg tctcgaccgg ttccggccgc gttcagggcc  120
gccgccgacg cagcgggagc acggcagcgg cgccgatctg tgggccggtc tcggcgtcga  180
gatcgggcac ggcgatgatc ggcgcgccgc gcaggtcccg gcgcatgacg atagcgccgc  240
gctcctccag atagcccagc atgcgccggg cacgccccgc cgaggaggtg ccgtaggcct  300
ccgcgagcgc cgcgtcggaa gggcagggcg aaccttcgag cgccgtgcgg gcgatgagca  360
ggaacaaccc ggccagatcc tccggcagac cggcggcgat ctcctgcgcc cgctcccaac  420
cgggtccctc ggcggtggcg ccctggacgc cggcccgcgc cacggcgagc cgccgcttga  480
actcgggcag gcccatcgcc                                              500

SEQ ID NO: 7            moltype = DNA  length = 178
FEATURE                 Location/Qualifiers
source                  1..178
                        mol_type = unassigned DNA
                        organism = Paracoccus zeaxanthinifaciens
SEQUENCE: 7
gactaggtct ttcccttgcc ggaacaatcg gctaaagcct tccgcagtcg gggcgtagcg  60
cagcctggta gcgcgacggt tttgggtacc gtaggtcgga ggttcgaatc ctctcgcccc  120
gaccatcttc gggaaaacat taatatttcc agcgacggaa cgcgtgatgc gcctgccg    178

SEQ ID NO: 8            moltype = DNA  length = 227
FEATURE                 Location/Qualifiers
source                  1..227
                        mol_type = unassigned DNA
                        organism = Paracoccus zeaxanthinifaciens
SEQUENCE: 8
ccgcatccgt ctgcatcggc gggggcgagg cgacggccat cgcgctggaa cggctgagct  60
aattcatttg cgcgaatccg cgtttttcgt gcacgatggg ggaaccggaa acggccacgc  120
ctgttgtggt tgcgtcgacc tgtcttcggg ccatgcccgt gacgcgatgt ggcaggcgca  180
tggggcgttg ccgatccggt cgcatgactg acgcaacgaa ggcaccg                227

SEQ ID NO: 9            moltype = DNA  length = 5479
FEATURE                 Location/Qualifiers
source                  1..5479
                        mol_type = unassigned DNA
                        organism = Paracoccus zeaxanthinifaciens
SEQUENCE: 9
gactaggtct ttcccttgcc ggaacaatcg gctaaagcct tccgcagtcg gggcgtagcg  60
cagcctggta gcgcgacggt tttgggtacc gtaggtcgga ggttcgaatc ctctcgcccc  120
gaccatcttc gggaaaacat taatatttcc agcgacggaa cgcgtgatgc gcctgccgcg  180
ttcggcggcg aatgtcacgg atgatccgcc tatgagccct gaacgcagat gtcacgcgat  240
gccctttggt cgcaccccga tgggctggtc atgcaccgcg cggcagcgta gcctgttccc  300
tgtcatatca agcaaggggc cggcatgagc acttgggccg caatcctgac cgtcatcctg  360
accgtcgccg cgatggagct gacggcctac tccgtccatc ggtggatcat gcatggcccc  420
ctgggctggg gctggcataa atcgcaccac gacgaggatc acgaccacgc gctcgagaag  480
aacgacctct atggcgtcat cttcgcggta atctcgatcg tgctgttcgc gatcggcgcg  540
atggggtcgg atctggcctg gtggctggcg gtgggggtca cctgctacgg gctgatctac  600
tatttcctgc atgacggctt ggtgcatggg cgctggccgt tccgctatgt ccccaagcgc  660
ggctatcttc gtcgcgtcta ccaggcacac aggatgcatc acgcggtcca tggccgcgag  720
aactgcgtca gcttcggttt catctgggcg ccctcggtcg acagcctcaa ggcagagctg  780
aaacgctcgg gcgcgctgct gaaggaccgc gaaggggcgg atcgcaatac atgagccatg  840
atctgctgat cgcgggcgcg gggctgtccg gtgcgctgat cgcgcttgcc gttcgcgacc  900
gcagaccgga tgcgcgcatc gtgatgctcg acgcgcggtc cggcccctcg gaccagcaca  960
cctggtcctg ccacgacacg gatctttcgc ccgaatggct ggcgcgcctg tcgcccattc  1020
gtcgcggcga atggacggat caggaggtcg cgtttcccga ccattcgcgc cgcctgacga  1080
caggctatgg ctcgatcgag gcgggcgcgc tgatcgggct gctgcagggt gtcgatctgc  1140
ggtggaatac gcatgtcgcg acgctggacg ataccggcgc gacgctgacg gacggctcgc  1200
ggatcgaggc tgcctgcgtg atcgacgccc gtggtgccgt cgagacccccg cacctgaccg  1260
tgggtttcca gaaattcgtg ggcgtcgaga tcgagaccga cgcccccccat ggcgtcgagc  1320
gcccgatgat catggacgcg accgttccgc agatggacgg gtaccgcttc atctatctgc  1380
tgcccttcag tcccacccgc atcctgatcg aggatacgcg ctacagcgac ggcggcgatc  1440
tggacgatgg cgcgctggcg caggcgtcgc tggactatgc cgccaggcgg ggctggaccg  1500
ggcaggagat gcggcgcgaa aggggcatcc tgcccatcgc gctggcccat gacgccatag  1560
gcttctggcg cgaccacgcg caggggggcgg tgccggttgg gctgggggca gggctgttcc  1620
accccgtcac cggatattcg ctgccctatg ccgcgcaggt cgcggatgcc atcgcggcgc  1680
gcgacctgac gaccgcgtcc gcccgtcgcg cggtgcgcgg ctgggccatc gatcgcgcgg  1740
atcgcgaccg cttcctgcgg ctgctgaacc ggatgctgtt ccgcggctgc ccgcccgacc  1800
gtcgctatcg cctgctgcag cggttctacc gcctgccgca gccgctgatc gagcgcttct  1860
```

```
atgccgggcg cctgacattg gccgaccggc ttcgcatcgt caccggacgc ccgcccattc  1920
cgctgtcgca ggccgtgcgc tgcctgcccg aacgccccct gctgcaggag agagcatgag  1980
ttccgccatc gtcatcggcg caggtttcgg cgggcttgcg cttgccatcc gcctgcaatc  2040
ggccggcatc gcgaccacca tcgtcgaggc ccgcgacaag cccggcggcc gcgcctatgt  2100
ctggaacgat cagggccacg tcttcgatgc aggcccgacg gtcgtgaccg accccgacag  2160
cctgcgagag ctgtgggccc tcagcggcca accgatggag cgtgacgtga cgctgctgcc  2220
ggtctcgccc ttctaccggc tgacatgggc ggacggccgc agcttcgaat acgtgaacga  2280
cgacgacgag ctgatccgcc aggtcgcctc cttcaatccc gccgatgtcg atggctatcg  2340
ccgcttccac gattacgccg aggaggtcta tcgcgagggg tatctgaagc tggggaccac  2400
gcccttcctg aagctgggcc agatgctgaa cgccgcgccc gcgctgatgc gcctgcaggc  2460
ataccgctcg gtccacagca tggtggcgcg cttcatccag gacccgcatc tgcggcaggc  2520
cttctcgttc cacacgctgc tggtcggcgg gaacccgttt tcgaccagct cgatctatgc  2580
gctgatccat gcgctggaac ggcgcggcgg cgtctggttc gccaagggcg gcaccaacca  2640
gctggtcgcg ggcatggtcg ccctgttcga gcgtcttggc ggcacgctgc tgctgaatgc  2700
ccgcgtcacg cggatcgaca ccgagggcga tcgcgccacg ggcgtcacgc tgctggacgg  2760
gcggcagttg cgcgcggata cggtggccag caacggcgac gtgatgcaca gctatcgcga  2820
cctgctgggc catacccgcc gcgggcgcac caaggccgcg atcctgaacc ggcagcgctg  2880
gtcgatgtcg ctgttcgtgc tgcatttcgg cctgtccaag cgccccgaga acctggccca  2940
ccacagcgtc atcttcggcc cgcgctacaa ggggctggtg aacgagatct tcaacgggcc  3000
acgcctgccg gacgatttct cgatgtatct gcattcgccc tgcgtgaccg atcccagcct  3060
ggcccccgag gggatgtcca cgcattacgt ccttgcgccc gttccgcatc tgggccgcgc  3120
cgatgtcgat tgggaagccg aggccccggg ctatgccgag cgcatcttcg aggaactgga  3180
gcgccgcgcc atccccgacc tgcgcaagca cctgaccgtc agccgcatct tcagccccgc  3240
cgatttcagc accgaactgt cggcccatca cggcagcgcc ttctcggtcg agccgatcct  3300
gacgcaatcc gcctggttcc gcccgcataa ccgcgaccgc gcgatcccga acttctacat  3360
cgtgggggcg ggcacgcatc cgggtgcggg catcccgggt gtcgttggca gcgccaaggc  3420
cacggcgcag gtcatgctgt cggacctggc cgtcgcatga ccgatctgac ggcgacttcc  3480
gaagcggcca tcgcgcaggg ttcgcaaagc ttcgcgcagg cggccaagct gatgccgccc  3540
ggcatccgcg aggatacggt catgctctat gcctggtgca ggcatgcgga tgacgtgatc  3600
gacgggcagg tcatgggttc tgcccccgag gcgggcggcg acccacaggc gcggctggat  3660
gcgctgcgcg ccgacacgct ggccgcgctg cacgaggacg gcccgatgtc gccgcccttc  3720
gcggcgctgc gccaggtcgc ccggcggcat gatttcccgg acctttggcc gatggacctg  3780
atcgagggtt tcgcgatgga tgtcgcggat cgcgaatacc gcagcctgga tgacgtgctg  3840
gaatattcct accacgtcgc gggggtcgtg ggcgtgatga tggcgcgggt gatgggcgtg  3900
caggacgatg cggtgctgga tcgcgcctgc gatctgggcc ttgcgttcca gctgacgaac  3960
atcgctcgcg acgtgatcga cgatgccgcc atcgggcgct gctatctgcc tgccgactgg  4020
ctggccgagg cgggggcgac ggttgagggt ccggtgcctt cggacgcgct ctattccgtc  4080
atcatccgcc tgcttgacgc ggccgagccc tattatgcct cggcgcggca ggggcttccg  4140
catctgccgc cgcgctgcgc gtggtcgatc gccgccgcgc tgcgtatcta tcgcgcaatc  4200
gggacgcgca tccggcaggg tggccccgag gcctatcgcc agcggatcag cacgtcgaag  4260
gctgccaaga tcgggcttct ggcgcgcgga ggcttggacg cggccgcatc gcgcctgcgc  4320
ggcggtgaaa tcagccgcga cggcctgtgg acccgaccgc gcgcctaggc gctgcggcgg  4380
atgtcatgcg gcagcacgcg ggccagcagg tccgcgatct gccccccgcg gaacagccgg  4440
gtgcgcatca gctcgtccag ttgcgcgcgg ctggcgcggt aatgctgcgc cacgtcgccc  4500
atctgtccga ccgccatcag gccgcgcttt gggccggggg cggcggtgtc gcgccccgta  4560
tccttgccgg tgctggcctt gtcgccgatc acgtccagca ggtcgtcata ggactggaag  4620
acccgaccaa gctgacgccc gaaggccatg agctgctcgg tctcggcctt gtccagaccc  4680
ttaataatgg acagcatctc gaggcccgcg acgaacagca cgccggtctt gaggtcctgt  4740
tcacgttcga tcccggcggc gtccttgggg gcgtgcaggt ccagatcctg ccctgcgcac  4800
agccccaccg gtcccatcgc gcgcgacatg gatgcgacca gccttgcgcg ctgatccggc  4860
gtcgcgccgc gcgcctcgcc caaaatccgc atggcctcgg tgatcagggc gatgcccgca  4920
agcaccgcgc gcccctcgcc atgggcgaca tgggtggcgg gctgaccgcg acgggtcctg  4980
gcatcgtcca tgcagggcat gtcgtcgaag atcagcgatg cggcatggac catctcgacc  5040
gcgcaggcgg catcgaccat cgcatcgcag accccgcccg agctttcggc gaccatcagc  5100
atcagcacgg cgcgaaagcg tttgccgggg gacagggcgg catcgctcat ggccgcgccg  5160
agcggggccg agaccacgcc gaactggccc gagatctgcg ccagcctgat ctcgaccaga  5220
tcgcgtaggg ggaattgctg cttgggcgtc atcggtgcct tcgttgcgtc agtcatgcga  5280
ccggatcggc aacgccccat gcgcctgcca catcgcgtca cgggcatggc ccgaagacag  5340
gtcgacgcaa ccacaacagg cgtggccgtt tccggttccc ccatcgtgca cgaaaaacgc  5400
ggattcgcgc aaatgaatta gctcagccgt tccagcgcga tggccgtcgc ctcgcccccg  5460
ccgatgcaga cggatgcgg                                                5479
```

```
SEQ ID NO: 10          moltype = AA  length = 169
FEATURE                Location/Qualifiers
source                 1..169
                       mol_type = protein
                       organism = Paracoccus zeaxanthinifaciens
SEQUENCE: 10
MSTWAAILTV ILTVAAMELT AYSVHRWIMH GPLGWGWHKS HHDEDHDHAL EKNDLYGVIF  60
AVISIVLFAI GAMGSDLAWW LAVGVTCYGL IYYFLHDGLV HGRWPFRYVP KRGYLRRVYQ  120
AHRMHHAVHG RENCVSFGFI WAPSVDSLKA ELKRSGALLK DREGADRNT              169
```

```
SEQ ID NO: 11          moltype = AA  length = 382
FEATURE                Location/Qualifiers
source                 1..382
                       mol_type = protein
                       organism = Paracoccus zeaxanthinifaciens
SEQUENCE: 11
MSHDLLIAGA GLSGALIALA VRDRRPDARI VMLDARSGPS DQHTWSCHDT DLSPEWLARL  60
```

```
SPIRRGEWTD QEVAFPDHSR RLTTGYGSIE AGALIGLLQG VDLRWNTHVA TLDDTGATLT  120
DGSRIEAACV IDARGAVETP HLTVGFQKFV GVEIETDAPH GVERPMIMDA TVPQMDGYRF  180
IYLLPFSPTR ILIEDTRYSD GGDLDDGALA QASLDYAARR GWTGQEMRRE RGILPIALAH  240
DAIGFWRDHA QGAVPVGLGA GLFHPVTGYS LPYAAQVADA IAARDLTTAS ARRAVRGWAI  300
DRADRDRFLR LLNRMLFRGC PPDRRYRLLQ RFYRLPQPLI ERFYAGRLTL ADRLRIVTGR  360
PPIPLSQAVR CLPERPLLQE RA                                           382

SEQ ID NO: 12           moltype = AA  length = 494
FEATURE                 Location/Qualifiers
source                  1..494
                        mol_type = protein
                        organism = Paracoccus zeaxanthinifaciens
SEQUENCE: 12
MSSAIVIGAG FGGLALAIRL QSAGIATTIV EARDKPGGRA YVWNDQGHVF DAGPTVVTDP  60
DSLRELWALS GQPMERDVTL LPVSPFYRLT WADGRSFEYV NDDDELIRQV ASFNPADVDG  120
YRRFHDYAEE VYREGYLKLG TTPFLKLGQM LNAAPALMRL QAYRSVHSMV ARFIQDPHLR  180
QAFSFHTLLV GGNPFSTSSI YALIHALERR GGVWFAKGGT NQLVAGMVAL FERLGGTLLL  240
NARVTRIDTE GDRATGVTLL DGRQLRADTV ASNGDVMHSY RDLLGHTRRG RTKAAILNRQ  300
RWSMSLFVLH FGLSKRPENL AHHSVIFGPR YKGLVNEIFN GPRLPDDFSM YLHSPCVTDP  360
SLAPEGMSTH YVLAPVPHLG RADVDWEAEA PGYAERIFEE LERRAIPDLR KHLTVSRIFS  420
PADFSTELSA HHGSAFSVEP ILTQSAWFRP HNRDRAIPNF YIVGAGTHPG AGIPGVVGSA  480
KATAQVMLSD LAVA                                                    494

SEQ ID NO: 13           moltype = AA  length = 303
FEATURE                 Location/Qualifiers
source                  1..303
                        mol_type = protein
                        organism = Paracoccus zeaxanthinifaciens
SEQUENCE: 13
MTDLTATSEA AIAQGSQSFA QAAKLMPPGI REDTVMLYAW CRHADDVIDG QVMGSAPEAG  60
GDPQARLDAL RADTLAALHE DGPMSPPFAA LRQVARRHDF PDLWPMDLIE GFAMDVADRE  120
YRSLDDVLEY SYHVAGVVGV MMARVMGVQD DAVLDRACDL GLAFQLTNIA RDVIDDAAIG  180
RCYLPADWLA EAGATVEGPV PSDALYSVII RLLDAAEPYY ASARQGLPHL PPRCAWSIAA  240
ALRIYRAIGT RIRQGGPEAY RQRISTSKAA KIGLLARGGL DAAASRLRGG EISRDGLWTR  300
PRA                                                                303

SEQ ID NO: 14           moltype = AA  length = 295
FEATURE                 Location/Qualifiers
source                  1..295
                        mol_type = protein
                        organism = Paracoccus zeaxanthinifaciens
SEQUENCE: 14
MTPKQQFPLR DLVEIRLAQI SGQFGVVSAP LGAAMSDAAL SPGKRFRAVL MLMVAESSGG  60
VCDAMVDAAC AVEMVHAASL IFDDMPCMDD ARTRRGQPAT HVAHGEGRAV LAGIALITEA  120
MRILGEARGA TPDQRARLVA SMSRAMGPVG LCAGQDLDLH APKDAAGIER EQDLKTGVLF  180
VAGLEMLSII KGLDKAETEQ LMAFGRQLGR VFQSYDDLLD VIGDKASTGK DTGRDTAAPG  240
PKRGLMAVGQ MGDVAQHYRA SRAQLDELMR TRLFRGGQIA DLLARVLPHD IRRSA       295

SEQ ID NO: 15           moltype = DNA  length = 4019
FEATURE                 Location/Qualifiers
source                  1..4019
                        mol_type = unassigned DNA
                        organism = Sphingomonas astaxanthinifaciens
SEQUENCE: 15
atgatgaagc gcgcggacct ggtgatcgtc ggtggaggac tggccggcgg cctgtgcgcc  60
ctcgcccttc gccgccgccg ccctgacctc aggctgctgc tggtcgagcc ggggccaagc  120
atcggcggca accatctctg gtccttcttc gaaagcgacg tcgcccccgc cgaccgctgg  180
ctgaccgacc cgctgatccg gcatcgctgg cccgattacg aggtccgctt cccggcgcac  240
cagcgccacc tcgccgaagc ctatcagacc atcgagagcg aggcgctcga cgaggccgtg  300
cgcaaggccc tttccgccga ggagatcgtc cgggccgaag ccaccgacct tggcccgacc  360
cacgtcaccc tcgcgaccgg cgagcggatc gaggcgaagg cggtgctcga cgcgcgcggg  420
ggcaaagccg aggggctcga tctcggctgg cagaaattcc tcggccagct gctgaccatc  480
ccgcagggcc acggcctcac ccgtccgatc gtgatggacg cgacggtcga ccagcatgac  540
ggctatcgct tcgtctactg cctgcccttc agcccgaccg aactcttcgt cgaggacact  600
tattacagcg acgggcccga gctcgaccac gaccgattgc gtgaccggat cggcgattat  660
gccgcggcac agggctggca ggtcgcggac cgcagccgcg aggagcatgg cgcgctgcca  720
gtggtgatcg gcggcgattt cgaccggctg tggcccgccg ccgaccatgt cgcccgggcc  780
ggcgcgcgcg gcggtttctt ccatccgctg accagctatt cgctgcccga cgcggtccgc  840
ttcgccatct ggctggcgga caaggccacg ttcgacgccc ggctcggggc cgcgacccgc  900
gcgcggggcc gccgccactg gaggtcgggt gccttctacc ggctgctcac cgcgctcctg  960
ttccacgccg ccgagcccgg ccagcgctac ctcgtgctgg agcgtttcta ccgcctttcc  1020
ggcccccttga tcggccgctt ctacgcgggg atgagcaccg gctatgacaa ggcgcgcgtg  1080
ctcgcgggca agccgccggt gcccttcttc cgggcactca gggtattgag ggacagcttg  1140
tgaagagtgc aatcgtgatc ggtgccggct tcggcggcct ggcgctggcc atccgcctcc  1200
agtcggccgg ggtgaagacc accatcgtcg aggcccgcga ccggcccggc ggccgcgcct  1260
atgtctggga aaaggacggc cacgtgttcg acgcgggccc gaccgtgatc accgatcccg  1320
actgtctcca gcggctgtgg aagctgtcgg gccacgacat gtcggaggat gtcgagctcg  1380
tcccggtcaa gcccttctac cggctctcct ggcccgacgg cgtggtgttc gattacacca  1440
atgacgacgc cgagctcaaa gccgcgatgg acgcactcaa tcccgacgac tgggcgggct  1500
```

```
accagcgctt cctcgcctat agcgccgggg tctataacga gggctatgtg aagctcggga  1560
ccaaggcgtt tgaaagcctc ggcgacatgc tcaaggccgc gcccgcgctc gccaaatatc  1620
aggcttggcg gtcggtctat tcgatcgtgt cgagcttcgt gaaggacgag cacctgcgcc  1680
agaccttgtc cttccacacg ctgctggtcg gcggcaatcc gatgacctgc tcgtcgatct  1740
acgcgctgat ccacaagctc gagcgcgacg gcggggtgtg gttcgccaag ggcgggacca  1800
acaagctgat cgccggcatg gtccgccagt tcgagcggat cggcgggacc attcgccttg  1860
gcgatccggt cactgcgatc ctggccgaga acgatcgggt caccggggtg cgcaccgcct  1920
cgggttggag cgccaccgcc gacgcggtcg cctccaatgg cgacgtggtc cacagctatg  1980
gcctgatcga gggttccgac cgcggccagc aacaggtccg cgccctcaag cgcaagcgtt  2040
tctcgcccgg cctgttcgtg ctccatttcg ggctcgaggg gacgtcggac ctcgcccacc  2100
acacgatcct gttcggcccg cgctacggcg gcctcgtcaa cgacatctac aagaccgggc  2160
ggctcgcgac cgacccgtcg ctctacatcc accacccgac catcaccgac ccgtccatgg  2220
cgccgccggg ctgctcgacc ttctacgcgc ttgccccgt ccccaatgcc ggcaaggccg  2280
atgtcgactg ggcggtcgag ggccgaaat atcaggaggt cgtgctcgac acgatcgccg  2340
agcggctgat ccccgacgtg cgccagcgga tccggaccat cttccattac accccggccg  2400
atttctcggc cgacctcgcc gcccacctcg gctccgcatt cagcctcgag ccggtgctgt  2460
ggcagtcggc ctggttccgc acccacaatc gcgacgacaa gctcaggaac ctctatttcg  2520
tcggtgccgg cactcaccca ggcgcgggga tcccgggggt ggtcggaagc gccgaggcga  2580
ctgcggggct gatgctggcg tgagcgaagc tgacgaacgg gcacggctgg tccaggccgc  2640
gctggaaagc atttcggcgg gctccaagag ttttcgcttc gccagccagt tgttcgacca  2700
gcagacccga gagcgcagct ggctgctcta cagctggtgc cgcgcctgcg acgacgtgac  2760
cgacggccag accctgggcc atgatgcgga gcgggtcgac gatcccgccg cccgcctcgc  2820
cttcctcaag gcgaagaccg ccgaggcgtt cgcgggccaa ccgacgggac ttgtcccctt  2880
cgacgcactg cgcgtggtcg ccgccgaatg cgcgattccc caggccgtcg ccggcgacca  2940
tctcgccggg ttcgagcgcg acgccggggg gtggcggccg accacgaccg acgacctcct  3000
ctcttattgc taccaggttg ctggcgcggt gggcgtgatg atggcgcacg tcatgggcgt  3060
gccgcccgag gacgaggaca cgctcaaccg cgcagccgac ttggggatcg ccttccagct  3120
cgccaatatc gcccgcgaca tcgtcgacga tgccaaggtc gggcgggtct atctgcccgc  3180
cgaatggctt gccgccgagg ggctggccgg ggccgacctc gccgatcccg cgcatcgccc  3240
ggccctcgcg cgcctcgccc accgcctcgc cgacatggcc gacgcctatc gccgctcggc  3300
ccgggtcggc gcggcccgcc tgcccttccg cagccgctgg gcggtgctcg cggccagcgg  3360
catctacggc gagatcgcga cccgcgccgc cgcgctcggg ccccgcgcct gggacgagcg  3420
gatcaccacc tcgaaggcgg aaaaggccgc gctggtgatg gaggccttct gggaagcctt  3480
gtggcgggtc aggcccgctc ctcgtgacgg gctgtggacc cgccccgcgc acgcctgagc  3540
tgcgcctcgc ggctggcctg gagcgcctgc ttcagccgct cgaccggcgg ggcgtaaagg  3600
aagccgaagc tcaccgcccc gtcgcggctc tcgaccgcat ggtgcagctt gtgcgcctgg  3660
acgatccgct tgaaataggt cgaacgcggc acgatccggt gcggcagccg gccgtggacg  3720
atgacgtcgt gaaagccgaa atagatcacc ccgtagaagg ccaccccggc ccccatccac  3780
gtcgcccagt cgccccagcc gccattgagc ccgccccaga tcagcaggat cgagggcaaa  3840
gcgaagacca cggcatagag gtcgttccgc tcgaaccagc cggtccgcgc gcgatgatgg  3900
ctttcgtgcc agttccagcc gagccgcgag tgcatcacga agcggtggag gacataggcg  3960
aagccctcca tcagaaggac cgtcgatacg aacagggcga gaccggcagg ccaggacat   4019
```

```
SEQ ID NO: 16          moltype = AA  length = 176
FEATURE                Location/Qualifiers
source                 1..176
                       mol_type = protein
                       organism = Sphingomonas astaxanthinifaciens
SEQUENCE: 16
MSWPAGLALF VSTVLLMEGF AYVLHRFVMH SRLGWNWHES HHRARTGWFE RNDLYAVVFA  60
LPSILLIWGG LNGGWGDWAT WMGAGVAFYG VIYFGFHDVI VHGRLPHRIV PRSTYFKRIV  120
QAHKLHHAVE SRDGAVSFGF LYAPPVERLK QALQASREAQ LRRARGGSTA RHEERA      176

SEQ ID NO: 17          moltype = AA  length = 380
FEATURE                Location/Qualifiers
source                 1..380
                       mol_type = protein
                       organism = Sphingomonas astaxanthinifaciens
SEQUENCE: 17
MMKRADLVIV GGGLAGGLCA LALRRRRPDL RLLLVEPGPS IGGNHLWSFF ESDVAPADRW  60
LTDPLIRHRW PDYEVRFPAH QRHLAEAYQT IESEALDEAV RKALSAEEIV RAEATDLGPT  120
HVTLATGERI EAKAVLDARG GKAEGLDLGW QKFLGQLLTI PQGHGLTRPI VMDATVDQHD  180
GYRFVYCLPF SPTELFVEDT YYSDGPELDH DRLRDRIGDY AAAQGWQVAD RSREEHGALP  240
VVIGGDFDRL WPAADHVARA GARGGFFHPL TSYSLPDAVR FAIWLADKAT FDARLGAATR  300
ARGRRHWRSG AFYRLLTALL FHAAEPGQRY LVLERFYRLS GPLIGRFYAG MSTGYDKARV  360
LAGKPPVPFF RALRVLRDSL                                              380

SEQ ID NO: 18          moltype = AA  length = 487
FEATURE                Location/Qualifiers
source                 1..487
                       mol_type = protein
                       organism = Sphingomonas astaxanthinifaciens
SEQUENCE: 18
VKSAIVIGAG FGGLALAIRL QSAGVKTTIV EARDRPGGRA YVWEKDGHVF DAGPTVITDP  60
DCLQRLWKLS GHDMSEDVEL VPVKPFYRLS WPDGVVFDYT NDDAELKAAM DALNPDDWAG  120
YQRFLAYSAG VYNEGYVKLG TKAFESLGDM LKAAPALAKY QAWRSVYSIV SSFVKDEHLR  180
QTLSFHTLLV GGNPMTCSSI YALIHKLERD GGVWFAKGGT NKLIAGMVRQ FERIGGTIRL  240
GDPVTAILAE NDRVTGVRTA SGWSATADAV ASNGDVVHSY GLIEGSDRGQ QQVRALKRKR  300
FSPGLFVLHF GLEGTSDLAH HTILFGPRYG GLVNDIYKTG RLATDPSLYI HHPTITDPSM  360
```

```
APPGCSTFYA LAPVPNAGKA DVDWAVEGPK YQEVVLDTIA ERLIPDVRQR IRTIFHYTPA  420
DFSADLAAHL GSAFSLEPVL WQSAWFRTHN RDDKLRNLYF VGAGTHPGAG IPGVVGSAEA  480
TAGLMLA                                                            487

SEQ ID NO: 19          moltype = AA  length = 312
FEATURE                Location/Qualifiers
source                 1..312
                       mol_type = protein
                       organism = Sphingomonas astaxanthinifaciens
SEQUENCE: 19
VSEADERARL VQAALESISA GSKSFRFASQ LFDQQTRERS WLLYSWCRAC DDVTDGQTLG  60
HDAERVDDPA ARLAFLKAKT AEAFAGQPTG LVPFDALRVV AAECAIPQAV AGDHLAGFER  120
DAGGWRPTTT DDLLSYCYQV AGAVGVMMAH VMGVPPEDED TLNRAADLGI AFQLANIARD  180
IVDDAKVGRV YLPAEWLAAE GLAGADLADP AHRPALARLA HRLADMADAY RRSARVGAAR  240
LPFRSRWAVL AASGIYGEIA TRAAALGPRA WDERITTSKA EKAALVMEAF WEALWRVRPA  300
PRDGLWTRPA HA                                                      312

SEQ ID NO: 20          moltype = AA  length = 249
FEATURE                Location/Qualifiers
source                 1..249
                       mol_type = protein
                       organism = Sphingomonas astaxanthinifaciens
SEQUENCE: 20
MAPMLSDAQR RRQAMIGLGL AAAITAAFVA LHVWSVFFLP LEGAGWWLAL PIVAVQTWLS  60
VGLFIVAHDA MHGSLAPGRP ATNLFWGRLT LLLYAGFWLD RLSPKHFDHH RHVGTERDPD  120
FSVDHPTRFW PWYYAFMRRY FGLREYLVLN ALVLAYVLVL KAPLGNLLLF WALPSILSSI  180
QLFYFGTYLP HRHEDAPFAD QHNARSNDFP VWLSLLTCFH FGYHREHHLS PGTPWWQLPR  240
RRRELALPA                                                          249

SEQ ID NO: 21          moltype = DNA  length = 3935
FEATURE                Location/Qualifiers
source                 1..3935
                       mol_type = unassigned DNA
                       organism = unidentified
                       note = Siansivirga zeaxanthinifaciens
SEQUENCE: 21
atgaaaaaag aaataataat tatcggttca ggtttttcgt ctctagcagc atcctgctat  60
ttggcgaaag caggttataa tgtaacttta ttagaaaaaa acaacactat tggaggcaga  120
gctcgacaat tagttaaaga cggttttact ttcgatatag gtccaacttg gtattggatg  180
cccgatgtat ttgaacgctt cttcaatgat tttgataaaa aaccttcaga ttactatagt  240
cttgaaaaac tgaatcccgc atacagtgtt tattttggaa aaaacgacta cattaccatt  300
gaagatacat tagcgaaaat ttctgaagca tttgaaaaag aagaacctgg aagttcaaaa  360
aaactaaaca cctttattga aaaagctaaa agcaactacg atatagcaat taaagatttg  420
gtttataacc ctggcgtatc gcctctagaa ttggttacta ttgctactat aaaaaaatta  480
gaccaattct ttagtaacat aaaaagagat gttagaaaag aatttaaaaa tgaaaggtta  540
gtaaaaattc ttgaatttcc tgttttattt ttaggagcaa aaccaagcga tacaccttcg  600
ttttatagtt ttatgaatta tgcagatttt ggccttggga cgtttcatcc aaaaaaaggc  660
atgtatcaag ttatcctagc gcttgaaaat ctggcaaaat ctcttggtgt tattataaaa  720
acaaatgctc ccatagaaaa aattatcatt gaaaacaacg aagtaaaagg tgttatttca  780
aatggaaaaa caataaatac caacattgtt gttagtggag ccgattacca tcataccgaa  840
acgttattag ataaaacata cagacaatat agtgagtctt actggagtaa aaagactttt  900
gcaccgtcat cactactatt ttatgtaggt ttcgataaaa agattcaaaa tgtaaatcat  960
cacacattat tttttgatgt agattttgat gtacatgcag aagccatata cgatactcca  1020
aaatggcccg aagaaccact tttttacgca agtttcccta gtataacgga tgctaacagc  1080
gccccagaag gtaaagaagc tggcatattt ttaataccct tagcgccagg attagaagat  1140
acagaagcgt taagagaagc ctattttgaa aaaattatga cacgttttga ggccttaact  1200
agtcaaaata ttaaaaaaca tgttatattt aaagagagtt tttgtatcaa tgattttata  1260
aaagattata attcttacaa aggaaacgct tacggaatgg ctaatacaat tacccaaacc  1320
gcatttttaa gacccaaatt aaaaagtaaa aaagttaaag gtttattttt tacaggtcaa  1380
ttaacagttc ctggtcccgg tgtaccacca tcattaattt caggaaagtt agtagcagat  1440
ttagtaacca aacaccattc tttatgaaag cattatttga taccgtttca tacaattgca  1500
gcaaattagt aacaaaatct tatagcactt cattttcgct tgctactaaa atgctataca  1560
aatctataag acccgatatt tacaacattt acggatttgt tagatttgct gatgagattg  1620
tagattcgtt tcatgatttt aataaagaag aactacttaa caaatttgaa gccgatttag  1680
agcatgctct cgaacatagg gtaagtttaa accctatttt aaatgccttc cagtacacat  1740
accataagaa taaaatagag aaaagcatgg tcgatgcttt tatgaaaagt atgcgacttg  1800
atttacataa aactcaatac ctaacaaacg aagagtacaa agaatacatt tacggttctg  1860
cagatgttgt aggacttatg tgtttaaagg tttttgtgaa tggtgataac gaaaaatttg  1920
aagctttaaa agatacagcc atggcacttg gttctgcttt tcaaaaagtt aacttttttaa  1980
gagatttaaa agatgattac gaaggtttaa acagaacata tttcccgaat accgatttaa  2040
ataaccttga tgaacaatcg aaactagata ttattcaaga tattgaaaaa gattttgaaa  2100
aaggcttaac aggaattaaa aaattaccaa ttgaggctaa atttggtgtt tttatggctt  2160
acagatatta tcatcaattg cttaaaaaac ttaaaaaaac acctgctttt aatattaaaa  2220
acaccagaat acgcgtttca aatcctaaaa aaatagaatt attaatgcgt agttatgtaa  2280
aatatcaatt aaaattaatg taaatttata gtatgcaaac actattatgg ataatcattt  2340
ttttagcaac gtattgtatc atggaattta tggcgtggtt tacgcataaa tacattatgc  2400
atggcttttt atggagttta cacaaagacc atcacaagaa agatcacgat agttggttcg  2460
aaagaaacga tgcttttttt atattttatg ctattgttag cataggtttgt tttttacttt  2520
ggaaatacga catattttgg gctggtttac ccattggcgt tggtattttt gcttatggat  2580
```

```
tatcatactt tttggtacac gatatattta ttcatcaacg ttttaaatta tttagaaatg  2640
ccaataactg gtatgctaaa ggtgtaagac gtgctcacaa aatgcaccac aaacatattg  2700
gaaaagaaga tggcgaatgc tttggtatgt tgtttgttcc ttttaaatac ttcaagaaat  2760
aattttctat taattacatg atatctaaca cccatttcga ttatatcatt attggaaatg  2820
gattagcagg gcttcagttg gcattaaaaa tgagtgctga tgtttatttt aaagataaac  2880
gcatcgcttt aatagatggt tctaacaaaa acacaaacga taaaacctgg agtttttggg  2940
aagaaaactc atctcaatgg gatgccatta caactaaaag ttggaatatt gccaacattt  3000
acacttccaa aaaacatatt tcattagcac tttgcccta taaatataaa tctatacgtt  3060
ctatagattt atataattat gcgaaattcg agcttcaaaa acattctaat tttcatttta  3120
taattgattt tgtatgtact accacagaaa cagaagataa aaaggtatta gtagaaactt  3180
cctctaataa attcactgcc tcacatgttt ttgatagtag aattccagaa gatttttttc  3240
aaaaaaataa aaattacaca cacataattc aacactttaa aggctatgta attaaaacag  3300
aagaagccta ttttaatgac gacaccttca cgatgatgga ttatcgattg aaagatggtg  3360
aacaaaccac atttacctat gtactgcctt tttcaaaaac agaagcttta atagaattta  3420
cctattttac agaaaattta gttaatgaag ccgtttatga tgcattcatt gaaaaataca  3480
taaaaaacta tcttaaaatt gactcgtatt taattatgga aacagaaata ggtcaaattc  3540
ctatgactaa tttcccattt gcaaggttca atacaaaaaa tataacgaaa ataggcactg  3600
gtggtggatg ggtaaagggg tctacgggtt attcttttaa acataccgaa aaaaaaatat  3660
ctaaaatcat cgaaaatatt aaagctaaca acataccaag cgctcactta tttaagaaaa  3720
ggtatcgttt ttatgacaaa atatttttaa aggttttaaa agataacaac cacaaaggcg  3780
aatggatttt tgagcaattt tacaacaaaa attctcctca aaatatgttt aaatttcttg  3840
atgaagaatc tacttttttt gatgaattaa aaattatgta ttcattattc tctttgcctt  3900
ttattaaagc atttttcaag accctttca aataa                            3935

SEQ ID NO: 22          moltype = AA  length = 149
FEATURE                Location/Qualifiers
source                 1..149
                       mol_type = protein
                       organism = unidentified
                       note = Siansivirga zeaxanthinifaciens
SEQUENCE: 22
MQTLLWIIIF LATYCIMEFM AWFTHKYIMH GFLWSLHKDH HKKDHDSWFE RNDAFFIFYA  60
IVSIGCFLLW KYDIFWAGLP IGVGIFAYGL SYFLVHDIFI HQRFKLFRNA NNWYAKGVRR  120
AHKMHHKHIG KEDGECFGML FVPFKYFKK                                  149

SEQ ID NO: 23          moltype = AA  length = 385
FEATURE                Location/Qualifiers
source                 1..385
                       mol_type = protein
                       organism = unidentified
                       note = Siansivirga zeaxanthinifaciens
SEQUENCE: 23
MISNTHFDYI IIGNGLAGLQ LALKMSADVY FKDKRIALID GSNKNTNDKT WSFWEENSSQ  60
WDAITTKSWN IANIYTSKKH ISLALCPYKY KSIRSIDLYN YAKFELQKHS NFSFIIDFVC  120
TTTETEDKKV LVETSSNKFT ASHVFDSRIP EDFFQKNKNY THIIQHFKGY VIKTEEAYFN  180
DDTFTMMDYR LKDGEQTTFT YVLPFSKTEA LIEFTYFTEN LVNEAVYDAF IEKYIKNYLK  240
IDSYLIMETE IGQIPMTNFP FARFNTKNIT KIGTGGGWVK GSTGYSFKHT EKKISKIIEN  300
IKANNIPSAH LFKKRYRFYD KIFLKVLKDN NHKGEWIFEQ FYNKNSPQNM FKFLDEESTF  360
FDELKIMYSL FSLPFIKAFF KTLFK                                      385

SEQ ID NO: 24          moltype = AA  length = 488
FEATURE                Location/Qualifiers
source                 1..488
                       mol_type = protein
                       organism = unidentified
                       note = Siansivirga zeaxanthinifaciens
SEQUENCE: 24
MKKEIIIIGS GFSSLAASCY LAKAGYNVTL LEKNNTIGGR ARQLVKDGFT FDIGPTWYWM  60
PDVFERFFND FDKKPSDYYS LEKLNPAYSV YFGKNDYITI EDTLAKISEA FEKEEPGSSK  120
KLNTFIEKAK SNYDIAIKDL VYNPGVSPLE LVTIATIKKL DQFFSNIKRD VRKEFKNERL  180
VKILEFPVLF LGAKPSDTPS FYSFMNYADF GLGTFHPKKG MYQVILALEN LAKSLGVIIK  240
TNAPIEKIII ENNEVKGVIS NGKTINTNIV VSGADYHHTE TLLDKTYRQY SESYWSKKTF  300
APSSLLFYVG FDKKIQNVNH HTLFFDVDFD VHAEAIYDTP KWPEEPLFYA SFPSITDANS  360
APEGKEAGIF LIPLAPGLED TEALREAYFE KIMTRFEALT SQNIKKHVIF KESFCINDFI  420
KDYNSYKGNA YGMANTITQT AFLRPKLKSK KVKGLFFTGQ LTVPGPGVPP SLISGKLVAD  480
LVTKHHSL                                                         488

SEQ ID NO: 25          moltype = AA  length = 279
FEATURE                Location/Qualifiers
source                 1..279
                       mol_type = protein
                       organism = unidentified
                       note = Siansivirga zeaxanthinifaciens
SEQUENCE: 25
MKALFDTVSY NCSKLVTKSY STSFSLATKM LYKSIRPDIY NIYGFVRFAD EIVDSFHDFN  60
KEELLNKFEA DLEHALEHRV SLNPILNAFQ YTYHKNKIEK SMVDAFMKSM RLDLHKTQYL  120
TNEEYKEYII GSADVVGLMC LKVFVNGDNE KFEALKDTAM ALGSAFQKVN FLRDLKDDYE  180
GLNRTYFPNT DLNNLDEQSK LDIIQDIEKD FEKGLTGIKK LPIEAKFGVF MAYRYYHQLL  240
KKLKKTPAFN IKNTRIRVSN PKKIELLMRS YVKYQLKLM                        279
```

```
SEQ ID NO: 26           moltype = DNA  length = 3904
FEATURE                 Location/Qualifiers
source                  1..3904
                        mol_type = unassigned DNA
                        organism = Mesoflavibacter zeaxanthinifaciens
SEQUENCE: 26
atgaaaaata aaatagcaat aataggttct gggttttctg ctttatctgc tgcatgttat  60
cttgctaagg atggatttaa tgtttcagtt tttgaaaaaa atgatactgt aggaggacgt  120
tgtagacagt ttaaaaaaga tggatttact tttgatatgg gaccaagctg gtattggatg  180
cctgatatat ttgataagtt ttttaatgat tttgataaaa aaacttcaga tttttatcag  240
ctagacaagc tttctcctgc gtataaaatt ttctttaatg atgaagttat caccatagga  300
gatacaatgg agaaaatttg cgaagaattt gaacgcatag aaaaaggaag ttcaattcct  360
cttaaaaaat ttataaataa agctgcagat aattataaca ttgccataaa caaaattgta  420
ttaaaaccag gtgtttcacc cttagaattg gttactaaag atactgttac tagactagat  480
caatttttta aaacaataag cagtgatgtt agacgccagt ttaaaaaccc taaactaata  540
tctactttag agtttcctgt tttgttttg ggtgcaaaac caagcaatac accttctttt  600
tatagtttta tgaattacgc cgattttggc ttaggtactt ggcatcctaa aggcggaatg  660
tatcaaataa ttcttgcaat gagacaactt gcagaagaat taggtgtttc aataaatgta  720
aactctaatg ttactaatat taatgttgaa aataatacat caacatcaat tactgttaac  780
ggtaaaactt taaagtttga tgttgtttta agcggtgcag attatcatca ctcagaaacg  840
ttgttagata gaaaatatag acagtattca gaaaaatatt ggaacaataa aacctttgct  900
ccttcttctc tcctatttta cgtaggtttt gataagaaat tgaaaaatgt aaaccatcat  960
aacttatttt ttgataccaa ctttgaaacg catgcagaag atatttacga taatccaaaa  1020
tggcctaaag aacctctatt ttatgccaat ttcccatctg taacagataa cagcatggcg  1080
cctaatggta aagaaaatgg ttttttctta ataccaattg ctcctaactt agaagataca  1140
cctcaattaa gagaacaata ttttgatata atcatgtctc gttttgaaaa attaactcaa  1200
caagatgtta aaaatagtat tatctttaaa gaaagctttt gtgttaaaga ttttattgaa  1260
gcatataatt cctacaaagg aaacgcatac ggaatggcta atacgctaac gcaaaccgct  1320
tttttaagac caaatttaaa gagtaaaaaa gttaacaacc tctactttac aggacaatta  1380
actgttcctg gtccaggtgt gccgccagca cttatatctg gaaaattagt agcagaatta  1440
atccaaaaac accaccaaaa actatgaaag caatatttga ttctgtgtcg tacaattgta  1500
gtaaagttgt tactacatct tacagcactt cgttttcttt agctacaaaa atgcttgcaa  1560
agtctatcag acaggatatt tataatattt atggttttgt gaggtttgca gatgagattg  1620
tagacacttt tcatgattat gataaagaaa ctttatttaa caattttgaa aatgatttag  1680
aattagctct aaaaaacaaa attagcctaa atccaatatt aaatgcgttt caacatacat  1740
atcacaagta taacatcgaa aaacatatgg ttgatgcttt tatgaaaagt atgcgactag  1800
atttatctaa aactaaatac actacagacc aagagtataa agattatatt tatggttctg  1860
cagacgtagt tggactaatg tgtttaaaag tctttgttaa aggagataat gatcaatacg  1920
aaaaacttaa agacacagca atgtcattag gttctgcttt tcaaaaggtg aatttttac  1980
gagacttaaa agctgatcac gaattacttg atagaactta tttcccaaat acagatttaa  2040
ataatctaac tgaagaagat aaactattca tcattaatga tattgaaaac gattttaaaa  2100
aaggcttaga aggtataaaa caattaccta tggaggctaa atttggagta tttatggctt  2160
atagatacta tcaccagtta ctggcaaagc ttaaaaaaac accagcatta gaaattaaaa  2220
atactagaat aagagtacca aactacaaaa aggcagaact tttaactaga agctacgtaa  2280
agtatcagtt aaatttatta taattagaca tgaaaacatt gtattggata ttaatatttt  2340
taggcacatt ttctatcatg gaatttatgg catggtttac acataaatac atcatgcacg  2400
gatttttatg gtcactacat aaagaccatc atctaaaaga tcacgatagc tggtttgagc  2460
gtaatgatgc ctttttatc ttttatgcaa ttgtaagtat gactttgcttt tacttatgga  2520
gttacgaaga tatatggtat acattaccaa taggcttagg cattatggct tatggtgcag  2580
cttacttctt agtacacgat atttttatcc atcaacgctt taaaatgttt agaaatgcta  2640
ataattggta cgcacgtggt gttagacgtg cacacaaaat acatcacaag catataggca  2700
aagaagatgg agaaaacttt ggcatgttag tcgtaccatt taagtacttc aaaaaataga  2760
ctaaatgtct caaaaacatt atgattatat catagttggc aatggtttag ctggacttca  2820
attagcctta gcttttgcca aggattcata ttttaataat aaatccattg ctttaataga  2880
cgcttctact aaaactgaaa atgataaaac ttggagtttt tgggaacaaa acaatagcac  2940
ttttagtcat ttaacttacc aatcctggca acatgcaact atctacgcag aagaccaaaa  3000
aataagctta aatctaaaac cttatactta taaatctata cgtgcaatag acttttatac  3060
ggaagctaaa gcacaactca atcagcaaga caatattaca tttttggtgg aaaccgtgac  3120
ttcggttaaa gaaaaagaaa tagttgaagt cacaaccaaa acaaacaact atacgacaaa  3180
tcatgttttt gatagtcgga ttccagacgc gtttttttaaa gatgaaaaag ccacaacttt  3240
aatacaacat tttaaaggct ggattataga agctgaaaac gatgttttta atgaaaacag  3300
cttaacaatg atggattatc gattaaaaga taataatcaa acaaccttta tgtatgtgtt  3360
accgcataca aaaaataaag cgttagtaga atttacatat tttacggaaa acactgttaa  3420
aagtgaccat tacgacaact atttaaagca atatatttca gaatatttaa acattaataa  3480
ttataatatt gtcgaaactg aagttggtca aataccaatg acaactttta attttcaatt  3540
gtttaactct tccaaaatca ctaaaattgg tacagctggc ggttgggtaa aaccttctac  3600
gggatattct tttaaactca cagaaaaaag agttgcaaaa attattgaga atataaaaac  3660
caatcaacca accacaaacg gatttttttaa aaacaagtat aaattttacg acaaagtatt  3720
tttacaagtt ttaaaagata ataatgaaaa aggcgaatgg gtttttaatc aattttacag  3780
taaaaatagc acaccaacca tgtttaaatt tttagatgaa gagtcttcac tttttgaaga  3840
cattaaaatt atgtggtcgt tatttagttt cagttttatt aaagcttttt ttaaaacgct  3900
ttaa                                                                3904

SEQ ID NO: 27           moltype = AA  length = 149
FEATURE                 Location/Qualifiers
source                  1..149
                        mol_type = protein
                        organism = Mesoflavibacter zeaxanthinifaciens
```

```
SEQUENCE: 27
MKTLYWILIF LGTFSIMEFM AWFTHKYIMH GFLWSLHKDH HLKDHDSWFE RNDAFFIFYA  60
IVSMTCFYLW SYEDIWYTLP IGLGIMAYGA AYFLVHDIFI HQRFKMFRNA NNWYARGVRR  120
AHKIHHKHIG KEDGENFGML VVPFKYFKK                                    149

SEQ ID NO: 28          moltype = AA  length = 379
FEATURE                Location/Qualifiers
source                 1..379
                       mol_type = protein
                       organism = Mesoflavibacter zeaxanthinifaciens
SEQUENCE: 28
MSQKHYDYII VGNGLAGLQL ALAFAKDSYF NNKSIALIDA STKTENDKTW SFWEQNNSTF  60
SHLTYQSWQH ATIYAEDQKI SLNLKPYTYK SIRAIDFYTE AKAQLNQQDN ITFLVETVTS  120
VKEKEIVEVT TKTNNYTTNH VFDSRIPDAF FKDEKATTLI QHFKGWIIEA ENDVFNENSL  180
TMMDYRLKDN NQTTFMYVLP HTKNKALVEF TYFTENTVKS DHYDNYLKQY ISEYLNINNY  240
NIVETEVGQI PMTTFNFQLF NSSKITKIGT AGGWVKPSTG YSFKLTEKRV AKIIENIKTN  300
QPTTNGFFKN KYKFYDKVFL QVLKDNNEKG EWVFNQFYSK NSTPTMFKFL DEESSLFEDI  360
KIMWSLFSFS FIKAFFKTL                                               379

SEQ ID NO: 29          moltype = AA  length = 488
FEATURE                Location/Qualifiers
source                 1..488
                       mol_type = protein
                       organism = Mesoflavibacter zeaxanthinifaciens
SEQUENCE: 29
MKNKIAIIGS GFSALSAACY LAKDGFNVSV FEKNDTVGGR CRQFKKDGFT FDMGPSWYWM  60
PDIFDKFFND FDKKTSDFYQ LDKLSPAYKI FFNDEVITIG DTMEKICEEF ERIEKGSSIP  120
LKKFINKAAD NYNIAINKIV LKPGVSPLEL VTKDTVTRLD QFFKTISSDV RRQFKNPKLI  180
STLEFPVLFL GAKPSNTPSF YSFMNYADFG LGTWHPKGGM YQIILAMRQL AEELGVSINV  240
NSNVTNINVE NNTSTSITVN GKTLKFDVVL SGADYHHSET LLDRKYRQYS EKYWNNKTFA  300
PSSLLFYVGF DKKLKNVNHH NLFFDTNFET HAEDIYDNPK WPKEPLFYAN FPSVTDNSMA  360
PNGKENGFFL IPIAPNLEDT PQLREQYFDI IMSRFEKLTQ QDVKNSIIFK ESFCVKDFIE  420
AYNSYKGNAY GMANTLTQTA FLRPNLKSKK VNNLYFTGQL TVPGPGVPPA LISGKLVAEL  480
IQKHHQKL                                                           488

SEQ ID NO: 30          moltype = AA  length = 279
FEATURE                Location/Qualifiers
source                 1..279
                       mol_type = protein
                       organism = Mesoflavibacter zeaxanthinifaciens
SEQUENCE: 30
MKAIFDSVSY NCSKVVTTSY STSFSLATKM LAKSIRQDIY NIYGFVRFAD EIVDTFHDYD  60
KETLFNNFEN DLELALKNKI SLNPILNAFQ HTYHKYNIEK HMVDAFMKSM RLDLSKTKYT  120
TDQEYKDYIY GSADVVGLMC LKVFVKGDND QYEKLKDTAM SLGSAFQKVN FLRDLKADHE  180
LLDRTYFPNT DLNNLTEEDK LFIINDIEND FKKGLEGIKQ LPMEAKFGVF MAYRYYHQLL  240
AKLKKTPALE IKNTRIRVPN YKKAELLTRS YVKYQLNLL                         279

SEQ ID NO: 31          moltype = DNA  length = 7292
FEATURE                Location/Qualifiers
source                 1..7292
                       mol_type = unassigned DNA
                       organism = Escherichia vulneris
SEQUENCE: 31
atggtgagtg gcagtaaagc gggcgtttcg cctcatcgcg aaatagaagt aatgagacaa  60
tccattgacg atcacctggc tggcctgtta cctgaaaccg acagccagga tatcgtcagc  120
cttgcgatgc gtgaaggcgt catggcaccc ggtaaacgga tccgtccgct gctgatgctg  180
ctggccgccc gcgacctccg ctaccagggc agtatgccta cgctgctcga tctcgcctgc  240
gccgttgaac tgacccatac cgcgtcgctg atgctcgacg acatgccctg catggacaac  300
gccgagctgc gccgcggtca gcccactacc cacaaaaaat ttggtgagag cgtggcgatc  360
cttgcctccg ttgggctgct ctctaaagcc tttggtctga tcgccgccac cggcgatctg  420
ccgggggaga ggcgtgccca ggcggtcaac gagctctcta ccgccgtggg cgtgcagggc  480
ctggtactgg ggcagtttcg cgatcttaac gatgccgccc tcgaccgtac ccctgacgct  540
atcctcagca ccaaccacct caagaccggc attctgttca gcgcgatgct gcagatcgtc  600
gccattgctt ccgcctcgtc gccgagcacg cgagagacgc tgcacgcctt cgccctcgac  660
ttcggccagg cgtttcaact gctggacgat ctgcgtgacg atcacccgga aaccggtaaa  720
gatcgcaata aggacgcggg aaaatcgacg ctggtcaacc ggctgggcgc agacgcggcc  780
cggcaaaagc tgcgcgagca tattgattcc gccgacaaac acctcacttt tgcctgtccg  840
cagggcggcg ccatccgaca gtttatgcat ctgtggtttg gccatcacct tgccgactgg  900
tcaccggtca tgaaaatcgc ctgataccgc ccttttgggt tcaagcagta cataacgatg  960
gaaccacatt acaggagtag tgatgaatga aggacgagcg ccttgttcag cgtaagaacg  1020
atcatctgga tatcgttctc gacccccgtc gcgccgtaac tcaggctagc gcaggttttg  1080
agcgctggcg ctttacccac tgcgccctgc cagagctgaa ttttagcgac atcacgctgg  1140
aaaccacctt cctgaatcgg cagctacagg ctccgctgct gatcagctcc atgaccggcg  1200
gcgttgagcg ctcgcgccat atcaaccgcc acctcgccga ggcggcgcag gtgctaaaaa  1260
ttgcgatggg ggtgggctcc cagcgcgtcg ccattgagag cgacgcgggc ttagggctgg  1320
ataaaaccct gcggcagctg gctccggacg tgccgctgct ggcgaacctc ggcgcggcgc  1380
agctgaccgg cagaaaaggt attgattacg cccgacgggc cgtggagatg atcgaggcgg  1440
atgcgctgat tgtgcaccta aacccgctgc aggaggcgct acagcccggc ggcgatcgcg  1500
actggcgcgg acggctggcg gctattgaaa ctctggtccg cgagctgccc gttccgctgg  1560
```

```
tggtgaaaga ggtgggagcc ggtatctccc gaaccgtggc cgggcagctg atcgatgccg  1620
gcgttaccgt gattgacgtc gcgggcgcgg gcggcaccag ctgggccgcc gttgaaggcg  1680
agcgggcggc caccgagcag cagcgcagcg tggccaacgt ctttgccgac tgggggatcc  1740
ccaccgctga ggcgctggtt gacattgccg aggcctggcc gcagatgccc cttattgcct  1800
cgggcgggat taaaaacggc gtcgacgcgg cgaaagcgct gcggctcggc gcgtgcatgg  1860
tagggcaggc cgccgccgtg ctcggcagcg caggcgtctc cacggagaag gtgatcgatc  1920
acttcaacgt gattattgag cagctgcggg tggcctgctt ctgcaccggc agccgcagcc  1980
tgagcgatct aaagcaggct gatatccgct atgtgcggga tacgccatga gccattttgc  2040
cattgtggca ccgccgctct acagtcatgc ggtggcgctg catgccctgg cgctggagat  2100
ggcccaacgc ggccaccggg tgacctttct caccggcaac gtcgcctcgc tggcagagca  2160
ggaaacggag cgggtggcgt tctatccact tcccgccagc gtgcaacagg cccagcgcaa  2220
cgtccagcag cagagtaacg gcaacctgct gcggctgatt gcggccatgt catccctgac  2280
cgatgtgctc tgccagcagt tgcccgctat tctacagcgg ctggcggtgg acgcgctgat  2340
tgtcgatgag atggagcccg ccggaagcct ggtcgccgag gcgctgggac taccatttat  2400
ctctattgcc tgcgcgctgc cggtcaaccg cgagccgggt ctgccgctgc cggtgatgcc  2460
gtttcactac gccgaggata agagagccct gcggcgtttt caggtcagcg aacggatcta  2520
cgatgcgctg atgtacccgc acgggcagac gatcctgcgc cacgcccagc gctttggttt  2580
gccggagcgc aggcgtctcg acgagtgtct ctcgccgctg gcgcagatta gccagtccgt  2640
tccggccctc gacttcccac gccgggcgct gccgaactgt tttcactacg tgggagcact  2700
gcgctatcag ccgccgccgc aggtagaacg ctcgccacgc agcacgccgc ggatctttgc  2760
ctcgctgggc accctccagg gccaccgtct acgcctgttt cagaagatcg cccgcgcctg  2820
tgccagcgtg gggcggaggg tgaccattgc ccactgcgat ggcctgacgc ccgcccaggc  2880
cgactcgctc tacgcctgcg gcgcgacgga ggtggtcagc tttgtcgacc agccgcgcta  2940
cgttgccgag gctaatctgg tgatcaccca cggcggtctc aataccgtac tggatgcgct  3000
ggctgccgcg acgccggtgc tggcggtgcc actctctttc gaccagcccg ccgtggctgc  3060
ccggctggtc tataacgggc tgggtcgccg ggtatcgcgc tttgccagac agcagacgct  3120
ggcggatgag attgcccaac tgctggggga tgagacgctg catcagcgtc tggcgacggc  3180
ccgccagcag cttaacgacg ccgggggcac gccccgtgcg gcgaccctga ttgaacaggc  3240
catagcaggg agtgagagcg tatcgtgagg gatctgattt tagtcggcgg cggcctggcc  3300
aacgggctga tcgcctggcg tctgcgccag cgctacccgc agcttaacct gctgctgatc  3360
gaggccgggg agcagcccgg cgggaaccat acctggtcat tccatgaaga cgatctgact  3420
cccgggcagc acgcctggct ggccccgctg gtggcccacg cctggccggg ctatgaggtg  3480
cagtttcccg atcttcgccg tcgcctcgcg cgcggctact actccattac ctcagagcgc  3540
tttgccgagg ccctgcatca ggcgctgggg gagaacatct ggctaaactg ttcggtgagc  3600
gaggtgttac ccaatagcgt gcgccttgcc aacggtgagg cgctgcttgc cggagcggtg  3660
attgacggac gcggcgtgac cgccagttcg gcgatgcaaa ccggctatca gctctttctt  3720
ggtcagcagt ggcggctgac acagccccac ggcctgaccg taccgatcct gatggatgcc  3780
acggtggcgc agcagcaggg ctatcgcttt gtctacacgc tgccgctctc cgccgacacg  3840
ctgctgatcg aggatacgcg ctacgccaat gtcccgcagc gtgatgataa tgccctacgc  3900
cagacggtta ccgactatgc tcacagcaaa gggtggcagc tggcccagct tgaacgcgag  3960
gagaccggct gtctgccgat taccctggcg ggtgacatcc aggctctgtg ggccgatgcg  4020
ccgggcgtgc cgcgctcggg aatgcgggct gggctatttc accctaccac tggctattcg  4080
ctgccgctgg cggtggccct tgccgacgcg attgccgaca gcccgcggct gggcagcgtt  4140
ccgctctatc agctcacccg gcagtttgcc gaacgccact ggcgcaggca gggattcttc  4200
cgcctgctga accggatgct tttcctggcc gggcgcgagg agaaccgctg gcgggtgatg  4260
cagcgctttt atgggctgcc ggagcccacc gtagagcgct tttacgccgg tcggctctct  4320
ctctttgata aggcccgcat tttgacgggc aagccaccgg ttccgctggg cgaagcctgg  4380
cgggcggcgc tgaaccattt tcctgacaga cgagataaag gatgaaaaaa accgttgtga  4440
ttggcgcagg ctttggtggc ctggcgctgg cgattcgcct gcaggcggca gggatcccaa  4500
ccgtactgct ggagcagcgg gacaagcccg gcggtcgggc ctacgtctgg catgaccagg  4560
gctttacctt tgacgccggg ccgacggtga tcaccgatcc taccgcgctt gaggcgctgt  4620
tcaccctggc cggcaggcgc atggaggatt acgtcaggct gctgccggta aaacccttct  4680
accgactctg ctgggagtcc gggaagaccc tcgactatgc taacgacagc gccgagcttg  4740
aggcgcagat tacccagttc aacccccgcg acgtcgaggg ctaccggcgc tttctggctt  4800
actcccaggc ggtattccag gagggatatt tgcgcctcgg cagcgtgccg ttcctctctt  4860
ttcgcgacat gctgcgcgcc gggccgcagc tgcttaagct ccaggcgtgg cagagcgtct  4920
accagtcggt ttcgcgcttt attgaggatg agcatctgcg gcaggccttc tcgttccact  4980
ccctgctggt aggcggcaac cccttcacca cctcgtccat ctacaccctg atccacgccc  5040
ttgagcggga gtggggggtc tggttccctg agggcggcac cggggcgctg gtgaacggca  5100
tggtgaagct gtttaccgat ctgggcgggg agatcgaact caacgcccgg gtcgaagagc  5160
tggtggtggc cgataaccgc gtaagccagg tccggctggc ggatggtcgg atctttgaca  5220
ccgacgccgt agcctcgaac gctgacgtgg tgaacaccta taaaaagctg ctcggccacc  5280
atccggtggg gcagaagcgg gcggcagcgc tggagcgcaa gagcatgagc aactcgctgt  5340
ttgtgctcta cttcggcctg aaccagcctc attcccagct ggcgcaccat accatctgtt  5400
ttggtccccg ctaccgggag ctgatcgacg agatctttac cggcagcgcg ctggcggatg  5460
acttctcgct ctacctgcac tcgccctgcg tgaccgatcc ctcgctcgcg cctcccggct  5520
gcgccagctt ctacgtgctg gccccggtgc cgcatcttgg caacgcgccg ctggactggg  5580
cgcaggaggg gccgaagctg cgcgaccgca tctttgacta ccttgaagag cgctatatgc  5640
ccggcctgcg tagccagctg gtgacccagc ggatctttac cccggcagac ttccacgaca  5700
cgctggatgc gcatctggga tcggccttct ccatcgagcc gctgctgacc caaagcgcct  5760
ggttccgccc gcacaaccgc gacagcgaca ttgccaacct ctacctggtg ggcgcaggta  5820
ctcaccctgg ggcgggcatt cctggcgtag tggcctcggc gaaagccacc gccagcctga  5880
tgattgagga tctgcaatga gccaaccgcc gctgcttgac cacgccacgc agaccatggc  5940
caacggctcg aaaagttttg ccaccgctgc gaagctgttc gacccggcca cccgccgtag  6000
cgtgctgatg ctctacacct ggtgccgcca ctgcgatgac gtcattgacg accagaccca  6060
cggcttcgcc agcgaggccg cggcggagga ggaggccacc cagcgcctgg cccggctgcg  6120
cacgctgacc ctggcggcgt ttgaaggggc cgagatgcag gatccggcct tcgctgcctt  6180
tcaggaggtg gcgctgaccc acggtattac gccccgcatg gcgctcgatc acctcgacgg  6240
ctttgcgatg gacgtggctc agacccgcta tgtcaccttt gaggatacgc tgcgctactg  6300
```

```
ctatcacgtg gcgggcgtgg tgggtctgat gatggccagg gtgatgggcg tgcgggatga  6360
gcgggtgctg gatcgcgcct gcgatctggg gctggccttc cagctgacga atatcgcccg  6420
ggatattatt gacgatgcgg ctattgaccg ctgctatctg cccgccgagt ggctgcagga  6480
tgccgggctg accccggaga actatgccgc gcgggagaat cgggccgcgc tggcgcgggt  6540
ggcggagcgg cttattgatg ccgcagagcc gtactacatc tcctcccagg ccgggctaca  6600
cgatctgccg ccgcgctgcg cctgggcgat cgccaccgcc cgcagcgtct accgggagat  6660
cggtattaag gtaaaagcgg cgggaggcag cgcctgggat cgccgccagc acaccagcaa  6720
aggtgaaaaa attgccatgc tgatggcggc accggggcag gttattcggg cgaagacgac  6780
gagggtgacg ccgcgtccgg ccggtctttg gcagcgtccc gtttaggcgg gcggccatga  6840
cgttcacgca ggatcgcctg taggtcggca ggcttgcggg cgtaaataaa accgaaggag  6900
acgcagccct cccggccgcg caccgcgtgg tgcaggcggt gggcgacgta gagccgcttc  6960
aggtagcccc ggcgcgggat ccagtggaag ggccagcgct gatgcaccag accgtcgtgc  7020
accaggaagt agagcaggcc atagaccgtc atgccgcagc caatccactg caggggccaa  7080
acgcccgccg tgcccacggc aatcagcgcg atagccaccc cggcaaacac caccgcaaag  7140
agatcgttta gctcaaatac gcccttgcgc ggggtatggt gtgactcatg ccagcgccat  7200
ccccagccgt gcataatgta gcggtgggta aacgcggcga tgccctccat cgcaataacg  7260
ctcaagatga cgattaaact atttactagc at                                7292

SEQ ID NO: 32           moltype = AA  length = 176
FEATURE                 Location/Qualifiers
source                  1..176
                        mol_type = protein
                        organism = Escherichia vulneris
SEQUENCE: 32
MLVNSLIVIL SVIAMEGIAA FTHRYIMHGW GWRWHESHHT PRKGVFELND LFAVVFAGVA  60
IALIAVGTAG VWPLQWIGCG MTVYGLLYFL VHDGLVHQRW PFHWIPRRGY LKRLYVAHRL  120
HHAVRGREGC VSFGFIYARK PADLQAILRE RHGRPPKRDA AKDRPDAASP SSSSPE      176

SEQ ID NO: 33           moltype = AA  length = 386
FEATURE                 Location/Qualifiers
source                  1..386
                        mol_type = protein
                        organism = Escherichia vulneris
SEQUENCE: 33
VRDLILVGGG LANGLIAWRL RQRYPQLNLL LIEAGEQPGG NHTWSFHEDD LTPGQHAWLA  60
PLVAHAWPGY EVQFPDLRRR LARGYYSITS ERFAEALHQA LGENIWLNCS VSEVLPNSVR  120
LANGEALLAG AVIDGRGVTA SSAMQTGYQL FLGQQWRLTQ PHGLTVPILM DATVAQQQGY  180
RFVYTLPLSA DTLLIEDTRY ANVPQRDDNA LRQTVTDYAH SKGWQLAQLE REETGCLPIT  240
LAGDIQALWA DAPGVPRSGM RAGLFHPTTG YSLPLAVALA DAIADSPRLG SVPLYQLTRQ  300
FAERHWRRQG FFRLLNRMLF LAGREENRWR VMQRFYGLPE PTVERFYAGR LSLFDKARIL  360
TGKPPVPLGE AWRAALNHFP DRRDKG                                      386

SEQ ID NO: 34           moltype = AA  length = 486
FEATURE                 Location/Qualifiers
source                  1..486
                        mol_type = protein
                        organism = Escherichia vulneris
SEQUENCE: 34
MKKTVVIGAG FGGLALAIRL QAAGIPTVLL EQRDKPGGRA YVWHDQGFTF DAGPTVITDP  60
TALEALFTLA GRRMEDYVRL LPVKPFYRLC WESGKTLDYA NDSAELEAQI TQFNPRDVEG  120
YRRFLAYSQA VFQEGYLRLG SVPFLSFRDM LRAGPQLLKL QAWQSVYQSV SRFIEDEHLR  180
QAFSFHSLLV GGNPFTTSSI YTLIHALERE WGVWFPEGGT GALVNGMVKL FTDLGGEIEL  240
NARVEELVVA DNRVSQVRLA DGRIFDTDAV ASNADVVNTY KKLLGHHPVG QKRAAALERK  300
SMSNSLFVLY FGLNQPHSQL AHHTICFGPR YRELIDEIFT GSALADDFSL YLHSPCVTDP  360
SLAPPGCASF YVLAPVPHLG NAPLDWAQEG PKLRDRIFDY LEERYMPGLR SQLVTQRIFT  420
PADFHDTLDA HLGSAFSIEP LLTQSAWFRP HNRDSDIANL YLVGAGTHPG AGIPGVVASA  480
KATASL                                                            486

SEQ ID NO: 35           moltype = AA  length = 309
FEATURE                 Location/Qualifiers
source                  1..309
                        mol_type = protein
                        organism = Escherichia vulneris
SEQUENCE: 35
MSQPPLLDHA TQTMANGSKS FATAAKLFDP ATRRSVLMLY TWCRHCDDVI DDQTHGFASE  60
AAAEEEATQR LARLRTLTLA AFEGAEMQDP AFAAFQEVAL THGITPRMAL DHLDGFAMDV  120
AQTRYVTFED TLRYCYHVAG VVGLMMARVM GVRDERVLDR ACDLGLAFQL TNIARDIIDD  180
AAIDRCYLPA EWLQDAGLTP ENYAARENRA ALARVAERLI DAAEPYYISS QAGLHDLPPR  240
CAWAIATARS VYREIGIKVK AAGGSAWDRR QHTSKGEKIA MLMAAPGQVI RAKTTRVTPR  300
PAGLWQRPV                                                         309

SEQ ID NO: 36           moltype = AA  length = 307
FEATURE                 Location/Qualifiers
source                  1..307
                        mol_type = protein
                        organism = Escherichia vulneris
SEQUENCE: 36
MVSGSKAGVS PHREIEVMRQ SIDDHLAGLL PETDSQDIVS LAMREGVMAP GKRIRPLLML  60
LAARDLRYQG SMPTLLDLAC AVELTHTASL MLDDMPCMDN AELRRGQPTT HKKFGESVAI  120
```

```
LASVGLLSKA FGLIAATGDL PGERRAQAVN ELSTAVGVQG LVLGQFRDLN DAALDRTPDA  180
ILSTNHLKTG ILFSAMLQIV AIASASSPST RETLHAFALD FGQAFQLLDD LRDDHPETGK  240
DRNKDAGKST LVNRLGADAA RQKLREHIDS ADKHLTFACP QGGAIRQFMH LWFGHHLADW  300
SPVMKIA                                                            307

SEQ ID NO: 37          moltype = AA  length = 347
FEATURE                Location/Qualifiers
source                 1..347
                       mol_type = protein
                       organism = Escherichia vulneris
SEQUENCE: 37
MKDERLVQRK NDHLDIVLDP RRAVTQASAG FERWRFTHCA LPELNFSDIT LETTFLNRQL  60
QAPLLISSMT GGVERSRHIN RHLAEAAQVL KIAMGVGSQR VAIESDAGLG LDKTLRQLAP  120
DVPLLANLGA AQLTGRKGID YARRAVEMIE ADALIVHLNP LQEALQPGGD RDWRGRLAAI  180
ETLVRELPVP LVVKEVGAGI SRTVAGQLID AGVTVIDVAG AGGTSWAAVE GERAATEQQR  240
SVANVFADWG IPTAEALVDI AEAWPQMPLI ASGGIKNGVD AAKALRLGAC MVGQAAAVLG  300
SAGVSTEKVI DHFNVIIEQL RVACFCTGSR SLSDLKQADI RYVRDTP                347

SEQ ID NO: 38          moltype = DNA  length = 6228
FEATURE                Location/Qualifiers
source                 1..6228
                       mol_type = unassigned DNA
                       organism = Pantoea ananatis
SEQUENCE: 38
atgacggtct gcgcaaaaaa acacgttcat ctcactcgcg atgctgcgga gcagttactg  60
gctgatattg atcgacgcct tgatcagtta ttgcccgtgg agggagaacg ggatgttgtg  120
ggtgccgcga tgcgtgaagg tgcgctggca ccgggaaaac gtattcgccc catgttgctg  180
ttgctgaccg cccgcgatct gggttgcgct gtcagccatg acggattact ggatttggcc  240
tgtgcggtgg aaatggtcca cgcggcttcg ctgatccttg acgatatgcc ctgcatggac  300
gatgcgaagc tgcggcgcgg acgccctacc attcattctc attacggaga gcatgtggca  360
atactggcgg cggttgcctt gctgagtaaa gcctttggcg taattgccga tgcagatggc  420
ctcacgccgc tggcaaaaaa tcgggcggtt tctgaactgt caaacgccat cggcatgcaa  480
ggattggttc agggtcagtt caaggatctg tctgaagggg ataagccgcg cagcgctgaa  540
gctattttga tgacgaatca ctttaaaacc agcacgctgt tttgtgcctc catgcagatg  600
gcctcgattg ttgcgaatgc ctccagcgaa gcgcgtgatt gcctgcatcg tttttcactt  660
gatcttggtc aggcatttca actgctggac gatttgaccg atggcatgac cgacaccggt  720
aaggatagca atcaggacgc cggtaaatcg acgctggtca atctgttagg cccgagggcg  780
gttgaagaac gtctgagaca acatcttcag cttgccagtg agcatctctc tgcggcctgc  840
caacacgggc acgccactca acattttatt caggcctggt ttgacaaaaa actcgctgcc  900
gtcagttaag gatgctgcat gagccatttc gcggcgatcg caccgccttt ttacagccat  960
gttcgcgcat tacagaatct cgctcaggaa ctggtcgcgc gcggtcatcg ggtgaccttt  1020
attcagcaat acgatattaa acacttgatc gatagcgaaa ccattggatt tcattccgtc  1080
gggacagaca gccatccccc cggcgcgtta acgcgcgtgc tacacctggc ggctcatcct  1140
ctggggccgt caatgctgaa gctcatcaat gaaatggcgc gcaccaccga tatgctgtgc  1200
cgcgaactcc cccaggcatt taacgatctg gccgtcgatg gcgtcattgt tgatcaaatg  1260
gaaccggcag gcgcgctcgt tgctgaagca ctgggactgc cgtttatctc tgtcgcctgc  1320
gcgctgcctc tcaatcgtga accggatatg cccctggcgg ttatgccttt cgaatacggg  1380
accagcgacg cggctcgcga acgttatgcc gccagtgaaa aaatttatga ctggctaatg  1440
cgtcgtcatg accgtgtcat tgccgaacac agccacagaa tgggcttagc cccccggcaa  1500
aagcttcacc agtgttttc gccactggcg caaatcagcc agcttgttcc tgaactggat  1560
tttccccgca aagcgttacc ggcttgtttt catgccgtcg ggcctctgcg cgaaacgcac  1620
gcaccgtcaa cgtcttcatc ccgttatttt acatcctcag aaaaaccccg gattttcgcc  1680
tcgctgggca cgcttcaggg acaccgttat gggctgttta aaacgatagt gaaagcctgt  1740
gaagaaattg acggtcagct cctgttagcc cactgtggtc gtcttacgga ctctcagtgt  1800
gaagagctgg cgcgaagccg tcatacacag gtggtggatt ttgccgatca gtcagccgcg  1860
ctgtctcagg cgcagctggc gatcacccac ggcggcatga atacggtact ggacgcgatt  1920
aattaccgga cgccccttt agcgcttccg ctggcctttg atcagcccgg cgtcgcgtca  1980
cgcatcgttt atcacggcat cggcaagcgt gcttcccgct ttaccaccag ccatgctttg  2040
gctcgtcaga tgcgttcatt gctgaccaac gtcgactttc agcagcgcat ggcgaaaatc  2100
cagacagccc ttcgtttggc agggggcacc atggccgctg ccgatatcat tgagcaggtt  2160
atgtgcaccg gtcagcctgt cttaagtggg agcggctatg caaccgcatt atgatctgat  2220
tctcgtgggg gctggactcg cgaatggcct tatcgccctg cgtcttcagc agcagcaacc  2280
tgatatgcgt attttgctta tcgacgccgc accccaggcg ggcgggaatc atacgtggtc  2340
atttcaccac gatgatttga ctgagagcca acatcgttgg atagctccgc tggtggttca  2400
tcactggccc gactatcagg tacgctttcc cacacgccgt cgtaagctga acagcggcta  2460
cttttgtatt acttctcagc gtttcgctga ggttttacag cgacagtttg gcccgcactt  2520
gtggatggat accgcggtcg cagaggttaa tgcggaatct gttcggttga aaaagggtca  2580
ggttatcggt gcccgcgcgg tgattgacgg gcggggttat gcggcaaatt cagcactgag  2640
cgtgggcttc caggcgttta ttggccagga atggcgattg agccacccgc atggtttatc  2700
gtctcccatt atcatggatg ccacggtcga tcagcaaaat ggttatcgct tcgtgtacag  2760
cctgccgctc tcgccgacca gattgttaat tgaagacacg cactatattg ataatgcgac  2820
attagatcct gaatgcgcgc ggcaaaatat ttgcgactat gccgcgcaac agggttggca  2880
gcttcagaca ctgctgcgag aagaacaggg cgccttaccc attactctgt cgggcaatgc  2940
cgacgcattc tggcagcagc gcccccctggc ctgtagtgga ttacgtgccg gtctgttcca  3000
tcctaccacc ggctattcac tgccgctggc ggttgccgtg gccgaccgcc tgagtgcact  3060
tgatgtcttt acgtcggcct caattcacca tgccattacg cattttgccc gcgagcgctg  3120
gcagcagcag ggcttttttcc gcatgctgaa tcgcatgctg tttttagccg gacccgccga  3180
ttcacgctgg cgggttatgc agcgttttta tggtttacct gaagatttaa ttgcccgttt  3240
ttatgcggga aaactcacgc tgaccgatcg gctacgtatt ctgagcggca agccgcctgt  3300
```

```
tccggtatta gcagcattgc aagccattat gacgactcat cgttaaagag cgactacatg  3360
aaaccaacta cggtaattgg tgcaggcttc ggtggcctgg cactggcaat tcgtctacaa  3420
gctgcgggga tccccgtctt actgcttgaa caacgtgata aacccggcgg tcgggcttat  3480
gtctacgagg atcaggggtt tacctttgat gcaggcccga cggttatcac cgatcccagt  3540
gccattgaag aactgtttgc actggcagga aaacagttaa aagagtatgt cgaactgctg  3600
ccggttacgc cgttttaccg cctgtgttgg gagtcaggga aggtctttaa ttacgataac  3660
gatcaaaccc ggctcgaagc gcagattcag cagtttaatc cccgcgatgt cgaaggttat  3720
cgtcagtttc tggactattc acgcgcggtg tttaaagaag gctatctaaa gctcggtact  3780
gtcccttttt tatcgttcag agacatgctt cgcgccgcac ctcaactggc gaaactgcag  3840
gcatggagaa gcgtttacag taaggttgcc agttacatcg aagatgaaca tctgcgccag  3900
gcgttttctt tccactcgct gttggtgggc ggcaatccct tcgccacctc atccatttat  3960
acgttgatac acgcgctgga gcgtgagtgg ggcgtctggt ttccgcgtgg cggcaccggc  4020
gcattagttc aggggatgat aaagctgttt caggatctgg gtggcgaagt cgtgttaaac  4080
gccagagtca gccatatgga aacgacagga aacaagattg aagccgtgca tttagaggac  4140
ggtcgcaggt tcctgacgca agccgtcgcg tcaaatgcag atgtggttca tacctatcgc  4200
gacctgttaa gccagcaccc tgccgcggtt aagcagtcca acaaactgca gactaagcgc  4260
atgagtaact ctctgtttgt gctctatttt ggtttgaatc accatcatga tcagctcgcg  4320
catcacacgg tttgtttcgg cccgcgttac cgcgagctga ttgacgaaat ttttaatcat  4380
gatggcctcg cagaggactt ctcactttat ctgcacgcgc cctgtgtcac ggattcgtca  4440
ctggcgcctg aaggttgcgg cagttactat gtgttggcgc cggtgccgca tttaggcacc  4500
gcgaacctcg actggacggt tgaggggcca aaactacgcg accgtatttt tgcgtacctt  4560
gagcagcatt acatgcctgg cttacggagt cagctggtca cgcaccggat gtttacgccg  4620
tttgattttc gcgaccagct taatgcctat catggctcag ccttttctgt ggagcccgtt  4680
cttacccaga gcgcctggtt tcggccgcat aaccgcgata aaaccattac taatctctac  4740
ctggtcggcg caggcacgca tcccggcgca ggcattcctg gcgtcatcgg ctcggcaaaa  4800
gcgacagcag gtttgatgct ggaggatctg atatgaataa tccgtcgtta ctcaatcatg  4860
cggtcgaaac gatggcagtt ggctcgaaaa gttttgcgac agcctcaaag ttatttgatg  4920
caaaaacccg gcgcagcgta ctgatgctct acgcctggtg ccgccattgt gacgatgtta  4980
ttgacgatca gacgctgggc tttcaggccc ggcagcctgc cttacaaacg cccgaacaac  5040
gtctgatgca acttgagatg aaaacgcgcc aggcctatgc aggatcgcag atgcacgaac  5100
cggcgtttgc ggcttttcag gaagtggcta tggctcatga tatcgccccg gcttacgcgt  5160
ttgatcatct ggaaggcttc gccatggatg tacgcgaagc gcaatacagc caactggatg  5220
atacgctgcg ctattgctat cacgttgcag gcgttgtcgg cttgatgatg gcgcaaatca  5280
tgggcgtgcg ggataacgcc acgctggacc gcgcctgtga ccttgggctg gcatttcagt  5340
tgaccaatat tgctcgcgat attgtggacg atgcgcatgc gggccgctgt tatctgccgg  5400
caagctggct ggagcatgaa ggtctgaaca aagagaatta tgcggcacct gaaaaccgtc  5460
aggcgctgag ccgtatcgcc cgtcgtttgg tgcaggaagc agaaccttac tatttgtctg  5520
ccacagccgg cctggcaggg ttgcccctgc gttccgcctg ggcaatcgct acggcgaagc  5580
aggtttaccg gaaaataggt gtcaaagttg aacaggccgg tcagcaagcc tgggatcagc  5640
ggcagtcaac gaccacgccc gaaaaattaa cgctgctgct ggccgcctct ggtcaggccc  5700
ttacttcccg gatgcgggct catcctcccc gccctgcgca tctctggcag cgcccgctct  5760
agcgccatgt ctttcccgga gcgtcgcctg aagttttgac aggggcggcg catagaggaa  5820
gccaaaagaa acacaacctt ctttgcccct gacggcgtga tgcatacggt gcgccatata  5880
caaccgtttg aggtagccct tgcgtggaat atagcggaat ggccaacgtt gatgcaccag  5940
cccgtcgtgc accataaaat agagtaatcc atacgccgtc atacctgcgc caatccactg  6000
gagcggccac attcctgtac tgcccagata aatcagcagg atcgataatg cagcaaaaac  6060
cacggcataa agatcgttaa cttcaaacgc acctttacgc ggttcatgat gtgaaagatg  6120
ccatccccaa ccccagccgt gcatgatgta tttgtgtgcc agtgcagcaa tcacttccat  6180
gccaatcacg gtaacgaaaa cgatcagggc attccaaatc cacaacat               6228

SEQ ID NO: 39          moltype = AA  length = 175
FEATURE                Location/Qualifiers
source                 1..175
                       mol_type = protein
                       organism = Pantoea ananatis
SEQUENCE: 39
MLWIWNALIV FVTVIGMEVI AALAHKYIMH GWGWGWHLSH HEPRKGAFEV NDLYAVVFAA  60
LSILLIYLGS TGMWPLQWIG AGMTAYGLLY FMVHDGLVHQ RWPFRYIPRK GYLKRLYMAH  120
RMHHAVRGKE GCVSFGFLYA PPLSKLQATL RERHGARAGA ARDAQGGEDE PASGK       175

SEQ ID NO: 40          moltype = AA  length = 382
FEATURE                Location/Qualifiers
source                 1..382
                       mol_type = protein
                       organism = Pantoea ananatis
SEQUENCE: 40
MQPHYDLILV GAGLANGLIA LRLQQQQPDM RILLIDAAPQ AGGNHTWSFH HDDLTESQHR  60
WIAPLVVHHW PDYQVRFPTR RRKLNSGYFC ITSQRFAEVL QRQFGPHLWM DTAVAEVNAE  120
SVRLKKGQVI GARAVIDGRG YAANSALSVG FQAFIGQEWR LSHPHGLSSP IIMDATVDQQ  180
NGYRFVYSLP LSPTRLLIED THYIDNATLD PECARQNICD YAAQQGWQLQ TLLREEQGAL  240
PITLSGNADA FWQQRPLACS GLRAGLFHPT TGYSLPLAVA VADRLSALDV FTSASIHHAI  300
THFARERWQQ QGFFRMLNRM LFLAGPADSR WRVMQRFYGL PEDLIARFYA GKLTLTDRLR  360
ILSGKPPVPV LAALQAIMTT HR                                           382

SEQ ID NO: 41          moltype = AA  length = 492
FEATURE                Location/Qualifiers
source                 1..492
                       mol_type = protein
                       organism = Pantoea ananatis
```

```
SEQUENCE: 41
MKPTTVIGAG FGGLALAIRL QAAGIPVLLL EQRDKPGGRA YVYEDQGFTF DAGPTVITDP  60
SAIEELFALA GKQLKEYVEL LPVTPFYRLC WESGKVFNYD NDQTRLEAQI QQFNPRDVEG  120
YRQFLDYSRA VFKEGYLKLG TVPFLSFRDM LRAAPQLAKL QAWRSVYSKV ASYIEDEHLR  180
QAFSFHSLLV GGNPFATSSI YTLIHALERE WGVWFPRGGT GALVQGMIKL FQDLGGEVVL  240
NARVSHMETT GNKIEAVHLE DGRRFLTQAV ASNADVVHTY RDLLSQHPAA VKQSNKLQTK  300
RMSNSLFVLY FGLNHHHDQL AHHTVCFGPR YRELIDEIFN HDGLAEDFSL YLHAPCVTDS  360
SLAPEGCGSY YVLAPVPHLG TANLDWTVEG PKLRDRIFAY LEQHYMPGLR SQLVTHRMFT  420
PFDFRDQLNA YHGSAFSVEP VLTQSAWFRP HNRDKTITNL YLVGAGTHPG AGIPGVIGSA  480
KATAGLMLED LI                                                    492

SEQ ID NO: 42          moltype = AA  length = 309
FEATURE                Location/Qualifiers
source                 1..309
                       mol_type = protein
                       organism = Pantoea ananatis
SEQUENCE: 42
MNNPSLLNHA VETMAVGSKS FATASKLFDA KTRRSVLMLY AWCRHCDDVI DDQTLGFQAR  60
QPALQTPEQR LMQLEMKTRQ AYAGSQMHEP AFAAFQEVAM AHDIAPAYAF DHLEGFAMDV  120
REAQYSQLDD TLRYCYHVAG VVGLMMAQIM GVRDNATLDR ACDLGLAFQL TNIARDIVDD  180
AHAGRCYLPA SWLEHEGLNK ENYAAPENRQ ALSRIARRLV QEAEPYYLSA TAGLAGLPLR  240
SAWAIATAKQ VYRKIGVKVE QAGQQAWDQR QSTTTPEKLT LLLAASGQAL TSRMRAHPPR  300
PAHLWQRPL                                                        309

SEQ ID NO: 43          moltype = AA  length = 302
FEATURE                Location/Qualifiers
source                 1..302
                       mol_type = protein
                       organism = Pantoea ananatis
SEQUENCE: 43
MTVCAKKHVH LTRDAAEQLL ADIDRRLDQL LPVEGERDVV GAAMREGALA PGKRIRPMLL  60
LLTARDLGCA VSHDGLLDLA CAVEMVHAAS LILDDMPCMD DAKLRRGRPT IHSHYGEHVA  120
ILAAVALLSK AFGVIADADG LTPLAKNRAV SELSNAIGMQ GLVQGQFKDL SEGDKPRSAE  180
AILMTNHFKT STLFCASMQM ASIVANASSE ARDCLHRFSL DLGQAFQLLD DLTDGMTDTG  240
KDSNQDAGKS TLVNLLGPRA VEERLRQHLQ LASEHLSAAC QHGHATQHFI QAWFDKKLAA  300
VS                                                               302

SEQ ID NO: 44          moltype = DNA  length = 3760
FEATURE                Location/Qualifiers
source                 1..3760
                       mol_type = unassigned DNA
                       organism = Fulvimarina pelagi
SEQUENCE: 44
ttgacgtctt ctgcgaaaca gaaggtcgac attgctcttg tgggcggtgg acttgccaat  60
gggctgatcg cctggcggct tgccgaattg cggccggatc tcagcatcgt cgtcctcgaa  120
gccggtgagg cgcctggcgg caaccacaca tggtcgtttc acgaacacga ccttacaccc  180
gccgctcatc ggtggatcgc gcctttcgtc gctcatcgct ggaccaccaa cgaggtgcaa  240
ttccccgacc gccatcgtca tctctcgacg gggtatttga gcgcgtcctc ggatctattt  300
cgcgaaaggc tgacgacgcg tctcggcttg cgtatccgca ccggctgtcc ggccgtttct  360
gtcacggcgc gcaaggtgcg actcgaaaac ggcgaagtga tcgaggccgg ctcggtgatt  420
gacgggcgcg gctaccgatc gagcgaacac ctcacgctcg gctttcagaa gtttctcggt  480
caggagatcg aattcgaggc accgcacggc gttgcccgac cggtcatcat ggatgctacc  540
gtcccccagg cggacggcta tcggttcgtc tatcttcttc ccatgacgcc gacgcggttg  600
ctggtcgagg acacctacta tgccgatggc gacgccctcg atcgcggaac gatccggcgc  660
aacatcgcgg cttaccgggc ggcgaagggc tggcctgcgg ggaaagtcgt tcgcgaagaa  720
gatggtgtcc tgccgatcgc gctcgccggc gatatcgagg ccttctggga ggagaagcag  780
ggcgtcccat ccagcggcct caacgctgcg cttttccacc cgacgactgg gtattccttg  840
ccggacgccg tgtatctcgc cgatctgatt gcaggcctgc cggactattc ggccgcaacc  900
ctttatgctg cgacacgccg ccactcggtc gcaacgtgga agcggcgcgg cttcttccgt  960
atgctgaacc gccttctcta tctcgccggt gatccgttga aacgttatgt catcctccag  1020
catttttatc gcctgcccga accattggtg tcgcggttct acgctgcgcg gctgacccga  1080
ggtgacaagg tgcggatcct caccggcaag ccgccggtca gtgttatcag cgcgctcaaa  1140
gttctttccc cgagttctgt cgagggagcg cccgcatgaa ccagatgccg cgcgaccttc  1200
ctaacaagac aaagaccgca gtcgttatcg gagcaggctt cggcggactg gcgcttgcga  1260
ttcgacttca ggcggccggt atccaaacga cgcttctcga aaagcgcgac aagcccggcg  1320
gacgggctta cgtctacgag gatcagggct tcaccttcga tgccggccca accgtgatca  1380
ccgacccctc cgcgctcgaa gagctgttcg agacggcgaa cgccaagctt tcggactatg  1440
tcgaactgct tcccgtcaag cctttctacc gtctcgcctg ggaagacggc ttcgtcttcg  1500
actatgcaga cgatcaggag gatctcgacc gccagatcgg cgcgaagaac ccgaaggatg  1560
tcgagggcta tcgccgcttc ctcgcttatt cgcgggacgt gttccacgag ggttacgaaa  1620
agctcggcac cgtccctttc ctgaatttca aggatatgat gcgggcagcg ccccagctcg  1680
ttcggctcga ggcctatcgc tcggtctatt cgaaggtcgc ccagttcatc gaggacgacc  1740
agttacggca ggccttttcc ttccactcgc tcctcgtcgg cggcaatccg ttcgccactt  1800
cttcgatcta cgcgctcatc cacgcgttgg agcgcaaatg ggcgtcttc ttcccgcgcg  1860
gcggcaccgg cgcgctggtc cgcggcatgg ccaagctctt caccgacatt ggcgggagga  1920
tcgaggtgaa tgccgaggtc gagaatatcg cgatcgagaa cgggcgcgcg aagtccgtga  1980
cgactaaggg cggtcaaacc tttcccgcag acttcgtcgc ctcgaatgcc gacgtcgtcc  2040
acacctatgc caagctgatg ggtcgcagcg agcgcggcaa aaagcacggc aattcgctga  2100
agaagaagcg cttttccatg tcgctcttcg tcatctattt cggcctgaag acccaccggc  2160
```

```
cggacattgc ccatcacacg gtctgtttcg gtccgcgcta tcgcccgctg atcgacgaga  2220
ttttcaaggg caaagagctc gcgggcgact tctcgctcta tctccataac ccgtgcgtca  2280
ccgatccctc gctcgcgccg gagggcatgg gctccttcta cgttctgtcc cctgtccccc  2340
atctcggtaa cgccgatata gattgggcgg ttgaggggcc gaaatatcgc gacaggatcc  2400
tcgactatct ggaagagctg tacatccccg gcctgaagga cgatctcgtc accagccgca  2460
tcttcacccc ggctgatttc aagaccgaac tgaacgccca tctcggctcg gccttctcgc  2520
tcgatccggt actgacgcag agcgcttggt tccgccctca caatcgcgac gatcagattc  2580
ccaacctcta cgtcgtcggg gctggtacgc atccaggtgc cggcgttccg ggcgtcgtcg  2640
gttcggccaa ggcgactgcc ggcctgatga tcgaggacgc gggtctcgcg tgcgtgcctg  2700
catgagtttc gccgaccgcc tcgacgtacc gatcgtcggc ggccttccgt tcgaaaagcg  2760
cgagcgcgcc gcgctggccg ccgaagccga agcgacgatc gcgcaaggct cgaagagttt  2820
cgctgccgcc gcccgcctgt ttgatccgga gatgcgggtc agcgcgctta tgctctatgc  2880
ctggtgccgg cattgcgacg atgtggtcga tgaccagatc cttggttttc gccagccagg  2940
ccgccgggac cgagccggcg atcgcgcacg tctcgatgaa ctcgaggcca agacccttgc  3000
ggcggttcga ggccgatcca cgggcgaagc accattcgac gcgatcggcg atgtcgccct  3060
gcggcatgag ctgccggaat cgctcttgac cgcgcacctc gaaggcttcc ggatggatgt  3120
cgacggccgg gtctacgagg tgattgagga tacgctcgat tattgctacc gggtcgcagg  3180
tgtcgtcggc gtgatgatgg cgcgggtcat gggcatcagg gtcgaaaacg gttcgaaatt  3240
cgacctgacg ctgaccctcg atcgagcctg cgacctcggc atggcctttc agctcaccaa  3300
tatcgcacgt gacatagtcg acgacggcga ggccggacgg gtctacgtgc cgaagacatg  3360
gctcgatgcg gctggcgtcc cggcagcgc catccaccac ccgcgcaatc gggaggcggc  3420
agcggtgttc gctctgcgtc tcctcgatct ggccgagcca tactacgcgt cggcctcgaa  3480
ggggctagcc gcgctgccgc ctcgtgccgc atgggccgtc gcgactgcgc ttggcgtcta  3540
ccgtgagatc gggaccgtca tccgccggcg tggaagtcaa gcctgggacg atcgttcatc  3600
gacaagcgcg gcgaccaagt tcctgcacgc cttcaagggt gtcggttgga cgatgggatc  3660
acgtgtctca agcaggcgcg gcgttcggcc gccggagctc tggacgcgtc ctcgactgct  3720
tgagctcggt gatgcgccca caacaggtct atcggcctga                        3760

SEQ ID NO: 45          moltype = DNA  length = 3581
FEATURE                Location/Qualifiers
source                 1..3581
                       mol_type = unassigned DNA
                       organism = Fulvimarina pelagi
SEQUENCE: 45
ttaggactgg cgagtatgcg gcagagccca ccaaggcgtc catggcgcca aatggtgctc  60
atggtggtag ccaaaatgga agcaggagaa tagcgaggcc acgtaaccga attcgctcga  120
acgtgtgtta tgcgcgtcgg caaaggtgcc cgattcttcg tgtcgatgcg ggcggtaggt  180
tccgaagtag aagagctgca atgacgaaag cagtgacggc aagccgtaaa atagaaccac  240
gttcgtcaca gatgcatcca gtatgacgag ataaaacgtc acgacggtcg agacgaatgc  300
gaccgatctc catccgaaat aacgtgagaa gaaggtgccg aaccaaggcc agaaattctc  360
cggatcatct gcgtagaaat ccgggtcggc cggtgtaccg ggtgcgtcgt ggtgtgcgaa  420
gtgagcatct ctgatctttt tccacgcaaa tcccgcgtag acgaacagga tgaacccgcc  480
gattacggca ttcaaacgcg ttcgacccgg cgccagcgaa ccatgcatgg cgtcgtgagc  540
caggatgaaa agccccaccg tcaaccagca ctggaacacc gtgatcaatg gtgcgagagg  600
caacgtgctg aaattgatgt cgaggaagaa tatcgctgag acgtgtattg cgaaccacga  660
tgccagcagc acggcacaga gcgtcaggcc aatcgtcgtt tggtagggtc tgattttggg  720
tgagtcggcg ggtgtggatc gcggtaacgc acttgccggg atcaggcgtg aggttgggct  780
gagggtcatg acctcgcaaa taagccgaac cgtccgggtg caaaatcgtt tgccgcctcg  840
tttggcgcgg cataacgtcg tccatcctcg ctctgtgcgc tcgcgagaac acgatcgacg  900
gcttctgcag cagcacgcgc accgcctgcg ttggcgattt ccgcctggat cggagcgatc  960
cggttcacga aggctgctcg gtttgcaatc aaatcggaaa gtgcattcgc aatggttcgc  1020
ggcttggccc gcttggcggc gatagcctta cccacgccgt gatggagtat acgggcaccg  1080
acacccggct gatcgtagcc aattggcagc gccaacatag gcgtaccgac cgccagacag  1140
tcgagaacgg tgttgagccc cccgtgagtc acgcagacat ctgcgcgtgc gagcatcgcg  1200
cgttgatcga cgaaactgac tacccacttg gccggaagcc tcgaagcttg tcgtggcgag  1260
agccccccgc aatgcgcgat catcaattgc acatcgagcg tctcgcaggc ggatgcgatc  1320
tttttgaata aactgtaacg atgaccttgc accgtgccga gagacgcgaa cacgaagggg  1380
cgcgtcgggt cgatcgtgag acatgtttcc ttcgtcagtc ttgcgactga ggcactgcgg  1440
atgggtccaa ccggcttcag tttcgtcccc ctcggtctcg gaaagtcgaa aacgctgacg  1500
gtctgcgaca aacgcaacac tggcgagaga caggcaacgt cgtcctcccg cggccccagt  1560
ccgaagcgcg tcgcccaggc ttggatcacc ttccgttgct tgcgcatgaa gaatttgccg  1620
acacgctccc cgccgcgatt gcgagcaagt ccctcttcgg tgggatcgta gggccaatcg  1680
agaaacggca gaggcatcgc cacatcccgt tcgattggta gggccgacgc caaggagatg  1740
tgtggcaggc cgagataagc tgcgaccaga ccggcgcctg gctcgaattc atctgcgatg  1800
attgcatcga tttgcatcga acgcatgatg tccggagcga tgcgacaaaa ctgatctgtt  1860
tctcttgctc gatcggcaac tgcccgcaag ataccgagaa tcccggcgcc gccgccgtca  1920
cgccgacgat gccgaacacc agacatgatt gaagcagaag ccgctagcgt aacaatctcg  1980
atgtcagact ggcagaccat cgtctccgcc tctttcggca gtatgaagac gacgtcgtgg  2040
ccgcgaacct tgagcgcttg ccccagaact tcgaacgcct tgatatggct gtagaacgcc  2100
ggacagacca aagctatgcg tgccaattac atcaatccct cagccgaaac gaatcgacgc  2160
agacaagcac cgccctatcg atagcaaccg accttaacat agttccgggt gacgatagtc  2220
gaggtagggt atgatcagga cattcctgaa cggcgatgga agcgttcggg tcgatcgaga  2280
aacggctttt aacgtgacga aagaggattg atgtcggccg cgcgcggttc atgctcccta  2340
agcgagatcg ctagccgctc ggctcggttg cgccgacctc gctcgatcgc gaaagtctgg  2400
cccgtcgctt cgacacttgc atgcctgttg ctgacaaacg gcctcgtcgt actctacctc  2460
tgggcgatcg gtagaccgtt catcgcgccg accgaacctc tcaagctgtt tagcgacaac  2520
ctcgccgctg cgaattcgct ttatctctcc gatccctact cgcttctgca cgtcatcttc  2580
ggaatcggtc tcttcctgta tctcgactgg atgaaacctt tctggccgac gagggaaaaa  2640
ctgattgtcg cggtcttggg gagcgcaatc tgggaagtcg tcgagaacac gccatatgtt  2700
```

```
gtgggtctgt tcaacgacac gagtgacacg gcagcttaca acggggacag tgtcgcgaat  2760
tcgattggcg atacgatctc tgcggtaatt ggttttttgt tcgcgaatcg gacagggcgc  2820
cgagtttccc tgttcgttgc attcgcgctt gaatcaatcg ttacagtatg gattggcgat  2880
ggaatcgtta ttggcacgct cagacttctg ggtctgtacc cgatctgatc gacgcgactc  2940
ttgcgcccat cgtcacggcc atgtgtgtgt gccaagatcg agttatatat gtacctcggc  3000
ctgaacgact gaaccaaaac tagaaacgtc gataagaaac gatgacgatc tggactctct  3060
actacgtctg tctcaccctc gtcacgatcg gtttgatgga ggtttatgca tggtgggcgc  3120
acaagttcat catgcatggc aaattcggtt ggggctggca taagtcccac cacgaggaaa  3180
ccgaagggtg gttcgagaag aacgatctct acgctgtcgt tttcgccggc ttcgcgatag  3240
cgctgttcat ggtcggacat ttcctttctc cgaccctgct cgccatcgcc tggggcatca  3300
cgctttacgg attactctac ttcgttgccc atgatggact tgtccatcag cgctggccgt  3360
tcaactacgt gccgcatcga ggttatgcaa aacgcctggt tcaagctcat cgtctgcacc  3420
atgcggtgga aggccgcgag cactgcgtct cgttcggctt tctctatgcg ccgccgattg  3480
aaaagctgaa gcgcgatttg cgtgagtccg gaattctcga acgggagcgc atcgagcggt  3540
ctctggacca gcaaggctcc gcccacgcgc cggttcggtg a                        3581

SEQ ID NO: 46          moltype = AA  length = 392
FEATURE                Location/Qualifiers
source                 1..392
                       mol_type = protein
                       organism = Fulvimarina pelagi
SEQUENCE: 46
LTSSAKQKVD IALVGGGLAN GLIAWRLAEL RPDLSIVVLE AGEAPGGNHT WSFHEHDLTP  60
AAHRWIAPFV AHRWTTNEVQ FPDRHRHLST GYLSASSDLF RERLTTRLGL RIRTGCPAVS  120
VTARKVRLEN GEVIEAGSVI DGRGYRSSEH LTLGFQKFLG QEIEFEAPHG VARPVIMDAT  180
VPQADGYRFV YLLPMTPTRL LVEDTYYADG DALDRGTIRR NIAAYRAAKG WPAGKVVREE  240
DGVLPIALAG DIEAFWEEKQ GVPSSGLNAA LFHPTTGYSL PDAVYLADLI AGLPDYSAAT  300
LYAATRRHSV ATWKRRGFFR MLNRLLYLAG DPLKRYVILQ HFYRLPEPLV SRFYAARLTR  360
GDKVRILTGK PPVSVISALK VLSPSSVEGA PA                                 392

SEQ ID NO: 47          moltype = AA  length = 509
FEATURE                Location/Qualifiers
source                 1..509
                       mol_type = protein
                       organism = Fulvimarina pelagi
SEQUENCE: 47
MNQMPRDLPN KTKTAVVIGA GFGGLALAIR LQAAGIQTTL LEKRDKPGGR AYVYEDQGFT  60
FDAGPTVITD PSALEELFET ANAKLSDYVE LLPVKPFYRL AWEDGFVFDY ADDQEDLDRQ  120
IGAKNPKDVE GYRRFLAYSR DVFHEGYEKL GTVPFLNFKD MMRAAPQLVR LEAYRSVYSK  180
VAQFIEDDQL RQAFSFHSLL VGGNPFATSS IYALIHALER KWGVFFPRGG TGALVRGMAK  240
LFTDIGGRIE VNAEVENIAI ENGRAKSVTT KGGQTFPADF VASNADVVHT YAKLMGRSER  300
GKKHGNSLKK KRFSMSLFVI YFGLKTHRPD IAHHTVCFGP RYRPLIDEIF KGKELAGDFS  360
LYLHNPCVTD PSLAPEGMGS FYVLSPVPHL GNADIDWAVE GPKYRDRILD YLEELYIPGL  420
KDDLVTSRIF TPADFKTELN AHLGSAFSLD PVLTQSAWFR PHNRDDQIPN LYVVGAGTHP  480
GAGVPGVVGS AKATAGLMIE DAGLACVPA                                     509

SEQ ID NO: 48          moltype = AA  length = 352
FEATURE                Location/Qualifiers
source                 1..352
                       mol_type = protein
                       organism = Fulvimarina pelagi
SEQUENCE: 48
MSFADRLDVP IVGGLPFEKR ERAALAAEAE ATIAQGSKSF AAAARLFDPE MRVSALMLYA  60
WCRHCDDVVD DQILGFRQPG RRDRAGDRAR LDELEAKTLA AVRGRSTGEA PFDAIGDVAL  120
RHELPESLLT AHLEGFRMDV DGRVYEVIED TLDYCYRVAG VVGVMMARVM GIRVENGSKF  180
DLTLTLDRAC DLGMAFQLTN IARDIVDDGE AGRVYVPKTW LDAAGVPGSA IHHPRNREAA  240
AVFALRLLDL AEPYYASASK GLAALPPRAA WAVATALGVY REIGTVIRRR GSQAWDDRSS  300
TSAATKFLHA FKGVGWTMGS RVSSRRGVRP PELWTRPRLL ELGDAPTTGL SA           352

SEQ ID NO: 49          moltype = AA  length = 262
FEATURE                Location/Qualifiers
source                 1..262
                       mol_type = protein
                       organism = Fulvimarina pelagi
SEQUENCE: 49
MTLSPTSRLI PASALPRSTP ADSPKIRPYQ TTIGLTLCAV LLASWFAIHV SAIFFLDINF  60
STLPLAPLIT VFQCWLTVGL FILAHDAMHG SLAPGRTRLN AVIGGFILFV YAGFAWKKIR  120
DAHFAHHDAP GTPADPDFYA DDPENFWPWF GTFFSRYFGW RSVAFVSTVV TFYLVILDAS  180
VTNVVLFYGL PSLLSSLQLF YFGTYRPHRH EESGTFADAH NTRSSEFGYV ASLFSCFHFG  240
YHHEHHLAPW TPWWALPHTR QS                                            262

SEQ ID NO: 50          moltype = AA  length = 179
FEATURE                Location/Qualifiers
source                 1..179
                       mol_type = protein
                       organism = Fulvimarina pelagi
SEQUENCE: 50
MTIWTLYYVC LTLVTIGLME VYAWWAHKFI MHGKFGWGWH KSHHEETEGW FEKNDLYAVV  60
FAGFAIALFM VGHFLSPTLL AIAWGITLYG LLYFVAHDGL VHQRWPFNYV PHRGYAKRLV  120
```

-continued

```
QAHRLHHAVE GREHCVSFGF LYAPPIEKLK RDLRESGILE RERIERSLDQ QGSAHAPVR   179

SEQ ID NO: 51          moltype = DNA  length = 496
FEATURE                Location/Qualifiers
source                 1..496
                       mol_type = unassigned DNA
                       organism = Methylobacterium extorquens
SEQUENCE: 51
gtgtcgccag cttcctcttc cccggcatcg cccggatgct gttcctgaac cccgtgacgc  60
ccaaagtttt cgcctggagc gccgaccggg cggcggtgcg tcgcctcatc gacggcaccg  120
gctcgcgcct cgacccgcag gggctcgacc tctaccggcg gctgttcacc cgccccggcc  180
atgtcgcggg cgccctcggc atgatggcga actgggatct tccggcactc gcccgcgacc  240
tgccggggct cgaaacccgt acgctgctgg tcgtcggcgg ggacgacaag gcgatcaagc  300
ccgacgattc cttcgccttg cgcgagcggt tgcggagcgc acgcgtagaa ttgctgcgtg  360
ggctcggcca cctcgcgcac gaggaggcgc cggagcgggt ggcggagatc attctggcag  420
aagcggacgc ccttggcgcc tcggtatcct gagacgcctc ttgcgctgac gaaaatccca  480
gccatagtgt caacct                                                  496

SEQ ID NO: 52          moltype = DNA  length = 2573
FEATURE                Location/Qualifiers
source                 1..2573
                       mol_type = unassigned DNA
                       organism = Methylobacterium extorquens
SEQUENCE: 52
atgttgacac tggccgtcaa accgactgtc acgtccgact ccgatgcccg gccgcatgcg  60
gtcgtgatcg gggccggctt cggcgggctg gccgcggcgg ttcggctcgg cgcccgcggc  120
tatcgcgtca ccgttctgga acggctcgac cagcccggcg gccgcgcccg cgtccaccgc  180
caggacggct tcaccttcga tgcggggccc accatcgtca ccgcgccgtt cctgttcgag  240
gagctgtggc ggttgtgcgg gcgggagatg cgcgaggacg tgactctcgt gccgatgcag  300
ccattctacc gcattcgctt cgaggatggg cagagcttcg cctatagcgg cgaccgcgcg  360
gcgatgcggg ccgaggtcgc ccgcttctcg cccgacgacg tgtccggcta cgaacgcttc  420
atggcccata gcgaggcggt gtgccggatg ggcttcgagg aactcggcca cgtcccgttc  480
ggcagcctcg gctcgatgct gcggatcgcg cccgatctgc tgcgcttgtc gggccaccgc  540
agcgtctacg acgtggtgtc ccgcttcatc cgcgacgagc ggctgcgcac catcttcagc  600
ttccatcccc tgctcatcgg cggcaacccg tttcgcgcca gcggcatcta ctgcctgatc  660
gcccatctgg agcggcaatg gggcgtccat ttcgccatgg gcggtaccgg acgactggtg  720
gacgggctct gcggcttgat ccgggggcag ggaggccgcg tccgctgcgg cgaggacgtt  780
tcgcgcatcc gcgtcgagga tgcgcgggcg acgggtgtgg tgctggcggg cggcgaggtc  840
atccccgccg acaccgtcgt ctcgaacgcc gattccgcct tcacctacgg cacgctgctc  900
ggcggccgga cccggcgctg gagcgcgcgg cgcctggcgc gcgcctcgtc ctccatgggg  960
ctgttcgtct ggtatttcgg tacccggaag aagtacccgg aggtcgatca ccacatgatc  1020
ctgatgggcc cgcgctatcg cggcctgttg caggacatct tcgaccgcaa gcacttggcg  1080
aacgatttca gcctctatct ccaccgcccg accgcgaccg acccgctgct cgcgccgccc  1140
ggctgcgacg cgttctacgt gctcgccccg gtgccgaacc tcgacggcgg ccaggattgg  1200
gcacagcttg ccgagcccta ccgccagcgg atcgcgcgct tcctcgaagg ctcggtgctg  1260
ccggggctgt ccgacgccct cgtcacctcg cgggtgacga cgccgcagga cttttccgac  1320
gacttcctga gcttccgcgg ctccgggttc gggctggagc cggtgctgac gcaatcggcg  1380
tggttccgtc cgcacaaccg ctcggaagac gtggccaacc tcttcctcgt cggcgcgggg  1440
acgcatcccg gcgccggtct gccgggcgtg ctgtcctcgg cgcgtgtcct cgattccgtg  1500
gtgccggatg cccgtgtttg cgcctgaccc tttcgccgcc agcgcggcgg accgctctgc  1560
ctgccgggcc gcgatccgcg ccggctccaa gagcttcttc gcggcctcgc tgctgctgcc  1620
gccctcagtg cgggtctcgg cctacggcct ctacgccttc tgccgccttt ccgacgatgc  1680
ggtggacgag gcggggggca accgtgctgc ggccctcgcc cgcctggaac gacggctgac  1740
agcggcctgt gccggccggc ccgacaacca cccggccgac cgggcgctcg ccgaggtgct  1800
cgcccgccac gccatcccgg aaaagctgcc gcgggcgctg ctcgaagggt tggcctggga  1860
cacgcaaggc cggcgctacg acaccctgtc ggagctggcc gcctatgccg cccgggtcgc  1920
gggcgcggtc ggggcgatga tgacactggt gatgggggtg cgcgacggcc ccgcgctcgc  1980
ccgcgcctgc gatctcggcg tggccatgca attcaccaac atcgcccgcg atgtcggcga  2040
ggatgcccgc gccgggcgcc tctacctgcc tcgcgagtgg ctcgacgcgg ccggcatcga  2100
cccggacgcc ttcctcgccg agcctcggct cggccccagc ctgcaacggg tggtggccga  2160
gctgctggcg gcggccgacg aactctacgc ccgcgccgaa cccggcatcg ccgcgctccc  2220
gttgagctgc cgcccggcga tccgcgccgc cggcctgatc tacgcggaga tcggccgtgc  2280
cgtggaggcg aacgagctcg attcggtcac gcgccgcgcc cgcgtcaccg gcgcgcgcaa  2340
ggccgggctt ctggccaccg cgatcctgcc cgcgggcggc ggccagggac tatcggcgcc  2400
gccattgccc gagaccgcct tcctcgtgga agccgtgacg caccatccgg tcccagccgc  2460
gcggcgcttg ccaccgtggt ggaacgtgtc ggggcaggtc gtgcgggtgc tcgacctgat  2520
cgaggtgctg gaggagcgcg acgccttccg ccgctcggcc gcgtcgtaag gaa         2573
```